(12) United States Patent
Canan Koch et al.

(10) Patent No.: US 6,953,858 B2
(45) Date of Patent: Oct. 11, 2005

(54) HIV PROTEASE INHIBITORS, COMPOSITIONS CONTAINING THE SAME, THEIR PHARMACEUTICAL USES AND MATERIALS FOR THEIR SYNTHESIS

(75) Inventors: Stacie S. Canan Koch, La Jolla, CA (US); Therese N. Alexander, San Diego, CA (US); Mark Barvian, Ann Arbor, MI (US); Gary Bolton, Ann Arbor, MI (US); Frederick Earl Boyer, Jr., Canton Township, MI (US); Benjamin J. Burke, San Diego, CA (US); Tod Holler, Ann Arbor, MI (US); Tanya M. Jewell, Encinitas, CA (US); Vara Prasad Josyula, Ann Arbor, MI (US); David J. Kucera, Del Mar, CA (US); Maria Angelica Linton, San Diego, CA (US); Jeffrey J. Machak, Shelby Township, MI (US); Lennert J. Mitchell, Jr., Chula Vista, CA (US); Sean T. Murphy, Ypsilanti, MI (US); Siegfried H. Reich, Solana Beach, CA (US); Donald J. Skalitzky, San Diego, CA (US); John H. Tatlock, San Diego, CA (US); Michael D. Varney, Solana Beach, CA (US); Scott C. Virgil, San Diego, CA (US); Stephen E. Webber, San Diego, CA (US); Stephen T. Worland, Del Mar, CA (US); Michael Melnick, Ann Arbor, MI (US)

(73) Assignee: Agouron Pharmaceuticals, Inc., San Diego, CA (US)

(*) Notice: Subject to any disclaimer, the term of this patent is extended or adjusted under 35 U.S.C. 154(b) by 39 days.

(21) Appl. No.: 10/166,957

(22) Filed: Jun. 11, 2002

(65) Prior Publication Data

US 2003/0153507 A1 Aug. 14, 2003

Related U.S. Application Data

(60) Provisional application No. 60/297,460, filed on Jun. 11, 2001, and provisional application No. 60/297,729, filed on Jun. 11, 2001.

(51) Int. Cl.[7] ............................................. C07D 277/06
(52) U.S. Cl. ..................................................... 548/200
(58) Field of Search .......................................... 548/200

(56) References Cited

U.S. PATENT DOCUMENTS

| | | | |
|---|---|---|---|
| 5,629,406 A | 5/1997 | Higashida et al. | |
| 5,644,028 A | 7/1997 | Mimoto et al. | |
| 5,932,550 A | 8/1999 | Kato et al. | 514/19 |
| 5,962,640 A | 10/1999 | Kato et al. | 530/337 |
| 6,222,043 B1 | 4/2001 | Kato et al. | |
| 6,313,094 B1 | 11/2001 | Mimoto et al. | |
| 6,329,502 B1 | 12/2001 | Mimoto et al. | |
| 2002/0049165 A1 | 4/2002 | Mimoto et al. | |

FOREIGN PATENT DOCUMENTS

| | | |
|---|---|---|
| AU | 705193 | 2/1997 |
| CA | 2179935 | 6/1996 |
| EP | 0490667 | 6/1992 |
| EP | 0498680 | 8/1992 |
| EP | 0574135 B1 | 12/1993 |
| EP | 0706794 | 4/1996 |
| EP | 0751145 A2 | 6/1996 |
| JP | 8259532 | 10/1996 |
| JP | 10-87489 | 4/1998 |
| JP | 10101654 | 4/1998 |
| JP | 2003119137 | 4/2003 |
| WO | WO93/13066 | 7/1993 |
| WO | WO 93/13066 | 7/1993 |
| WO | WO 95/09843 | 4/1995 |
| WO | WO 98/46582 | 10/1998 |
| WO | WO 00/48466 | 8/2000 |
| WO | WO 02/100844 | 12/2002 |
| WO | WO 02/100845 | 12/2002 |
| WO | WO 03/035076 | 5/2003 |
| WO | WO 03/035650 | 5/2003 |
| WO | WO 03/047564 | 6/2003 |
| WO | WO 03/049690 | 6/2003 |
| WO | WO 03/062204 | 7/2003 |
| WO | WO 03/062238 | 7/2003 |

OTHER PUBLICATIONS

Carlsen et al.. "Thermolysis of N–Allylic 1,2,4–Triazoles" *Institute of Organic Chemistry* 34:797–805 (1997).

Demange et al., "Practical Synthesis of Boe and Fmoc Protected 4–Fluoro and 4–Difluoroprolines from Trans–4–Hydrozyproline," *Tetrahedron Letters* 39:1169–1172 (1998).

Harada et al., "Synthesis and Resolution of – N–I1–methyl–4(3–methylbenzyl)hexahydro–1H–1,14–dize-pin–6–yl/]–1/H–indazole–3–Carboxamide By Preferential Crystallization," *Tetrahedron Asymmetry* 8(14):2367–2374 (1997).

(Continued)

*Primary Examiner*—Laura L. Stockton
(74) *Attorney, Agent, or Firm*—Fitzpatrick, Cella, Harper & Scinto

(57) ABSTRACT

Compounds of the formula:

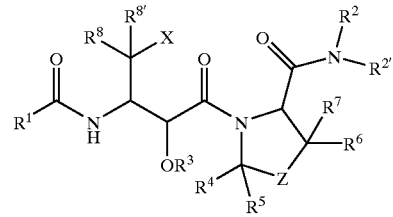

where the formula variables are as defined herein, are disclosed that advantageously inhibit or block the biological activity of the HIV protease. These compounds, as well as pharmaceutical compositions containing these compounds, are useful for treating patients or hosts infected with the HIV virus. Intermediates and synthetic methods for preparing such compounds are also described.

16 Claims, No Drawings

OTHER PUBLICATIONS

Holzgrabe, U., "Cer(IV)sulfat–Oxidationen: Intramolekulare Cyclisierung von N–Benzyl–β–Aminoketonen zu 4–Benzoyl–1,2,3,4–tetrahydro–isochinolinen," *Arch. Pharm.* 320:647–654 (1987).

Karanewsky et al.. "Phosphinyloxy)acyl Amino Acid Inhibitors Of Angiotensin Converting Enzyme," *J. Med. Chem.* 33:1459–1469 (1990).

Ludeman et al. "Synthesis and Antitumor Activity of Cyclophosphamide Analogs. I. Benzo Annulated Cyclophosphamide and Related Systems," *Journal of Medicinal Chemistry* 18(12):1251 (1975).

Matayoshi et al.. "Novel Fluorogenic Substrates For Assaying Retroviral Proteases By Resonance Energy Transfer," *Science* 247:954–958 (1990).

Mimoto et al., "Structure–Activity Relationship of Small–Sized HIV Protease Inhibitors Containing Allophenylnorstatine," *J. Med. Chem.* 42:1789–1802 (1999).

O'Brien et al., "Inhibitors of Acyl–CoA:Choloesterol O–Acyl Transferase (ACAT) as Hypocholesterolemic Agents. Incorporation of Amide or Amine Functionalities into a Series of Disubstituted Ureas And Carbamates. Effects on ACAT Inhibition In Vitro and Efficacy In Vivo," *J. Med. Chem.* 37:1810–1822 (1994).

Pauwels et al.. "Rapid and Automated Tetrazolium–Based Colorimetric Assay For The Detection Of Anti–HIV Compounds," *Journal of Virological Methods* 20:309–321 (1988).

Weislow et al.. "New Soluble–Formazan Assay For HIV–1 Cytopathic Effects: Application To High–Flux For AIDS–Antiviral Activity," *Journal of the National Cancer Institute* 81(8):577–586 (1989).

Wipf et al., "SN2'–Reactions of Peptide Aziridines. A Cuprate–Based Approach to (E)–Alkene Isosteres" *J. Org. Chem.* 59:4875–4886 (1994).

Yoshimura et al., "JE–2147: A Dipeptide Protease Inhibitor (PI) That Potently Inhibits Multi–PI–Resistant HIV–1," *Proc. Natl. Acad. Sci. USA* 96:8675–8680 (Jul. 1999).

Yoshiaki, Patent Abstracts of Japan, Publication No. 10182601, 1998, No. 12.

Sheha et al., Euro J. Med. Chem., vol. 35 (10), 2000, pp. 887–894.

Kitzaki et al., Chem & Pharm. Bulletin, Pharm. Soc. of Japan, vol. 42(12), 1994, pp. 2636–2640.

Slee, J.A.C.S., vol. 117(48), 1995, pp. 11867–11878.

Komai et al., Biorg. Med. Chem., vol. 4 (8), 1996, pp. 1356–1377.

Kiso et al., Arch. Pharm., Pharm. Med. Chem., vol. 331, 1998, pp. 87–89.

Matsumoto et al., Biorg. Med. Chem., vol. 9(2), 2001, pp. 417–430.

Tam et al., J. Med. Chem., vol. 35, No. 7, 1992, pp. 1318–1320.

Bell et al., J. Med. Chem. 41:2146–2163 (1998).

Bobbitt et al., J. Org. Chem. 25:560 (1960).

Charlesworth et al., Can. J. Chem. 41:1071–1077 (1963).

Dondoni et al., J. Org. Chem. 60:4749–4754 (1995).

Fujiwara et al., Can. J. Chem. 48:1346–1349 (1970).

Huang et al., Synthetic Communications 28 (7): 1197–1200 (1998).

Hursthouse et al., J. Chem. Soc. 1:2419–2425 (1995).

Miller et al., J. Org. Chem 24:560–561 (1958).

Nagasawa et al., J. Med. Chem. 30:1373 (1991).

Nussbaumer et al., J. Med. Chem. 34:65–73 (1991).

Onda et al., Chem. Pharm. Bull. 19 (10): 2013–2019 (1971).

Petropoulos et al., Antimicrob Agents Chemother 44(4): 920–928 (2000).

Van–Duc Le, Bioorg. Med. Chem. vol. 9, 2001, pp. 1185–1195.

Mimoto et al., Chem. & Pharm. Soc. Japan 48(9), 2000, pp. 1310–1326.

Sodergren, J. Am. Chem. Soc. 122(28),2000, pp. 6610–6618.

Falorni et al., Tetrahedron; Asymmetry, vol. 6 (1), 1995, pp. 287–294.

Andrés, "Stereoselective Cyanation of Chiral α–Amino Aldehydes By Reaction With Nagata's Reagent: A Route To Enantiopure β–Amino–α–Hydroxy Acids," *Tetrahedron Asymm.*, 2001, pp. 347–353, vol. 12.

Blanco, M. et al., "Enantiospecific And Stereoselective Synthesis Of Polyhydroxylated Pyrrolidines And Indolizidnes From Trans–4–Hydroxy–L–Proline," *J. Org. Chem.*, 1996, pp. 4748–4755, vol. 61.

Humphrey, J. et al., "Chemical Synthesis Of Natural Product Peptides: Coupling Methods For The Incorporation Of Noncoded Amino Acids Into Peptides," *Chemical Reviews,* 1997, 2243–2266 vol. 97.

Ikunaka, et al., "A Concise Synthesis of (2S,3S)–BocAHPBA and ®–BocDMTA, Chiral Building Blocks for Peptide–Mimetic HIV Protease Inhibitors," *Tetrahedron Asymmetry,* 2002, vol. 13, 1201.

Jacques, et al., Enantiomers, Racemates, and Resolutions, 1981, John Wiley & Sons, New York, Table of Contents only.

Larock, et al., Comprehensive Organic Transformation, 1989, Chapter 9, New York, p. 273–280.

Sasai, H., et al., "Diastereoselective Catalytic Asymmetric Nitroaldol Reaction Utilizing Rare Earth–Li–(R)–BINOL Complex. A Highly Efficient Synthesis of Norstatine," *Tetrahedron Letters,* 1994, pp. 6123–6126, vol. 35, No. 33.

Sharma, R. et al., "Regioselective Enolization And Alkylation Of 4–Oxo–N–(9–Phenylfluoren–9–yl)Proline: Synthesis Of Enantiopure Proline–Valine And Hydroxyproline–Valine Chimeras," *J. Org. Chem.,*1996, pp. 202–209, vol. 61.

Sustmann, et al., Comprehensive Organic Synthesis, 1991, vol. 6, 301–321, Trost.

Patrick, et al., "Protease Inhibitors as Antiviral Agents", Clinical Microbio. Reviews, Oct. 1998, pp. 614–627.

HIV PROTEASE INHIBITORS, COMPOSITIONS CONTAINING THE SAME, THEIR PHARMACEUTICAL USES AND MATERIALS FOR THEIR SYNTHESIS

This application claims the benefit of U.S. Provisional Application No. 60/297,460, filed on Jun. 11, 2001, and U.S. Provisional Application No. 60/297,729, filed on June 11, 2001.

BACKGROUND OF THE INVENTION

1. Field of the Invention

This invention relates to novel compounds as useful as HIV protease inhibitors and to the use of such compounds as antiviral agents for treatment of HIV infected individuals. This invention also relates to methods of preparation of these compounds and to intermediates that are useful in the preparation thereof.

2. Related Background Art

Acquired Immune Deficiency Syndrome (AIDS) causes a gradual breakdown of the body's immune system as well as progressive deterioration of the central and peripheral nervous systems. Since its initial recognition in the early 1980's, AIDS has spread rapidly and has now reached epidemic proportions within a relatively limited segment of the population. Intensive research has led to the discovery of the responsible agent, human T-lymphotropic retrovirus III (HTLV-III), now more commonly referred to as the human immunodeficiency virus or HIV.

HIV is a member of the class of viruses known as retroviruses. The retroviral genome is composed of RNA, which is converted to DNA by reverse transcription. This retroviral DNA is then stably integrated into a host cell's chromosome and, employing the replicative processes of the host cells, produces new retroviral particles and advances the infection to other cells. HIV appears to have a particular affinity for the human T-4 lymphocyte cell, which plays a vital role in the body's immune system. HIV infection of these white blood cells depletes this white cell population. Eventually, the immune system is rendered inoperative and ineffective against various opportunistic diseases such as, among others, pneumocystic carini pneumonia, Kaposi's sarcoma, and cancer of the lymph system.

Although the exact mechanism of the formation and working of the HIV virus is not understood, identification of the virus has led to some progress in controlling the disease. For example, the drug azidothymidine (AZT) has been found effective for inhibiting the reverse transcription of the retroviral genome of the HIV virus, thus giving a measure of control, though not a cure, for patients afflicted with AIDS. The search continues for drugs that can cure or at least provide an improved measure of control of the deadly HIV virus.

Retroviral replication routinely features post-translational processing of polyproteins. This processing is accomplished by virally encoded HIV protease enzyme. This yields mature polypeptides that will subsequently aid in the formation and function of infectious virus. If this molecular processing is stifled, then the normal production of HIV is terminated. Therefore, inhibitors of HIV protease may function as anti-HIV viral agents.

HIV protease is one of the translated products from the HIV structural protein pol gene. This retroviral protease specifically cleaves other structural polypeptides at discrete sites to release these newly activated structural proteins and enzymes, thereby rendering the virion replication-competent. As such, inhibition of the HIV protease by potent compounds may prevent proviral integration of infected T-lymphocytes during the early phase of the HIV-1 life cycle, as well as inhibit viral proteolytic processing during its late stage. Additionally, the protease inhibitors may have the advantages of being more readily available, longer lived in virus, and less toxic than currently available drugs, possibly due to their specificity for the retroviral protease.

Related inhibitors of HIV proteases have been described in, e.g., U.S. Pat. No. 5,962,640, U.S. Pat. No. 5,932,550, Australian Patent No. 705193, Canadian Patent Application No. 2,179,935, European Patent Application No. 0 751 145, and Japanese Patent Application No. 10087489. Other related HIV protease inhibitors have been described in K. Yoshimura, et al., *Proct. Natl. Acad. Sci. USA*, 96, 8675–8680 (1999) and T. Mimoto, et al., *J. Med. Chem.*, 42, 1789–1802 (1999).

On-going treatment of HIV-infected individuals with compounds that inhibit HIV protease has led to the development of mutant viruses that possess protesases that are resistant to the inhibitory effect of these compounds. Thus, to be effective, new HIV protease inhibitors must be effective not only against wild-type strains of HIV, but must also demonstrate efficacy against the newly emerging mutant strains that are resistant to the commercially available protease inhibitors. Accordingly, there continues to be a need for new inhibitors targeting the HIV protease in both wild type and mutant strains of HIV.

SUMMARY OF THE INVENTION

This invention relates to compounds useful for inhibiting the activity of HIV-protease of Formula I:

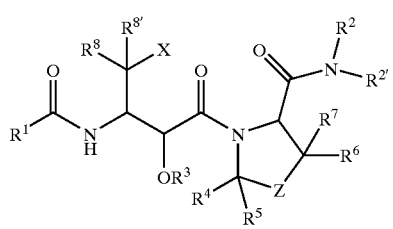

wherein:

$R^1$ is a 5- or 6-membered mono-cyclic carbocyclic or heterocyclic group, wherein said carbocyclic or heterocyclic group is saturated, partially unsaturated or fully unsaturated and is unsubstituted or substituted by one or more suitable substituents;

$R^2$ is a substituted alkyl group, a substituted or unsubstituted alkenyl group, a substituted or unsubstituted alkynyl group, a substituted phenyl group, a substituted phenylalkyl group, a substituted or unsubstituted phenylalkenyl group or a substituted or unsubstituted phenylalkynyl group, $R^{2'}$ is H or a substituted or unsubstituted $C_1$–$C_4$ alkyl group;

X is

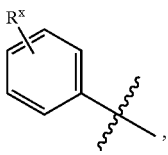

wherein $R^x$ is H or one or more suitable substituents;

Z is S, O, SO, $SO_2$, $CH_2$ or CFH;

$R^3$ is H or a substituted or unsubstituted $C_1$–$C_4$ alkyl group;

$R^4$, $R^5$, $R^6$ and $R^7$ are independently selected from H or a $C_1$–$C_6$ alkyl group; and $R^8$ and $R^{8'}$ are independently selected from H, halo, a $C_1$–$C_4$ aliphatic group or a $C_1$–$C_4$ halo-substituted aliphatic group;

where any of said substituted alkyl, alkenyl or alkynyl groups are substituted by one or more suitable substituents provided that said 5- or 6-membered mono-cyclic heterocycloalkyl, heterocycloalkenyl or heteroaryl group contains at least two heteroatoms when $R^2$ is a substituted phenyl group, a substituted phenylalkyl group, a substituted or unsubstituted phenylalkenyl group or a substituted or unsubstituted phenylalkynyl group; or provided that said alkyl, alkenyl or alkynyl moiety of said substituted phenylalkyl, phenylalkenyl or phenylalkynyl group is substituted by one or more substituents selected from halo or keto; or provided that said substituted phenyl group or phenyl moiety of said substituted phenylalkyl, phenylalkenyl or phenylalkynyl group is substituted by one or more suitable substituents other than halo or methyl.

The present invention relates to compounds of Formula I below, and prodrugs, pharmaceutically active metabolites, and pharmaceutically acceptable salts and solvates thereof that inhibit the protease encoded by human immunodeficiency virus (HIV) type 1 (HIV-1) or type 2 (HIV-2), as well as mutant strains thereof. These compounds are useful in the treatment of infection by HIV and the treatment of the acquired immune deficiency syndrome (AIDS). The compounds, their pharmaceutically acceptable salts, and the pharmaceutical compositions of the present invention can be used alone or in combination with other antivirals, immunomodulators, antibiotics or vaccines. Compounds of the present invention can also be converted to prodrugs, by derivatization, according to conventional techniques. Methods of treating AIDS, methods of treating HIV infection and methods of inhibiting HIV protease are disclosed.

DETAILED DESCRIPTION OF INVENTION AND PREFERRED EMBODIMENTS

In accordance with a convention used in the art,

is used in structural formulas herein to depict the bond that is the point of attachment of the moiety or substituent to the core or backbone structure.

As used herein, the term "aliphatic" represents a saturated or unsaturated, straight- or branched-chain hydrocarbon, containing 1 to 10 carbon atoms which may be unsubstituted or substituted by one or more of the substituents described below. The term "aliphatic" is intended to encompass alkyl, alkenyl and alkynyl groups.

As used herein, the term "alkyl" represents a straight- or branched-chain saturated or unsaturated hydrocarbon, containing 1 to 10 carbon atoms which may be unsubstituted or substituted by one or more of the substituents described below. Exemplary alkyl substituents include, but are not limited to methyl (Me), ethyl (Et), propyl, isopropyl, butyl, isobutyl, t-butyl, and the like. The term "lower alkyl" refers to an alkyl group containing from 1 to 6 carbon atoms The term "alkenyl" represents a straight- or branched-chain hydrocarbon, containing one or more carbon-carbon double bonds and having 2 to 10 carbon atoms which may be unsubstituted or substituted by one or more of the substituents described below. Exemplary alkenyl substituents include, but are not limited to ethenyl, propenyl, butenyl, allyl, pentenyl and the like.

The term "alkynyl" represents a straight- or branched-chain hydrocarbon, containing one or more carbon-carbon triple bonds and having 2 to 10 carbon atoms which may be unsubstituted or substituted by one or more of the substituents described below. An alkynyl moiety may also contain one or more carbon-carbon double bonds. Exemplary alkynyl substituents include, but are not limited to ethynyl, butynyl, propynyl (propargyl) isopropynyl. pentynyl, hexynyl and the like.

The term "carbocyclic" represents a saturated, partially saturated, or fully unsaturated (aromatic) cyclic hydrocarbon group containing from 3 to 14 carbon atoms which may be unsubstituted or substituted by one or more of the substituents described herein below. The term "carbocyclic" is intended to encompass mono-, bi- and tri-cyclic saturated, partially saturated, or fully unsaturated hydrocarbon groups; for example, cycloalkyl, cycloalkenyl and aryl groups. The term "carbocyclic" is also intended to encompass bi- and tri-cyclic hydrocarbon groups which contain any combination of ring moieties that are saturated, partially saturated, or fully unsaturated (aromatic). Partially saturated carbocycles include, for example, dihydro-arenes (e.g., indanyl) or tetrahydro-arenes (e.g. tetrahydronaphthalene), wherein any one or more points of saturation may occur in any ring moiety of the carbocycle. In addition, it is understood that bonding between any bi- or tri-cyclic carbocyclic group and any other substituent or variable group may be made at any suitable position of the carbocycle. The term "carbocyclic-aliphatic" group is intended to encompass aliphatic groups having a carbocyclic substituent (e.g., phenylmethyl-(benzyl), phenylethyl-, cyclopropylmethyl-, etc.), wherein the carbocyclic moiety and the aliphatic moiety thereof may be independently substituted by one or more suitable substituents.

"Cycloalkyl" represents a group comprising a non-aromatic monocyclic, bicyclic, or tricyclic hydrocarbon containing from 3 to 14 carbon atoms which may be unsubstituted or substituted by one or more of the substituents described below. Exemplary cycloalkyls include monocyclic rings having from 3–8 carbon atoms, such as cyclopropyl, cyclobutyl, cyclopentyl, cyclohexyl, cycloheptyl and the like. Illustrative examples of cycloalkyl groups include the following:

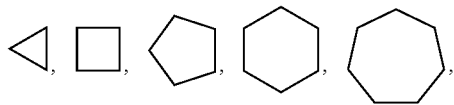

-continued

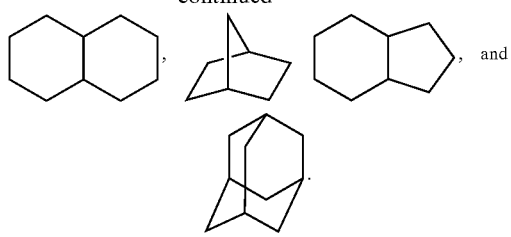

"Cycloalkenyl" represents a group comprising a non-aromatic monocyclic, bicyclic, or tricyclic hydrocarbon containing from 4 to 14 carbon atoms which may be unsubstituted or substituted by one or more of the substituents described below and contains at least one carbon-carbon double bond. Exemplary monocyclic cycloalkenyls include groups having from 4–8, preferably 5–6, carbon atoms, such as cyclopentenyl, cyclopentadienyl, cyclohexenyl, cycloheptenyl and the like. Illustrative examples of cycloalkenyl groups include the following:

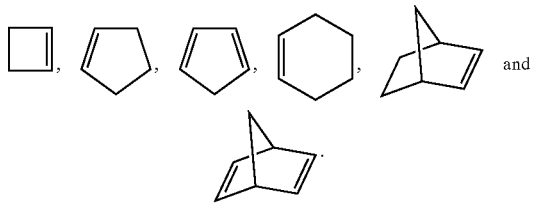

"Aryl" represents a group comprising an aromatic, monovalent monocyclic, bicyclic, or tricyclic radical containing from 6 to 18 carbon ring atoms, which may be unsubstituted or substituted by one or more of the substituents described below. Illustrative examples of aryl groups include the following:

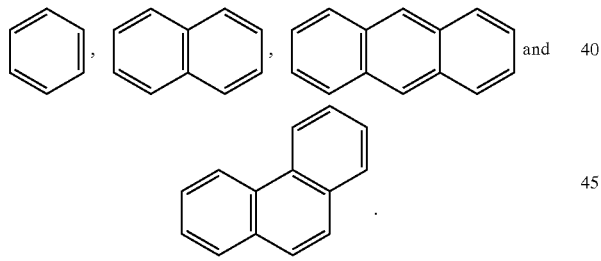

The term "carbocyclic" also to encompasses mixed bi- and tri-cyclic cycloalkyl/cycloalkenyl/aryl groups, which may be unsubstituted or substituted by one or more of the substituents described below. Illustrative examples of such mixed bi-and tri-cyclic groups include the following:

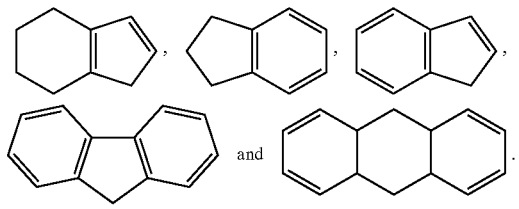

It is understood that bonding or substitution of any bi-cyclic or tri-cyclic carbocyclic or heterocyclic group described herein may be at any suitable position on any ring.

Illustrative examples of such bonding in mixed bi-and tri-cyclic carbocyclic groups include the following:

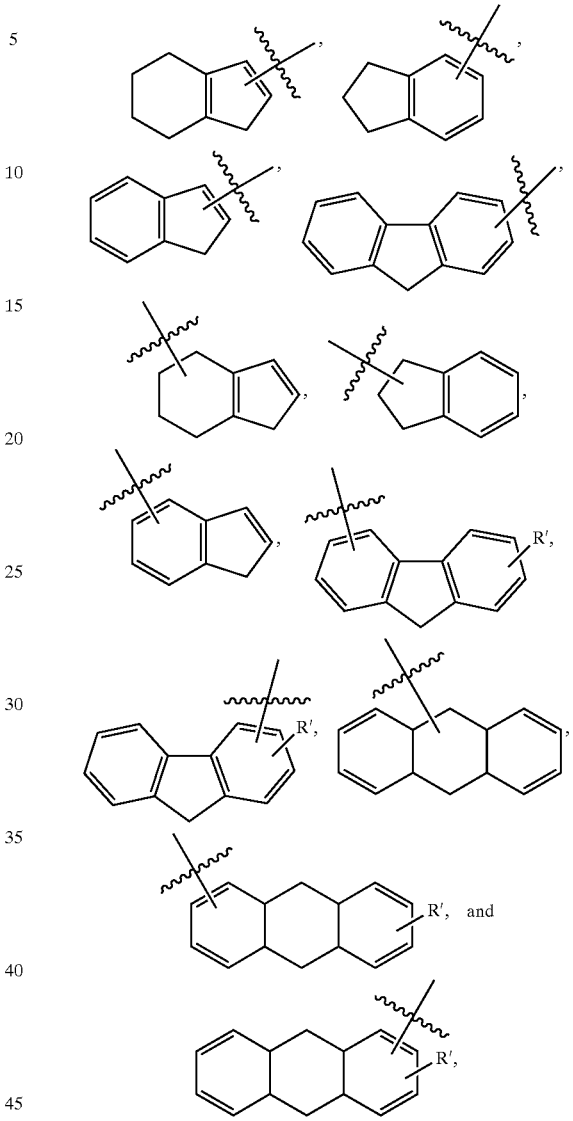

wherein R' is any suitable substituent.

The term "heterocyclic" represents a saturated, partially saturated, or fully unsaturated (aromatic) cyclic group containing from 3 to 18 ring atoms, which includes 1 to 5 heteroatoms selected from nitrogen, oxygen and sulfur, and which may be unsubstituted or substituted by one or more of the substituents described herein below. The term "heterocyclic" is intended to encompass mono-, bi- and tri-cyclic saturated, partially saturated, or fully unsaturated heteroatom-containing cyclic groups; for example, heterocycloalkyl, heterocycloalkenyl and heteroaryl groups. The term "heterocyclic" is also intended to encompass bi- and tri-cyclic groups which contain any combination of ring moieties that are saturated, partially saturated, or fully unsaturated (aromatic). Partially saturated heterocycles include, for example, dihydroheteroarenes (e.g., dihydroindole) or tetrahydro-heteroarenes (e.g. tetrahydroquinoline), wherein any one or more points of saturation may occur in any ring moiety of the heterocycle. In addition, it is understood that bonding between any bi- or tri-cyclic heterocyclic group and any other substituent or variable group may be made at any suitable position of the heterocycle (i.e., there is no restriction that a substituent or variable group must be bonded to the heteroatom-containing moiety of a bi- or tri-cyclic heterocyclic group). The term "heterocyclic-aliphatic" group is intended to encompass aliphatic groups having a heterocyclic substituent (e.g., pyridylmethyl-, thiazolylmethyl-, tetrahydrofuranylmethyl-, etc.) wherein the heterocyclic moiety and the aliphatic moiety thereof may be independently substituted by one or more suitable substituents.

"Heterocycloalkyl" represents a group comprising a saturated monovalent monocyclic, bicyclic, or tricyclic radical, containing 3 to 18 ring atoms, which includes 1 to 5 heteroatoms selected from nitrogen, oxygen and sulfur, and which may be unsubstituted or substituted by one or more of the substituents described below. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, tetrahydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3 .3.1]nonyl, azabicylo[4.3.0]nonyl, oxabicylo[2.2.1]heptyl, 1,5,9-triazacyclododecyl, and the like. Illustrative examples of heterocycloalkyl groups include the following:

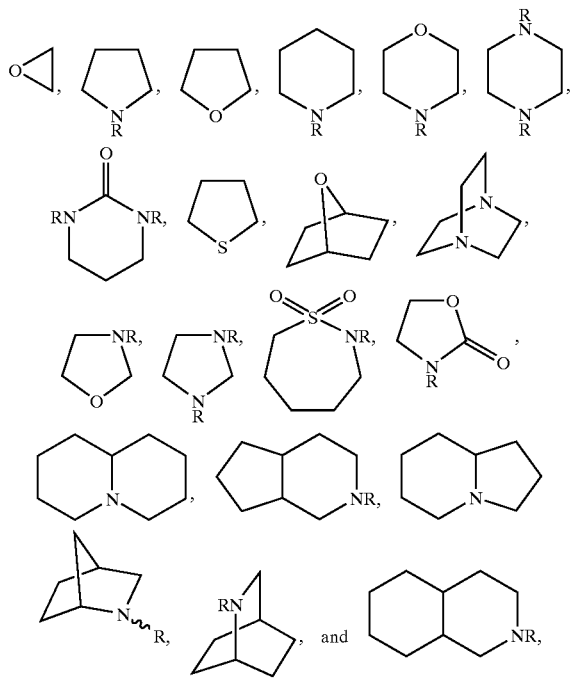

wherein R is H, alkyl, hydroxyl or represents a compound according to Formula I, and the bond depicted as

"⌇", represents bonding to either face of the bi-cyclic moiety (i.e., endo or exo).

The term "heterocycloalkenyl" is used herein to represent a non-aromatic, monovalent monocyclic, bicyclic, or tricyclic radical, containing 4 to 18 ring atoms, which may include from 1 to 5 heteroatoms selected from nitrogen, oxygen and sulfur, and which may be unsubstituted or substituted by one or more of the substituents described below and which contains at least one carbon-carbon or carbon-heteroatom double bond. Exemplary monocyclic heterocycloalkenyls include groups having from 4–8, preferably 5–6, ring atoms. Illustrative examples of heterocycloalkenyl groups include, but are not limited to, dihydrofuryl, dihydropyranyl, isoxazolinyl, dihydropyridyl, tetrahydropyridyl, and the like. Illustrative examples of heterocycloalkenyl groups include the following:

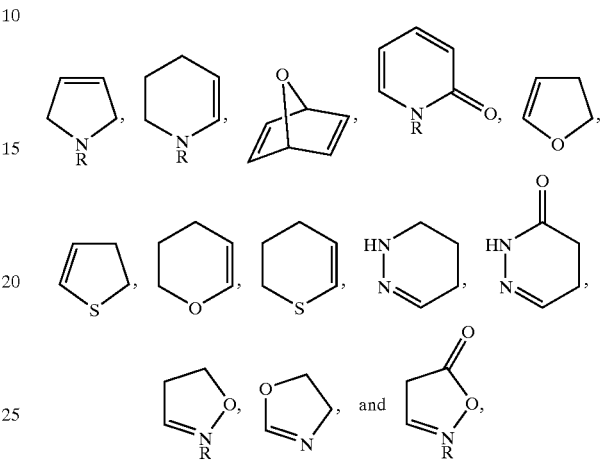

wherein R is H, alkyl, hydroxyl or represents a compound according to Formula I.

"Heteroaryl" represents a group comprising an aromatic monovalent monocyclic, bicyclic, or tricyclic radical, containing 5 to 18 ring atoms, including 1 to 5 heteroatoms selected from nitrogen, oxygen and sulfur, which may be unsubstituted or substituted by one or more of the substituents described below. As used herein, the term "heteroaryl" is also intended to encompass the N-oxide derivative (or N-oxide derivatives, if the heteroaryl group contains more than one nitrogen such that more than one N-oxide derivative may be formed) of the nitrogen-containing heteroaryl groups described herein. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl. Illustrative examples of N-oxide derivatives of heteroaryl groups include, but are not limited to, pyridyl N-oxide, pyrazinyl N-oxide, pyrimidinyl N-oxide, pyridazinyl N-oxide, triazinyl N-oxide, isoquinolyl N-oxide, and quinolyl N-oxide. Further examples of heteroaryl groups include the following moieties:

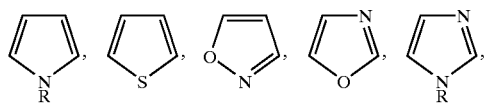

-continued

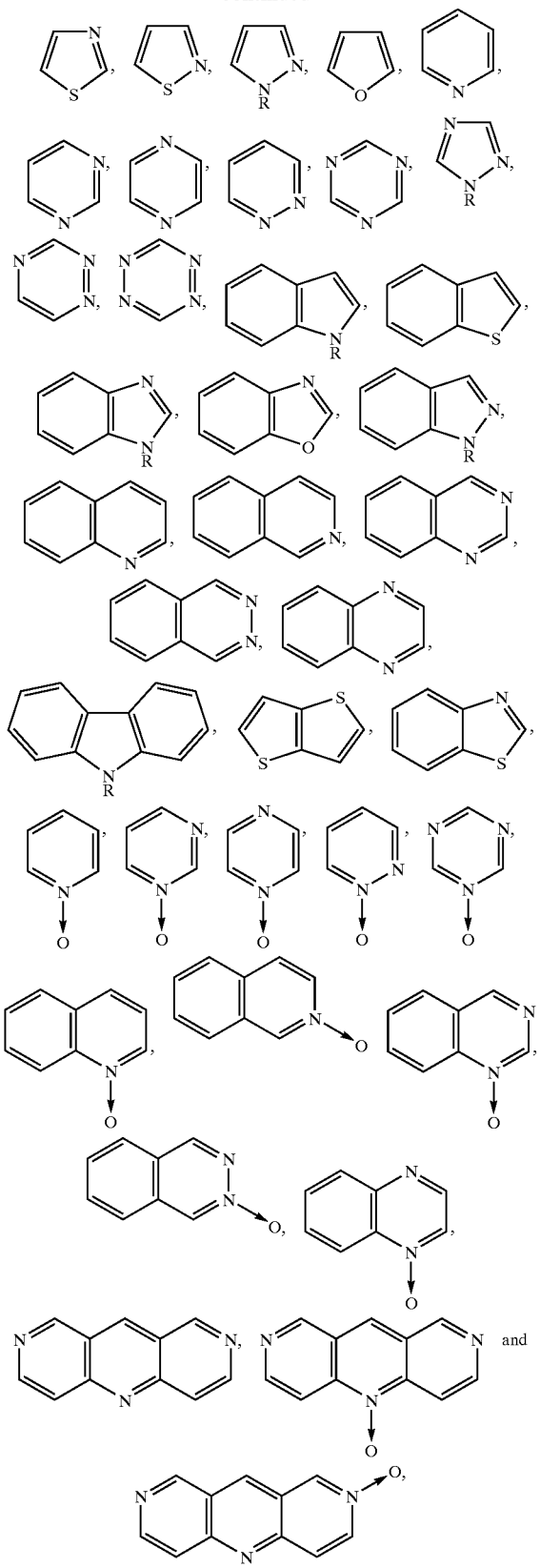

wherein R is H, alkyl, hydroxyl or represents a compound according to Formula I.

The term "heterocyclic" also to encompasses mixed bi- and tri-cyclic heterocycloalkyl/heterocycloalkenyl/heteroaryl groups, which may be unsubstituted or substituted by one or more of the substituents described below. Illustrative examples of such mixed bi-and tri-cyclic heterocyclic groups include the following:

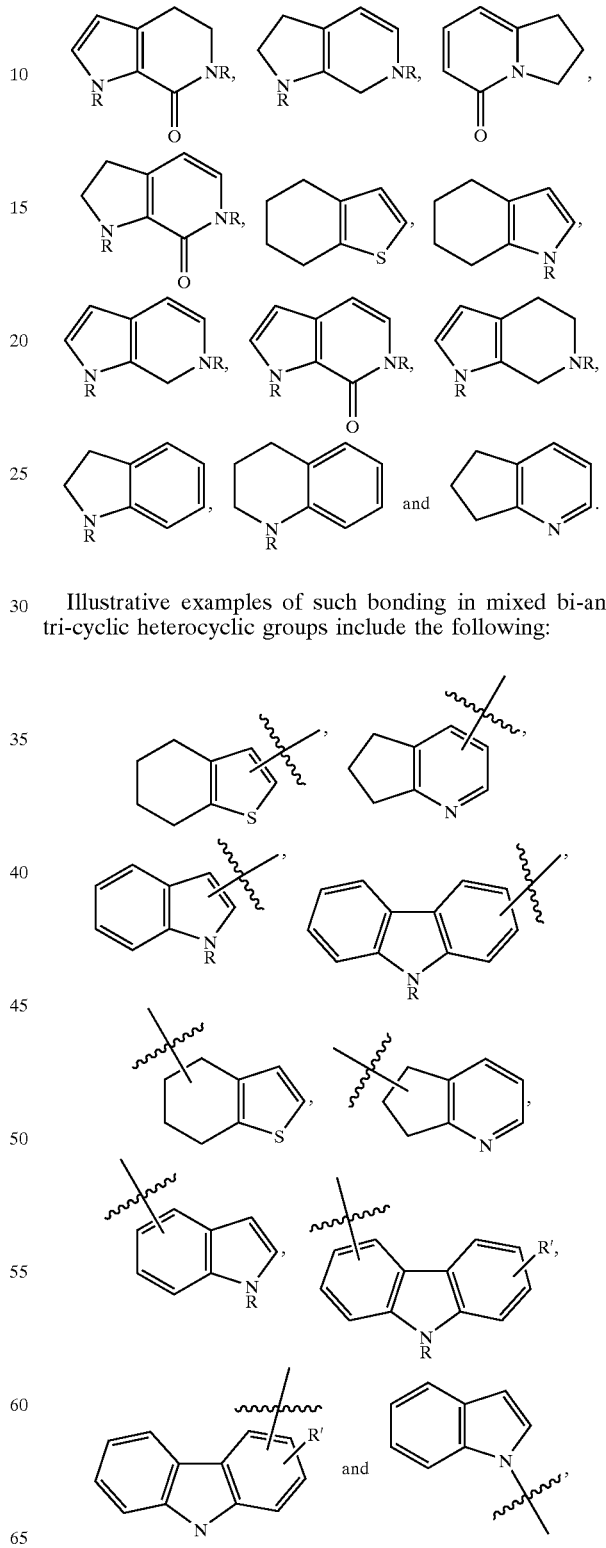

Illustrative examples of such bonding in mixed bi-and tri-cyclic heterocyclic groups include the following:

wherein R' is any suitable substituent.

In the compounds of this invention, the alkyl, alkenyl and alkynyl groups may be optionally substituted by one or more suitable substituents independently selected from phenyl, nitro, amino, cyano, halogen, hydroxyl, alkoxy, haloalkoxy, aryloxy, cycloalkyloxy, cycloalkylalkyloxy, cycloalkenyloxy, cycloalkenylalkyloxy, heterocycloalkoxy, heterocycloalkylalkyloxy, heterocycloalkenyloxy, heterocycloalkenylalkyloxy, heteroaryloxy, alkylcarbonyl, alkenylcarbonyl, alkynylcarbonyl, alkyloxycarbonyl, alkenyloxycarbonyl, alkynyloxycarbonyl, alkylcarbonyloxy, alkenylcarbonyloxy, alkynylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, alkenylamino, alkynylamino, cycloalkylamino, cycloalkenylamino, arylamino, heterocycloalkylamino, heterocycloalkenylamino, heteroarylamino, dialkylamino, alkylaminocarbonyl, alkenylaminocarbonyl, alkynylaminocarbonyl, cycloalkylaminocarbonyl, cycloalkenylamino, arylaminocarbonyl, heterocycloalkylaminocarbonyl, heterocycloalkenyl-carbonyl, heteroarylaminocarbonyl, dialkylaminocarbonyl, alkylaminothiocarbonyl, cycloalkylaminothiocarbonyl, arylaminothiocarbonyl, heterocycloalkylamino-thiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthio-carbonylamino, heteroarylthiocarbonylamino, alkylsulfonyloxy, arylsulfonyloxy, alkylsulfonylamino, arylsulfonylamino, mercapto, alkylthio, haloalkylthio, arylthio and heteroarylthio groups, wherein any of the alkyl, alkenyl, alkynyl, aryl, cycloalkyl, cycloalkenyl, heterocycloalkyl, heterocycloalkenyl, heteroaryl moieties present in the above substituents may be further substituted. The alkyl, alkenyl, alkynyl, cycloalkyl, cycloalkenyl, heterocycloalkyl, heterocycloalkenyl, aryl, and heteroaryl moieties of any of the above substituents may be optionally substituted by one or more groups independently selected from alkyl (except for alkyl), haloalkyl, aryl, nitro, amino, alkylamino, dialkylamino, halogen, hydroxyl, alkoxy, haloalkoxy, aryloxy, mercapto, alkylthio, haloalkylthio or arylthio groups.

In the compounds of this invention the substituted carbocyclic or heterocyclic groups may be optionally substituted by one or more suitable substituents independently selected from alkyl, haloalkyl, alkenyl, alkynyl, aryl, cycloalkyl, cycloalkenyl, heterocycloalkyl, heterocycloalkenyl, heteroaryl, nitro, amino, cyano, halogen, hydroxyl, alkoxy, haloalkoxy, alkenyloxy, alkynyloxy, alkylenedioxy, aryloxy, cycloalkyloxy, cycloalkylalkyloxy, cycloalkenyloxy, cycloalkenylalkyloxy, heterocycloalkoxy, heterocycloalkylalkyloxy, heterocycloalkenyloxy, heterocycloalkenylalkyloxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxy-carbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylamino-thiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthio-carbonylamino, heteroarylthiocarbonylamino, alkylsulfonyloxy, arylsulfonyloxy, alkylsulfonylamino, arylsulfonylamino, mercapto, alkylthio, haloalkylthio, arylthio and heteroarylthio groups, wherein any of the alkyl, alkylene, aryl, cycloalkyl, heterocycloalkyl, heteroaryl moieties present in the above substituents may be further substituted. Preferred "suitable substituents" include alkyl, alkenyl, alkynyl, aryl, cycloalkyl, heterocycloalkyl, heteroaryl, halogen, hydroxyl, alkoxy, alkylenedioxy, aryloxy, cycloalkoxy, heteroaryloxy, alkylthio, haloalkylthio and carboxyl. The alkyl, alkylene, cycloalkyl, heterocycloalkyl, aryl, and heteroaryl moieties of any of the above substituents may be optionally substituted by one or more groups independently selected from: alkyl, haloalkyl, nitro, amino, alkylamino, dialkylamino, halogen, hydroxyl, alkoxy, haloalkoxy, mercapto, alkylthio, haloalkylthio or arylthio groups.

For example, in the compounds of this invention, the substituted phenyl or phenyl moiety of $R^2$ may comprise at least one substituent (other than halo or methyl) selected from haloalkyl, hydroxyalkyl, alkoxyalkyl, cycloalkoxyalkyl, alkylcarbonylalkyl, haloalkoxyalkyl, aryloxyalkyl, alkylthioalkyl, haloalkylthioalkyl, arylthioalkyl, cyanoalkyl, aminoalkyl, alkylaminoalkyl, alkenyl, alkynyl, aryl, cycloalkyl, cycloalkenyl, heterocycloalkyl, heterocycloalkenyl, heteroaryl, nitro, amino, cyano, hydroxyl, alkoxy, haloalkoxy, alkenyloxy, alkynyloxy, alkylenedioxy, aryloxy, cycloalkyloxy, cycloalkylalkyloxy, cycloalkenyloxy, cycloalkenylalkyloxy, heterocycloalkoxy, heterocycloalkylalkyloxy, heterocycloalkenyloxy, heterocycloalkenylalkyloxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylamino-thiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, haloalkylthio, arylthio and heteroarylthio groups, wherein any of the alkyl, alkylene, aryl, cycloalkyl, heterocycloalkyl, heteroaryl moieties present in the above substituents may be further substituted. Preferred "suitable substituents" include alkyl, alkenyl, alkynyl, aryl, cycloalkyl, heterocycloalkyl, heteroaryl, halogen, hydroxyl, alkoxy, alkylenedioxy, aryloxy, cycloalkoxy, heteroaryloxy, alkylthio, haloalkylthio and carboxyl. The alkyl, alkylene, cycloalkyl, heterocycloalkyl, aryl, and heteroaryl moieties of any of the above substituents may be optionally substituted by one or more groups independently selected from: alkyl, haloalkyl, nitro, amino, alkylamino, dialkylamino, halogen, hydroxyl, alkoxy, haloalkoxy, mercapto, alkylthio, haloalkylthio or arylthio groups.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3$^{rd}$ ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

In the compounds of this invention, $R^2$ and $R^{2'}$, independently or taken together, may be a suitable nitrogen protecting group. As indicated above, nitrogen protecting groups are well known in the art and any nitrogen protecting group that is useful in the methods of preparing the compounds of this invention or may be useful in the HIV protease inhibitory compounds of this invention may be used. Exemplary nitrogen protecting groups include alkyl, substituted alkyl, carbamate, urea, amide, imide, enamine, sulfenyl, sulfonyl, nitro, nitroso, oxide, phosphinyl, phosphoryl, silyl, organometallic, borinic acid and boronic acid groups. Examples of each of these groups, methods for protecting nitrogen moieties using these groups and methods for removing these groups from nitrogen moieties are disclosed in T. Greene and P. Wuts, supra. Preferably, when $R^2$ and/or $R^{2'}$ are independently suitable nitrogen protecting groups, suitable $R^2$ and $R^{2'}$ substituents include, but are not limited to, carbamate protecting groups such as alkyloxycarbonyl (e.g., Boc: t-butyloxycarbonyl) and aryloxycarbonyl (e.g., Cbz: benzyloxycarbonyl, or FMOC: fluorene-9-methyloxycarbonyl), alkyloxycarbonyls (e.g., methyloxycarbonyl), alkyl or arylcarbonyl, substituted alkyl, especially arylalkyl (e.g., trityl (triphenylmethyl), benzyl and substituted benzyl), and the like. When $R^2$ and $R^{2'}$ taken together are a suitable nitrogen protecting group, suitable $R^2/R^{2'}$ substituents include phthalimido and a stabase (1,2-bis (dialkylsilyl))ethylene).

The terms "halogen" and "halo" represent chloro, fluoro, bromo or iodo substituents. "Heterocycle" is intended to mean a heteroaryl or heterocycloalkyl group. "Acyl" is intended to mean a —C(O)—R radical, where R is a substituted or unsubstituted alkyl. cycloalkyl, aryl, heterocycloalkyl or heteroaryl group. "Acyloxy" is intended to mean an —OC(O)—R radical, where R is a substituted or unsubstituted alkyl, cycloalkyl, aryl, heterocycloalkyl or heteroaryl group. "Thioacyl" is intended to mean a —C(S)—R radical, where R is a substituted or unsubstituted alkyl, cycloalkyl, aryl, heterocycloalkyl or heteroaryl group. "Sulfonyl" is intended to mean an —SO$_2$— biradical. "Sulfenyl" is intended to mean an —SO— biradical. "Sulfo" is intended to mean an —SO$_2$H radical. "Hydroxy" is intended to mean the radical —OH. "Amine" or "amino" is intended to mean the radical —NH$_2$. "Alkylamino" is intended to mean the radical —NHR$_a$, where R$_a$ is an alkyl group. "Dialkylamino" is intended to mean the radical —NR$_a$R$_b$, where R$_a$ and R$_b$ are each independently an alkyl group, and is intended to include heterocycloalkyl groups, wherein R$_a$ and R$_b$, taken together, form a heterocyclic ring that includes the amine nitrogen. "Alkoxy" is intended to mean the radical —OR$_a$, where R$_a$ is an alkyl group. Exemplary alkoxy groups include methoxy, ethoxy, propoxy, and the like. "Lower alkoxy" groups have alkyl moieties having from 1 to 4 carbons. "Alkoxycarbonyl" is intended to mean the radical —C(O)OR$_a$, where R$_a$ is an alkyl group. "Alkylsulfonyl" is intended to mean the radical —SO$_2$R$_a$, where R$_a$ is an alkyl group. "Alkylenedioxy" is intended to mean the divalent radical —OR$_a$O— which is bonded to adjacent atoms (e.g., adjacent atoms on a phenyl or naphthyl ring), wherein R$_a$ is a lower alkyl group. "Alkylaminocarbonyl" is intended to mean the radical —C(O)NHR$_a$, where R$_a$ is an alkyl group. "Dialkylaminocarbonyl" is intended to mean the radical —C(O)NR$_a$R$_b$, where R$_a$ and R$_b$ are each independently an alkyl group. "Mercapto" is intended to mean the radical —SH. "Alkylthio" is intended to mean the radical —SR$_a$, where R$_a$ is an alkyl group. "Carboxy" is intended to mean the radical —C(O)OH. "Keto" or "oxo" is intended to mean the diradical =O. "Thioketo" is intended to mean the diradical =S. "Carbamoyl" is intended to mean the radical —C(O)NH$_2$. "Cycloalkylalkyl" is intended to mean the radical -alkylcycloalkyl, wherein alkyl and cycloalkyl are defined as above, and is represented by the bonding arrangement present in the groups —CH$_2$-cyclohexane or —CH$_2$-cyclohexene. "Arylalkyl" is intended to mean the radical -alkylaryl, wherein alkyl and aryl are defined as above, and is represented by the bonding arrangement present in a benzyl group. "Aminocarbonylalkyl" is intended to mean the radical -alkylC(O)NH$_2$ and is represented by the bonding arrangement present in the group —CH$_2$CH$_2$C(O)NH$_2$. "Alkylaminocarbonylalkyl" is intended to mean the radical -alkylC(O)NHR$_a$, where R$_a$ is an alkyl group and is represented by the bonding arrangement present in the group —CH$_2$CH$_2$C(O)NHCH$_3$. "Alkylcarbonylaminoalkyl is intended to mean the radical -alkylNHC(O)-alkyl and is represented by the bonding arrangement present in the group —CH$_2$NHC(O)CH$_3$. "Dialkylaminocarbonylalkyl" is intended to mean the radical -alkylC(O)NR$_a$R$_b$, where R$_a$ and R$_b$ are each independently an alkyl group. "Aryloxy" is intended to mean the radical —OR$_c$, where R$_c$ is an aryl group. "Heteroaryloxy" is intended to mean the radical —OR$_d$, where R$_d$ is a heteroaryl group. "Arylthio" is intended to mean the radical —SR$_c$, where R$_c$ is an aryl group. "Heteroarylthio" is intended to mean the radical —SR$_d$, where R$_d$ is a heteroaryl group.

If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

Specific embodiments of the compounds of this invention comprising the compounds depicted by Formula I may also be described. For example, this invention relates to compounds useful for inhibiting the activity of HIV-protease of Formula I, above, wherein:

$R^1$ is a 5- or 6-membered monocyclic cycloalkyl, cycloalkenyl, aryl, heterocycloalkyl, heterocycloalkenyl or heteroaryl group, where said cycloalkyl, cycloalkenyl, aryl, heterocycloalkyl, heterocycloalkenyl or heteroaryl group is unsubstituted or substituted with one or more substituents independently selected from alkyl, haloalkyl, amino, cyano, halogen, hydroxyl, alkoxy, haloalkoxy, alkylenedioxy, di-haloalkylenedioxy, aryloxy, cycloalkoxy, cycloalkylalkoxy, cycloalkenyloxy, cycloalkenylalkoxy, heterocycloalkoxy, heterocycloalkylalkoxy, heterocycloalkenyloxy, heterocycloalkenylalkoxy, heteroaryloxy, alkylcarbonyloxy, arylcarbonyloxy, heteroarylcarbonyloxy, alkylamino, dialkylamino, keto, alkylsulfonyl, arylsulfonyl, alkylcarbonylamino, alkylthio, haloalkylthio and arylthio, wherein any of the alkyl, alkylene, aryl, cycloalkyl, heterocycloalkyl, heteroaryl moieties present in the above substituents may be further substituted by one or more groups independently selected from alkyl, haloalkyl, aryl, nitro, amino, alkylamino, dialkylamino, halogen, hydroxyl, alkoxy, haloalkoxy, aryloxy, mercapto, alkylthio, haloalkylthio and arylthio groups;

$R^2$ is a substituted alkyl group, a substituted or unsubstituted alkenyl group, or a substituted or unsubstituted alkynyl group, wherein said alkyl, alkenyl or alkynyl group is a straight or branched chained group, and where said substituted alkyl, alkenyl or alkynyl group is substituted by one or more substituents independently selected from amino, cyano, halogen, hydroxyl, alkoxy, haloalkoxy, aryloxy, cycloalkoxy, cycloalkylalkoxy, cycloalkenyloxy, cycloalkenylalkoxy, heterocycloalkoxy, heterocycloalkylalkoxy, heterocycloalkenyloxy, heterocycloalkenlalkoxy, heteroaryloxy, alkylamino, dialkylamino, alkylsulfonyl, arylsulfonyl, alkylsulfenyl, arylsulfenyl, alkylthio, haloalkylthio, arylthio and heteroarylthio groups, wherein any of the alkyl, alkenyl, alkynyl, aryl, cycloalkyl, cycloalkenyl, heterocycloalkyl, heterocycloalkenyl, heteroaryl moieties present in the above substituents may be further substituted by one or more groups independently selected from alkyl, haloalkyl, halogen, hydroxyl, alkoxy, haloalkoxy, alkylthio and haloalkylthio groups;

$R^{2'}$ is H, methyl, ethyl or propyl, where said methyl, ethyl or propyl is unsubstituted or substituted by halo or hydroxyl;

X is

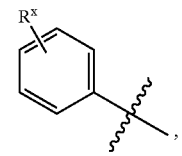

wherein $R^x$ is H or one or more substituents independently selected from halogen, alkyl, haloalkyl, alkoxy, haloalkoxy, hydroxyl, alkylenedioxy, di-haloalkylenedioxy, alkylamino, dialkylamino, alkylthio and haloalkylthio;

Z is S, O, SO, $SO_2$, $CH_2$ or CFH;

$R^3$ is H;

$R^4$, $R^5$, $R^6$ and $R^7$ are independently selected from H or methyl; and $R^8$ and $R^{8'}$ are independently selected from H, halogen, methyl, monohalo-methyl, dihalo-methyl and tri-halomethyl;

or a prodrug, pharmaceutically active metabolite or pharmaceutically active salt or solvate thereof.

In more specific embodiments, this invention relates to compounds of Formula I, above, wherein:

$R^1$ is phenyl, pyrrolyl, pyrrolidinyl, isoxazolyl, pyrazolyl, thiazolyl, tetrahydrofuranyl, furanyl, thienyl or tetrahydropyridazinyl, where said phenyl, pyrrolyl, pyrrolidinyl, isoxazolyl, pyrazolyl, thiazolyl, tetrahydrofuranyl, furanyl, thienyl or tetrahydropyridazinyl is unsubstituted or substituted with one or more substituents independently selected from alkyl, haloalkyl, halogen, and hydroxyl;

$R^2$ is a substituted alkyl group, a substituted or unsubstituted $C_1$–$C_6$ alkenyl group, or a substituted or unsubstituted $C_1$–$C_6$ alkynyl group, wherein said alkyl, alkenyl or alkynyl group is a straight or branched chained group, and where said substituted alkyl, alkenyl or alkynyl group is substituted by one or more substituents independently selected from cyano, halogen and alkylamino;

$R^{2'}$ is H, methyl or ethyl;

X is

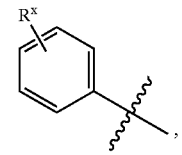

wherein $R^x$ is H, halogen, or alkoxy;

Z is S, O, $CH_2$ or CFH;

$R^3$, $R^4$, $R^5$, $R^8$ and $R^{8'}$ are each H; and $R^6$ and $R^7$ are independently selected from H or methyl;

or a prodrug, pharmaceutically active metabolite or pharmaceutically active salt or solvate thereof.

In preferred specific embodiments, this invention relates to compounds of Formula I, above, wherein:

$R^1$ is phenyl, where said phenyl is substituted with one or more substituents independently selected from alkyl, halogen or hydroxyl;

$R^2$ is a $C_1$–$C_6$ alkenyl group or a $C_1$–$C_6$ alkynyl group, wherein said alkenyl or alkynyl group is a straight or branched chained group, and where said alkenyl or alkynyl group is unsubstituted or is substituted by one or more halogen substituents;

$R^{2'}$ is H;

X is

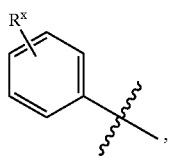

wherein $R^x$ is H;

Z is S;

$R^3$, $R^4$, $R^5$, $R^8$ and $R^{8'}$ are each H; and $R^6$ and $R^7$ are each methyl;

or a prodrug, pharmaceutically active metabolite or pharmaceutically active salt or solvate thereof.

More specifically, this invention relates to compounds useful for inhibiting the activity of HIV-protease of Formula I, above, wherein:

$R^1$ is a 5- or 6-membered mono-cyclic cycloalkyl, cycloalkenyl, aryl, heterocycloalkyl, heterocycloalkenyl or heteroaryl group, where said cycloalkyl, cycloalkenyl, aryl, heterocycloalkyl, heterocycloalkenyl or heteroaryl group is unsubstituted or substituted with one or more substituents independently selected from alkyl, haloalkyl, amino, cyano, halogen, hydroxyl, alkoxy, haloalkoxy, alkylenedioxy, dihaloalkylenedioxy, aryloxy, cycloalkoxy, cycloalkylalkoxy, cycloalkenyloxy, cycloalkenylalkoxy, heterocycloalkoxy, heterocycloalkylalkoxy, heterocycloalkenyloxy, heterocycloalkenylalkoxy, heteroaryloxy, alkylcarbonyloxy, arylcarbonyloxy, heteroarylcarbonyloxy, alkylamino, dialkylamino, alkylsulfonyl, arylsulfonyl, alkylcarbonylamino, alkylthio, haloalkylthio and arylthio, wherein any of the alkyl, alkylene, aryl, cycloalkyl, heterocycloalkyl, heteroaryl moieties present in the above substituents are substituted by one or more groups independently selected from alkyl, haloalkyl, aryl, nitro, amino, alkylamino, dialkylamino, halogen, hydroxyl, alkoxy, haloalkoxy, aryloxy, mercapto, alkylthio, haloalkylthio and arylthio groups;

$R^2$ is a substituted phenyl group, a substituted phenylalkyl group, a substituted or unsubstituted phenylalkenyl group or a substituted or unsubstituted phenylalkynyl group;

where said alkyl, alkenyl or alkynyl moiety of said phenylalkyl, phenylalkenyl or phenylalkynyl group is a straight or branched chain moiety;

$R^{2'}$ is H, methyl, ethyl or propyl, where said methyl, ethyl or propyl is unsubstituted or substituted with halo or hydroxyl;

X is

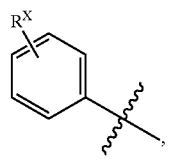

wherein $R^x$ is H or one or more substituents independently selected from halogen, alkyl, haloalkyl, alkoxy, haloalkoxy, hydroxyl, alkylenedioxy, di-haloalkylenedioxy, alkylamino, dialkylamino, alkylthio and haloalkylthio;

Z is S, O, SO, $SO_2$, $CH_2$ or CFH;

$R^3$ is H;

$R^4$, $R^5$, $R^6$ and $R^7$ are independently selected from H or methyl; and $R^8$ and $R^{8'}$ are independently selected from H, halogen, methyl, monohalo-methyl, dihalo-methyl and tri-halomethyl;

provided that said 5- or 6-membered mono-cyclic heterocycloalkyl, heterocycloalkenyl or heteroaryl group contains at least two heteroatoms; or provided that said alkyl, alkenyl or alkynyl moiety of said substituted phenylalkyl, phenylalkenyl or phenylalkynyl group is substituted by one or more substituents selected from halo or keto; or provided that said substituted phenyl group or phenyl moiety of said substituted phenylalkyl, phenylalkenyl or phenylalkynyl group is substituted by one or more substituents other than halo or methyl, where said one or more substituents is independently selected from haloalkyl, hydroxyalkyl, alkoxyalkyl, cycloalkoxyalkyl, alkylcarbonylalkyl, haloalkoxyalkyl, aryloxyalkyl, alkylthioalkyl, haloalkylthioalkyl, arylthioalkyl, cyanoalkyl, aminoalkyl, alkylaminoalkyl, alkenyl, alkynyl, aryl, cycloalkyl, cycloalkenyl, heterocycloalkyl, heterocycloalkenyl, heteroaryl, nitro, amino, cyano, hydroxyl, alkoxy, haloalkoxy, alkenyloxy, alkynyloxy, alkylenedioxy, aryloxy, cycloalkoxy, cycloalkylalkoxy, cycloalkenyloxy, cycloalkenylalkoxy, heterocycloalkoxy, heterocycloalkylalkoxy, heterocycloalkenoxy, heterocycloalkenylalkoxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto, thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino. heteroarylthiocarbonylamino, alkylsulfonyloxy, arylsulfonyloxy, alkylsulfonylamino, aryl sulfonylamino, mercapto, alkylthio, haloalkylthio, arylthio and heteroarylthio groups, wherein any of the alkyl, alkylene, aryl, cycloalkyl, heterocycloalkyl, or heteroaryl moieties present in the above substituents are unsubstituted or substituted by one or more groups independently selected from alkyl, haloalkyl, halogen, hydroxyl, alkoxy, haloalkoxy, alkylthio and haloalkylthio groups;

or a prodrug, pharmaceutically active metabolite or pharmaceutically active salt or solvate thereof. If the phenyl group or phenyl moiety of $R^2$ contains more than one substituent, the substituents may be the same or different, and may be independently selected from the above-described substituents.

More specifically, this invention relates to compounds useful for inhibiting the activity of HIV-protease of Formula I, above, wherein:

$R^1$ is phenyl, pyrrolyl, pyrrolidinyl, isoxazolyl, pyrazolyl, thiazolyl, tetrahydrofuranyl, furanyl, thienyl or tetrahydropyridazinyl, where said phenyl, pyrrolyl, pyrrolidinyl, isoxazolyl, pyrazolyl, thiazolyl, tetrahydrofuranyl, furanyl, thienyl or tetrahydropyridazinyl is unsubstituted or substituted with one or more substituents independently selected from alkyl, haloalkyl, halogen, and hydroxyl;

$R^2$ is a substituted phenylalkyl group, where said alkyl moiety of said substituted phenylalkyl group is a straight or branched chain alkyl moiety;

$R^{2'}$ is H, methyl, ethyl or propyl, where said methyl, ethyl or propyl is unsubstituted or substituted with hydroxyl;

X is

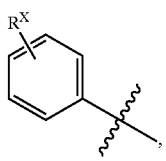

wherein $R^x$ is H, halogen, or alkoxy;

Z is S, O, $CH_2$ or CFH;

$R^3$, $R^4$, $R^5$, $R^8$ and $R^{8'}$ are each H; and $R^6$ and $R^7$ are independently selected from H or methyl;

provided that $R^1$ is selected from isoxazolyl, pyrazolyl, thiazolyl or tetrahydropyridazinyl, where said is isoxazolyl, pyrazolyl, thiazolyl or tetrahydropyridazinyl is unsubstituted or substituted with one or more substituents independently selected from alkyl, haloalkyl, halogen, and hydroxyl when $R^2$ is a substituted or unsubstituted phenylalkyl group or provided that $R^1$ is selected from phenyl, pyrrolyl, pyrrolidinyl, isoxazolyl, pyrazolyl, thiazolyl, tetrahydrofuranyl, furanyl, thienyl or tetrahydropyridazinyl when $R^2$ is a substituted phenylalkyl group and said phenyl moiety of said substituted phenylalkyl group comprises one or more substituents other than halo or methyl, where said one or more substituents is independently selected from haloalkyl, amino, hydroxyl, alkoxy, haloalkoxy, alkylenedioxy, di-haloalkylenedioxy, cycloalkylalkyloxy, dialkylamino, alkylsulfonyl and alkylthio;

or a prodrug, pharmaceutically active metabolite or pharmaceutically active salt or solvate thereof.

In preferred embodiments, this invention relates to compounds of Formula I, above, wherein:

$R^1$ is phenyl, where said phenyl is substituted with one or more substituents independently selected from methyl, halogen or hydroxyl;

$R^2$ is a substituted phenylalkyl group, where said alkyl moiety of said substituted phenylalkyl group is a straight or branched chain alky moiety;

where said phenyl moiety of said substituted phenylalkyl group comprises one or more substituents other than halo or methyl, where said one or more substituents is independently selected from trifluoromethyl, amino, hydroxyl, $C_1$–$C_4$alkoxy, alkylenedioxy, di-fluoro-alkylenedioxy, cyclopropylmethoxy, di-methyl-amino, methanesulfonyl and methylthio;

$R^{2'}$ is H, methyl or ethyl;

X is

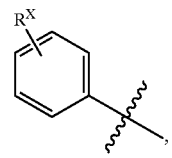

wherein $R^x$ is H;

Z is S or O; and $R^3$, $R^4$, $R^5$, $R^6$, $R^7$, $R^8$ and $R^{8'}$ are each H;

or a prodrug, pharmaceutically active metabolite or pharmaceutically active salt or solvate thereof.

All compounds of this invention contain at least one chiral center and may exist as single stereoisomers (e.g., single enantiomers or single diastereomers), any mixture of stereoisomers (e.g., any mixture of enantiomers or diastereomers) or racemic mixtures thereof. All such single stereoisomers, mixtures and racemates are intended to be encompassed within the broad scope of the present invention. Compounds identified herein as single stereoisomers are meant to describe compounds that are present in a form that contains at least 90% of a single stereoisomer of each chiral center present in the compounds. Where the stereochemistry of the chiral carbons present in the chemical structures illustrated herein is not specified, the chemical structure is intended to encompass compounds containing either stereoisomer of each chiral center present in the compound. Preferably, however, the inventive compounds are used in optically pure, that is, stereoisomerically pure, form or substantially optically pure (substantially stereoisomerically pure) form. As used herein, the term "stereoisomeric" purity (or "optical" purity) refers to the "enantiomeric" purity and/or "diastereomeric" purity of a compound. Compounds that are substantially enantiomerically pure contain at least 90% of a single isomer and preferably contain at least 95% of a single isomer of each chiral center present in the enantiomer. Compounds that are substantially diastereomerically pure contain at least 90% of a single isomer of each chiral center present in the diastereomer, and preferably contain at least 95% of a single isomer of each chiral center. More preferably, the substantially enantiomerically and diastereomerically pure compounds in this invention contain at least 97.5% of a single isomer and most preferably contain at least 99% of a single isomer of each chiral center in the compound. The term "racemic" or "racemic mixture" refers to a mixture of equal amounts of enantiomeric compounds, which encompasses mixtures of enantiomers and mixtures of enantiomeric diastereomers. The compounds of this invention may be obtained in stereoisomerically pure (i.e., enantiomerically and/or diastereomerically pure) or substantially stereoisomerically pure (i.e., substantially enantiomerically and/or diastereomerically pure) form. Such compounds may be obtained synthetically, according to the procedures described herein using optically pure or substantially optically pure materials. Alternatively, these compounds may be obtained by resolution/separation of a mixture of stereoisomers, including racemic mixtures, using conventional procedures. Exemplary methods that may be useful for the resolution/separation of stereoisomeric mixtures include chromatography and crystallization/recrystallization. Other useful methods may be found in "*Enantiomers, Racemates, and Resolutions*," J. Jacques et al., 1981, John Wiley and Sons, New York, N.Y., the disclosure of which is incorporated herein by reference. Preferred stereoisomers of the compounds of this invention are described herein.

Especially preferred embodiments of this invention comprise compounds, wherein the stereogenic centers (chiral carbons) have the following designated stereochemistry:

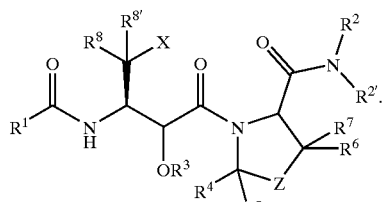

More preferably, at least two of the stereogenic centers have the following designated stereochemistry:

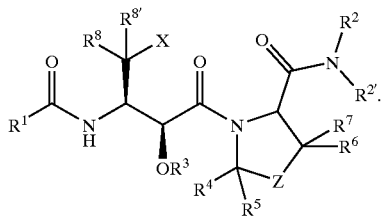

Even more preferably, at least three of the stereogenic centers have the following designated stereochemistry:

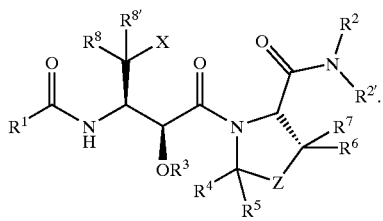

Exemplary compounds of this invention include:

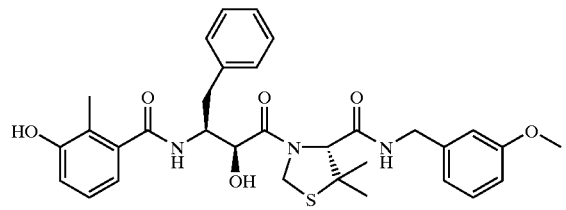

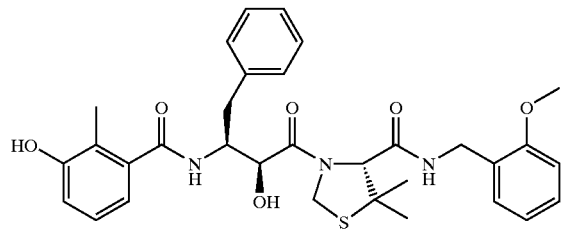

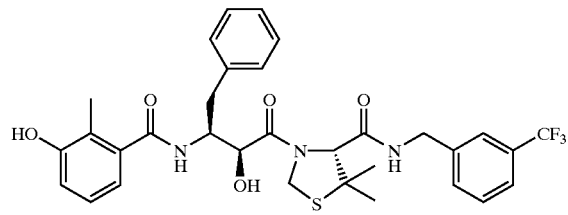

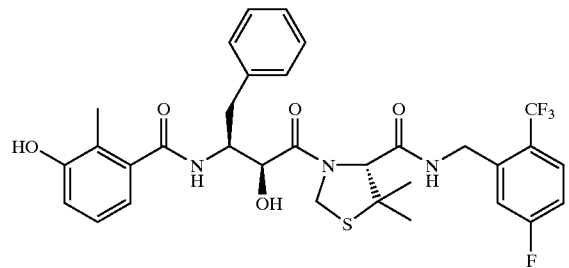

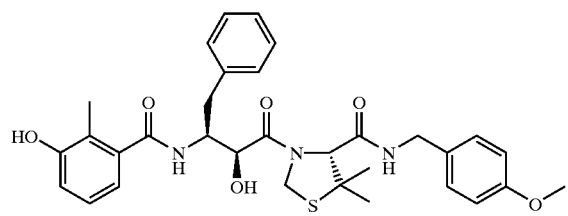

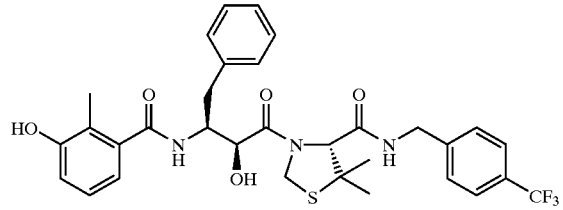

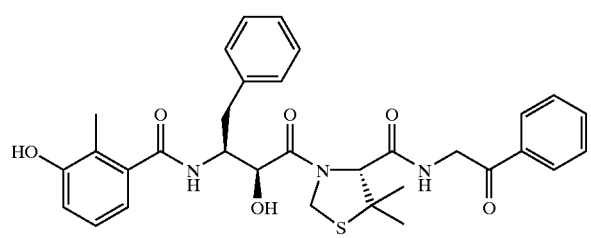

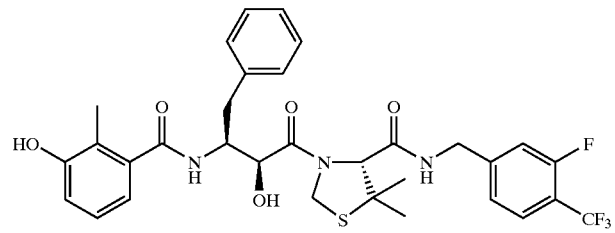

-continued
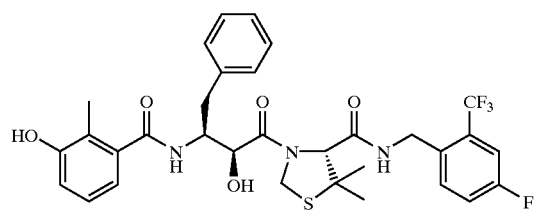
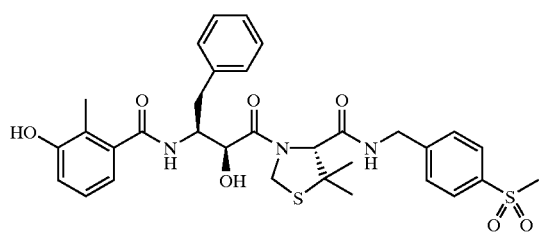
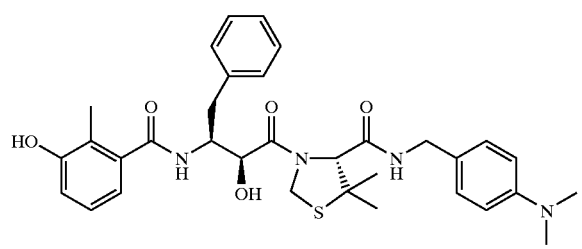
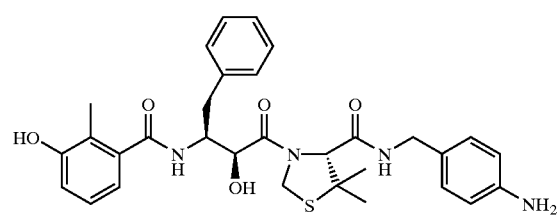
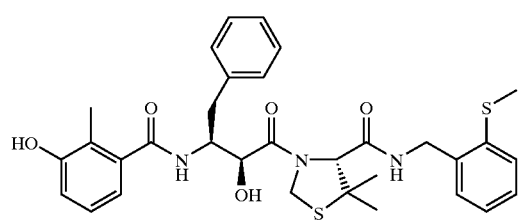
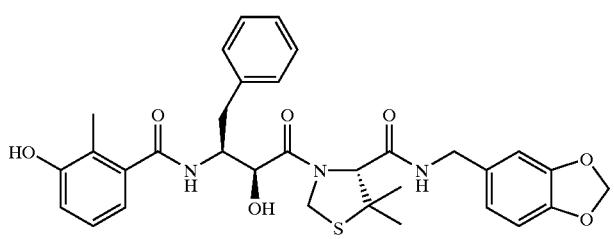
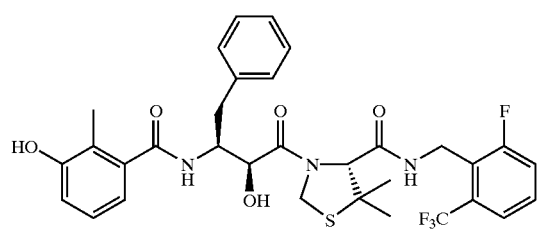
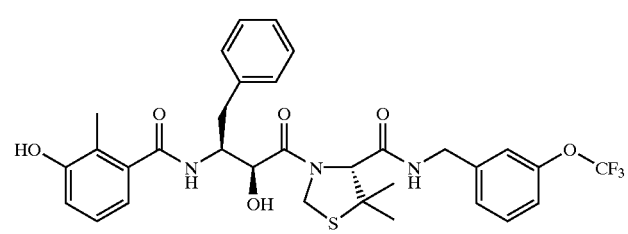
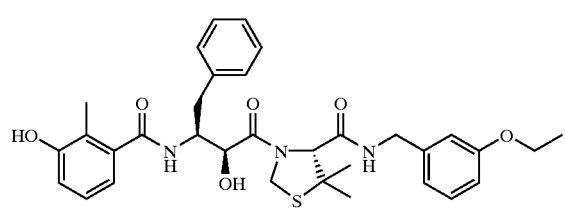
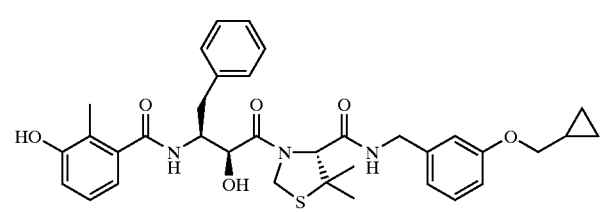
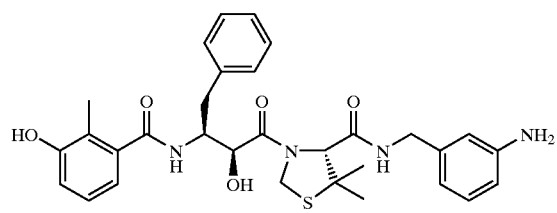
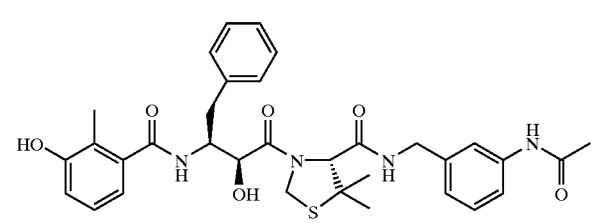
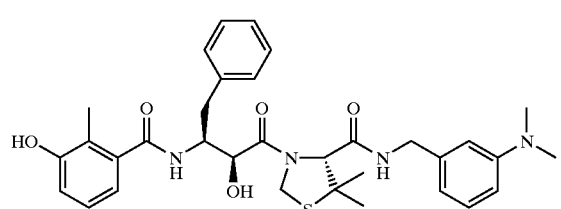
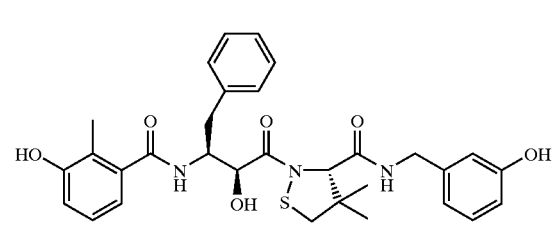

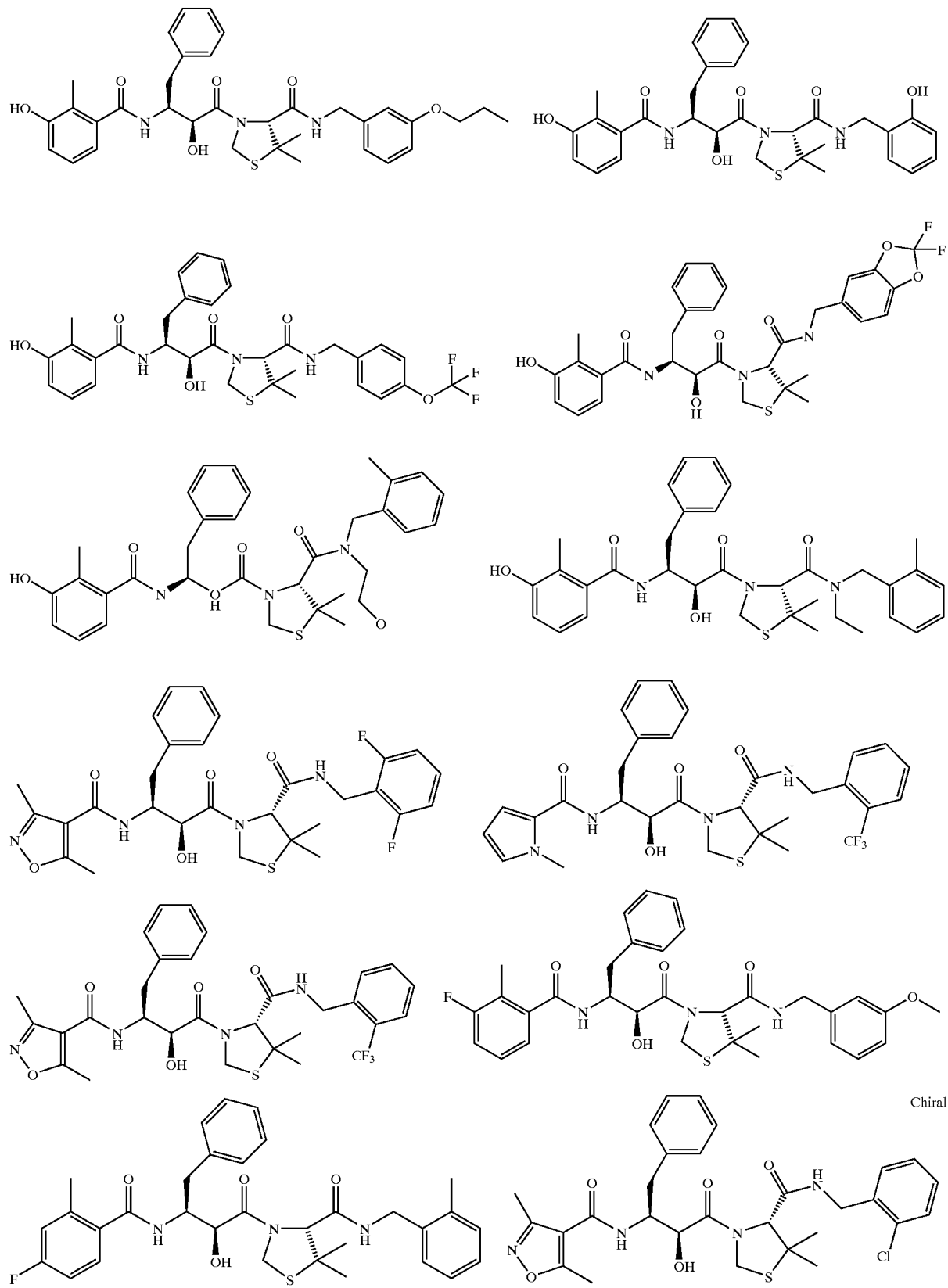

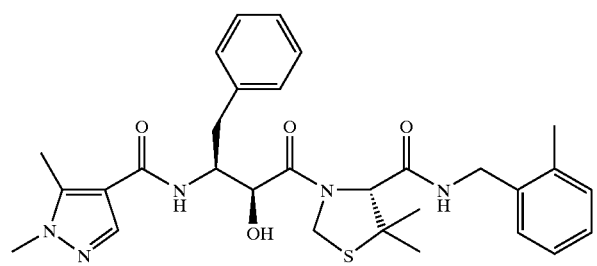
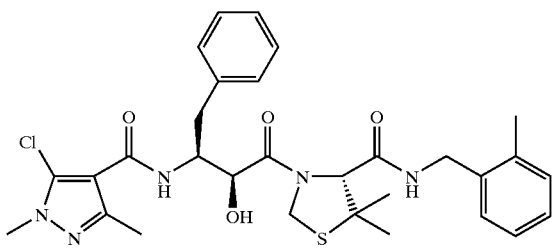
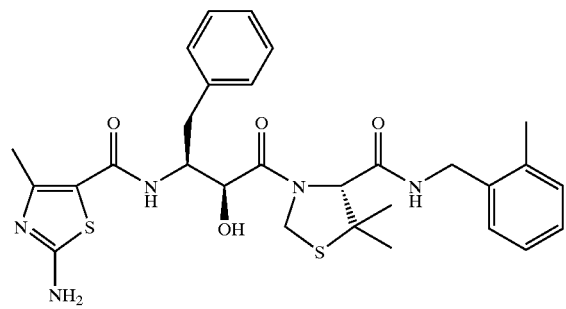
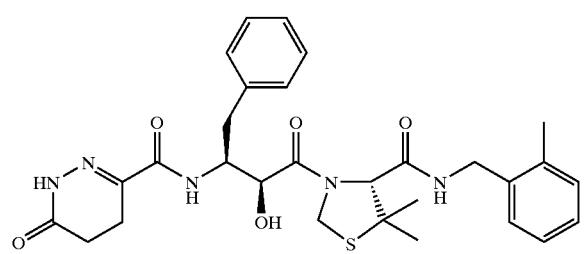
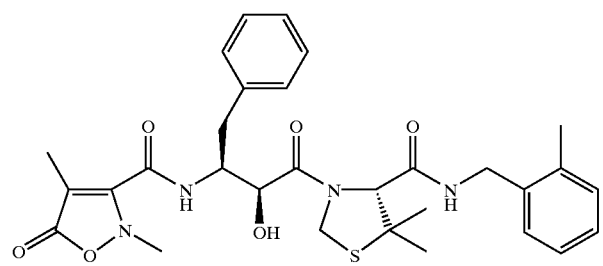
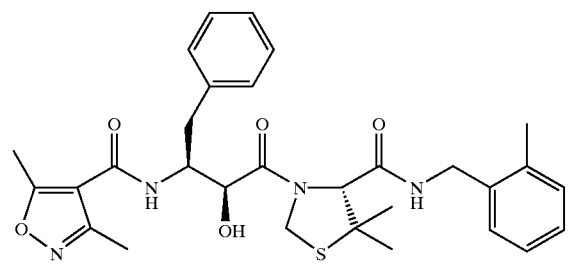
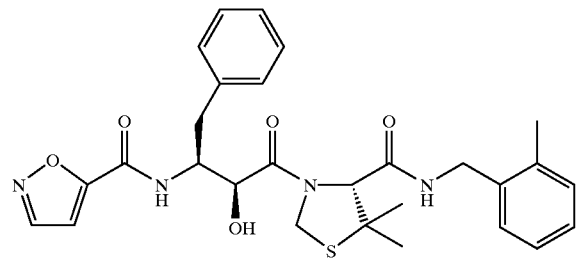
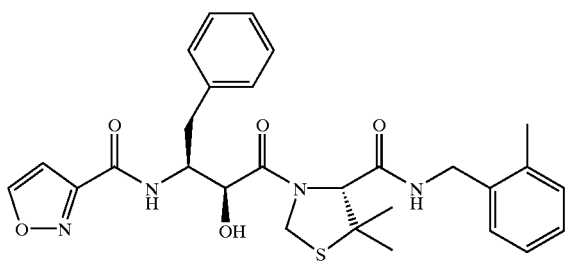
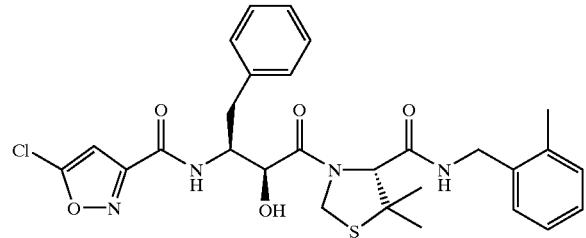
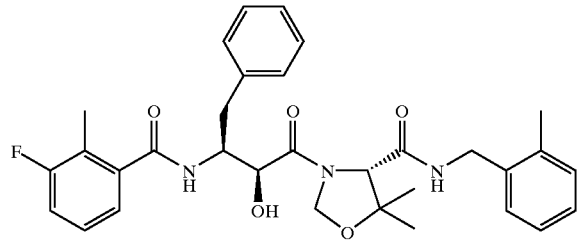
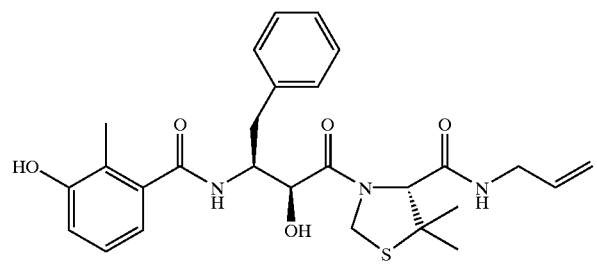
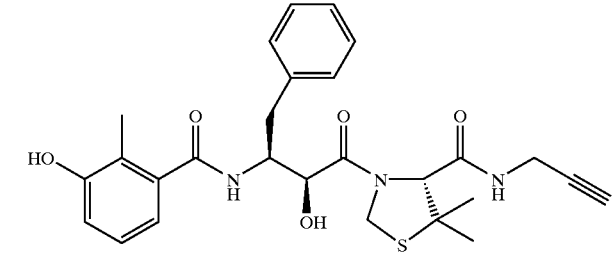

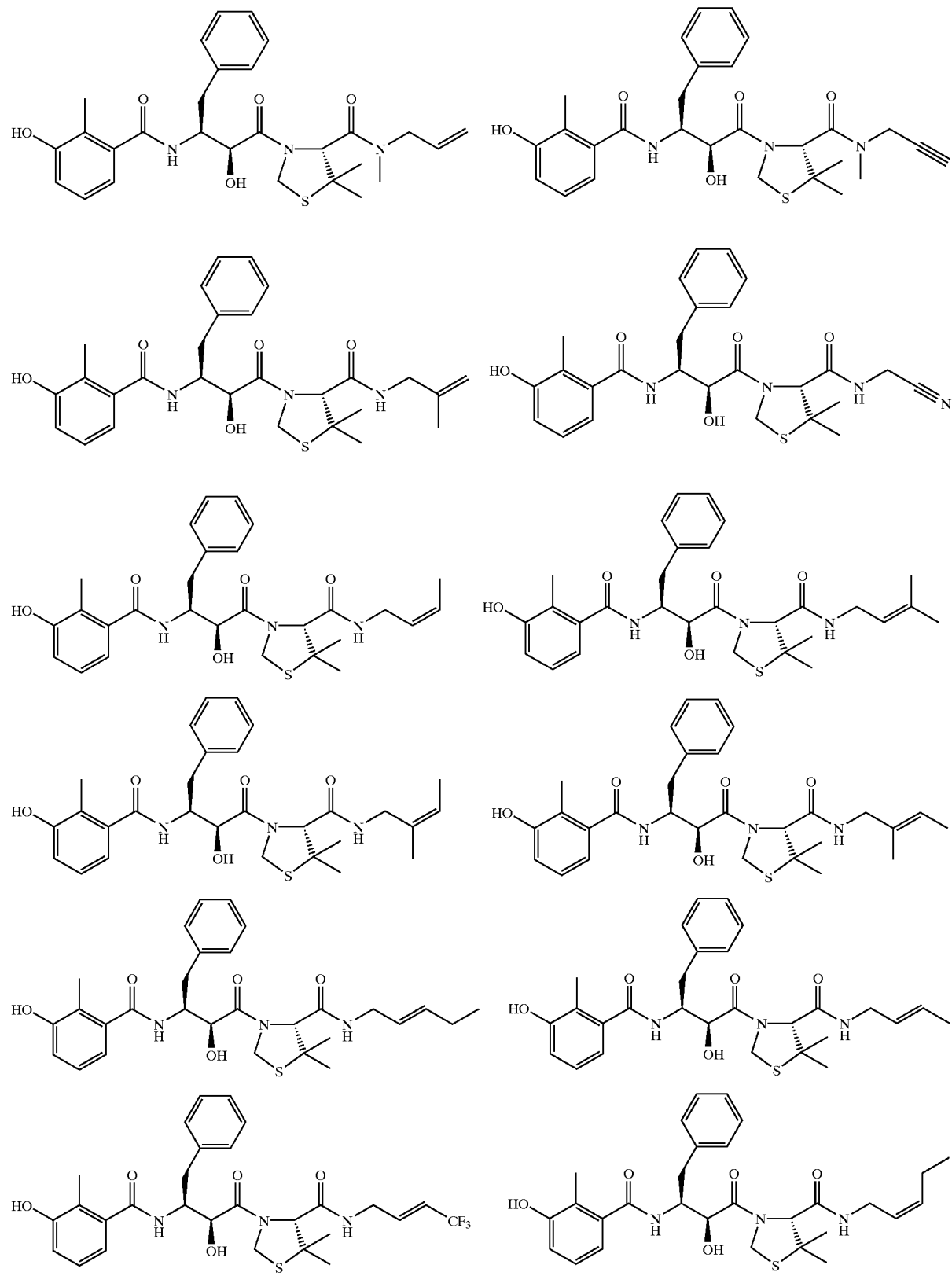

31 32
-continued
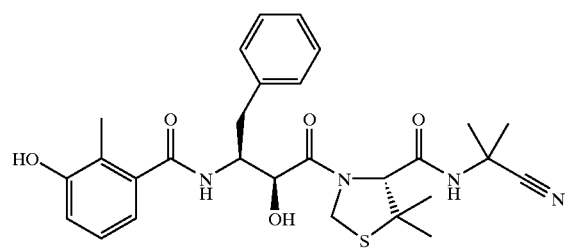
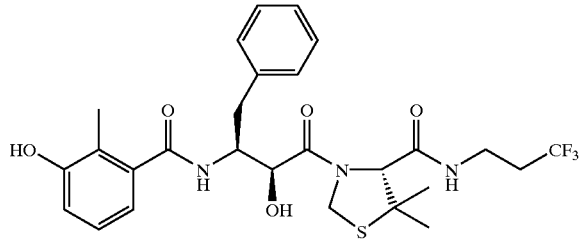
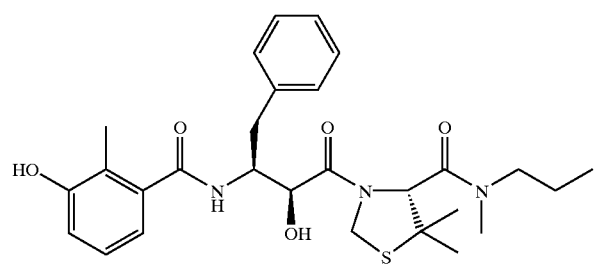
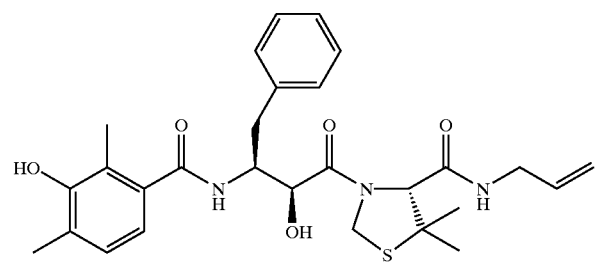
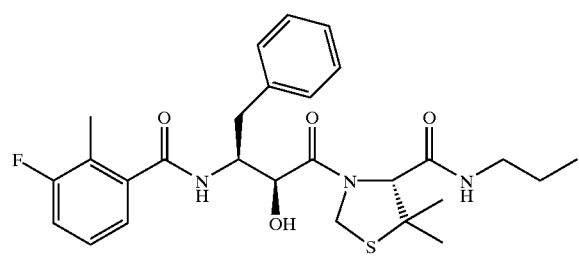
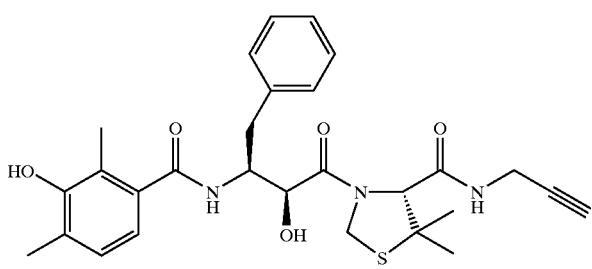
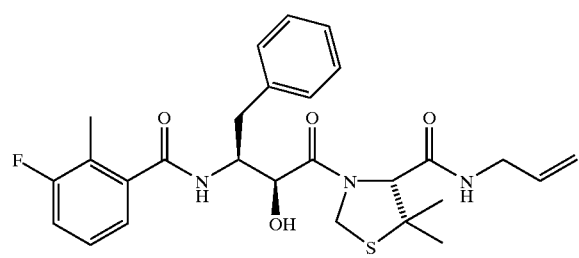
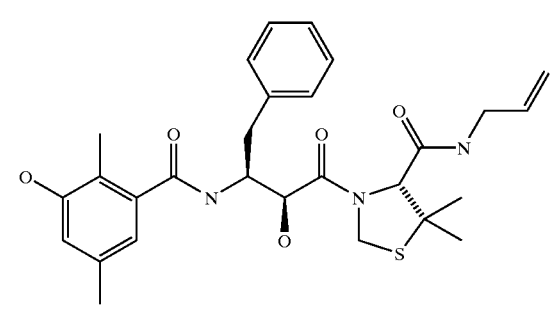
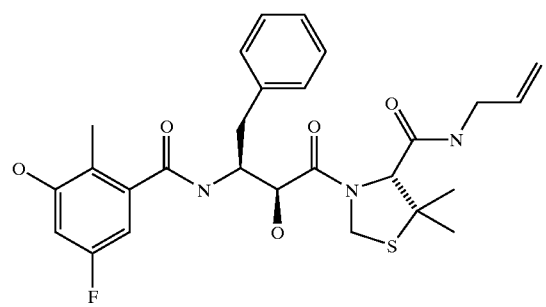
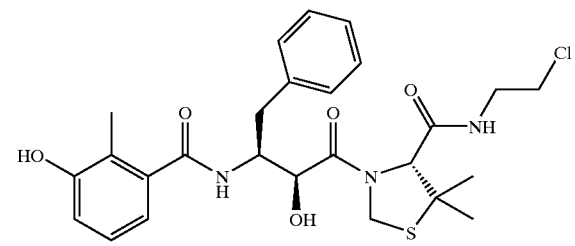
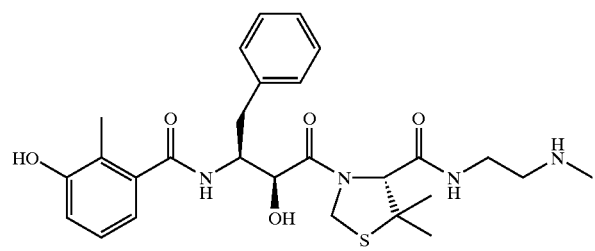
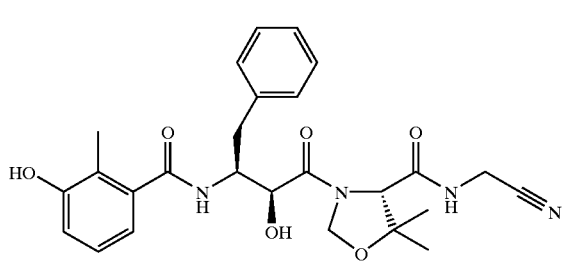

and the prodrugs, pharmaceutically active metabolites, and pharmaceutically acceptable salts and solvates thereof.

The invention is also directed to the intermediates of Formula II, which are useful in the synthesis of certain compounds of Formula I:

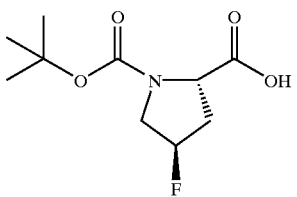

20a

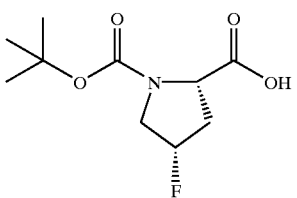

20b

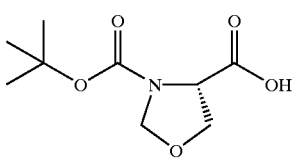

20c

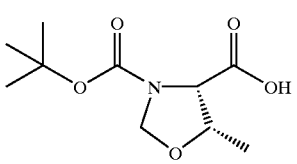

20d

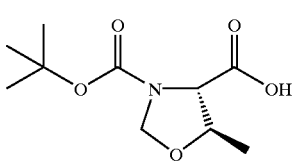

20e

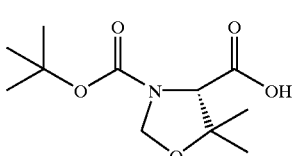

20f

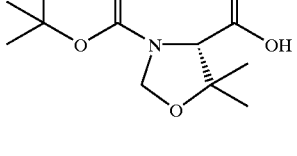

The HIV protease inhibitor compounds of this invention include prodrugs, the pharmaceutically active metabolites, and the pharmaceutically acceptable salts and solvates thereof. In preferred embodiments, the compounds of Formula I, prodrugs, pharmaceutically acceptable salts, and pharmaceutically active metabolites and solvates thereof demonstrate an HIV-protease inhibitory activity, corresponding to $K_i$ of at least 100 nM, an $EC_{50}$ of at least 10 mM or an $IC_{50}$ of at least 10 mM. Preferably, the compounds of this invention demonstrate an HIV-protease inhibitory activity, corresponding to a $K_i$ of at least 10 nM, an $EC_{50}$ of at least 1 mM or an $IC_{50}$ of at least 1 mM. More preferably, the compounds of this invention demonstrate an HIV-protease inhibitory activity against mutant strains of HIV, corresponding to a $K_i$ of at least 100 nM, an $EC_{50}$ of at least 10 mM or an $IC_{50}$ of at least 10 mM. Even more preferably, the compounds of this invention demonstrate protease inhibitory activity against mutant strains corresponding to a $K_i$ of at least 10 nM, an $EC_{50}$ of at least 1 mM or an $IC_{50}$ of at least 1 mM.

A "prodrug" is intended to mean a compound that is converted under physiological conditions or by solvolysis or metabolically to a specified compound that is pharmaceutically active. A prodrug may be a derivative of one of the compounds of this invention that contains a moiety, such as for example —CO₂R, —PO(OR)₂ or —C=NR, that may be cleaved under physiological conditions or by solvolysis. Any suitable R substituent may be used that provides a pharmaceutically acceptable solvolysis or cleavage product. A prodrug containing such a moiety may be prepared according to conventional procedures by treatment of a compound of this invention containing, for example, an amido, carboxylic acid, or hydroxyl moiety with a suitable reagent. A "pharmaceutically active metabolite" is intended to mean a pharmacologically active compound produced through metabolism in the body of a specified compound. Prodrugs and active metabolites of compounds of this invention of the above-described Formulas may be determined using techniques known in the art, for example, through metabolic studies. See, e.g., "Design of Prodrugs," (Bundgaard, ed.), 1985, Elsevier Publishers B.V., Amsterdam, The Netherlands. The following is an example of a prodrug that can be converted to the compound of this invention under physiological conditions, by solvolysis or metabolically:

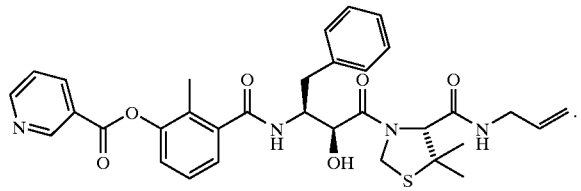

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates (mesylates), propanesulfonates, naphthalene-1-sulfonates, naphthalene-2-sulfonates, and mandelates. A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the inventive compounds, salts, and solvates may exist in different crystal forms, all of which are intended to be within the scope of the present invention and specified formulas.

The present invention is also directed to a method of inhibiting HIV protease activity, comprising contacting the protease with an effective amount of a compound of Formula I, or a pharmaceutically acceptable salt, prodrug, pharmaceutically active metabolite, or solvate thereof. For example, HIV protease activity may be inhibited in mammalian tissue by administering a compound of Formula I or a pharmaceutically acceptable salt, prodrug, pharmaceutically active metabolite, or solvate thereof. More preferably, the present method is directed at inhibiting HIV-protease activity. "Treating" or "treatment" is intended to mean at least the mitigation of a disease condition in a mammal, such as a human, that is alleviated by the inhibition of the activity of HIV proteases. The methods of treatment for mitigation of a disease condition include the use of the compounds in this invention in any conventionally acceptable manner, for example, as a prophylactic. The activity of the inventive compounds as inhibitors of HIV protease activity may be measured by any of the suitable methods known to those skilled in the art, including in vivo and in vitro assays. Examples of suitable assays for activity measurements are escribed herein. Administration of the compounds of the Formula I and their pharmaceutically acceptable prodrugs, salts, active metabolites, and solvates may be performed according to any of the generally accepted modes of administration available to those skilled in the art. Illustrative examples of suitable modes of administration include oral, nasal, parenteral, topical, transdermal, and rectal.

An inventive compound of Formula I or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use or mode of administration. Acceptable methods of preparing suitable pharmaceutical forms of the pharmaceutical compositions may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

The present invention includes pharmaceutical compositions useful for inhibiting HIV protease, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV protease, and a method of treating infection by HIV, or of treating AIDS or ARC. Additionally, the present invention is directed to a pharmaceutical composition comprising a therapeutically effective amount of a compound of the present invention in combination with a therapeutically effective amount of an HIV infection/AIDS treatment agent selected from:

1) an HIV/AIDS antiviral agent,
2) an anti-infective agent, and
3) an immunomodulator.

The present invention also includes the use of a compound of the present invention as described above in the preparation of a medicament for (a) inhibiting HIV protease, (b) preventing or treating infection by HIV, or (c) treating AIDS or ARC.

The present invention further includes the use of any of the HIV protease inhibiting compounds of the present invention as described above in combination with one or more HIV infection/AIDS treatment agents selected from an HIV/AIDS antiviral agent, an anti-infective agent, and an immunomodulator for the manufacture of a medicament for (a) inhibiting HIV protease, (b) preventing or treating infection by HIV, or (c) treating AIDS or ARC, said medicament comprising an effective amount of the HIV protease inhibitor compound and an effective amount of the one or more treatment agents.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a non-aqueous or aqueous liquid suspension. A dose of the pharmaceutical composition contains at least a therapeutically effective amount of the active compound (i.e., a compound of Formula I or a pharmaceutically acceptable salt, prodrug, active metabolite, or solvate thereof), and preferably is made up of one or more pharmaceutical dosage units. The selected dose may be administered to a mammal, for example, a human patient, in need of treatment mediated by inhibition of HIV protease activity, by any known or suitable method of administering the dose, including: topically (for example, as an ointment or cream), orally, rectally (for example, as a suppository), parenterally (by injection) or continuously by intravaginal, intranasal, intrabronchial, intraaural, or intraocular infusion. A "therapeutically effective amount" is intended to mean the amount of an inventive agent that when administered to a mammal in need thereof, is sufficient to effect treatment for disease conditions alleviated by the inhibition of the activity of one or more variant of the HIV protease. The amount of a given compound of the invention that will be therapeutically effective will vary depending upon factors such as the particular compound, the disease condition and the severity thereof, the identity of the mammal in need thereof, which amount may be routinely determined by artisans.

The compounds of this invention are also useful in the preparation and execution of screening assays for antiviral compounds. For example, the compounds of this invention are useful for isolating enzyme mutants that are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

General Synthetic Methods

Preferably, the inventive compounds are prepared by the methods of the present invention, including the General Methods shown below. When stereochemistry is not specified in chemical structures, either stereocenter may be utilized. The following abbreviations also apply: Boc (tert-butoxycarbonyl), Ac (acetyl), Cbz (benzyloxycarbonyl), DMB (2,4-dimethoxybenzyl), TBS (tert-butyldimethylsilyl), TBDPS (tert-butyldiphenylsilyl), Ms (methanesulfonate), Ts (toluenesulfonate), Bn (benzyl), and Tr (triphenylmethyl)

All reactions were performed in septum-sealed flasks under a slight positive pressure of argon unless otherwise noted. All commercial reagents and solvents were used as received from their respective suppliers with the following exceptions: Tetrahydrofuran (THF) was distilled from sodium benzophenone ketyl prior to use. Dichloromethane ($CH_2Cl_2$) was distilled from calcium hydride prior to use. Flash chromatography was performed using silica gel 60 (Merck art. 9385). $^1H$ NMR spectra were recorded at 300 MHz utilizing a Varian UNITY plus 300 spectrometer. Chemical shifts are reported in ppm (δ) downfield relative to internal tetramethylsilane, and coupling constants are given in Hertz. Infrared absorption spectra were recorded using a Perkin-Elmer 1600 series FTIR spectrometer. Elemental analyses were performed by Atlantic Microlab, Inc., Norcross, Ga. Melting points are uncorrected.

All P2' amine variants mentioned in General Methods A–E described hereinbelow were either purchased and used directly or synthesized as follows.

Method A: Representative Procedure for Reduction of Ketones to Alcohols.

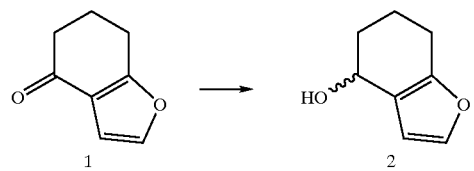

6,7-Dihydro-4-(5H)-benzofuranone (1) (1.00 g 7.34 mmol) was dissolved in methanol (55 mL). The mixture was cooled to 0° C. and $NaBH_4$ (0.31 g, 8.08 mmol) was added in portions. The reaction was stirred for 2 h at 0° C. at which time the methanol was evaporated. The residue was dissolved in EtOAc and poured into $NaHCO_3$ (saturated aqueous) and extracted with EtOAc (3×10 mL). The combined organic extracts were washed with brine (10 mL), passed over a short plug of $Na_2SO_4$, and concentrated in vacuo to give 2 (1.01 g, 99%, as a mixture of isomers) as a pale yellow, thick oil, which was of sufficient quality to be advanced to the next step without further purification. Rf (50% EtOAc/hexanes): 0.53.

Method B: Representative Procedure for Reduction of Acids to Alcohols.

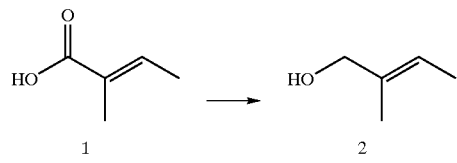

Tiglic acid (1) (20.0 g, 0.200 mol) was dissolved in ether (80 ml) and added dropwise over 30 min to a suspension of $LiAlH_4$ (15.0 g, 0.417 mol) in ether (80 ml) at 0° C. and the reaction mixture was allowed to warm to room temperature. After 3 h the mixture was re-cooled to 0° C. and quenched slowly by the addition of $H_2O$ (15 ml), 15% NaOH (15 ml) and $H_2O$ (15 ml). The reaction mixture was filtered to remove the granular precipitate and washed thoroughly with ether. The filtrate was washed successively with 1N HCl, $NaHCO_3$ (saturated aqueous), and brine. The combined organic layers were dried over $MgSO_4$ and concentrated in vacuo to give (E)-2-methyl-but-2-en-1-ol (2) as a clear oil (12.8 g, 74%).

Method C: Representative Procedure for Alkylation of Phenols Alcohols.

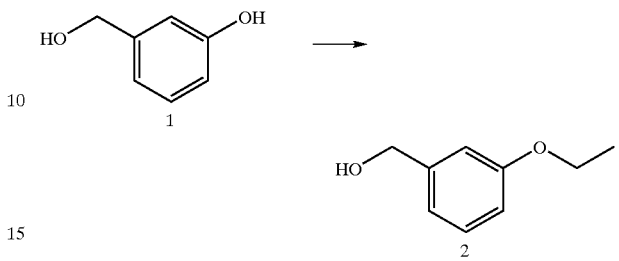

3-Hydroxybenzylalcohol (1) (0.500 g 4.03 mmol) was dissolved in DMF (2 mL) at ambient temperature. Ethyl bromide (0.900 mL, 12.1 mmol) and finely crushed $K_2CO_3$ (2.78 g, 20.1 mmol) were added and the reaction mixture was stirred for 5 h. The DMF was then removed in vacuo and the residue was partitioned between EtOAc and $H_2O$, and extracted with EtOAc (3×10 mL). The organic layers were washed with brine (10 mL) and passed over a short plug of $Na_2SO_4$. The solvents were removed in vacuo to give alcohol 2 (0.55 g, 90%) as a pale yellow, thick oil, which was of sufficient quality to be advanced to the next step without further purification. Rf (40% EtOAC/hexanes): 0.69.

Method D: Representative Procedure for Conversion of Alcohols to Amines.

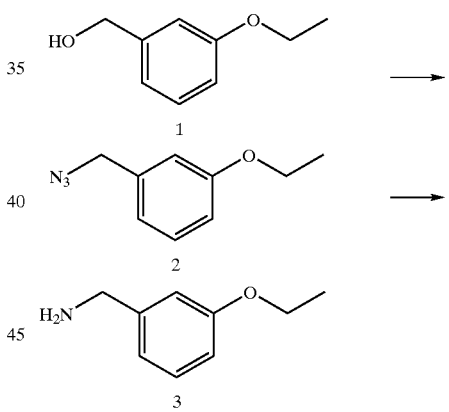

3-Ethoxy-phenyl-methanol (1) (1.23 g 8.08 mmol) was dissolved in $CH_2Cl_2$ (10 mL) at ambient temperature and diphenylphosphoryl azide (2.67 g, 9.70 mmol) and 1,8-diazabicyclo [5.4.0] undec-7-ene (1.45 mL, 9.70 mmol) were added. The mixture was stirred for 5 h at which time the $CH_2Cl_2$ was removed in vacuo and the crude residue was partitioned between EtOAc and $H_2O$ and extracted with EtOAc (3×10 mL). The combined organic layers were washed with brine (10 mL), passed over a short plug of $Na_2SO_4$, and concentrated in vacuo to give a yellow oil that was loaded directly onto a flash silica gel column and was quickly eluted with 10% EtOAc/hexanes. The solvents were removed in vacuo to give azide 2 (1.43 g, 84%) as a colorless oil. Rf (30% EtOAc/hexanes): 0.79.

1-Azidomethyl-3-ethoxy-benzene (2) (1.19 g 6.71 mmol) was dissolved in MeOH (15 mL) and palladium 10% on activated carbon, wet (20% in weight) was added. The reaction was hydrogenated for 30 min at 40 PSI in a Parr Hydrogenator. The black suspension was then filtered through compacted celite and the methanol was removed in vacuo to give amine 3 (0.88 g, 88%) as a pale yellow, thick oil, which was of sufficient quality to be advanced to the coupling reactions without further purification.

Method E: Representative Procedure for Conversion of Alcohols to Bromides.

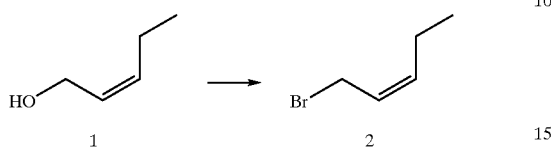

Cis-2-penten-1-ol (1) (1.00 g, 11.6 mmol) and carbon tetrabromide (3.85 g, 13.9 mmol) were dissolved in $CH_2Cl_2$ (75 mL). The mixture was cooled to 0° C. and triphenylphosphine (3.65 mL, 13.9 mmol) dissolved in $CH_2Cl_2$ (50 mL) was added dropwise. The mixture was allowed to warm to room temperature and was stirred overnight. The $CH_2Cl_2$ was removed in vacuo and the crude residue was loaded directly onto a flash silica gel column and eluted quickly with 20% EtOAc/hexanes. The solvents were removed in vacuo to give bromide 2 (1.53 g, 88%) as a colorless volatile oil. Rf (30% EtOAC/hexanes): 0.89.

Method F: Representative Procedure for Conversion of Bromides to Amines.

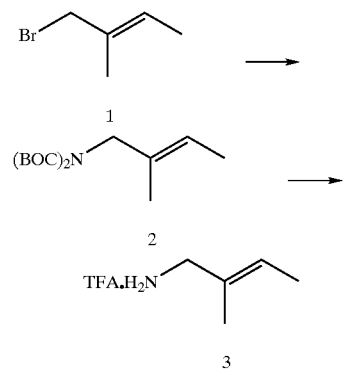

A mixture of bromide 1 (3.00 g, 20.1 mmol), di-tert-butyl-iminodicarboxylate (4.8 g, 22 mmol), and $K_2CO_3$ (3.10 g, 80.4 mmol) in DMF (30 ml) was stirred at ambient temperature overnight. The mixture was partitioned between 1N HCl and EtOAc. The organic layer was washed with $H_2O$ and brine, then dried over $NaSO_4$. Concentration in vacuo afforded a yellow oil which upon purification by flash column chromatography (hexanes to 5% EtOAc/Hexane gradient) yielded protected amine 2 as a clear oil (2.0 g, 35%).

A mixture of the diBOC amine 2 (2.0 g, 7.0 mmol), trifluoroacetic acid (2.7 ml, 35 mmol) and $CH_2Cl_2$ (40 ml) was stirred at ambient temperature overnight. The reaction mixture was concentrated in vacuo to give the TFA salt of (E)-2-methyl-but-2-enylamine (3).

Method G: Representative Procedure for Reduction of Aromatic Nitro Groups by Hydrogenation.

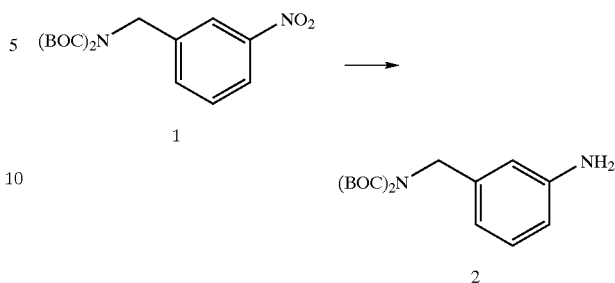

Compound 1 (2.04, 5.79 mmol) was dissolved in EtOAc (20 mL) and palladium 10% on activated carbon, wet (20% in weight) was added. The reaction was hydrogenated for 4 h at 45 PSI in a Parr Hydrogenator. The black suspension was then filtered through compacted celite and the methanol was removed in vacuo to give aniline 2 (1.65 g, 88%) as a pale yellow, thick oil, which was of sufficient quality to be advanced to the acetylation reaction without further purification.

Method H: Representative Procedure for Acetylation of Anilines.

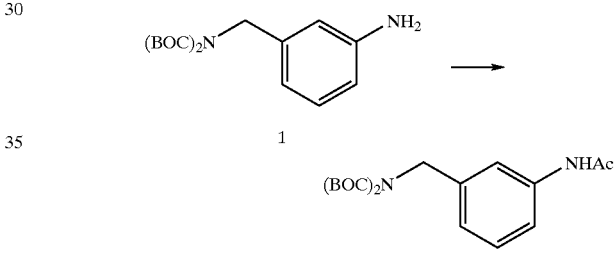

Aniline 1 (1.65 g, 5.12 mmol) was dissolved in $CH_2Cl_2$ (25 mL) at ambient temperature. Acetyl chloride (0.48 g, 6.14 mmol) and N,N-Diisopropylethylamine (0.79 g, 6.14 mmol) were added, and the reaction was stirred overnight. The $CH_2Cl_2$ was removed in vacuo and the crude residue was partitioned between EtOAc and 5% $KHSO_4$ and extracted with EtOAc (3×10 mL). The combined organic extracts were washed with $NaHCO_3$ (saturated aqueous, 10 mL), brine (10 mL), and dried over $Na_2SO_4$. The solvents were removed in vacuo to give an orange oil which was of sufficient quality to be advanced to the next step without further purification. Rf (50% EtOAC/hexanes): 0.42.

Method I: Representative Procedure for Reduction of Aldehydes to Amines.

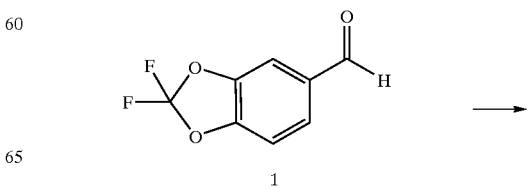

-continued

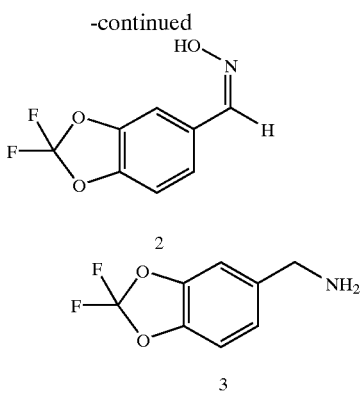

Hydroxyl amine hydrochloride (758 mg, 10.7 mmol) and pyridine (2.16 mL) was added to a solution of 2,2-difluoro-5-formyl benzodioxole (1) (2.00 g, 10.7 mmol) in MeOH (10 mL). After 18 hours the MeOH was removed in vacuo. The reaction mixture was diluted with EtOAc and was washed sequentially with $H_2O$, 10% w/v $CuSO_4$, and brine and then dried over $MgSO_4$. The solution was concentrated in vacuo. The hydroxy imine was purified by column chromatography using 20% EtOAc/Hexanes to give 1.37 g (64% yield) of a white solid. Imine was then subjected to LAH reduction as described above to provide amine 3.

The following amines were synthesized for the corresponding example numbers:

EXAMPLE A26

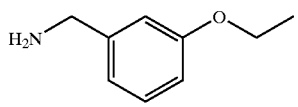

Amine was generated by alkylation of 3-hydroxybenzyl alcohol with ethyl bromide as describe in method C above followed by conversion of the alcohol to the amine as described in method D above provided desired amine.

EXAMPLE A43

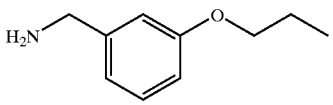

Amine was generated as described above for Example A43 using propylbromide as the alkylating agent.

EXAMPLE A33

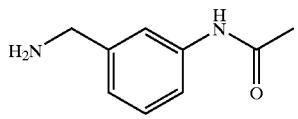

Amine was generated from displacement of bromide in 3-nitrobenzylbromide with di BOC amine as described in method F above. Reduction of the nitro moiety to the aniline (method G above) followed by acetylation (method H above) and BOC removal (method F above) provided desired amine.

EXAMPLE A36, EXAMPLE A37 and EXAMPLE A40

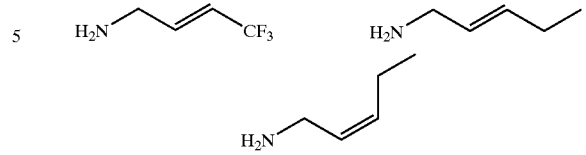

Amines were generated from conversion of the corresponding primary alcohols as described in method E above. Displacement of the bromide with di BOC amine and deprotection with TFA (method F above) provided the desired amines.

EXAMPLE A39

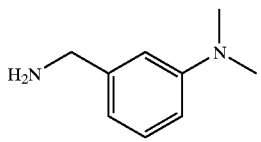

Amine was generated from 3-dimethylaminobenzyl alcohol as described in method D above.

EXAMPLE A34

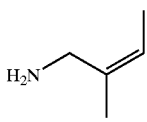

Amine was generated by reduction of the corresponding methyl ester to the primary alcohol (Wipf, *J. Org. Chem.* 1994, 59, 4875–86.). Conversion to the bromide (method E above) followed by displacement with diBOC amine and deprotection (method F above) provided desired amine.

EXAMPLE A35

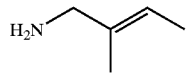

Amine was generated from the corresponding carboxylic acid. Reduction of the acid as described in method B above followed by bromide displacement as described in method E above gave the primary bromide. Conversion of the bromide to the primary amine followed the procedure described in method F above.

EXAMPLE A42

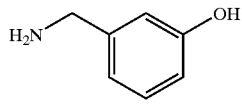

Amine was generated from 3-benzyloxybenzyl alcohol. Conversion to the azide and reduction of both the azide and benzyl protecting group were accomplished using method D as described above with longer hydrogenation time.

EXAMPLE A44

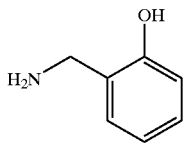

Amine was generated by LiAlH₄ reduction of 2-cyanophenol (Ludeman, S. M., et. al. *J. Med. Chem.* 1975, 18, 1252–3.).

EXAMPLE A50

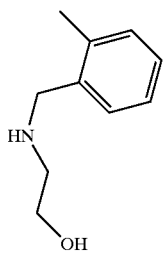

Amine was generated from the condensation of o-tolualdehyde with 2-aminoethanol followed by reduction with sodium borohydride (*Tetrahedron Assym.* 1997, 8, 2367–74.).

EXAMPLE A48

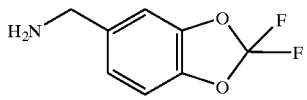

Amine was generated from the corresponding aldehyde by the reductive amination procedure described in method I above.

EXAMPLE A7

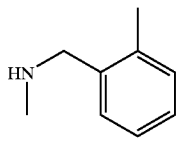

Amine was generated by a reductive amination with the corresponding aldehyde (*Arch. Pharm.* 1987, 320, 647–54.).

EXAMPLE A49

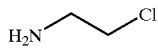

Amine was generated on the thiazolidine core as follows:
Diphenylchlorophosphate (1.0 ml, 4.2 mmol) followed by triethylamine (0.59 ml, 4.2 mmol) were added to a cooled 0° C. solution of BOC-DMTA 1 (1.0 g, 3.8 mmol) in EtOAc (10 ml). The mixture was stirred for 1 h and at which time triethylamine (0.59 ml, 4.2 mmol) and ethanolamine (0.25 ml, 4.2 mmol) were added. The reaction was left to stir overnight at ambient temperature and then partitioned between 1N HCl and EtOAc. The organic layer was washed with NaHCO₃(saturated aqueous) and brine. The organic layer was dried over Na₂SO₄ and concentrated in vacuo to a pale yellow oil 2. The oil was stirred with thionyl chloride (2 ml) for 45 min at room temperature. The mixture was concentrated in vacuo and the residual oil was partitioned between 1N NaOH and EtOAc. The organic layer was extracted with 1N HCl (2×20 ml). The combined aqueous layers were made basic with 1N NaOH and then extracted with EtOAc (3×60 ml). The organic layers were washed with brine, dried over Na₂SO₄ and concentrated in vacuo to give (R)-5,5-Dimethyl-thiazolidine-4-carboxylic acid (2-chloro-ethyl)-amide 3 as a clear oil (0.39 g, 55%).

The following amines were prepared as described:

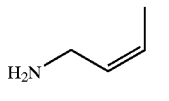

Example A31

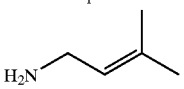

Example A32

Example A38

The above amines were prepared according to Carlsen, H. J., *J. Heterocycle Chem.* 1997, 34, 797–806.

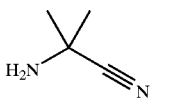

EXAMPLE A41

The above amine was prepared according to O'Brien, P. M., *J. Med. Chem.* 1994, 37, 1810–1822.

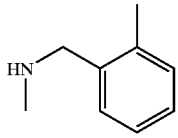

EXAMPLE A7

The above amine was prepared according to Weinheim, G. *Arch. Pharm.* 1987, 320, 647–654.

General Method A

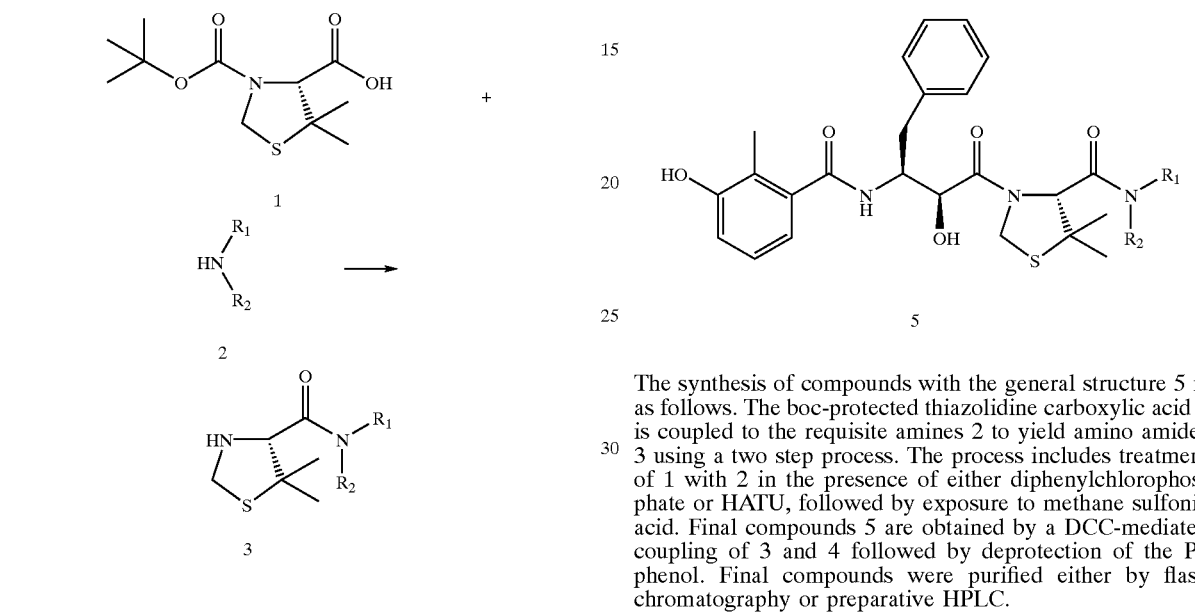

The synthesis of compounds with the general structure 5 is as follows. The boc-protected thiazolidine carboxylic acid 1 is coupled to the requisite amines 2 to yield amino amides 3 using a two step process. The process includes treatment of 1 with 2 in the presence of either diphenylchlorophosphate or HATU, followed by exposure to methane sulfonic acid. Final compounds 5 are obtained by a DCC-mediated coupling of 3 and 4 followed by deprotection of the P2 phenol. Final compounds were purified either by flash chromatography or preparative HPLC.

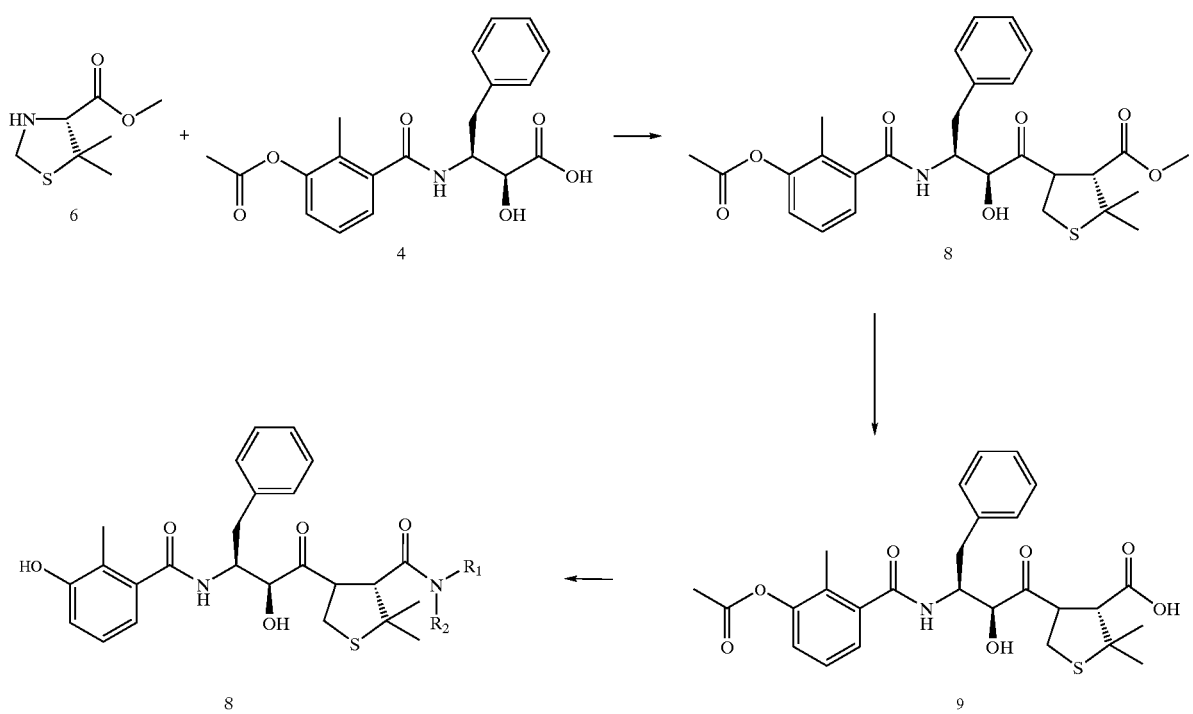

An alternative approach to the general structure 5 is as follows. The thiazolidine ester 6 is coupled to acid 7 under carbodiimide reaction conditions, resulting in product 8 which is converted to acid 9 by mild base hydrolysis. Acid 9 is combined with various amines, using diphenylphosphoryl azide, followed by cleavage of the P2 acetate to yield final compounds 5. The products were purified by either flash chromatography or preparative HPLC.

Specific Method A.

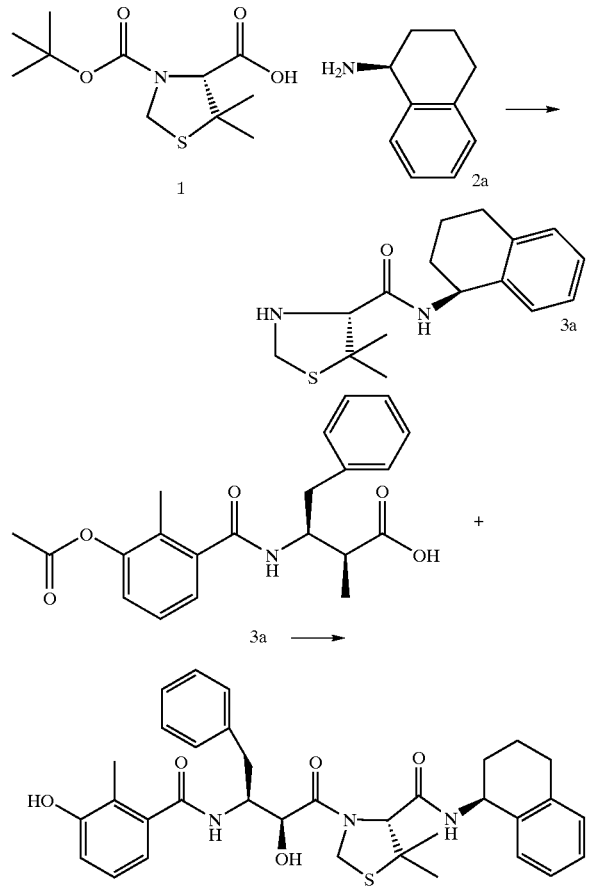

EXAMPLE A1

3-[2-Hydroxy-3-(3-hydroxy-2-methyl-benzoylamino)-4-phenyl-butyryl]-5,5-dimethyl-thiazolidine-4-carboxylic Acid (1,2,3,4-tetrahydro-naphthalen-1-yl)-amide The title compound was prepared as follows. (R)-5,5-Dimethyl-thiazolidine-3,4-dicarboxylic acid 3-tert-butyl ester 1 (0.3 g, 1.15 mmol) was dissolved in EtOAc (3 mL) and cooled to 0° C. Diphenyl chlorophosphate (0.26 mL, 1.26 mmol) was added followed by TEA (0.18 mL, 1.26 mmol). The reaction was stirred at 0° C. for 1 h, and treated with (S)-1,2,3,4-Tetrahydro-1-naphthylamine (0.19 g, 1.26 mmol). The reaction mixture was stirred at room temperature overnight, then partitioned between 1N HCl (5 mL) and EtOAc (10 mL). The organic layer was washed with saturated NaHCO$_3$, brine, dried over Na$_2$SO$_4$ and concentrated to a light yellow oil. The resulting crude oil was dissolved in EtOAc (5 mL) and the cooled to 0° C. Methanesulfonic acid (0.36 mL, 5.32 mmol) was added and the solution was stirred at 0° C. for 15 minutes, then at room temperature for 1 h. The mixture was re-cooled to 0° C. and quenched with 5% Na$_2$CO$_3$ (5 mL) then extracted with EtOAc (10 mL). The organic layer was washed with brine, dried over Na$_2$SO$_4$ and concentrated in vacuo to give 3a as a yellow oil. The yellow oil 3a (0.34 g, 1.15 mmol) was dissolved in EtOAc (12 mL). AMB-AHPBA 4 (0.40 g, 1.09 mmol) was added followed by HOBt (0.15 g, 1.09 mmol). The mixture was stirred at room temperature 1 h, then cooled to 0° C. DCC (0.24 g, 1.15 mmol) was slowly added as solution in EtOAc (6 mL). The mixture was warmed to room temperature and stirred overnight. The mixture was filtered and the filtrate was washed with 1N HCl (10 mL), saturated NaHCO$_3$ (10 mL), brine (10 mL), dried over Na$_2$SO$_4$ and concentrated to give a crude white solid (contaminated with DCU). The DCU was removed by flash chromatography (30% to 50% EtOAc in hexanes) to provide a white solid, which was dissolved in MeOH (2 mL) and treated with 4N HCl in 1,4-dioxane (0.26 mL, 1.1 mmol). The reaction was stirred at room temperature overnight then partitioned between 1N HCl (10 mL) and EtOAc (10 mL). The organic layer was washed with saturated NaHCO$_3$, dried over Na$_2$SO$_4$ and concentrated to a residue which was purified by flash chromatography (60% EtOAc in hexanes) to provide the title compound as a white solid: mp=125–126° C.; IR (cm$^{-1}$) 3320, 2932, 1704, 1644, 1530, 1454, 1361, 1284; $^1$H NMR (DMSO-d$_6$) δ 9.36 (s, 1H), 8.28 (d, J=8.6, 1H), 8.21 (d, J=8.8, 1H), 7.35–6.91 (m, 10H), 6.76 (d, J=8.0, 1H), 6.54 (d, J=7.5, 1H), 5.34 (d, J=6.0, 1H), 5.13 (d, J=9.0, 1H), 5.02 (d, J=9.0, 1H), 4.60–4.30 (m, 4H), 2.81–2.68 (m, 4H), 1.81 (s, 3H), 1.78–1.60 (m, 4H), 1.48 (s, 3H), 1.45 (s, 3 H); Anal. Calcd for C$_{34}$H$_{39}$N$_3$O$_5$S.1.5 H$_2$O: C, 64.95; H, 6.73; N, 6.68. Found: C, 64.88; H, 6.31; N, 6.18.

EXAMPLE A2

(R)-3-((2S,3R)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 3-methoxy-benzylamide

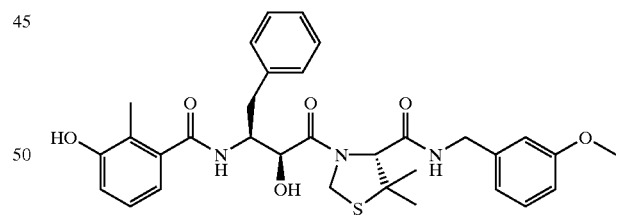

White solid: mp 108–110° C.; IR (neat, cm$^{-1}$) 3310, 2965, 1644, 1586, 1531, 1455, 1359, 1284; $^1$H NMR (DMSO-d$_6$) δ 9.37 (s, 1H), 8.40 (t, J=6.0, 1H), 8.09 (d, J=8.1, 1H), 7.31–6.52 (m, 12H), 5.49 (d, J=6.0, 1H), 5.12 (d, J=9.3, 1H), 5.00 (d, J=9.3, 1H), 4.44–4.35 (m, 3H), 4.42 (s, 1H), 4.09 (dd, J=15.0, 6.0, 1H), 3.69 (s, 3H), 2.87–2.67 (m, 2H), 1.82 (s, 3H), 1.49 (s, 3H), 1.34 (s, 3 H); Anal. Calcd for C$_{32}$H$_{37}$N$_3$O$_6$S.0.75 H$_2$O: C, 63.50; H, 6.41; N, 6.94. Found: C, 63.60; H, 6.23; N, 6.80.

The following examples were prepared by the specific method outlined above using the requisite amine 2.

EXAMPLE A3

(R)-3-(2-Hydroxy-3-{[1-(3-hydroxy-2-methyl-phenyl)-methanoyl]-amino}-4-phenyl-butanoyl)-5,5-dimethyl-thiazolidine-4-carboxylic Acid 2-methoxy-benzylamide

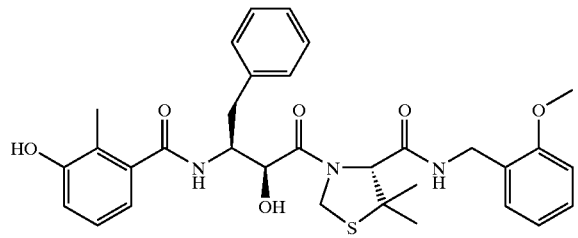

White solid: mp=123–125° C.; IR (cm$^{-1}$) 3318, 2965, 1644, 1525, 1495, 1464, 1286, 1246, 1120, 1030; $^1$H NMR (DMSO-d$_6$) δ 9.36 (s, 1H), 8.26 (t, J=5.9, 1H), 8.14 (d, J=8.0. 1H), 7.39–7.13 (m, 6H), 6.95–6.76 (m, 5H), 6.53 (d, J=7.5, 1H), 5.49 (d, J=6.0, 1H), 5.13 (d, J=9.0, 1H), 5.01 (d, J=9.0, 1H), 4.47 (s, 1H), 4.41–4.16 (m, 4H), 3.78 (s, 3H), 2.90–2.62 (m, 2H), 1.81 (s, 3H), 1.49 (s, 3H), 1.32 (s, 3H); Anal. Calcd for C$_{32}$H$_{37}$N$_3$O$_6$S.0.75 H$_2$O: C, 63.50; H, 6.41; N, 6.94. Found: C, 63.68; H, 6.20; N, 6.54.

EXAMPLE A4

3-(2-Hydroxy-3-{[1-(3-hydroxy-2-methyl-phenyl)-methanoyl]-amino}-4-phenyl-butanoyl)-5,5-dimethyl-thiazolidine-4-carboxylic Acid 3-trifluoromethyl-benzylamide

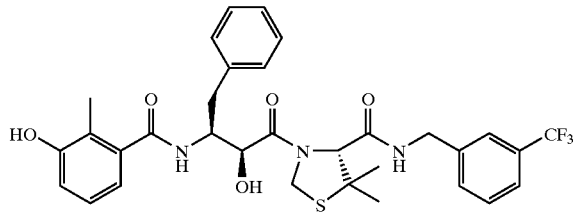

Whitesolid: mp=108–110° C.; IR (cm$^{-1}$) 3308, 3065, 1646, 1540, 1456, 1362, 1329, 1284, 1165, 1125, 1074; $^1$H NMR (DMSO-d$_6$) δ 9.38 (s, 1H), 8.56 (t, J=6.0, 1H), 8.12 (d, J=8.2, 1H), 7.65 (s, 1H), 7.60–7.47 (m, 3H), 7.28–7.13 (m, 5H), 6.96–6.92 (m, 1H), 6.77 (d, J=8.0, 1H), 6.53 (d, J=7.5, 1H), 5.45 (d, J=6.0, 1H), 5.14 (d, J=9.2, 1H), 5.00 (d, J=9.2, 1H), 4.53–4.41 (m, 4H), 4.22 (dd, J=16.0, 6.0, 1H), 2.86–2.66 (m, 2H), 1.81 (s, 3H), 1.49 (s, 3H), 1.31 (s, 3H); Anal. Calcd for C$_{32}$H$_{34}$F$_3$N$_3$O$_5$S: C, 61.04; H, 5.44; N, 6.67. Found: C, 61.03; H, 5.56; N, 6.51.

EXAMPLE A5

3-(2-Hydroxy-3-{[1-(3-hydroxy-2-methyl-phenyl)-methanoyl]-amino}-4-phenyl-butanoyl)-5,5-dimethyl-thiazolidine-4-carboxylic Acid Fluoro trifluoromethyl-benzylamide

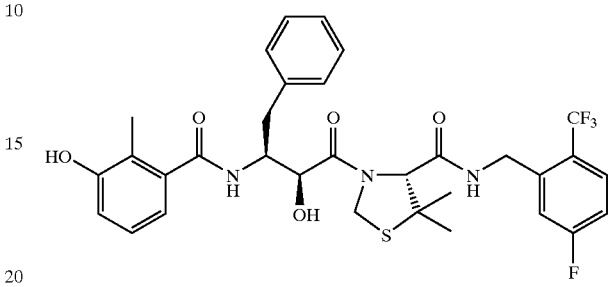

$^1$H NMR (DMSO-d$_6$) δ 9.33 (s, 1H), 8.69 (t, J=5.6, 1H), 8.12–6.56 (m, 11H), 5.50 (d, J=6.0, 1H), 5.22 (d, J=9.3, 1H), 5.06 (d, J=9.3, 1H), 4.60–4.36 (m, 5H), 4.50 (s, 1H), 2.89–2.67 (m, 2H), 1.83 (s, 3H), 1.55 (s, 3H), 1.39 (s, 3H); Anal. Calcd for C$_{32}$H$_{33}$N$_3$O$_5$SF$_4$: C, 59.34; H, 5.14; N, 6.49; S, 4.95. Found: C, 59.06; H, 5.31; N, 6.22; S, 4.66.

EXAMPLE A6

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 4-methoxy-benylamide

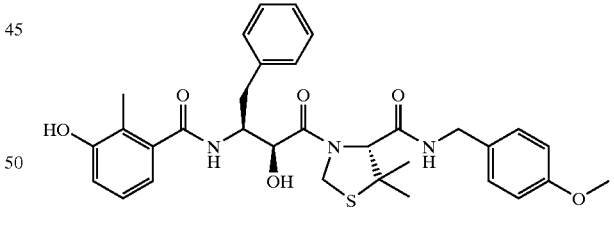

IR (neat cm$^{-1}$) 3335, 2920, 1641, 1516, 1463, 1374, 1285, 1249, 1172, 1118; $^1$H NMR (DMSO-d$_6$) δ 9.38 (s, 1H), 8.37 (t, J=5.5, 1H), 8.12 (d, J=8.2, 1H), 7.33–7.13 (m, 7H), 6.94 (t, J=7.7, 1H), 6.84–6.79 (m, 3H), 6.54 (d, J=7.0, 1H), 5.48 (d, J=6.6, 1H), 5.12 (d, J=9.2, 1H), 5.00 (d, J=9.2, 1H), 4.49–4.42 (m, 3H), 4.32 (dd, J=6.2, 14.8, 6., 1H), 4.09 (dd, J=14.8, 5.3, 1H), 3.67 (s, 3H), 2.87–2.68 (m, 2H), 1.82 (s, 3H), 1.48 (s, 3H), 1.32 (s, 3H); HRMS (ESI) m/z calcd for C$_{32}$H$_{37}$N$_3$O$_6$SNa (M+Na)$^+$ 614.2301, found 614.2305; Anal. Calcd for C$_{32}$H$_{37}$N$_3$O$_6$S.0.75 H$_2$O: C, 63.50; H, 6.41; N, 6.94. Found: C, 63.65; H, 6.43; N, 6.74.

EXAMPLE A7

3-[2-Hydroxy-3-(3-hydroxy-2-methyl-benzoylamino)-4-phenyl-butyryl]-5,5-dimethyl-thiiazolidine-4-carboxylic Acid methyl-(2-methyl-benzyl)-amide

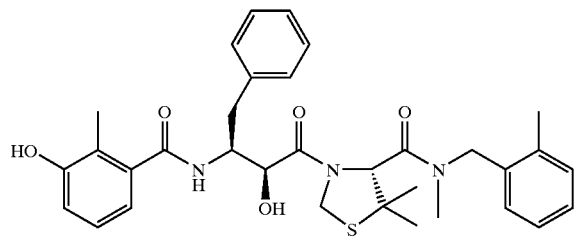

$^1$H NMR (DMSO-$d_6$) δ 9.3 (s, 1H), 8.44 (t, J=7.98, 1 H), 8.13–8.07 (m, 2H), 7.34–7.13 (m, 9H), 6.93 (t, J=7.9, 1H), 6.78 (d, J=7.7, 1H), 6.53 (d, J=7.1, 1H), 5.58 (d, J=6.8, 1H), 5.45 (d, J=7.0, 1H), 5.12 (dd J=7.8 8.2 1H), 4.51–4.31 (m, 6H), 2.86–2.67 (m, 2H), 2.19 (s, 3H), 1.81 (s, 3H), 1.51 (s, 3H), 1.34 (s, 3H); Anal. Calcd for $C_{33}N_{39}N_3O_5S.0.37$ $H_2O$: C, 66.45; H, 6.72; N, 7.15. Found: C, 66.34; H, 7.28; N, 7.45.

EXAMPLE A8

3-[2-Hydroxy-3-(3-hydroxy-2-methyl-benzolyamino)-4-phenyl-butyryl]-5,5-dimethyl-thiiazolidine-4-carboxylic Acid methyl-(3-methyl-thiophen-2ylmethyl)-amide

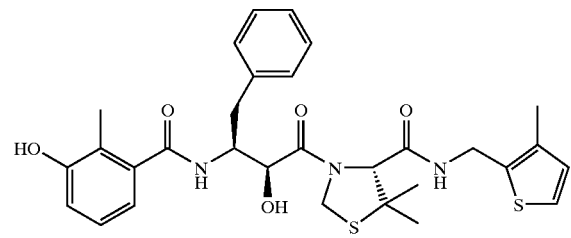

IR (neat or KBr cm$^{-1}$) 3150, 3000, 2942, 2187, 1712, 1600, 1567, 1505; $^1$H NMR (DMSO-$d_6$) δ 9.36 (s, 1H), 8.44 (t, J=7.98, 1H), 8.13–8.07 (m, 2H), 7.34–7.13 (m, 5H), 6.93 (t, J=7.9, 1H), 6.78 (d, J=7.7, 1H), 6.53 (d, J=7.1, 1H), 5.45 (d, J=7.0, 1H), 5.12 (dd, J=7.8, 8.2 1H), 4.51–4.31(m, 4H), 2.86–2.67 (m, 2H), 2.19 (s, 3H), 1.81 (s, 3H), 1.51 (s, 3H), 1.34 (s, 3H); Anal. Calcd for $C_{30}H_{35}N_3O_5S_2$: calculated C, 61.94H, 6.06 N, 7.22. Found C, 62.38 H, 6.23, N, 7.17.

EXAMPLE A9

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 4-trifluoromethyl-benzylamide

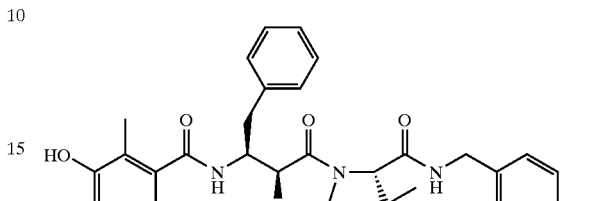

IR (neat cm$^{-1}$) 3343, 2931, 1543, 1530, 1454, 1326, 1122; $^1$HNMR(DMSO-$d_6$) δ 9.38(s, 1H), 8.57 (t, J=5.0, 1H), 8.15 (d, J=8.4, 1H), 7.59 (d, J=8.2, 2H), 7.50 (d, J=8.2, 2H), 7.28–7.13 (m, 5H), 6.93 (t, J=7.5, 1H), 6.77 (d, J=7.7, 1H), 6.54 (d, J=7.3, 1H), 5.50 (s br, 1H), 5.15 (d, J=9.2, 1H), 5.02 (d, J=9.2, 1H), 4.47–4.21 (m, 5H), 2.85–2.67 (m, 2H), 1.81 (s, 3H), 1.51 (s, 3H), 1.34 (s, 3H); ); HRMS (ESI) m/z calcd for $C_{32}H_{34}F_3N_3O_5SNa$ (M+Na)$^+$ 652.2063, found 652.2044; Anal. Calcd for $C_{32}H_{34}F_3N_3O_5S.0.25$ $H_2O$: C, 60.60; H, 5.48; N, 6.63. Found: C, 60.50; H, 5.29; N, 6.48.

EXAMPLE A10

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (2-oxo-2-phenyl-ethyl)-amide

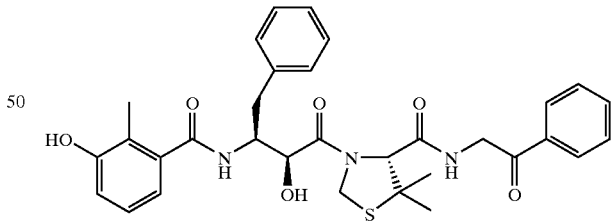

$^1$H NMR (DMSO-$d_6$) δ 9.39 (s, 1H), 8.36 (t, J=4.8, 1H), 8.15 (d, J=8.1, 1H), 7.98 (d, J=7.4, 1H), 7.65 (m, 1H), 7.52 (m, 2H), 7.32–7.11 (m, 6H), 6.93 (t, J=7.9, 1H), 6.76 (d, J=7.9, 1H), 6.54 (d, J=7.5, 1H), 5.42 (d, J=6.4, 1H), 5.08 (d, J=9.3, 1H), 5.02 (d, J=9.0, 1H), 4.78–4.30 (m, 5H), 2.84–2.66 (m, 2H), 1.81 (s, 3H), 1.57 (s, 3H), 1.45 (s, 3H); HRMS (ESI) m/z calcd for $C_{32}H_{35}N_3O_6SNa$ (M+Na)$^+$ 612.2139, found 612.2141.

EXAMPLE A11

3-(2-Hydroxy-3-{[1-(3-hydroxy-2-methyl-phenyl)-methanoyl]-amino}-4-phenyl-butanoyl)-5,5-dimethyl-thiazolidine-4-carboxylic Acid 3-fluoro-4-trifluoromethyl-benzylamide

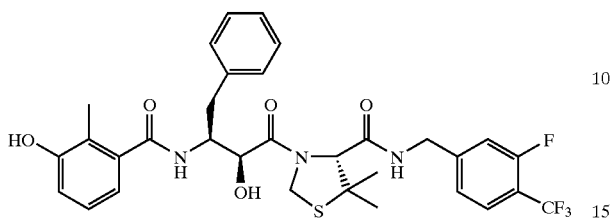

$^1$H NMR (DMSO-d$_6$) δ 9.34 (s, 1H), 8.62 (t, J=5.9, 1H), 8.09–6.54 (m, 11H), 5.45 (s br, 1H), 5.18 (d, J=9.2, 1H), 5.03 (d, J=9.2, 1H), 4.55–4.00 (m, 5H), 4.45 (s, 1H), 2.86–2.49 (m, 2H), 1.82 (s, 3H), 1.53 (s, 3H), 1.36 (s, 3H); Anal. Calcd for $C_{32}H_{33}N_3O_5SF_4$: C, 59.34; H, 5.14; N, 6.49; S, 4.95. Found: C, 59.14; H, 5.29; N, 6.21; S, 4.67.

EXAMPLE A12

3-(2-Hydroxy-3-{[1-(3-hydroxy-2-methyl-phenyl)-methyanoyl-amino}-4-phenyl-butanoyl)-5,5-dimethyl-thiazolidine-4-carboxylic acid-2-trifluoromethyl-4-fluoro-benzylamide

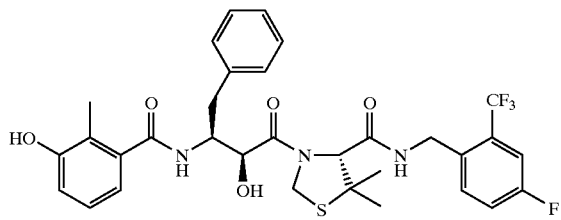

$^1$H NMR (DMSO-d$_6$) δ 9.33 (s, 1H), 8.65 (t, J=5.9, 1H), 8.12–6.54 (m, 11H), 5.45 (d, J=6.9, 1H), 5.18 (d, J=9.2, 1H), 5.05 (d, J=9.2, 1H), 4.59–4.34 (m, 5H), 4.50 (s, 1H), 2.85–2.67 (m, 2H), 1.82 (s, 3H), 1.53 (s, 3H), 1.37 (s, 3H); Anal. Calcd for $C_{32}H_{33}N_3O_5SF_4$: C, 59.34; H, 5.14; N, 6.49; S, 4.95. Found: C, 59.26; H, 5.35; N, 6.23; S, 4.69.

EXAMPLE A13

3-[2-Hydroxy-3-(3-hydroxy-2-methyl-benzoylamino)-4-phenyl-butyryl]-5,5-dimethyl-thiazolidine-4-carboxylic Acid 4-methanesulfonyl-benzamide

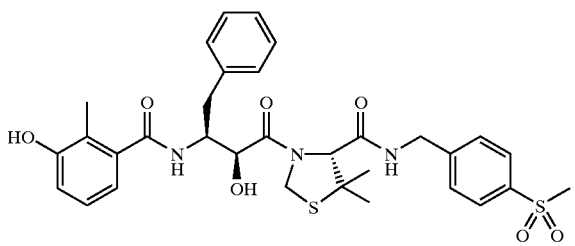

$^1$H NMR (DMSO-d$_6$) δ 9.38 (s, 1H), 8.37 (t, J=5.5, 1H,), 8.12 (d, 1H, J=8.2, 1H), 7.33–7.13 (m, 7H), 6.94 (t, 1H, J=7.7, 1H,), 6.84–6.79 (m, 3H), 6.54 (d, 1H, J=7.3, 1H), 5.48 (d, J=6.6, 1H), 5.12 (d, J=9.2, 1H,), 5.00 (d, 1H, J=9.2, 1H), 4.49–4.42 (m, 3H), 4.32 (dd, J=14.8, 6.2, 1H,), 4.09 (dd, 1H, J=14.8, 5.3, 1H), 3.47 (s, 3H), 2.87–2.68 (m, 2H), 1.82 (s, 3H), 1.48 (s, 3H), 1.32 (s, 3H); Anal. Calcd for $C_{32}H_{37}N_3O_7S_2$: C, 60.07; H, 5.83; N, 6.57. Found C, 60.25; H, 6.13; N, 6.74.

EXAMPLE A14

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid Allylamide

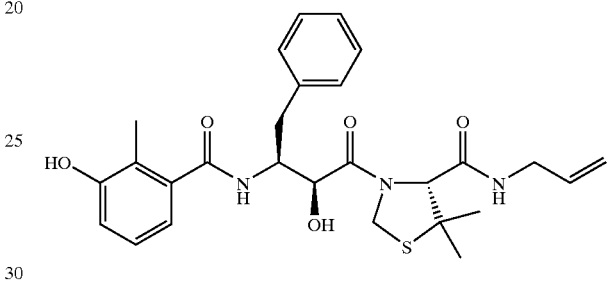

IR (neat cm$^{-1}$) 3342, 2966, 1637, 1531, 1460, 1366, 1284, 1108; $^1$H NMR (DMSO-d$_6$) δ 9.36 (s, 1H), 8.13–8.07 (m, 2H), 7.34–7.13 (m, 5H), 6.93 (t, J=7.9, 1H), 6.78 (d, J=7.7, 1H), 6.53 (d, J=7.0, 1H), 5.82–5.70 (m, 1H), 5.46 (d, J=6.6, 1H), 5.23–4.97 (m, 4H), 4.40 (m, 3H), 3.81–3.59 (m, 2H), 2.86–2.67 (m, 2H), 1.81 (s, 3H), 1.50 (s, 3H), 1.35 (s, 3H); HRMS (ESI) m/z calcd for $C_{27}H_{33}N_3O_5S$ Na (M+Na)$^+$ 534.2039, found 534.2062; Anal. Calcd for $C_{27}H_{33}N_3O_5S$: C, 63.38; H, 6.50; N, 8.21. Found: C, 63.68; H, 6.57; N, 8.29.

EXAMPLE A15

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 4-dimethylamino-benzylamide

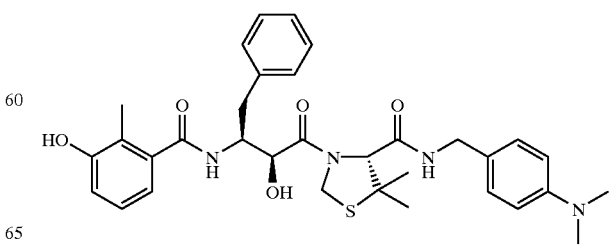

IR (neat cm⁻¹) 3331, 2931, 1643, 1519, 1455, 1349, 1284; ¹H NMR(DMSO-d₆) δ 9.37 (s, 1H), 8.26 (m, 1H), 8.12 (d, J=7.1, 1H), 7.38–6.92 (m, 8H), 6.78 (t, J=7.9, 1H), 6.60 (d, J=8.6, 1H), 6.55 (d, J=7.3, 1H), 6.42 (d, J=8.2, 1H), 5.46 (d, J=6.0, 1H), 5.11 (d, J=9.3, 1H), 5.00 (d, J=9.3, 1H), 4.45 (m, 3H), 4.25 (m, 1H), 4.03 (m, 1H), 2.80 (s, 3H), 2.87–2.73 (m, 2H), 1.82 (s, 3H), 1.48 (s, 3H), 1.32 (s, 3H); HRMS (ESI) m/z calcd for $C_{33}H_{40}N_4O_5SNa$ (M+Na)⁺ 627.2612, found 627.2607.

EXAMPLE A16

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 4-amino-benzylamide

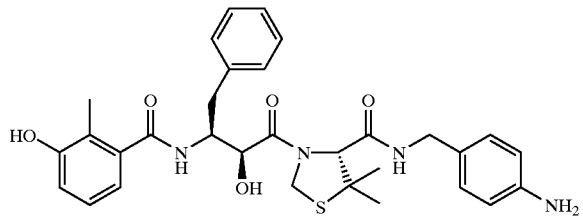

Pale yellow solid: mp=107–109° C.; IR (cm⁻¹) 3378, 2919, 1631, 1518, 1453, 1382, 1281, 1121; ¹H NMR (DMSO-d₆) δ 9.36 (s, 1H), 8.21 (t, J=6.0, 1H), 7.40–7.10 (m, 6H), 8.12 (d, J=8.1, 1H), 6.92 (d, J=8.4, 2H), 6.77 (d, J=7.2, 1H), 6.54 (d, J=7.2, 1H), 6.44 (d, J=8.4, 2H), 5.44 (d, J=6.0, 1H), 5.10 (d, J=9.2, 1H), 4.99 (d, J=9.2, 1H), 4.90 (s, 2H), 4.50–4.32 (m, 3H), 4.22–3.93 (m, 2H), 2.90–2.60 (m, 2H), 1.81 (s, 3H), 1.47 (s, 3H), 1.31 (s, 3H); Anal. Calcd for $C_{31}H_{36}N_4O_5S \cdot 0.25\ H_2O$: C, 64.06; H, 6.33; N. 9.64. Found: C, 64.17; H, 6.38; N, 9.60.

EXAMPLE A17

3-(2-Hydroxy-3-{[1-(3-hydroxy-2-methyl-phenyl)-methanoyl]-amino}-4-phenyl-butanoyl)-5,5-dimethyl-thiazolidine-4-carboxylic Acid prop-2-ynylamide

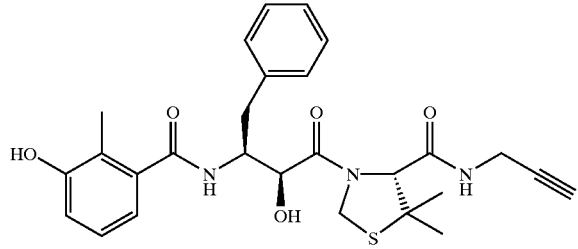

¹H NMR (DMSO-d₆) δ 9.33 (s, 1H), 8.38 (t, J=5.5, 1H), 8.08(d, J=8.3, 1H), 7.35–6.53 (m, 8H), 5.46 (d, J=6.6, 1H), 5.10 (d, J=9.2, 1H), 5.02 (d, J=9.2, 1H), 4.44–4.40 (m, 1H), 4.40 (s, 1H), 3.85 (m, 3H), 3.08 (t, J=2.5, 1H), 2.88–2.68 (m, 2H), 1.82 (s, 3H), 1.51 (s, 3H), 1.37 (s, 3H); Anal. Calcd for $C_{27}H_{31}N_3O_5S$: C, 63.63; H, 6.13; N, 8.24; S, 6.29. Found: C, 63.50; H, 6.33; N, 7.81; S, 5.68.

EXAMPLE A18

3-(2-Hydroxy-3-{[1-(3-hydroxy-2-methyl-phenyl)-methanoylamino}-4-phenyl-butanoyl)]-5,5-dimethyl-thiazolidine-4-carboxylic Acid (2-methylsulfanyl-phenyl)-amide

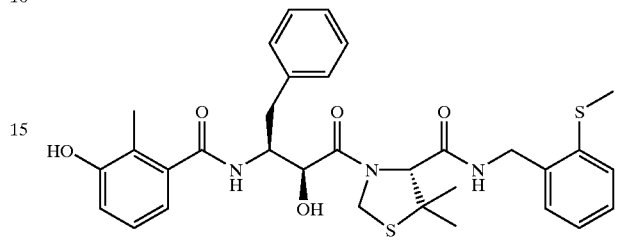

¹H NMR (DMSO-d₆) δ 9.33 (s, 1H), 8.41 (t, J=5.7, 1H), 8.10 (d, J=8.3, 1H), 8.09–6.54 (m, 12H), 5.46 (d, J=6.6, 1H), 5.14 (d, J=9.2, 1H), 5.04 (d, J=9.2, 1H), 4.50–4.02 (m, 4H), 4.50 (s, 1H), 2.89–2.69 (m, 2H), 2.51 (s, 3H), 1.84 (s, 3H), 1.53 (s, 3H), 1.39 (s, 3H); Anal. Calcd for $C_{32}H_{37}N_3O_5S_2$: C, 63.24; H, 6.14; N, 6.91. Found: C, 63.01; H, 6.30; N, 6.53.

EXAMPLE A19

(R)-3-((2S,3S)-2-Hydroxy-3-{[1-(3-hydroxyl-2-methyl-phenyl)-methanoyl]-amino}-4-phenyl-butanoyl)-5,5-dimethyl-thiazolidine-4-carboxylic Acid phenethyl-amide

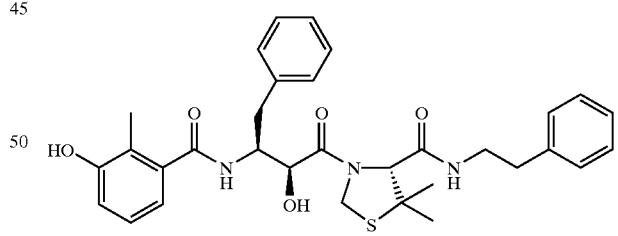

¹H NMR (DMSO-d₆) δ 9.41 (s, 1H), 8.38 (t, J=4.8, 1H), 8.16 (d, J=8.1, 1H), 8.01 (d, J=7.4, 1H), 7.64 (m, 1H), 7.52 (m, 2H), 7.32–7.11 (m, 6H), 6.93 (t, J=7.9, 1H), 6.76 (d, J=7.9, 1H), 6.54 (d, J=7.5, 1H), 5.42 (d, J=6.4, 1H), 5.10 (d, J=9.3, 1H), 5.05 (d, J=9.0, 1H), 4.80–4.32 (m, 5H), 2.84–2.66 (m, 4H), 1.80 (s, 3H), 1.56 (s, 3H), 1.45 (s, 3H); Anal. Calcd for $C_{32}H_{37}N_3O_5S$: C, 66.76; H, 6.48; N, 7.30. Found C, 66.50; H, 6.56; N, 7.23.

EXAMPLE A20

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid ((S)-1-phenyl-ethyl)-amide

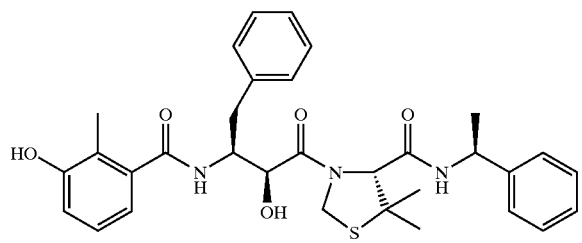

White solid: mp 114–115° C.; IR (neat, cm$^{-1}$) 3306, 2971, 1643, 1531, 1451, 1372, 1284, 1211, 1107; $^1$H NMR (DMSO-d$_6$) δ 9.36 (s, 1H), 8.45 (d, J=8.2, 1H), 8.19 (d, J=8.2, 1H), 77.32–7.18 (m, 10H), 6.96–6.91 (m, 1H), 6.76 (d, J=8.1, 1H), 6.54 (d, J=7.5, 1H), 5.36 (d, J=7.2, 1H), 5.08 (d, J=9.7, 1H), 5.01 (d, J=9.7, 1H), 4.95–4.85 (m, 2H), 4.48 (s, 1H), 4.45–4.30 (m, 1H), 2.80–2.60 (m, 2H), 1.79 (s, 3H), 1.47 (s, 3H), 1.36 (d, J=7.2, 3H), 1.30 (d, J=7.0, 3H); Anal. Calcd for C$_{32}$H$_{37}$N$_3$O$_5$S.0.25 H$_2$O: C, 66.24; H, 6.51; N, 7.24. Found C, 66.30; H, 6.56; N, 6.89.

EXAMPLE A21

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid ((R)-1-phenyl-ethyl)-amide

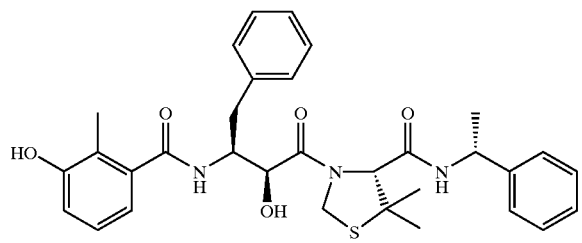

White solid: mp 114–115° C.; IR (neat, cm$^{-1}$) 3299, 1643, 1583, 1520, 1454, 1377, 1284, 1104; $^1$H NMR (DMSO-d$_6$) δ 9.35 (s, 1H), 8.36 (d, J=8.2, 1H), 8.15 (d, J=8.2, 1H), 7.44–7.13 (m, 10H), 6.96–6.91 (m, 1H), 6.75 (d, J=8.1, 1H), 6.52 (d, J=6.7, 1H), 5.38 (d, J=6.9, 1H), 5.15 (d, J=9.7, 1H), 4.99 (d, J=9.7, 1H), 5.28–4.74 (m, 1H), 4.52(s, 1H), 4.49–4.35 (m, 2H), 2.80–2.60 (m, 2H), 1.79 (s, 3H), 1.50 (s, 3H), 1.38 (s, 3H), 1.34 (d, J=7.0, 3H); Anal. Calcd for C$_{32}$H$_{37}$N$_3$O$_5$S.0.25 H$_2$O: C, 66.24; H, 6.51; N, 7.24. Found: C, 66.38; H, 6.52; N, 7.30.

EXAMPLE A22

3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (benzo[1,3]dioxol-5-ylmethyl)-amide

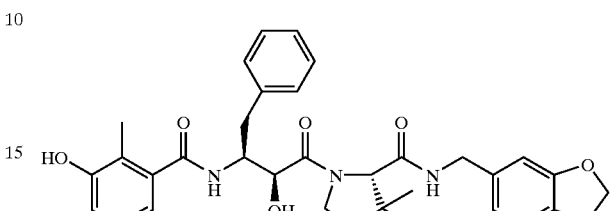

IR (neat or KBr cm$^{-1}$) 3302, 2922, 2351, 2333, 1768, 1750, 1646, 1537; $^1$HNMR (DMSO-d$_6$) δ 9.36 (s, 1H), 8.44 (s, 1H), 8.13 (d, J=7.9 1H), 7.34–7.13 (m, 5H), 6.99–6.77 (m, 4H), 6.78 (d, J=7.7, 1H), 5.93 (d, J=7.1, 2H), 5.15 (d, J=7.0, 1H), 5.08 (d, J=7.8, 1H), 4.43 (d, J=9.32, 2H), 4.34 (m, 2H), 4.12(d, J=6.18, 1H), 4.08 (d, J=6.08, 1H), 2.86–2.67 (m, 2H), 2.55 (s, 1H), 1.81 (s, 3H), 1.51 (s, 3H), 1.39 (s, 3H); Anal. Calcd C$_{32}$H$_{35}$N$_3$O$_7$S.0.65 TFA.1.0 H$_2$O: C, 57.31H, 5.44 N, 6.02. Found: C, 57.58H, 5.47 N, 5.85.

EXAMPLE A23

(R)-3-((2S,3S)-2-Hydroxy-3-{[1-hydroxy-2-methyl-phenyl)-methanoyl]-amino}-4-phenyl-butanoyl)-5,5-dimethyl-thiazolidine-4-carboxylic Acid allyl-methyl-amide

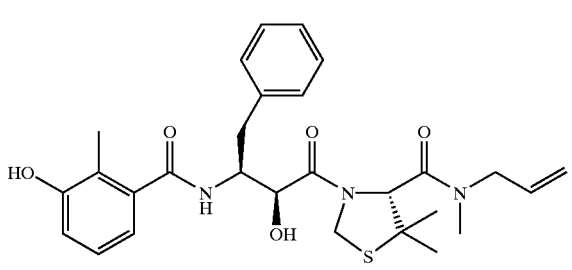

IR (neat, cm$^{-1}$) 3380, 2943, 1637, 1460, 1284, $^1$H NMR (DMSO-d$_6$) δ 9.37 (s, 1H), 8.24 (d, J=8.4, 1H), 7.34–7.15 (m, 5H), 6.94 (t, J=7.5, 1H), 6.77 (d, J=7.7, 1H), 6.53 (d, J=7.5, 1H), 5.99 (m, 1H), 5.70–5.65 (m, 1H), 5.49–5.00 (m, 5H), 4.30–3.85 (m, 4H), 3.08 (s, 3H), 2.78–2.65 (m, 2H), 1.80 (s, 3H), 1.58 (s, 3H), 1.38 (s, 3H); HRMS (ESI) m/z calcd for C$_{28}$H$_{35}$N$_3$O$_5$SNa (M+Na)$^+$ 548.2190, found 548.2178.

EXAMPLE A24

(R)-3-((2S,3S)-2-Hydroxy-3-{[1-hydroxy-2-methyl-phenyl)-methanoyl]-amino}-4-phenyl-butanoyl)-5,5-dimethyl-thiazolidine-4-carboxylic Acid fluoro-trifluoromethyl-benzylamide

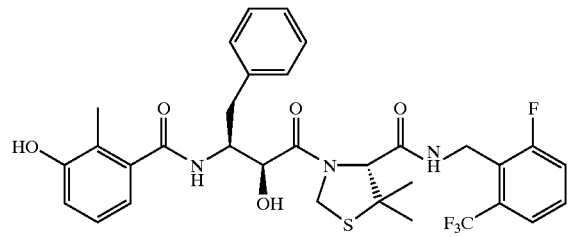

¹H NMR (DMSO-d₆) δ 9.34 (s, 1H), 8.32 (t, J=6.0, 1H, 8.20 (d, J=8.4, 1H), 7.70–7.56 (m,3H), 7.37 (d, J=6.9, 2H), 7.27 (t, J=7.5, 2H), 7.18 (t, J=7.4, 1H), 6.97 (t, J=7.0, 1H), 6.79 (d, J=7.0, 1H), 6.58 (d, J=6.6, 1H), 5.15 (d, J=9.0, 1H), 5.02 (d, J=9.0, 1H), 4.69–4.48 (m, 3H), 4.48–4.32 (m, 2H), 2.88–2.65 (m, 2H), 1.83 (s, 3H), 1.48 (s, 3H), 1.34 (s, 3H); HRMS (ESI) m/z calcd for $C_{32}H_{33}N_3O_5SF_4Na$ (M+Na)⁺ 670.1969, found 670.1999; Anal.1513 Calcd for $C_{32}H_{33}N_3O_5S$ $F_4$.1 $H_2O$, 0.3 TFA: C, 55.94; H, 5.08; N, 6.00. Found: C, 55.74; H, 4.98; N, 5.94.

EXAMPLE A25

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 3-trifluoromethyl-benzylamide

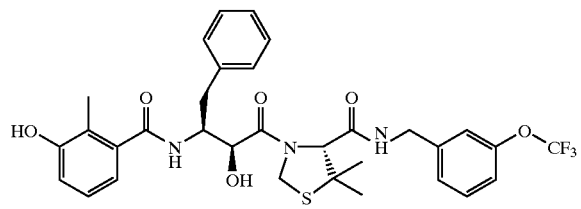

White solid: mp=102–105° C.; IR (cm⁻¹) 3306, 2966, 1644, 1586, 1520, 1216, 1166; ¹H NMR (DMSO-d₆) δ 9.38 (s, 1H), 8.53 (t, J=6.0, 1H), 8.12 (d, J=8.1, 1H), 7.40–7.13 (m, 9H), 6.96–6.91 (m, 1H), 6.77 (d, J=8.2, 1H), 6.54 (d, J=7.7, 1H), 5.48 (d, J=6.4, 1H), 5.13 (d, J=9.2, 1H), 5.00 (d, J=9.2, 1H), 4.46–3.97 (m, 5H), 2.87–2.67 (m, 2H), 1.81 (s, 3H), 1.50 (s, 3H), 1.30 (s, 3H); Anal. Calcd for $C_{32}H_{34}F_3$ $N_3O_6S$.0.25 $H_2O$: C, 59.11; H, 5.35; N, 6.46. Found: C, 58.91; H, 5.40; N, 6.30.

EXAMPLE A26

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 3-ethoxy-benzylamide

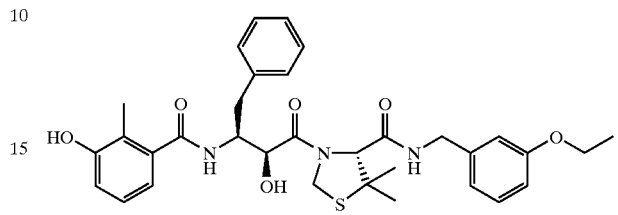

White solid: mp=105–107° C.; IR (cm⁻¹) 3322, 3063, 2978, 1643, 1585, 1538, 1454, 1354, 1265, 1159, 1050; ¹H NMR (DMSO-d₆) δ 9.38 (s, 1H), 8.40 (t, J=5.6, 1H), 8.11 (d, J=8.2, 1H), 7.30–6.70 (m, 11H), 6.53 (d, J=7.5, 1H), 5.48 (d, J=5.9, 1H), 5.11 (d, J=8.9, 1H), 5.00 (d, J=8.9, 1H), 4.50–4.20 (m, 4H), 4.07 (dd, J=15.0, 5.3, 1H), 3.94 (dd, J=14.0, 6.9, 2H), 2.90–2.62 (m, 2H), 1.81 (s, 3H), 1.49 (s, 3H), 1.34 (s, 3H), 1.25 (t, J=6.9, 3H); Anal. Calcd for $C_{33}H_{39}N_3O_6S$.0.75 $H_2O$: C, 64.01; H, 6.59; N, 6.79. Found: C, 63.89; H, 6.27; N, 6.44.

EXAMPLE A27

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid methyl-prop-2-ynyl-amide

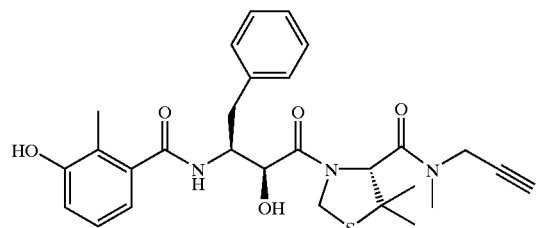

IR (neat, cm⁻¹) 3378, 1643, 1461, 1279, 1108, ¹H NMR (DMSO-d₆) δ 9.37 (s, 1H), 8.21 (d, J=9.2, 1H), 7.33–7.13 (m, 5H), 6.94 (t, J=7.7, 1H), 6.78 (d, J=8.1, 1H), 6.52 (d, J=7.0, 1H), 5.45 (d, J=6.8, 1H), 5.16 (d, J=9.2, 1H), 5.02 (d, J=9.2, 1H), 4.98 (s, 1H), 4.47–4.13 (s, 3H), 4.03–3.92 (m, 1H), 3.17 (s, 3H), 2.88 (s, 1H), 2.79–2.50 (m, 2H), 1.80 (s, 3H), 1.57 (s, 3H), 1.36 (s, 3H); Anal. Calcd for $C_{28}H_{33}N_3O_5S$.0.6$H_2O$: C, 62.95; H, 6.45; N, 7.86. Found: C, 62.95; H, 6.39; N, 7.69.

EXAMPLE A28

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (2-methyl-allyl)-amide

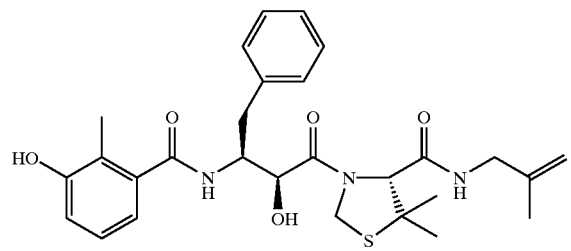

$^1$H NMR (DMSO-d$_6$) δ 9.33, (s, 1H), 8.18–7.79 (m, 2H), 7.39–7.12 (m, 5H), 6.92 (t, J=8.1, 1H), 6.75 (d, J=8.1, 1H), 6.53 (d, J=7.0, 1H), 5.09 (d, J=9.2, 1H), 4.96 (d, J=9.2, 1H), 4.70 (s, 1H), 4.43 (s, 1H), 4.40 (br s, 2H) 3.81–3.49 (m, 4H), 2.85–2.65 (m, 2H), 1.82 (s, 3H), 1.63 (s, 3H), 1.49 (s, 3H), 1.35 (s, 3H); Anal. Calcd for C$_{28}$H$_{35}$N$_3$O$_5$S: C, 63.97; H, 6.71; N, 7.99. Found: C, 63.85; H, 6.92; N, 7.65.

EXAMPLE A29

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 3-amino-benzylamide

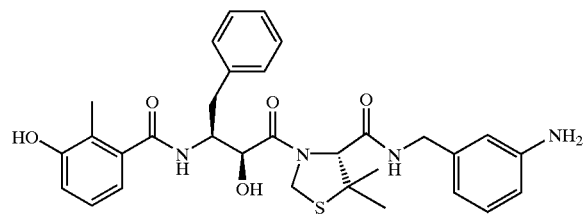

IR (neat, cm$^{-1}$) 3401, 2943, 1643, 1525, 1461, 1373; $^1$H NMR(DMSO-d$_6$) δ 9.36 (s, 1H), 8.28 (t, J=8.0, 1H), 8.12 (d, J=8.9, 1H), 7.33–6.37 (m, 12H), 5.45 (d, J=7.0, 1H), 5.10 (d, J=8.9, 1H), 4.99 (d, J=8.9, 1H), 4.50–4.35 (m, 3H), 4.30–3.90 (m 2H), 2.90–2.70 (m, 2H), 2.06 (s, 2H), 1.81 (s, 3H), 1.48 (s, 3H), 1.33 (s, 3H); Anal. Calcd for C$_{31}$H$_{36}$N$_4$O$_5$S·0.5 H$_2$O: C, 63.57; H, 6.37; N, 9.57. Found: C, 63.59; H, 6.38; N, 9.58.

EXAMPLE A30

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid cyanomethylamide

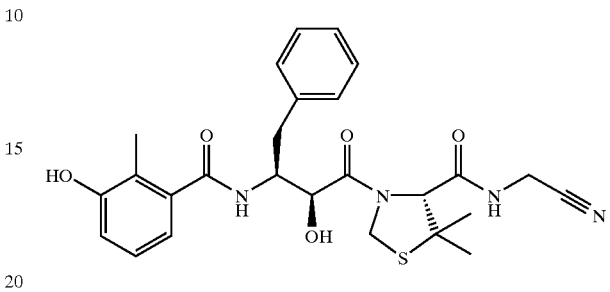

$^1$H NMR (DMSO-d$_6$) δ 9.34 (s, 1H), 8.65 (s, 1H), 8.15 (m, 1H), 7.42–7.19 (m, 5H), 6.94 (t, J=7.9, 1H), 6.81 (d, J=7.9, 1H), 6.62 (d, J=7.9, 1H), 5.22 (d, J=9.7, 1H), 5.05 (d, J=9.7, 1H), 4.61–4.36 (m, 4H), 3.01–2.71 (m, 4H), 1.84 (s, 3H), 1.47 (s, 3H), 1.34 (s, 3H); Anal. Calcd for C$_{26}$H$_{30}$N$_4$O$_5$S: C, 61.16; H, 5.92; N, 10.97. Found: C, 61.24; H, 6.14; N, 10.62.

EXAMPLE A31

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (Z)-but-2-enylamide

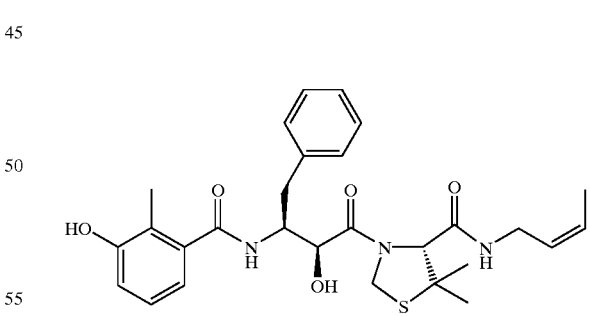

$^1$H NMR (DMSO-d$_6$) δ 9.37 (s, 1H), 8.35 (m, 1H), 8.12 (m, 1H), 7.15–6.98 (m, 6H), 6.77 (d, J=7.7, 1H), 6.68 (d, J=7.5, 1H), 5.60–5.33 (m, 3H), 5.18 (d, J=9.2, 1H), 5.02 (d, J=9.2, 1H), 4.52–4.39 (m, 3H), 3.79–3.68 (m, 2H), 2.92–2.62 (m, 2H), 1.80 (s, 3H), 1.61 (d, J=6.9, 3H), 1.51 (s, 3H), 1.38 (s, 3H); Anal. Calcd for C$_{28}$H$_{35}$N$_3$O$_5$S: C, 63.97; H, 6.71; N, 7.99. Found: C, 63.73; H, 6.75; N, 7.83.

EXAMPLE A32

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (3-methyl-but-2-enyl)-amide

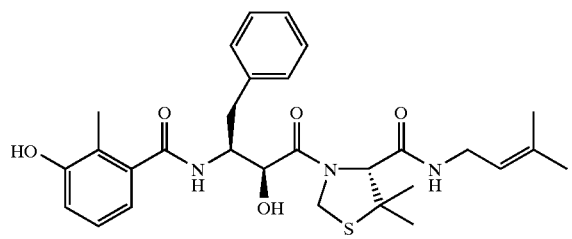

$^1$H NMR (DMSO-d$_6$) δ 9.33 (s, 1H), 8.19 (d, J=8.6, 1H), 7.96 (s br, 1H), 7.39–7.18 (m, 5H), 6.91 (t, J=7.6, 1H), 6.79 (d, J=7.9, 1H), 6.55 (d, J=7.1, 1H), 5.41 (m br, 1H), 5.21 (m, 2H), 5.02 (d, J=9.1, 1H), 4.57–4.37 (m, 3H), 3.79–3.61 (m, 2H), 2.90–2.71 (m, 2H), 1.81 (s, 3H), 1.63 (s, 6H), 1.52 (s, 3H), 1.40 (s, 3H); Anal. Calcd for C$_{29}$H$_{37}$N$_3$O$_5$S: C, 54.54; H, 6.91; N, 7.79. Found: C, 64.75; H, 6.82; N, 7.43.

EXAMPLE A33

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 3-acetylamino-benzylamide

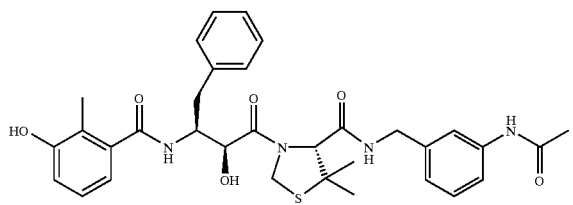

White solid: mp=145–147° C.; IR (neat, cm$^{-1}$) 3378, 2919, 1637, 1514, 1461, 1361; $^1$H NMR (DMSO-d$_6$) δ 9.87 (s, 1H), 9.36 (s, 1H), 8.45–8.40 (m, 1H), 8.12 (d, J=7.9, 1H), 7.49–6.91 (m, 10H), 6.77 (d, J=7.9, 1H), 6.55 (d, J=7.9, 1H), 5.49 (d, J=7.0, 1H), 5.10 (d, J=9.3, 1H), 5.00 (d, J=9.3, 1H), 4.44–3.95 (m, 5H), 2.90–2.62 (m, 2H), 2.00 (s, 3H), 1.80 (s, 3H), 1.48 (s, 3H), 1.32 (s, 3H); Anal. Calcd for C$_{32}$H$_{38}$N$_4$O$_6$S·1.5 H$_2$O: C, 61.38; H, 6.40; N, 8.68. Found: C, 61.49; H, 6.14; N, 8.35.

EXAMPLE A34

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid ((Z)-2-methyl-but-2-enyl)-amide

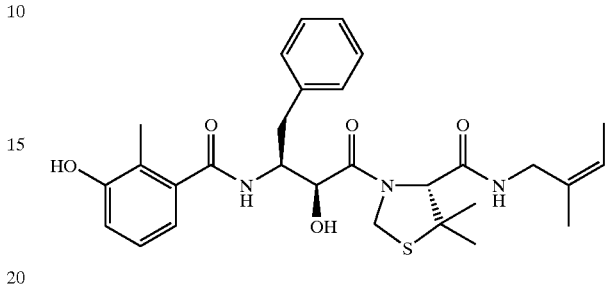

$^1$H NMR (DMSO-d$_6$) δ 9.36 (s, 1H), 8.16 (d, J=8.4, 1H), 8.00 (t, J=5.3, 1H), 7.36–7.13 (m, 5H), 6.94 (t, J=7.7, 1H), 6.77 (d, J=8.1, 1H), 6.53 (d, J=7.3, 1H), 5.37 (d, J=5.7, 1H), 5.24 (m, 1H), 5.12 (d, J=9.0, 1H), 5.00 (d, J=9.0, 1H), 4.48–4.39 (m, 3H), 3.71 (d, J=3.7, 2H), 2.82–2.65 (m, 2H), 1.80 (s, 3H), 1.61 (m, 6H), 1.49 (s, 3H), 1.35 (s, 3H); HRMS (ESI) m/z calcd for C$_{29}$H$_{37}$N$_3$O$_5$SNa (M+Na)$^+$ 562.2346, found 562.2360; Anal. Calcd for C$_{29}$H$_{37}$N$_3$O$_5$S: C, 64.54; H, 6.91; N, 7.79. Found: C, 64.33; H, 6.92; N, 7.60.

EXAMPLE A35

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid ((E)-2-methyl-but-2enyl)-amide

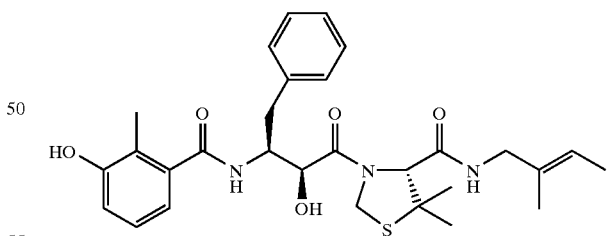

$^1$H NMR (DMSO-d$_6$) δ 9.37(s, 1H), 8.11 (d, J=8.2, 1H), 7.96 (t, J=5.5, 1H), 7.34–7.13 (m, 5H), 6.94 (t, J=7.7, 1H), 6.77 (d, J=8.1, 1H), 6.53 (d, J=7.3, 1H), 5.44 (d, J=6.6, 1H), (d, J=6.6, 1H), 5.10 (d, J=9.0, 1H), 4.98 (d, J=9.1, 1H), 4.47–4.36 (m, 3H), 3.71 (dd, J=14.7, 6.6, 1H), 3.46 (dd, J=14.5, 4.8, 1H), 2.85–2.67 (m, 2H), 1.81 (s, 3H), 1.50 (m, 9H), 1.35 (s, 3H); HRMS (ESI) m/z calcd for C$_{29}$H$_{37}$N$_3$O$_5$SNa (M+Na)$^+$ 562.2346, found 562.2220.

EXAMPLE A36

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (E)-pent-2-enylamide

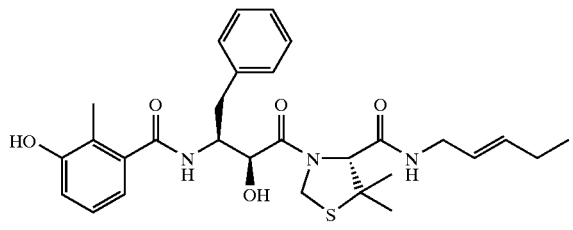

White solid: mp=113–115° C.; IR (neat, cm$^{-1}$) 3315, 2964, 1643, 1584, 1530, 1454, 1371, 1283, 1104, 969; $^1$H NMR (DMSO-d$_6$) δ 9.35 (s, 1H), 8.11 (d, J=8.2, 1H), 8.02 (t, J=5.6, 1H), 7.33–7.13 (m, 5H), 6.96–6.90 (m, 1H), 6.76 (d, J=8.2, 1H), 6.52 (d, J=7.5, 1H), 5.66–5.56 (m, 1H), 5.43(d, J=6.8, 1H), 5.38–5.31 (m, 1H), 5.10 (d, J=8.9, 1H), 4.99 (d, J=8.9, 1H), 4.47–4.39 (m, 2H), 4.38 (s, 1H), 3.72–3.53 (m, 2H), 2.84–2.66 (m, 2H), 1.98–1.83 (m, 2H), 1.80 (s, 3H), 1.48 (s, 3H), 1.34 (s, 3H), 0.87 (t, J=7.3, 3H); Anal. Calcd for C$_{29}$H$_{37}$N$_3$O$_5$S.0 5 H$_2$O: C, 63.48; H, 6.98; N, 7.66. Found: C, 63.30; H, 7.00; N, 7.28.

EXAMPLE A37

(R)-3-((2S,3S)-2-Hydroxy-3-{[1-(3-hydroxyy-2-methyl-phenyl)-methanoyl]-amino}-4-phenyl-butanoyl)-5,5-dimethyl-thiazolidine-4-carboxylic Acid (Z)-pent-2-enylamide

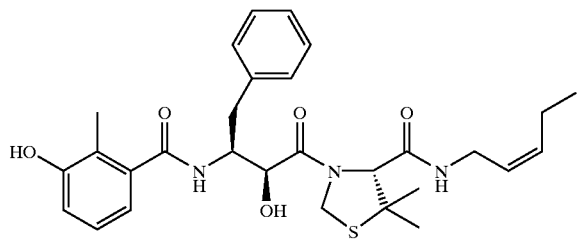

White solid: mp=112–113° C.; IR (neat, cm$^{-1}$) 3320, 2965, 1659, 1643, 1538, 1455, 1372, 1285, 1210, 1105, 1048; $^1$H NMR (DMSO-d$_6$) δ 9.35 (s, 1H), 8.11 (d, J=7.9, 1H), 8.03 (t, J=5.3, 1H), 7.35–7.13 (m, 5H), 6.96–6.90 (m, 1H), 6.76 (d, J=8.1, 1H), 6.53 (d, J=7.3, 1H), 5.42 (d, J=6.7, 1H), 5.37–5.35 (m, 1H), 5.29–5.23 (m, 1H), 5.09 (d, J=9.2, 1H), 4.99 (d, J=9.2, 1H), 4.45–4.38 (m, 2H), 4.36 (s, 1H), 3.80–3.62 (m, 2H), 2.84–2.70 (m, 2H), 2.07–1.97 (m, 2H), 1.80 (s, 3H), 1.48 (s, 3H), 1.34 (s, 3H), 0.90 (t, J=7.5, 3H); Anal. Calcd for C$_{29}$H$_{37}$N$_3$O$_5$S.0 5 H$_2$O: C, 63.48; H, 6.98; N, 7.66. Found: C, 63.60; H, 6.92; N, 7.48.

EXAMPLE A38

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (E)-but-2-enylamide

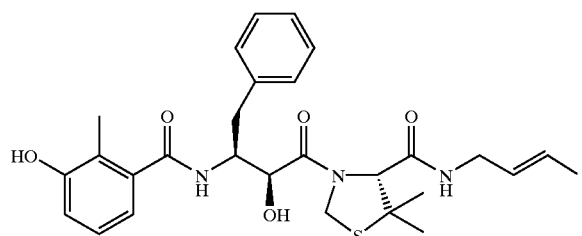

$^1$H NMR (DMSO-d$_6$) δ 9.39 (s, 1H), 8.19 (m br, 1H), 8.03 (m br, 1H), 7.40–7.16 (m, 5H), 6.94 (t, J=7.1, 1H), 6.79 (d, J=7.7, 1H), 6.55 (d, J=7.5, 1H), 5.64–5.31 (m, 3H), 5.19 (d, J=9.2, 1H), 5.02 (d, J=9.2, 1H), 4.55–4.38 (m, 3H), 3.80–3.69 (m, 2H), 2.84–2.7 (m, 2H), 1.80 (s, 3H), 1.61 (s br, 3H), 1.51 (s, 3H), 1.39 (s, 3H); Anal. Calcd for C$_{28}$H$_{35}$N$_3$O$_5$S: C, 63.73; H, 7.07; N, 7.96. Found: C, 63.41; H, 7.23; N, 7.71.

EXAMPLE A39

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 3-dimethylamino-benzylamide

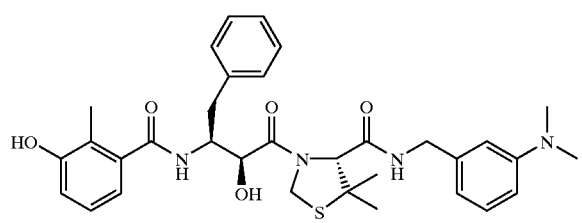

White solid: mp=105–106° C.; IR (neat, cm$^{-1}$) 2219, 2966, 1732, 1644, 1585, 1531, 1494, 1454, 1373, 1264, 1047; $^1$H NMR (DMSO-d$_6$) δ 9.37 (s, 1H), 8.33 (t, J=6.1, 1H), 8.08 (d, J=8.1, 1H), 7.32–6.52 (m, 12H), 5.54 (d, J=6.0, 1H), 5.10 (d, J=9.2, 1H), 4.99 (d, J=9.2, 1H), 4.43–4.31 (m, 4H), 4.03 (dd, J=15.3, 5.3, 1H), 2.84 (s, 6H), 2.84–2.67 (m, 2H), 1.81 (s, 3H), 1.49 (s, 3H), 1.35 (s, 3H). Anal. Calcd for C$_{33}$H$_{40}$N$_4$O$_5$S.0.1 H$_2$O: C, 65.35; H, 6.68; N, 9.24. Found: C, 65.49; H, 6.67; N, 9.30.

EXAMPLE A40

(R)-3-((2S,3S)-2-Hydrozy-3-{[1-(3-hydroxy-2-methyl-phenyl)-methanoyl]-amino}-4-phenyl-butanoyl)-5,5-dimethyl-thiazolidine-4-carboxylic Acid ((E)-4,4,4-trifluoro-but-2-enyl)-amide

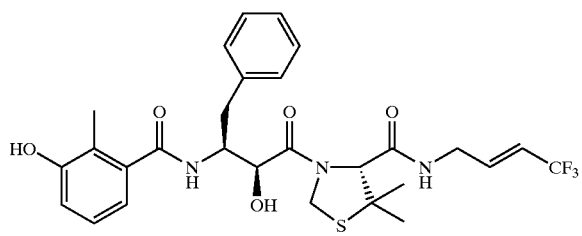

White foam; IR (neat, cm$^{-1}$) 3332, 1661, 1641, 1584, 1531, 1443, 1280, 1119; $^1$H NMR (DMSO-d$_6$) δ 9.36 (s, 1H), 8.32 (t, J=5.6, 1H), 8.15 (d, J=8.4, 1H), 7.35–7.12 (m, 5H), 7.00–6.90 (m, 1H), 6.77 (d, J=7.3, 1H), 6.52 (d, J=7.3, 1H), 6.49–6.40 (m, 1H), 6.08–6.00 (m, 1H), 5.49 (d, J=6.4, 1H), 5.15 (d, J=9.2, 1H), 5.01 (d, J=9.2, 1H), 4.50–4.40 (m, 2H), 4.38 (s, 1H), 4.10–3.90 (m, 1H), 3.80–3.70 (m, 1H), 2.90–2.60 (m, 2H), 1.80 (s, 3H), 1.51 (s, 3H), 1.34 (s, 3H); Anal. Calcd for C$_{28}$H$_{32}$F$_3$N$_3$O$_5$S: C, 58.02; H, 5.56; N, 7.25. Found: C, 58.37; H, 5.70; N, 6.91.

EXAMPLE A41

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (1-cyano-1,1-dimethyl-methyl)-amide

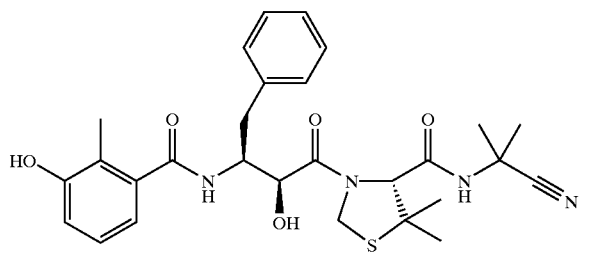

$^1$H NMR (DMSO-d$_6$) δ 9.39 (s, 1H), 8.31–8.12 (m, 2H), 7.38–7.17 (m, 5H), 6.97 (t, J=7.3, 1H), 6.79 (d, J=7.7, 1H), 6.59 (d, J=7.4, 1H), 5.41 (m br, 6H), 5.21 (d, J=9.2, 1H), 5.00 (d, J=9.2, 1H), 4.58–4.35 (m, 3H), 2.85–2.62 (m, 2H), 1.81 (s, 3H), 1.62 (s, 6H), 1.47 (s, 3H), 1.39 (s, 3H); Anal. Calcd for C$_{28}$H$_{34}$N$_4$O$_5$S: C, 62.43; H, 6.36; N, 10.40. Found: C, 62.12; H, 6.55; N, 10.13.

EXAMPLE A42

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 3-hydroxy-benzylamide

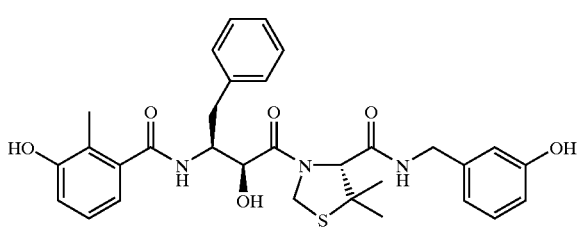

$^1$H NMR (DMSO-d$_6$) δ 9.37 (s, 1H), 9.30 (s, 1H), 8.35 (t, J=5.9, 1H), 8.11 (d, J=8.1, 1H), 7.33–7.15 (m, 5H), 7.04 (t, J=7.7, 1H), 6.94 (t, J=7.9, 1H), 6.77 (d, J=8.1, 1H), 6.70–6.54 (m, 4H), 5.49 (s br, 1H), 5.11 (d, J=9.2, 1H), 5.00 (d, J=9.3, 1H), 4.43 (m, 3H), 4.27 (dd, J=15.2, 6.0, 1H), 4.07 (dd, J=15.0, 5.5, 1H), 2.88–2.67 (m, 2H), 1.82 (s, 3H), 1.49 (s, 3H), 1.33 (s, 3H); Anal. Calcd for C$_{31}$H$_{35}$N$_3$O$_6$S.H$_2$O: C, 62.50; H, 6.26; N, 7.05. Found: C, 62.66; H, 6.19; N, 6.83.

EXAMPLE A43

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 3-propoxy-benzylamide

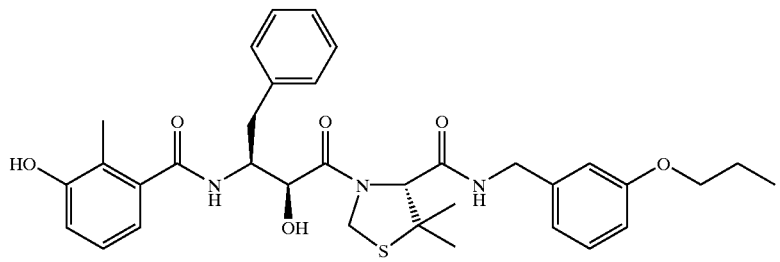

White foam; IR (cm$^{-1}$) 3319, 2966, 1644, 1585, 1531, 1454, 1373, 1264, 1047; $^1$H NMR (DMSO-d$_6$) δ 9.37 (s, 1H), 8.40 (t, J=5.8, 1H), 8.10 (d, J=8.4, 1H), 7.31–6.71 (m, 11H), 6.53 (d, J=7.3, 1H), 5.46 (d, J=6.4, 1H), 5.12 (d, J=9.2, 1H), 5.00 (d, J=9.2, 1H), 4.50–4.20 (m, 4H), 4.11–3.83 (m, 3H), 2.90–2.62 (m, 2H), 1.81 (s, 3H), 1.72–1.60 (m, 2H), 1.49 (s, 3H), 1.34 (s, 3H), 0.92 (t, J=7.3, 3H). Anal. Calcd for $C_{34}H_{41}N_3O_6S \cdot 0.25\ H_2O$: C, 65.42; H, 6.70; N, 6.73. Found: C, 65.49; H, 6.67; N, 6.70.

EXAMPLE A44

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 2-hydroxy-benzylamide

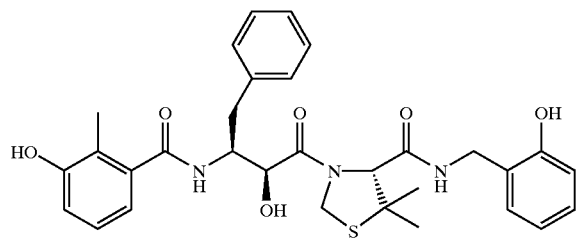

$^1$H NMR (DMSO-$d_6$) δ 9.50 (s, 1H), 9.36 (s, 1H), 8.33 (t, J=5.5, 1H), 8.14 (d, J=8.2, 1H), 7.32–7.12 (m, 6H), 7.04–6.91 (m, 2H), 6.76 (m, 2H), 6.68 (t, J=7.5, 1H), 6.54 (d, J=7.5, 1H), 5.46 (d, J=6.6, 1H), 5.13 (d, J=9.2, 1H), 5.01 (d, J=9.3, 1H), 4.47 (m, 3H), 4.28–4.19 (m, 2H), 2.86–2.67 (m, 2H), 1.82 (s, 3H), 1.49 (s, 3H), 1.32 (s, 3H); HRMS (ESI) m/z calcd for $C_{31}H_{36}N_3O_6S$ (M+H)$^+$ 578.2325, found 578.2325.

EXAMPLE A45

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (3,3,3-trifluoro-propyl)-amide

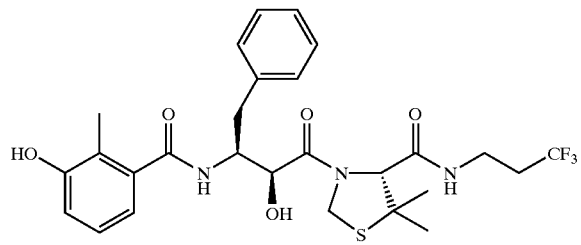

$^1$H NMR (DMSO-$d_6$) δ 9.36 (s, 1H), 8.20 (t, J=5.5, 1H), 8.13 (d, J=8.2, 1H), 7.34–7.13 (m, 5H), 6.93 (t, J=7.7, 1H), 6.76 (d, J=8.1, 1H), 6.08 (d, J=7.5, 1H), 5.44 (d, J=6.8, 1H), 5.10 (d, J=9.2, 1H), 5.05 (d, J=9.2, 1H), 4.48–4.38 (m, 2H), 4.35 (s, 1H), 3.32–3.25 (m, 2H), 2.75–2.70 (m, 2H), 2.44–2.35 (m, 2H), 1.80 (s, 3H), 1.49 (s, 3H), 1.34 (s, 3H); HRMS (ESI) m/z calcd for $C_{27}H_{33}N_3O_5SF_3$ (M+H)$^+$ 568.2093, found 568.2118.

EXAMPLE A46

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid methyl-propyl-amide

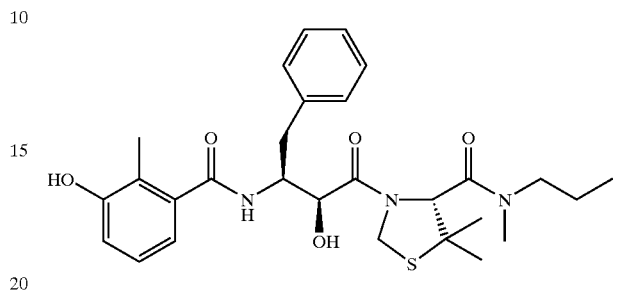

White solid: mp=108–110° C.; IR (cm$^{-1}$) 3325, 2964, 1637, 1522, 1456, 1372, 1284; $^1$H NMR (DMSO-$d_6$) δ 9.35 (s, 1H), 8.22 (d, J=8.6, 1H), 7.34–7.12 (m, 5H), 6.96–6.90 (m, 1H), 6.77–6.75 (m, 1H), 6.53–6.50 (m, 1H), 5.46 (d, J=6.4, 1H), 5.18–4.70 (m, 3H), 4.48–4.20 (m, 2H), 3.31 (s, 3H), 2.90–2.50 (m, 2H), 1.80 (s, 3H), 1.80–1.77 (m, 2H), 1.56 (s, 3H), 1.56–1.36 (m, 2H), 1.37 (s, 3H), 0.79 (t, J=7.5, 3H). Anal. Calcd for $C_{28}H_{37}N_3O_5S \cdot 1.0\ H_2O$: C, 61.63; H, 7.20; N, 7.60. Found: C, 62.03; H, 6.93; N, 7.33.

EXAMPLE A47

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid 4-trifluoromethoxy-benzylamide

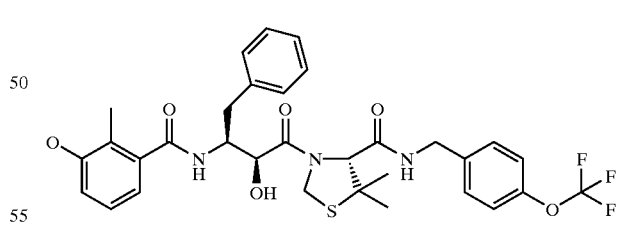

White solid: $^1$H NMR (DMSO) δ 9.37 (s, 1H), 8.51 (t, J=5.9, 1H), 8.13 (d, J=7.3, 1H), 7.39 (d, J=8.6, 1H), 7.32–7.10 (m, 8H), 7.00–6.90 (m, 1H), 6.76 (d, J=8.2, 1H), 6.53 (d, J=7.3, 1H), 5.49 (d, J=6.6, 1H), 5.14 (d, J=9.3, 1H), 5.00 (d, J=9.3, 1H), 4.49–4.37 (m, 4H), 4.17 (dd, J=15.0, 5.7, 1H), 2.90–2.64 (m, 2H), 1.81 (s, 3H), 1.49 (s, 3H), 1.32 (s, 3H), HRMS (ESI) m/z calcd for $C_{32}H_{35}N_3O_6F_3S$ (M+H)$^+$ 646.2199, found 646.2184.

EXAMPLE A48

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (2,2-difluoro-benzo[1,3]dioxol-5-ylmethyl)-amide

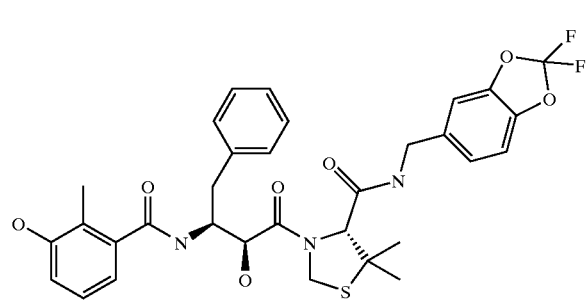

$^1$H NMR (DMSO-$d_6$) δ 9.36 (s, 1H), 8.55 (t, J=5.8, 1H), 8.14 (d, J=8.4, 1H), 7.29–7.11 (m, 8H), 6.94 (t, J=7.8, 1H), 6.77 (d, J=7.9, 1H), 6.54 (d, J=7.4, 1H), 5.58 (d, J=8.2, 1H), 5.17 (d, J=9.2, 1H), 5.02 (d, J=9.2, 1H), 4.49–4.39 (m, 3H), 4.43 (s, 1H), 4.21 (dd, J=5.4, 15.3, 1H), 2.83 (m, 1H), 2.71 (dd, J=13.5, 10.7, 1H), 2.20 (s, 3H), 1.51 (s, 3H), 1.34 (s, 3H); HRMS (ESI) m/z calcd for $C_{32}H_{34}F_2N_3O_7S$ (M+H)$^+$ 642.2086, found 642.2099; Anal. Calcd for $C_{32}H_{33}F_2N_3O_7S$: C, 59.90; H, 5.18; N, 6.55. Found: C, 60.01; H, 5.27; N, 6.29.

EXAMPLE A49

(R)-3-[(2S,3S)-2-Hydroxy-3-(3-hydroxy-2-methyl-benzoylamino)-4-phenyl-butyryl]-5,5-dimethyl-thiazolidine-4-carboxylic Acid (2-chloro-ethyl)-amide

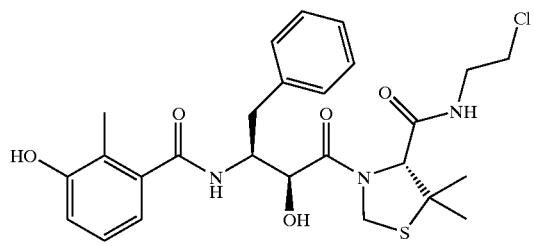

$^1$H NMR (DMSO-$d_6$) δ 9.40 (s, 1H), 8.31 (t, 1H, J=5.5), 8.17 (d, 1H, J=8.4), 7.37–7.16 (m, 5H), 6.96 (t, 1H, J=7.9), 6.79 (d, 1H, J=8.1), 6.55 (d, 1H, J=7.5), 5.47 (d, 1H, J=6.8), 5.11 (d, 1H, J=9.3), 5.03 (d, 1H, J=9.3), 4.50–4.45 (m, 2H), 4.41 (s, 1H), 3.64–3.58 (m, 2H), 3.46–3.34 (m, 2H), 2.86–2.69 (m, 2H), 1.82 (s, 3H), 1.53 (s, 3H), 1.40 (s, 3H), Exact mass calculated for $C_{26}H_{33}N_3O_5SCl$ (M+H)$^+$ 534.1829, found 534.1841.

EXAMPLE A50

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (2-hydroxy-ethyl)-(2-methyl-benzyl)-amide

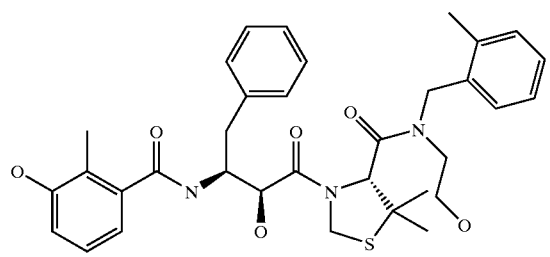

$^1$H NMR (DMSO-$d_6$) δ 9.38 (s, 1H), 8.29 (d, J=8.4, 1H), 7.42–6.87 (m, 10H), 6.78 (d, J=7.1, 1H), 6.55 (d, J=6.8, 1H), 5.44 (d, J=6.8, 1H), 5.26 (d, J=10.0, 1H), 5.08 (s, 1H), 5.04 (d, J=9.2, 1H), 4.82–4.67 (m, 2H), 4.55–4.24 (m, 3H), 3.67 (m, 2H), 3.47 (m, 2H), 2.78 (m, 2H), 2.24 (s, 3H), 1.82 (s, 3H), 1.61 (s, 3H), 1.45 (s, 3H); HRMS (ESI) m/z calcd for $C_{34}H_{42}N_3O_6S$ (M+H)$^+$ 620.2794, found 620.2798; Anal. Calcd for $C_{34}H_{41}N_3O_6S \cdot 1\ H_2O$: C, 64.03; H, 6.80; N, 6.59. Found: C, 63.66; H, 6.40; N, 6.59.

EXAMPLE A51

3-[2-Hydroxy-3-(3-hydroxy-2-methyl-benzoylamino)-4-phenyl-butyryl]-5,5-dimethyl-thiiazolidine-4-carboxylic Acid methyl-(2-ethyl-benzyl)-amide

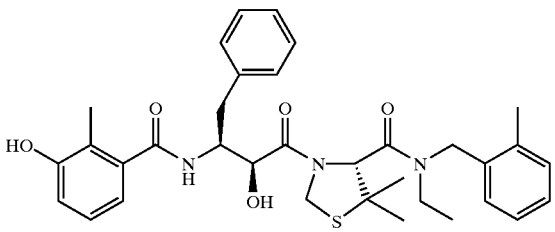

White solid: $^1$H NMR (DMSO-$d_6$) δ 9.40 (s, 1H), 8.45 (t, J=7.99, 1H), 8.10 (d, J=8.1, 1H), 7.41–6.91 (m, 12H), 6.62 (d, J=7.8, 1H), 5.41 (d, J=6.8, 1H), 5.12 (dd, J=8.1, 7.8, 1H), 4.44–4.35 (m, 3H), 4.42 (s, 1H), 2.91–2.67 (m, 2H), 2.54–2.21 (q, J=6.89, 2H), 2.1 (s, 3H), 1.88 (s, 3H), 1.56 (t, J=6.90, 3H), 1.49 (s, 3H), 1.34 (s, 3H); Anal. ($C_{34}H_{41}N_2O_5S \cdot 0.75\ H_2O$) calculated C (62.34), H (6.43), N (6.23), found C (62.72), H (6.52), N (5.97). HRMS (ESI) m/z calcd for 604.2845, found 604.2845.

EXAMPLE A52

3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic Acid (2-methylamino-ethyl)-amide

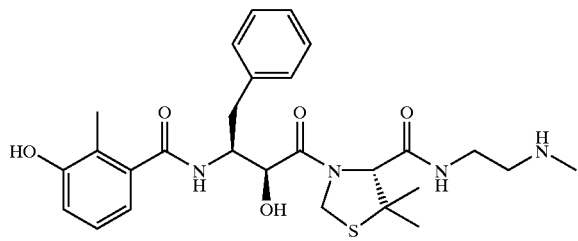

White solid: $^1$H NMR (DMSO-$d_6$) δ 9.40 (s, 1H), 8.45–8.01 (m, 1H), 7.41–7.13 (m, 12H), 6.98 (t, J=7.8, 1H), 6.78 (d, J—6.85, 1H), 6.55 (d, J=6.99, 1H), 5.41 (m, 1H), 5.12–4.98 (m, 2H), 4.44–4.35 (m, 2H), 3.15 (m, 2H), 2.91–2.67 (m, 2H), 1.84 (s, 3H), 1.66 (q, J=8.2, 4H), 1.34 (s, 3H); Anal. ($C_{27}H_{36}N_4O_5S \cdot 0.50\ H_2O$) calculated C (60.31), H (6.94), N (10.42), found C (60.59), H (6.50), N (8.08). HRMS (ESI) m/z calcd for 556.2771, found 556.2770.

General Method B

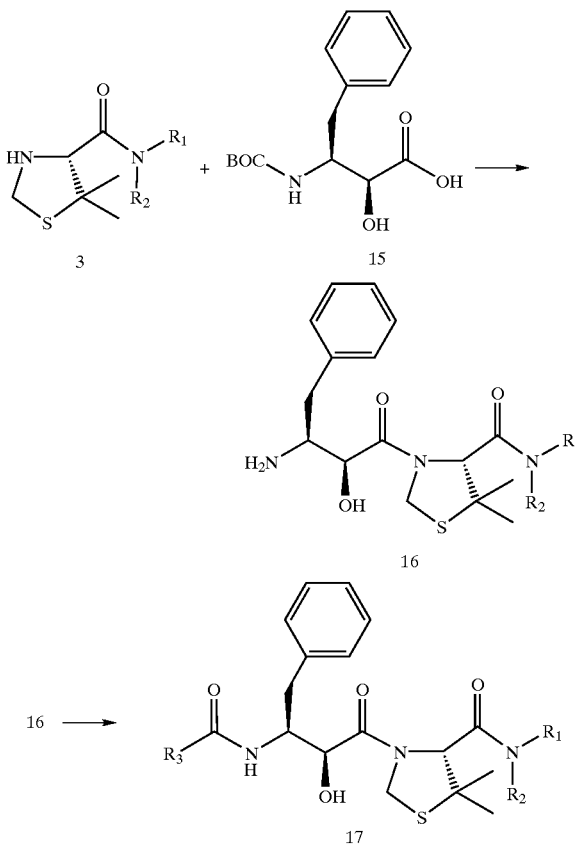

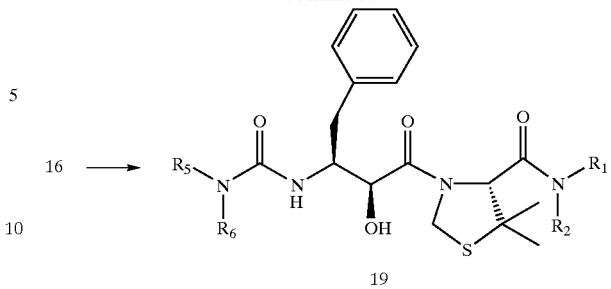

Amides of the general structure 3 (synthesized in the same manor as in the Methods A section) are coupled to boc-protected acid 15, and exposed to methane sulfonic acid to yield amines 16. Subjecting amines 16 to the reaction conditions depicted yielded a series of amides 17 and ureas 19.

Synthesis of amines of the general type 16.

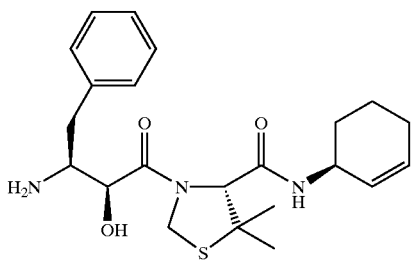

16a

The title compound was prepared as follows. (R)-5,5-Dimethyl-thiazolidine-3,4-dicarboxylic acid 3-tert-butyl ester 1 (1.95 g, 7.47 mmol) was dissolved in EtOAc (25 mL) and cooled to 0° C. Diphenyl chlorophosphate (1.71 mL, 8.23 mmol) was added followed by TEA (1.14 mL, 8.23 mmol). The reaction was stirred at 0° C. for 1 h, and treated with (S)-Cyclohex-2-enylamine (0.8 g, 8.23 mmol). The reaction mixture was stirred at room temperature overnight, then partitioned between 1N HCl (25 mL) and EtOAc (30 mL). The organic layer was washed with saturated NaHCO$_3$, brine, dried over Na$_2$SO$_4$ and concentrated to a yellow oil. The resulting oil (2.54 g, 7.47 mmol) was dissolved in EtOAc (30 mL) and then cooled to 0° C. Methanesulfonic acid (2.27 mL, 33.62 mmol) was added and the solution was stirred at 0° C. for 15 minutes, then at room temperature for 4 h. The mixture was re-cooled to 0° C. and quenched with 10% Na$_2$CO$_3$ (30 mL) then extracted with EtOAc (30 mL). Organic layer was washed with brine, dried over Na$_2$SO$_4$ and concentrated in vacuo to give a yellow oil 3. The resulting yellow oil (1.86 g, 7.74 mmol) was dissolved in EtOAc (77 mL). BOC-AHPBA 4 (2.29 g, 7.74 mmol) was added followed by HOBt (1.05 g, 7.74 mmol). The mixture was stirred at room temperature 1 h, then cooled to 0° C. DCC (1.60 g, 7.74 mmol) was slowly added as solution in EtOAc (30 mL). The mixture was allowed to gradually warm to room temperature and stirred overnight. The mixture was filtered and the filtrate was washed with 1N HCl (40 mL), saturated NaHCO$_3$ (40 mL), brine (40 mL), dried over Na$_2$SO$_4$ and concentrated to give a crude white solid (contaminated with DCU). The DCU was removed by flash chromatography (30% to 50% EtOAc in hexanes) to provide a white solid (4 g, 7.73 mmol), which was dissolved in EtOAc (30 mL) and then cooled to 0° C. Methanesulfonic acid (2.35 mL, 34.76 mmol) was added and the solution was stirred at 0° C. for 15 minutes, then at room temperature for 3 h. The mixture was re-cooled to 0° C. and quenched with 10% $Na_2CO_3$ (35 mL) then extracted with EtOAc (30 mL). Organic layer was washed with brine, dried over $Na_2SO_4$ and concentrated in vacuo to give a material which was recrystalized from 60% EtOAc in hexanes to provide the titled compound (2.41 g, 80%) as a white solid. $^1$H NMR (DMSO-$d_6$) δ 8.21 (d, J=8.1, 1H), 7.31–7.17 (m, 5H), 5.80 (d, J=5.6, 1H), 5.52–5.48 (m, 2H), 5.30–5.25 (m, 2H), 4.89 (s, 2H), 4.26 (s, 1H), 4.21–4.00 (m, 3H), 3.15–2.70 (m, 2H), 2.50–2.00 (m, 2H), 2.00–1.00 (m, 4H), 1.49 (s, 3H), 1.31 (s, 3H); Anal. Calcd for $C_{22}H_{31}N_3O_3S$: C, 63.28; H, 7.48; N, 10.06. Found: C, 63.40; H. 7.20; N, 9.98.

The following amines a-h were prepared by the specific method outlined above using the requisite amine.

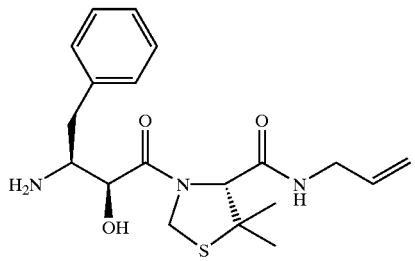

16a $^1$H NMR (DMSO-$d_6$) δ 8.36 (t, J=6.0, 1H), 7.36–7.14 (m, 5H), 5.70 (m, 1H), 5.34 (s, br, 1H), 5.12 (d, J=17.0, 1H), 4.96–4.88 (m, 3H), 4.34 (s, 1H), 4.10 (d, J=7.0, 1H), 3.80–3.55 (m, 2H), 3.06 (d, J=13.0, 1H), 2.87 (t, J=9.0, 1H), 2.38 (dd, J=13.0, 10.0, 1H), 1.52 (s, 3H), 1.33 (s, 3H).

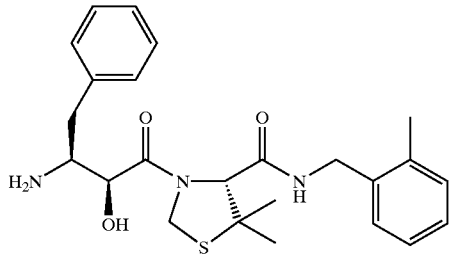

16b

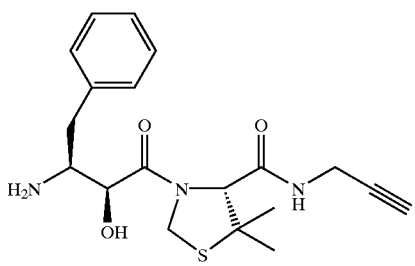

16c $^1$H NMR (DMSO-$d_6$) δ 8.69 (t, J=5.3, 1H), 7.34–7.14 (m, 5H), 5.34 (s br, 1H), 4.90 (s, 2H), 4.29 (s, 1H), 4.08 (d, J=7.0, 1H), 3.90–3.70 (m, 2H), 3.07 (dd, J=13.4, 2.5, 1H), 2.96 (t, J=2.6, 1H), 2.88, (ddd, J=9.8, 8.0, 2.8, 1H), 2.37 (dd, J=13.2, 9.9, 1H), 1.50 (s, 3H), 1.32 (s, 3H).

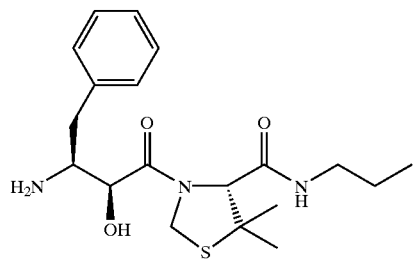

16d $^1$H NMR (DMSO-$d_6$) δ 8.13 (t, J=5.4, 1H), 7.35–7.15 (m, 5H), 5.28 (d, J=8.1, 1H), 4.79 (m, 2H), 4.27 (s, 1H), 4.07 (t, J=7.1, 1H), 3.10–2.71 (m, 4H), 2.37 (dd, J=13.2, 9.9, 1H), 1.49 (s, 3H), 1.34 (m, 2H), 1.33 (s, 3H), 0.77 (t, J=7.4, 3H).

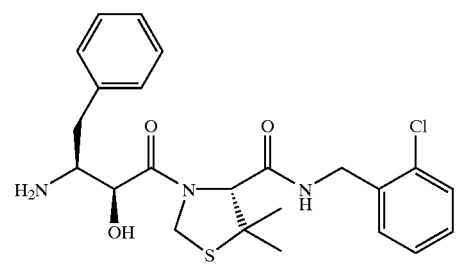

16e

Isolated yield: 84%; MS (APCI, m/z): 461, 463 (M+H)

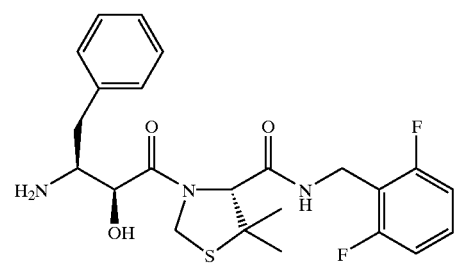

16f

Isolated yield: 93%; MS (APCI, m/z): 464 (M+H).

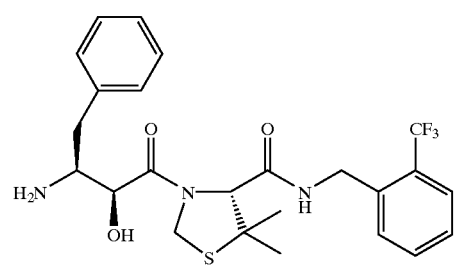

16g

Isolated yield: 86%; MS (APCI, m/z): 496 (M+H).

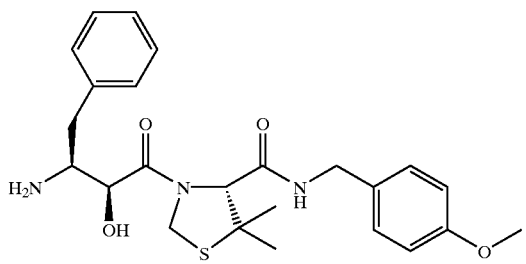

16h

Isolated yield: 87%. MS-APCI (m/z+): 458.

Synthesis of Final Products of the General Type 17 from 16a–h, General Methods:

Amide formation—To a solution of acid, amine 16 and HOBT in CH$_2$Cl$_2$ was added EDC and the solution stirred overnight at room temperature. The solution was concentrated in vacuo and the residue dissolved in ethyl acetate and a small portion of water. The solution was washed with saturated NH$_4$Cl or 0.5N HCl (2×), saturated NaHCO$_3$ (2×), brine (1×), dried with MgSO$_4$ and concentrated in vacuo. The resulting residue subjected to flash silica gel chromatography or preparative HPLC to afford the desired product.

Urea formation #1—The corresponding amine and isocyanate (1.1–1.2 eq.) were taken in dichloromethane and stirred at room temperature under nitrogen. (1.5 hr to overnight). The solvent was then removed in vacuo and the resulting residue subjected to flash silica gel chromatography or preparative HPLC to afford the desired product.

Urea formation #2—The corresponding amine was dissolved in CH$_2$Cl$_2$ and treated with diisopropylethylamine (1.5 eq.) and phosgene (1 eq., 20% soln. in toluene) at −78° C. The resulting solution was warmed to room temperature and treated with the amine of general structure 16. The resulting residue subjected to flash silica gel chromatography or preparative HPLC to afford the desired product.

Specific Urea Synthesis

EXAMPLE B1

3-(2-Hydroxy-3-{[1-(3-hydroxy-pyrrolidin-yl)-methanoyl]-amino}-4-phenyl-butanoyl)-5,5-dimethyl-thiazolidine-4-carboxylic acid-2-methyl-benzylamide

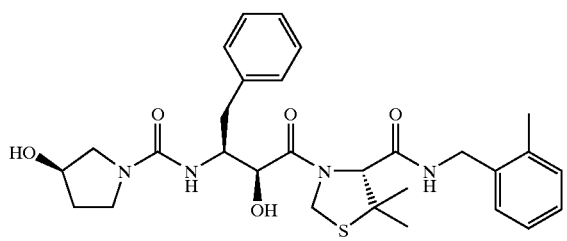

(R)-Pyrrolidin-3-ol (0.21 g, 2.40 mmol) was dissolved in dry CH$_2$Cl$_2$ (15 mL) and cooled to −78° C. under argon with magnetic stirring. To this solution was added Diisopropylethylamine (0.63 mL, 3.63 mmol) followed by Phosgene as a 20% solution in toluene (1.2 mL, 2.40 mmol). The resulting yellow solution was stirred for 20 min at −78° C. then allowed to warm to room temperature. The solution was concentrated and re-dissolved in dry CH$_2$Cl$_2$ (5 mL) and THF (5 mL). To this was added Diisopropylethylamine (0.31 mL, 1.81 mmol) followed by 16c. The result was stirred for 16 h at 23° C. then diluted with EtOAc (50 mL). The mixture was washed sequentially with 10% citric acid (1×50 mL), saturated NaHCO$_3$ (1×50 mL), H$_2$O (1×50 mL). The organics were dried over Na$_2$SO$_4$, filtered, and concentrated. The residue was purified by flash column chromatography (5% MeOH in EtOAc) to yield the title compound (0.12 g, 18%) as a white foam.

$^1$H NMR (DMSO-d$_6$) δ 8.38 (t, J=5.7, 1H), 7.34–7.09 (m, 10H), 5.99 (d, J=8.3, 1H), 5.04 (d, J=9.5, 1H), 4.96 (d, J=9.5, 1H), 4.49 (s, 1H), 4.48–4.38 (m, 3H), 4.22–3.83 (m, 4H), 3.29–3.04 (m, 3H), 2.77–2.70 (m, 2H), 2.28 (s, 3H), 1.52 (s, 3H), 1.32 (s, 3H), 1.82–1.69 (m, 2H); HRMS (ESI) m/z calcd for C$_{29}$H$_{38}$N$_4$O$_5$SNa (M+Na)$^+$ 577.2455, found 577.2440; Anal. Calcd for C$_{29}$H$_{38}$N$_4$O$_5$S.2H$_2$O: C, 58.96; H, 7.17; N, 9.48; S, 5.43. Found: C, 58.90; H, 6.40; N, 9.23; S, 5.24.

The following examples were prepared by the corresponding specific method outlined above using the requisite P2 fragment.

EXAMPLE B2

Isoxazole-5-carboxylic Acid {(1S,2S)-1-benzyl-3-[(R)-5,5-dimethyl-4-(2-methyl-benzylcarbamoyl)-thizolidin-3-yl]-2-hydroxy-3-oxo-propyl}-amide

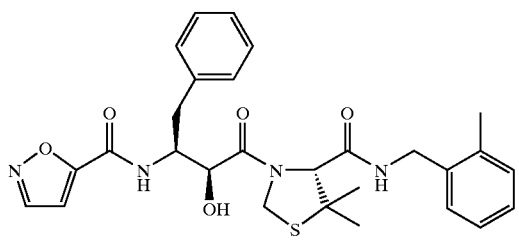

White solid: mp 82–84° C.; IR (neat, cm$^{-1}$) 3313, 2967, 1656, 1538, 1454, 1372, 1283, 1211, 1108, 916; $^1$H NMR (DMSO-d$_6$) 68.91 (d, J=8.6, 1H), 8.67 (d, J−2.0, 1H), 8.35 (t, J=5.0, 1H), 7.31–7.08 (m, 9H), 7.03 (d, J=2.0, 1H), 5.63 (d, J=6.9, 1H), 5.02 (d, J=8.6, 1H), 4.97 (d, J=8.6, 1H), 4.60–4.30 (m, 4H), 4.14–4.00 (m, 1H), 2.90–2.75 (m, 2H), 2.23 (s, 3H), 1.49 (s, 3H), 1.28 (s, 3H); HRMS (ESI) m/z calcd for C$_{28}$H$_{32}$N$_4$O$_5$SNa (M+Na)$^+$ 559.1986, found 559.1994; Anal. Calcd for C$_{28}$H$_{32}$N$_4$O$_5$S.0.5H$_2$O: C, 61.63; H, 6.10; N, 10.27. Found: C, 61.40; H, 5.91; N, 9.97.

EXAMPLE B3

Isoxazole-3-carboxylic Acid {(1S,2S)-1-benzyl-3-[(R)-5,5-dimethyl-4-(2-methyl-benzylcarbamoyl)-thizolidin-3-yl]-2-hydroxy-3-oxo-propyl}-amide

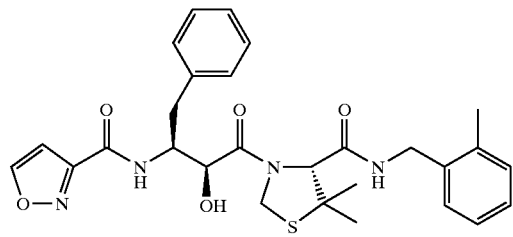

White solid; IR (neat, cm$^{-1}$) 3436, 1643, 1537,1425, 1378; $^1$H NMR (DMSO-d$_6$) δ 9.03 (s, 1H), 8.66 (d, J=8.7, 1H), 8.32 (t, J=5.3, 1H), 7.30–7.11 (m, 9H), 6.79 (s, 1H), 5.67 (d, J=6.8, 1H), 4.97 (s, 2H), 4.47–4.32 (m, 4H), 4.09 (dd, J=15.0, 5.0, 1H), 2.84 (m, 2H), 2.24 (s, 3H), 1.49 (s, 3H), 1.34 (m, 3H); HRMS (ESI) m/z calcd for C$_{28}$H$_{32}$N$_{4}$O$_{5}$SNa (M+Na)$^{+}$ 559.1986, found 559.1980.

EXAMPLE B4

5-Chloro-isoxazole-3-carboxylic Acid {(1S,2S)-1-benzyl-3-[(R)-5,5-dimethyl-4-(2-methyl-benzylcarbamoyl)-thiazolidin-3-yl]-2-hydroxy-3-oxo-propyl}-amide

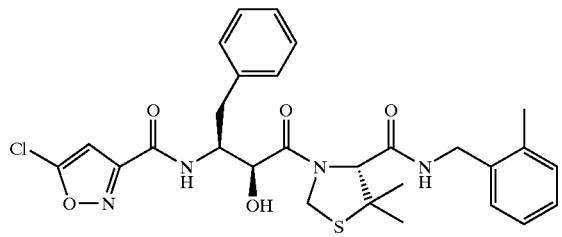

White solid; IR (neat, cm$^{-1}$) 3320, 2969, 1657, 1547, 1434, 1372, 1266; $^{1}$H NMR (DMSO-d$_{6}$) δ 8.74 (d, J=8.2, 1H), 8.29 (t, J=5.5, 1H), 7.28–7.08 (m, 9H), 6.90 (s, 1H), 5.72 (d, J=7.1, 1H), 4.96 (s, 2H), 4.44 (m, 3H), 4.32 (dd, J=15.2, 6.0, 1H), 4.09 (dd, J=15.2, 4.6, 1H), 2.85 (m, 2H), 2.83 (s, 3H), 1.49 (s, 3H), 1.33 (s, 3H); HRMS (ESI) m/z calcd for C$_{28}$H$_{31}$N$_{4}$O$_{5}$SClNa (M+Na)$^{+}$ 593.1596, found 593.1569.

EXAMPLE B5

(R)-3-{(2S,3S)-2-Hydroxy-4-phenyl-3-[(1-thiophen-2-yl-methanoyl)-amino]-butanoyl}-5,5,-dimethyl-thiazolidine-4-carboxylic Acid 2-methyl-benzylamide

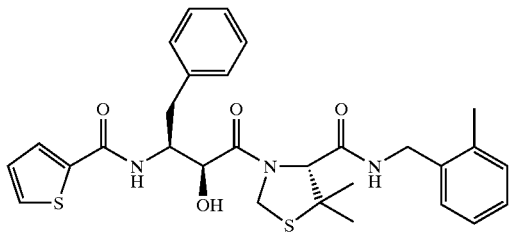

White solid: mp=98–101° C.; IR (neat, cm$^{-1}$) 3416, 1644, 1538, 1455, 1372, 1291, 1107; $^{1}$H NMR (DMSO-d$_{6}$) δ 8.56 (d, J=8.0, 1H), 8.38 (t, J=4.8, 1H), 7.85 (d, J=3.5, 1H), 7.69 (d, J=4.8, 1H), 7.36–7.08 (m, 10OH), 5.38 (d, J=7.2, 1H), 5.10 (d, J=8.8, 1H), 4.98 (d, J=8.8, 1H), 4.54–4.20 (m, 5H), 2.90–2.70 (m, 2H), 2.25 (s, 3H), 1.49 (s, 3H), 1.34 (s, 3H); HRMS (ESI) m/z calcd for C$_{29}$H$_{33}$N$_{3}$O$_{4}$S$_{2}$Na (M+Na)$^{+}$ 574.1805, found 574.1818; Anal. Calcd for C$_{29}$H$_{33}$N$_{3}$O$_{4}$S$_{2}$.0.75H$_{2}$O: C, 61.62; H, 6.15; N, 7.43. Found: C, 61.31; H, 5.97; N, 7.28.

EXAMPLE B6

(R)-3-{(2S,3S)-2-Hydroxy-4-phenyl-3-[(1-thiophen-3-yl-methanoyl)-amino]-butanoyl}-5,5,-dimethyl-thiazolidine-4-carboxylic Acid 2-methyl-benzylamide

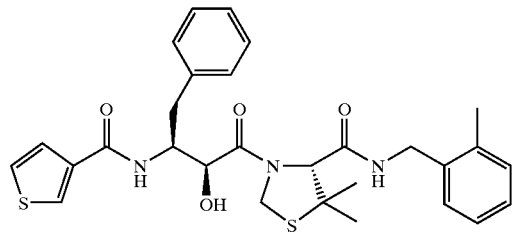

White solid: mp=98–100° C.; IR (neat, cm$^{-1}$) 3312, 3086, 2966, 1644, 1538, 1455, 1372, 1286, 1109; $^{1}$H NMR (DMSO-d$_{6}$) δ 8.42–8.34 (m, 2H), 8.14 (m, 1H), 7.54–7.06 (m, 11H), 5.74 (d, J=9.3, 1H), 5.35 (d, J=6.8, 1H), 4.99 (d, J=9.3, 1H), 4.53 (d, J=3.0, 1H), 4.50 (s, 1H), 4.42 (dd, J=15.0, 7.0, 1H), 4.40–4.30 (m, 1H), 4.15 (dd, J=15.0, 5.0, 1H), 2.90–2.70 (m, 2H), 2.26 (s, 3H), 1.50 (s, 3H), 1.35 (s, 3H); HRMS (ESI) m/z calcd for C$_{29}$H$_{33}$N$_{3}$O$_{4}$S$_{2}$Na (M+Na)$^{+}$ 574.1805, found 574.1789; Anal. Calcd for C$_{29}$H$_{33}$N$_{3}$O$_{4}$S$_{2}$.1H$_{2}$O: C, 61.14; H, 6.19; N, 7.38. Found: C, 60.74; H, 5.90; N, 7.15.

EXAMPLE B7

(R)-3-{(2S,3S)-2-Hydroxy-4-phenyl-3-[(((S)-1-tetrahydro-furan-2-yl-methanoyl)-amino]-butanoyl}-5,5,-dimethyl-thiazolidine-4-carboxylic Acid 2-methyl-benzylamide

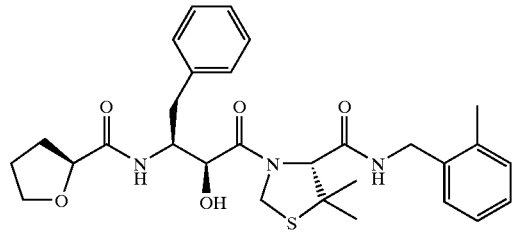

White solid: mp=82–84° C.; IR (neat, cm$^{-1}$) 3314, 2969, 1651, 1531, 1456, 1372, 1109, 1071; $^{1}$H NMR (DMSO-d$_{6}$) δ 8.35 (t, J=6.0, 1H), 7.60 (d, J=9.2, 1H), 7.31–7.09 (m, 9H), 5.45 (d, J=6.8, 1H), 4.97 (d, J=9.5, 1H), 4.93 (d, J=9.5, 1H), 4.46 (s, 1H), 4.41–4.07 (m, 4H), 3.77–3.65 (m, 3H), 2.78–2.64 (m, 2H), 2.26 (s, 3H), 2.00–1.80 (m, 1H), 1.60 (m, 1H), 1.49 (s, 3H), 1.44–1.38 (m, 2H), 1.34 (s, 3H); HRMS (ESI) m/z calcd for C$_{29}$H$_{37}$N$_{3}$O$_{5}$SNa (M+Na)$^{+}$ 562.2346, found 562.2345; Anal. Calcd for C$_{29}$H$_{37}$N$_{3}$O$_{5}$S.0.5 H$_{2}$O: C, 63.48; H, 6.98; N, 7.66. Found: C, 63.61; H, 6.85; N, 7.58.

EXAMPLE B8

3-(2-hydroxy-3-{[1-(3-hydroxy-pyrrolidin-yl)-methanoyl]-amino}-4-phenyl-butanoyl)-5,5,-dimethyl-thiazolidine-4-carboxylic acid-2-methyl-benzylamide

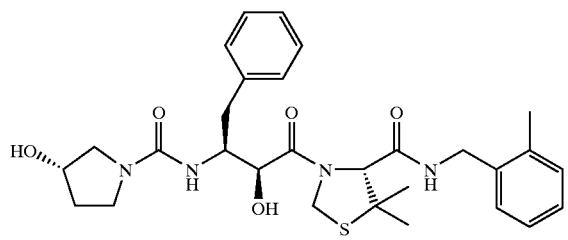

$^1$H NMR (DMSO-d$_6$) δ 8.38 (t, J=5.5, 1H), 7.34–7.09 (m, 10H), 5.99 (d, J=8.2, 1H), 5.04 (d, J=9.5, 1H), 4.96 (d, J=9.5, 1H), 4.49 (s, 1H),. 4.48–4.38 (m, 3H), 4.35–4.16 (m, 3H), 4.00 (m, 1H), 3.29–3.04 (m, 3H), 2.78–2.70 (m, 2H), 2.28 (s, 3H), 1.83–1.65 (m, 2H), 1.52 (s, 3H), 1.36 (s, 3H); HRMS (ESI) m/z calcd for C$_{29}$H$_{38}$N$_4$O$_5$SNa (M+Na)$^+$ 577.2455, found 577.2473; Anal. Calcd for C$_{29}$H$_{38}$N$_4$O$_5$S.2H$_2$O: C, 58.96; N, 9.48. Found: C, 58.68; N, 9.11.

EXAMPLE B9

(R)-3-{(2S,3S)-2-Hydroxy-4-phenyl-3-[(((S)-1-tetrahydro-furan-2-yl-methanoyl)-amino]-butanoyl}-5,5,-dimethyl-thiazolidine-4-carboxylic Acid 2-methyl-benzylamide

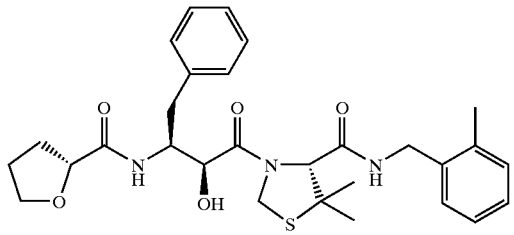

White solid; IR (neat, cm$^{-1}$) 3324, 2959, 2873, 1724, 1651, 1526, 1455, 1372, 1289, 1073; $^1$H NMR (DMSO-d$_6$) δ 8.35 (t, J=4.9, 1H), 7.77 (d, J=8.9, 1H), 7.52–7.09 (m, 9H), 5.51 (d, J=6.6, 1H), 4.97–4.89 (m, 2H), 4.52–3.66 (m, 8H), 2.90–2.60 (m, 2H), 2.25 (s, 3H), 1.99–1.63 (m, 4H), 1.48 (s, 3H), 1.33 (s, 3H); HRMS (ESI) m/z calcd for C$_{29}$H$_{37}$N$_3$O$_5$SNa (M+Na)$^+$ 562.2346, found 562.2366. Anal. Calcd for C$_{29}$H$_{37}$N$_3$O$_5$S.0.25 H$_2$O: C, 64.01; H, 6.95; N, 7.72. Found: C, 64.20; H, 6.90; N, 7.82.

EXAMPLE B10

3,5-Dimethyl-isoxazole-4-carboxylic Acid {(1S,2S)-1-benzyl-3-[(R)-5,5-dimethyl-4-(2-methyl-benzylcarbamoyl)-thiazolidin-3-yl]-2-hydroxy-3-oxo-propyl}-amide

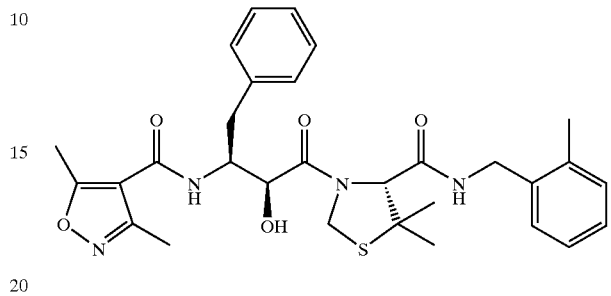

Isolated yield: 92%; $^1$H-NMR (400 MHz, dmso-d$_6$): δ 8.38 (t, 1H), 8.13 (d, 1H), 7.04–7.35 (m, 10H), 5.52 (d, 1H), 5.09 (d, 1H), 5.0 (d, 1H), 4.53 (m, 1H), 4.5 (s, 1H), 4.48 (m, 2H), 4.17 (dd, 1H), 2.87 (dd, 1H), 2.7 (q, 1H), 2.26 (s, 6H), 2.09 (s, 3H), 1.52 (s, 3H), 1.35 (s, 3H); IR (KBr in cm-1): 3313, 1643, 1521, 743; MS (APCI, n/z): 565 (M+H), 519, 265; C30H36N4O5S1.0.69 H$_2$O Calculated: C62.43, H6.53, N9.71, Observed: C63.81, H6.43, N9.92; HPLC: Rf (min.) 20.167; Purity: 98%.

EXAMPLE B11

2,4-Dimethyl-thiazole-5-carboxylic Acid {(1-benzyl-3-[5,5-dimethyl-4-(2-methyl-benzylcarbamoyl)-thiazolidin-3-yl]-2-hydroxy-3-oxo-propyl}-amide

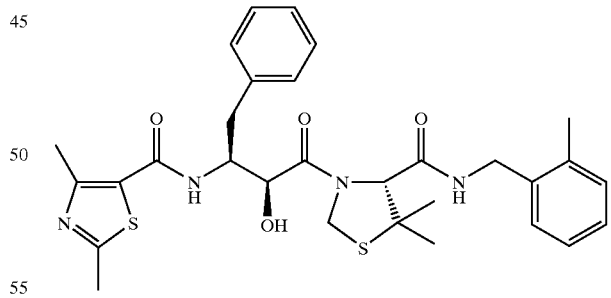

Isolated yield: 80%; $^1$H-NMR (400 MHz, dmso-d$_6$): δ 8.35 (t, 1H), 8.14 (d, 1H), 7.0–7.35 (m, 10H), 5.48 (d, 1H), 5.04 (d, 1H), 5.0 (d, 1H), 4.52 (m, 1H), 4.4 (s, 1H), 4.35 (m, 2H), 4.14 (dd, 1H), 2.78 (d, 2H), 2.57 (s, 3H), 2.30 (s, 3H), 2.26 (s, 3H), 1.48 (s, 3H), 1.35 (s, 3H); IR (KBr in cm-1): 3310, 1641, 1534, 743; MS (APCI, m/z): 581 (M+H), 317, 265,259; C30H36N4O4S2.0.39 H$_2$O Calculated: C61.30, H6.31, N9.53, Observed: C62.04, H6.25, N9.65; HPLC: Rf (min.) 19.613; Purity: 98%.

EXAMPLE B12

(R)-3-{(2S,3S)-2-Hydroxy-3-[(1-methyl-1H-pyrrole-2-carbonyl)-amino]-4-phenyl-butyryl}-5,5-dimethyl-thiazolidine-4-carboxic Acid 2-methyl-benzylamide

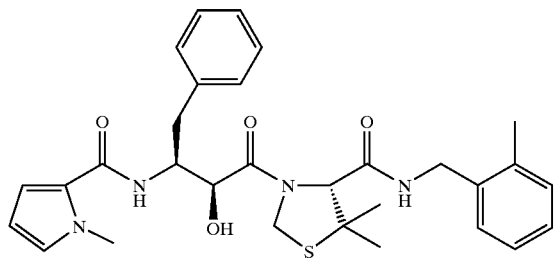

Isolated yield: 82%; $^1$H-NMR (400 MHz, dmso-d$_6$): δ 8.35 (t, 1H), 7.91 (d, 1H), 7.35–7.04 (m, 10H), 6.78 (s, 2H), 5.96 (s, 1H), 5.35 (d, 1H), 5.13 (s, 1H), 5.0 (d, 1H), 4.48 (s, 2H), 4.38 (dd, 1H), 4.30 (m, 1H), 4.13 (dd, 1H), 3.7 (s, 3H)), 2.8 (m, 2H), 2.26 (s, 3H), 1.52 (s, 3H), 1.35 (s, 3H); IR (KBr in cm−1): 3324, 1639, 1538, 735; MS (APCI, m/z): 549 (M+N), 503, 382, 285; C30NO36N4O4S1.2.44H$_2$O Calculated: C60.80, H6.95, N9.45, Observed: C65.67, H6.61, N10.21; NPLC: Rf (min.) 20.745; Purity: 100%.

EXAMPLE B13

(R)-3-{(2S,3S)-3-[(1,5-Dimethyl-1H-pyrazole-4-carbonyl)-amino]-2-hydroxy-4-phenyl-butyryl}-5,5-dimethyl-thiazolidine-4-carboxic Acid 2-methyl-benzylamide

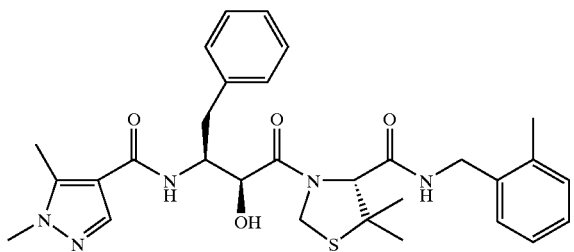

Isolated yield: 68%; 1H-NMR (400 MHz, dmso-d$_6$): δ 8.30 (t, 1H), 7.83 (d, 1H), 7.31–7.04 (m, 10H), 6.30 (s, 1H), 5.48 (d, 1H), 4.92 (s, 2H), 4.30–4.48 (m, 4H), 4.17 (dd, 1H), 3.7 (s, 3H), 2.74 (m, 2H), 2.26 (s, 3H), 2.18 (s, 3H), 1.48 (s, 3H), 1.30 (s, 3H); IR (KBr in cm−1): 3313, 1645, 1532, 744; MS (APCI, m/z): 564 (M+H), 300, 272; C30H37N5O4S1.0.5 H$_2$O Calculated: C62.86, H6.69, N12.22, Observed: C63.92, H6.62, N12.42; HPLC: Rf(min.) 19.724; Purity: 100%.

EXAMPLE B14

3-{(S)-3-[(5-Chloro-1,3-dimethyl-1H-pyrazole-4-carbonyl)-amino]-2-hydroxy-4-phenyl-butyryl}-5,5-dimethyl-thiazolidine-4-carboxic Acid 2-methyl-benzylamide

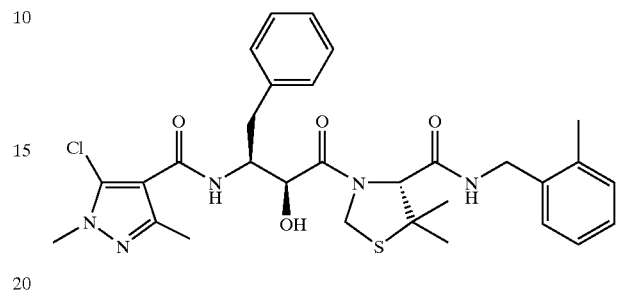

Isolated yield: 92%; $^1$H-NMR (400 MHz, dmso-d$_6$): δ 8.35 (t, 1H), 7.74 (d, 1H), 7.30–7.0 (m, 10H), 5.44 (d, 1H), 4.96 (q, 2H), 4.48 (m, 1H), 4.35 (m, 2H), 4.13 (dd, 1H), 2.74 (m, 2H), 2.22 (s, 3H), 2.09 (s, 3H), 1.48 (s, 3H), 1.26 (s, 3H); IR (KBr in cm−1): 3438, 3313, 1693, 1649, 1513, 1372, 754; MS (APCI, m/z): 598 (M+H), 334, 276, 174; C30H36N5O4S1Cl1.0.17 H2O Calculated: C59.93, H6.09, N11.65, Observed: C60.24, H6.07, N11.71; HPLC: Rf(min.) 19.829; Purity: 100%.

EXAMPLE B15

2-Amino-4-methyl-thiazole-5-carboxylic Acid {(S)-1-benzyl-3-[5,5-dimethyl-4-(2-methyl-benzylcarbamoyl)-thiazolidin-3-yl]-2-hydroxy-3-oxo-propyl}-amide

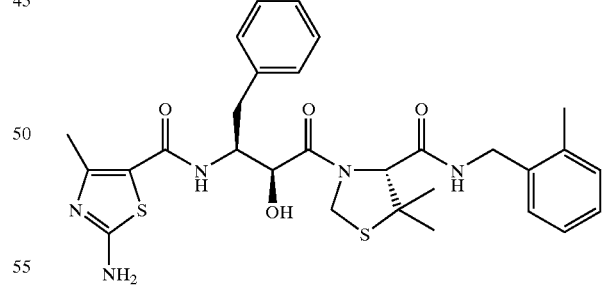

Isolated yield: 42%; 1H-NMR (400 MHz, dmso-d$_6$): δ 8.48 (brs, 1H), 8.35 (brs, 1H), 7.44 (d, 1H), 7.35–7.04 (m, 9H), 6.91 (s, 1H), 5.37 (d, 1H), 4.96 (q, 2H), 4.48–4.0 (m, 5H), 2,96 (m, 2H), 2.22 (2, 3H), 2.13 (s, 3H), 1.48 (s, 3H), 1.30 (s, 3H); IR (KBr in cm−1): 3307, 1625, 1495; MS (APCI, m/z): 582 (M+H), 442, 318; C29H35N5O4S2Cl1 Calculated: C60.13, H6.5, N10.82, Observed: C59.87, H6.06, N12.04; HPLC: Rf (min.) 17.981; Purity: 98%.

EXAMPLE B16

3-[2-Hydroxy-3-(2-methyl-benzoylamino)-4-phenyl-butyryl]-5,5-dimethyl-thiazolidine-4-carboxylic Acid 2-methyl-benzylamide

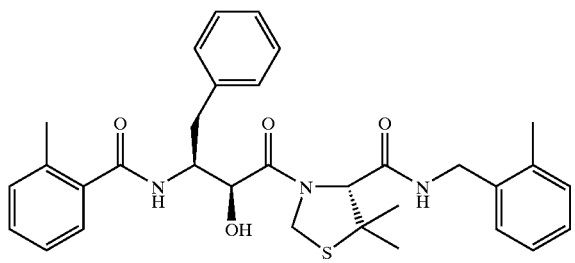

Isolated yield: 76%; 1H-NMR (400 MHz, dmso-$d_6$): δ 8.31 (t, 1H), 8.22 (d, 1H), 7.32–7.04 (m, 13H), 5.48 (d, 1H), 5.13 (d, 1H), 5.0 (d, 1H), 4.48 (s, 2H), 4.38 (dd, 2H), 4.09 (dd, 1H), 2.83 (d, 1H), 2.70 (t, 1H), 2.26 (s, 3H), 2.01 (s, 3H), 1.48 (s, 3H), 1.33 (s, 3H); IR (KBr in cm−1): 3309, 1641, 1520, 742; MS (APCI, m/z): 560 (M+H), 514, 296, 265; C32H37N3O4S1. 0.64 H2O Calculated: C67.40, H6.59, N7.37, Observed: C68.79, H6.49, N7.52; HPLC: Rf (min.) 21.024; Purity: 98%.

EXAMPLE B17

3-[3-(2,3-Dimethyl-benzoylamino)-2-hydroxy-4-phenyl-butyryl]-5,5-dimethyl-thiazolidine-4-carboxylic Acid 2-methyl-benzylamide

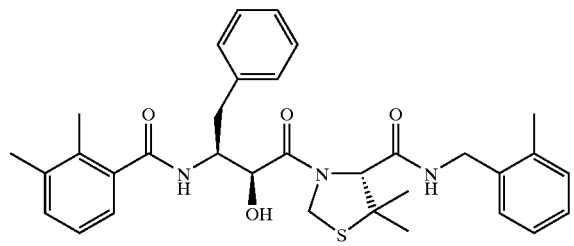

Isolated yield: 72%; 1H-NMR (400 MHz, dmso-$d_6$): δ 8.33 (t, 1H), 8.22 (d, 1H), 7.35–6.83 (m, 12H), 5.48 (d, 1H), 5.13 (d, 1H), 5.04 (d, 1H), 4.48–4.30 (m, 4H), 4.09 (dd, 1H), 2.84 (d, 1H), 2.70 (t, 1H), 2.26 (s, 3H), 2.17 (s, 3H), 1.87 (s, 3H), 1.48 (s, 3H), 1.30 (s, 3H); IR (KBr in cm−1): 3307, 1640, 1515, 743; MS (APCI, m/z): 574 (M+H), 528, 310, 265; C33H39N3O4S1. 0.54 H2O Calculated: C68.05, H6.76, N7.21, Observed: C69.20, H6.76, N7.34; HPLC: Rf (min.) 21.449; Purity: 99%.

EXAMPLE B18

6-Oxo-1,4,5,6-tetrahydro-pyridazine-3-carboxylic Acid {1-benzyl-3-[5,5-dimethyl-4-(2-methyl-benzylcarbamoyl)-thiazolidin-3-yl]-2-hydroxy-3-oxo-propyl}-amide

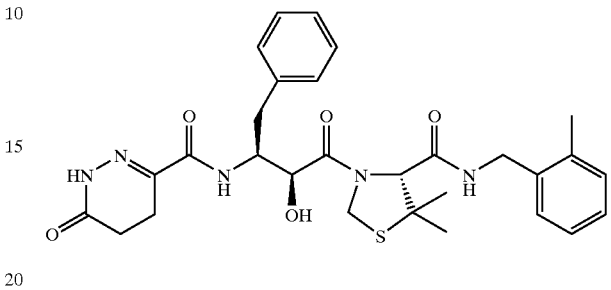

Isolated yield: 67%; 1H-NMR (400 MHz, dmso-$d_6$): δ 8.35 (t, 1H), 8.09 (d, 1H), 7.30–7.0 (m, 10H), 5.6 (d, 1H), 4.91 (d, 1H), 4.83 (d, 1H), 4.44 (s, 1H), 4.30 (m, 3H), 4.17 (dd, 1H), 2.78 (d, 2H), 2.61 (t, 2H), 2.30 (t, 2H), 2.22 (s, 3H), 1.48 (s, 3H), 1.30 (s, 3H); IR (KBr in cm−1): 3306, 1650, 1521, 742; MS (APCI, m/z): 566 (M+H), 520, 265; C29H35N5O5S1. 0.7 H2O Calculated: C60.23, H6.34, N12.11, Observed: C61.57, H6.24, N12.38; HPLC: Rf (min.) 18.455; Purity: 97%.

EXAMPLE B19

2,4-Dimethyl-5-oxo-2,5-dihydro-isoxazole-3-carboxylic Acid {1-benzyl-3-[5,5-dimethyl-4-(2-methyl-benzylcarbamoyl)-thizolidin-3-yl]-2-hydroxy-3-oxo-propyl}-amide

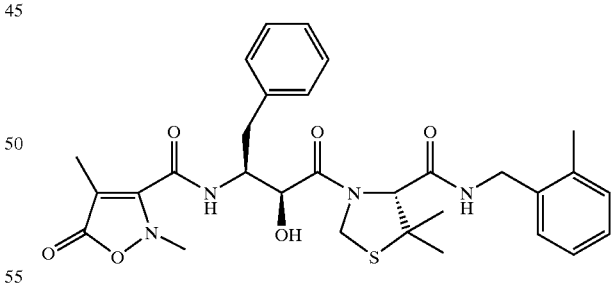

Isolated yield: 73%; 1H-NMR (400 MHz, dmso-$d_6$): δ 8.91 (d, 1H), 8.35 (t, 1H), 7.30–7.04 (m, 9H), 5.70 (d, 1H), 5.0 (d, 2H), 4.44 (s+m, 3H), 4.31 (dd, 1H), 4.13 (dd, 1H), 2.91 (s+m, 4H), 2.65 (t, 1H), 2.22 (s, 3H), 1.52 (s, 3H), 1.48 (s, 3H), 1.30 (s, 3H); IR (KBr in cm−1): 3325, 2932, 1729, 1649, 1527, 742; MS (APCI, m/z): 581 (M+H), 539, 493, 225; C30H36N4O6S1 Calculated: C62.29, H5.61, N9.19, Observed: C62.05, H6.25, N9.65; HPLC: Rf (min.) 19.638; Purity: 100%.

EXAMPLE B20

(R)-3-((2S,3S)-2-Hydroxy-3-{[1-(3-hydroxy-2,4-dimethyl-phenyl)-methanoyl]-amino}-4-phenyl-butanoyl)-5,5-dimethyl-thiazolidine-4-carboxylic Acid Allylamide

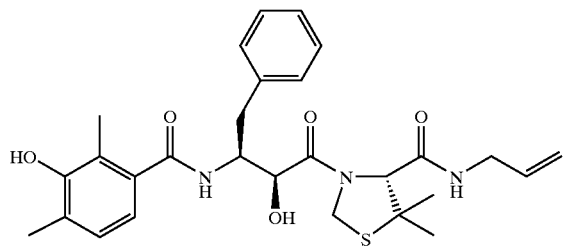

$^1$H NMR (DMSO-d$_6$) δ 8.23 (s, 1H), 8.10–8.03 (m, 2H), 7.33–7.12 (m, 5H), 6.85 (d, J=7.7, 1H), 6.51 (d, J=7.7, 1H), 5.82–5.70 (m, 1H), 5.44 (d, J=6.8, 1H), 5.22–4.97 (m, 4H), 4.50–4.30 (m, 3H), 3.84–3.60 (m, 2H), 2.84–2.66 (m, 2H), 2.13 (s, 3H), 1.85 (s, 3H), 1.49 (s, 3H), 1.35 (s, 3H); HRMS (ESI) m/z calcd for C$_{28}$H$_{36}$N$_3$O$_5$S (M+H)$^+$ 526.2376, found 526.2380; Anal. Calcd for C$_{28}$H$_{35}$N$_3$O$_5$S.0.2 TFA: C, 62.19; H, 6.47; N, 7.66. Found: C, 62.27; H, 6.78; N, 7.26.

EXAMPLE B21

3-(2-Hydroxy-3-{[1-(3-hydroxy-2,4-dimethyl-phenyl)-methyanoyl]-amino}-4-phenyl-butznoyl)-5,5-dimethyl-thiazolidine-4-carboxylic Acid prop-2-ynylamide

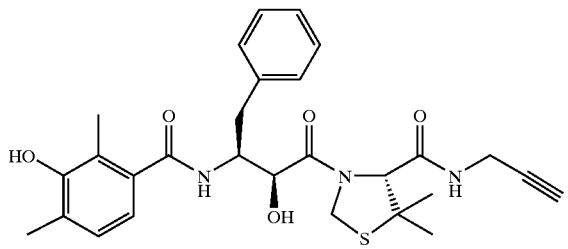

$^1$H NMR (DMSO-d$_6$) δ 8.40 (t, J=5.4, 1H), 8.22 (s, 1H), 8.02 (d, J=8.2, 1H), 7.35–6.52 (m, 7H), 5.44 (d, J=6.8, 1H), 5.10 (d, J=9.1, 1H), 5.02 (d, J=9.1, 1H), 4.46–4.40 (m, 2H), 4.40 (s, 1H), 3.86 (s br, 2H), 3.08 (t, J=1.8, 1H), 2.82–2.72 (m, 2H), 2.15 (s, 3H), 1.88 (s, 3H), 1.51 (s, 3H), 1.37 (s, 3H); HRMS (ESI) m/z calcd for C$_{28}$H$_{34}$N$_3$O$_5$S (M+H)$^+$ 524.2219, found 524.2219; Anal. Calcd for C$_{28}$H$_{33}$N$_3$O$_5$S.0.5H$_2$O: C, 63.13; H, 6.43; N, 7.89; S, 6.02. Found: C, 62.80; H, 6.64; N, 7.71; S, 5.69.

EXAMPLE B22

3-{2-Hyrdoxy-3-[(1-methyl-1H-pyrrole-2-carbonyl)-amino]-4-phenyl-butyryl}-5,5-dimethyl-thiazolidine-4-carboxylic Acid 2-chloro-benzylamide

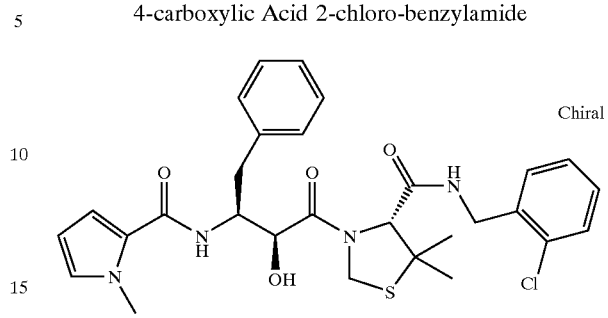

Isolated yield: 50%; 1H-NMR (400 MHz, dmso-d$^6$): 6.40–7.40 (m, 11H), 6.00 (m, 1H), 4.20–5.20 (m, 7H), 3.71, 3.54 (s 3H), 2.70–2.90 (m, 2H), 1.52 (d, J=2.0 Hz, 3H), 1.32 (d, J=2.1 Hz, 3H); MS (APCI, m/z): 570 (M+H).

EXAMPLE B23

3,5-Dimethyl-isoxazole-4-carboxylic Acid {1-benzyl-3-[4-(2-chloro-benzylcarbamoyl)-5,5-dimethyl-thiazolidin-3-yl]-2-hydroxy-3-oxo-propyl}-amide

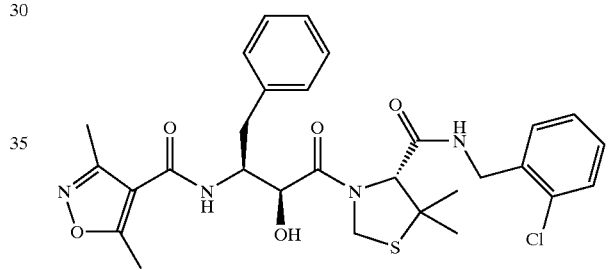

Isolated yield: 55%; 1H-NMR (400 MHz, dmso-d$^6$): 7.00–7.40 (m, 9H), 4.36–5.08 (m, 7H), 2.70–2.90 (m, 2H), 2.34, 2.25 (s, 3H), 2.18, 2.12 (s, 3H), 1.56 (d, J=8.5 Hz, 3H), 1.35 (d, J=6.2 Hz, 3H); MS (APCI, m/z): 586 (M+H); C$_{29}$H$_{33}$ClN$_4$O$_5$S. 0.42H$_2$O Calculated: C58.77, H5.75, N9.45, Observed: C58.37, H5.73, N9.19.

EXAMPLE B24

3-{2-Hydroxy-3-[(1-methyl-1H-pyrrole-2-carbonyl)-amino]-4-phenyl-butyryl}-5,5-dimethyl-thiazolidine-4-carboxylic Acid 2,6-difluoro-benzylamide

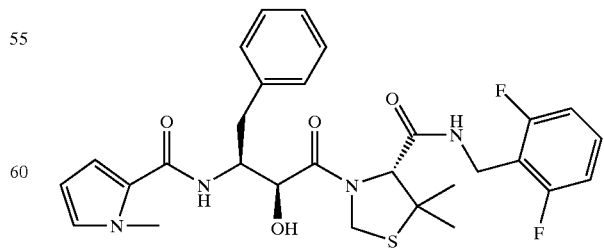

Isolated yield: 75%; 1H-NMR (400 MHz, dmso-d$^6$): 6.40–7.40 (m, 10H), 6.00 (m, 1H), 4.20–5.20 (m, 7H), 3.64, 3.61 (s 3H), 2.70–2.90 (m, 2H), 1.52, 1.49 (s, 3H), 1.33, 1.29 (s, 3H); MS (APCI, m/z): 571 (M+H); $C_{29}H_{32}F_2N_4O_4S$ Calculated: C61.04, H5.65, N9.82, Observed: C60.86, H5.94, N9.71.

EXAMPLE B25

3,5-Dimethyl-isoxazole-4-carboxylic Acid {(1-benzyl-3-[4-(2,6-difluoro-benzylcarbamoyl)-5,5-dimethyl-thiazolidin-3-yl]-2-hydroxy-3-oxo-propyl}-amide

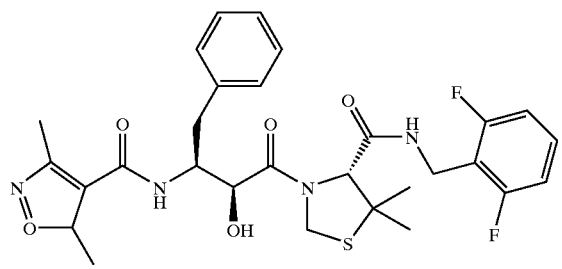

Isolated yield: 75%; 1H-NMR (400 MHz, dmso-d$^6$): 6.60–7.40 (m, 8H), 4.26–5.08 (m, 7H), 2.70–2.90 (m, 2H), 2.32, 2.28 (s, 3H), 2.16, 2.13 (s, 3H), 1.56, 1.53 (s, 3H), 1.37, 1.34 (s, 3H); MS (APCI, m/z): 587 (M+H); $C_{29}H_{32}F_2N_4O_5S$ Calculated: C59.37, H5.50, N9.55, Observed: C59.12, H5.88, N9.50.

EXAMPLE B26

3-{2-Hydroxy-3-[(1-methyl-1H-pyrrole-2-carbonyl)-amino]-4-phenyl-butyryl}-5,5-dimethyl-thiazolidine-4-carboxylic Acid 2-trifluoromethyl-benzylamide

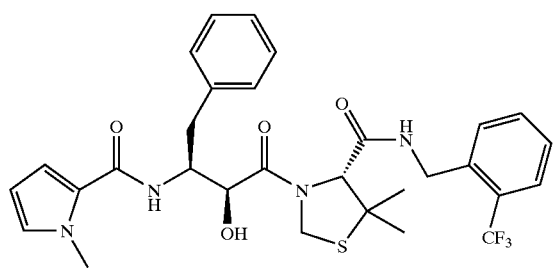

Isolated yield: 83%; 1H-NMR (400 MHz, dmso-d$^6$): 6.40–7.60 (m, 11H), 6.00 (m, 1H), 4.20–5.20 (m, 7H), 3.70, 3.54 (s 3H), 2.70–2.90 (m, 2H), 1.52 (s, 3H), 1.36, 1.29 (s, 3H); MS (APCI, m/z): 619 (M+H); $C_{30}H_{33}F_3N_4O_4S$ Calculated: C59.79, H5.52, N9.30, Observed: C59.42, H5.55, N9.06.

EXAMPLE B27

3,5-Dimethyl-isoxazole-4-carboxylic Acid {(1-benzyl-3-[5,5-dimethyl-4-(2-trifluoromethyl-benzylcarbamoyl)-thiazolidin-3-yl]-2-hydroxy-3-oxo-propyl}-amide

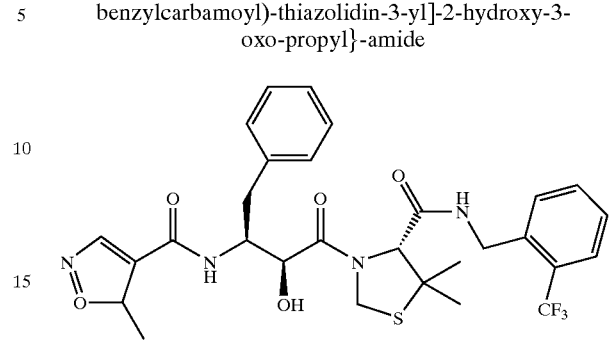

Isolated yield: 93%; 1H-NMR (400 MHz, dmso-d$^6$): 7.05–7.60 (m, 9H), 4.36–5.08 (m, 7H), 2.70–2.90 (m, 2H), 2.30, 2.21 (s, 3H), 2.15, 2.05 (s, 3H), 1.54, 1.52 (s, 3H), 1.39, 1.32 (s, 3H); MS (APCI, m/z): 619 (M+H); $C_{30}H_{33}F_3N_4O_5S$ Calculated: C58.24, H5.38, N9.06, Observed: C57.87, H5.68, N9.02.

EXAMPLE B28

N-[(1S,2S)-3-(4-Allylcarbamoyl-5,5-dimethyl-thiazolidin-3-yl)-1-benzyl-2-hydroxy-3-oxo-propyl]-nicotinamide

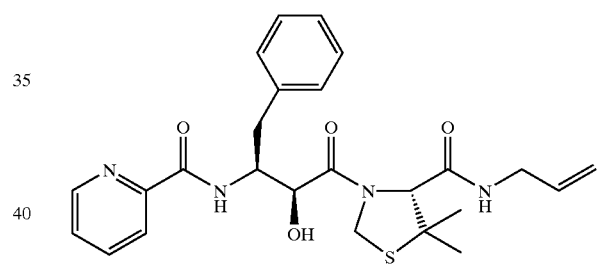

White solid: $^1$H NMR (DMSO-d$_6$) δ 8.81 (d, J=8.6, 1), 8.77 (d, J=6.2, 1H), 8.12 (m, 1H), 7.99 (m, 1H), 7.63 (m, 1H), 7.32–7.12 (m, 7H), 5.78 (m, 1H), 5.18 (m ,2H), 4.56(m ,3H), 4.40 (m, 4H), 2.87–2.67 (m, 2H), 1.49 (s, 3H), 1.34 (s, 3H); Anal. ($C_{26}H_{32}N_4O_4S.0.5\ H_2O.0.5$ TFA) calculated C (57.65), H (6.36), N (10.19), found C (57.73), H (5.91), N (10.15). HRMS (ESI) m/z calcd for 483.2075, found 497.2066.

EXAMPLE B29

3-[2-Hydroxy-3-(4-methoxy-2-methyl-benzoylamino)-4-phenyl-butyryl]-5,5-dimethyl-thiazolidine-4-carboxylic Acid 2-methyl-benzylamide

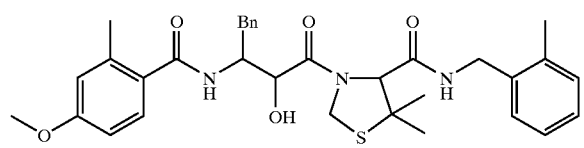

Isolated yield: 56%. $^1$H NMR (400 MHz, DMSO-d$_6$): δ 8.32 (t, 1H), 8.09 (d, 1H), 7.33–7.27 (m, 3H), 7.23–7.19 (m, 2H), 7.15–7.08 (m, 5H), 6.69 (d, 2H), 5.46 (d, 1H), 5.13 (d, 1H), 4.99 (d, 1H), 4.49 (s, 2H), 4.41–4.36 (m, 2H), 4.10 (dd, 1H), 3.71 (s,3H), 2.84–2.81 (m, 1H), 2.72 (t, 1H), 2.24 (s, 3H), 2.07 (s, 3H), 1.48 (s, 3H), 1.33 (s, 3H); MS-APCI (m/z+): 326, 590 (M+H). HPLC: Rf(min.) 21.26; Purity: 100%; C$_{33}$H$_{39}$N$_3$O$_5$S$_1$.0.4 H$_2$O: calcd: C66.40, H6.72, N7.04, found: C66.38, H6.71, N6.94.

EXAMPLE B30

(R)-3-{(2S,3S)-2-Hydroxy-4-phenyl-3-[(1-o-tolyl-methanoyl)-amino]-butanoyl}-5,5-dimethyl-thiazolidine-4-carboxylic Acid Propylamide

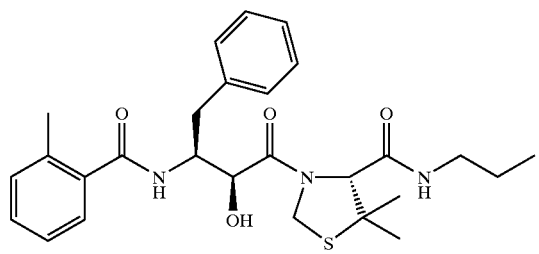

IR (neat, cm$^{-1}$) 3318, 2964, 1642, 1530, 1445, 1372, $^1$H NMR (DMSO) δ 8.21 (d, J=8.4, 1H), 7.90 (t, J=5.6, 1H), 7.35–7.07 (m, 9H), 5.45 (d, J=6.8, 1H), 5.09 (d, J=9.2, 1H), 5.00 (d, J=9.2, 1H), 4.50–4.38 (m, 2H), 4.37 (s, 1H), 3.01 (q, J=6.9, 2H), 2.90–2.60 (m, 2H), 2.02 (s, 3H), 1.49 (s, 3H), 1.44–1.35 (m, 2H), 1.34 (s, 3H), 0.82 (t, J=7.5, 3H); HRMS (ESI) m/z calcd for C$_{27}$H$_{36}$N$_3$O$_4$S (M+H)$^+$ 498.2424, found 498.2427.

EXAMPLE B31

(R)-3-((2S,3S)-3-{[1-(3-Fluoro-2-methyl-phenyl)-methanoyl]-amino}-2-hydroxy-4-phenyl-butanoyl)-5,5-dimethyl-thiazolidine-4-carboxylic Acid Propylamide

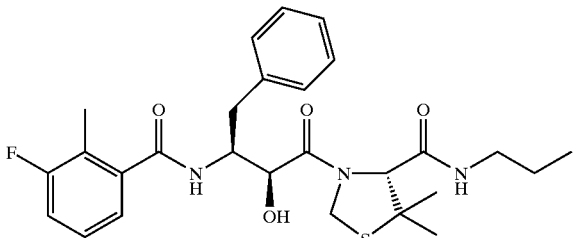

White solid: $^1$H NMR (DMSO) δ 8.34 (d, J=8.1, 1H), 7.91 (t, J=5.9, 1H), 7.40–7.10 (m, 7H), 6.93 (d, J=6.9, 1H), 5.51 (d, J=6.2, 1H), 5.08 (d, J=8.8, 1H), 5.00 (d, J=8.8, 1H), 4.50–4.39 (m, 2H), 4.38 (s, 1H), 3.00 (dd, J=12.3, 5.9, 2H), 2.90–2.60 (m, 2H), 1.89 (s, 3H), 1.49 (s, 3H), 1.40–1.34 (m, 2H), 1.34 (s, 3H), 0.82 (t, J=7.7, 3H); HRMS (ESI) m/z calcd for C$_{27}$H$_{35}$N$_3$O$_4$FS (M+H)$^+$ 516.2332, found 516.2339.

EXAMPLE B32

(R)-3-((2S,3S)-3-{[1-(3-Fluoro-2-methyl-phenyl)-methanoyl]-amino}-2-hydroxy-4-phenyl-butanoyl)-5,5-dimethyl-thiazolidine-4-carboxylic Acid 3-methoxy-benzylamide

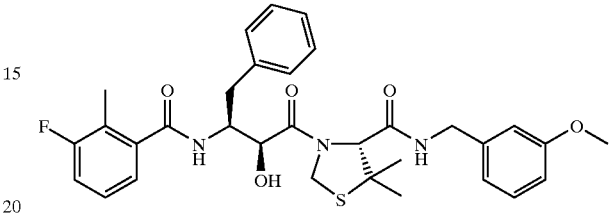

White solid: $^1$H NMR (DMSO) δ 8.43 (t, J=5.9, 1H), 8.34 (d, J=8.1, 1H), 7.31–6.72 (m, 12H), 5.57 (d, J=6.8, 1H), 5.12 (d, J=9.3, 1H), 5.01 (d, J=9.3, 1H), 4.50–4.30 (m, 4H), 4.12 (dd, J=15.7, 5.9, 1H), 3.69 (s, 3H), 2.95–2.62 (m, 2H), 1.90 (s, 3H), 1.49 (s, 3H), 1.34 (s, 3H); HRMS (ESI) m/z calcd for C$_{32}$H$_{37}$N$_3$O$_5$SF (M+H)$^+$ 594.2434, found 594.2438.

EXAMPLE B33

(R)-3-((2S,3S)-3-{[1-(3-Fluoro-2-methyl-phenyl)-methanoyl]-amino}-2-hydroxy-4-phenyl-butanoyl)-5,5-dimethyl-thiazolidine-4-carboxylic Acid Allylamide

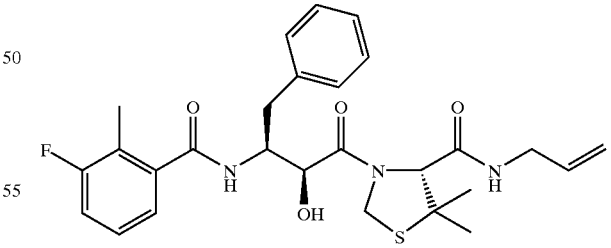

White solid: $^1$H NMR (DMSO) δ 8.34(d, J=8.3, 1H), 8.10(t, J=5.7, 1H), 7.40–6.90 (m, 8H), 5.81–5.69 (m, 1H), 5.54 (d, J=6.6, 1H), 5.30–4.90 (m, 4H), 4.50–4.35 (m, 3H), 3.80–3.65 (m, 2H), 2.90–2.60 (m, 2H), 1.89 (s, 3H), 1.49 (s, 3H), 1.35 (s, 3H); HRMS (ESI) m/z calcd for C$_{27}$H$_{33}$N$_3$O$_4$SF (M+H)$^+$ 514.2182, found 514.2176.

EXAMPLE B34

3-[(2S,3S)-2-Hydorxy-3-(3-hydroxy-2,5-dimethyl-benzoylamino)-4-phenyl-butyryl]-5,5-dimethyl-thiazolidine-4-carboxylic Acid Allylamide

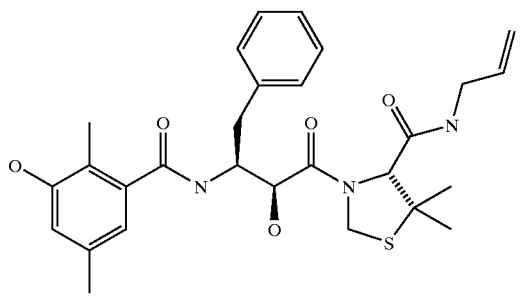

$^1$H NMR (DMSO-d$_6$) δ 9.23 (s, 1H), 8.09 (m, 2H), 7.35–7.17 (m, 5H), 6.60 (s, 1H), 6.37 (s, 1H), 5.74 (m, 1H), 5.41 (br s, 1H), 5.20 (dd, J=17.2, 1.6, 1H), 5.11 (d, J=9.2, 1H), 5.02 (dd, J=10.2, 1.5, 1H), 5.00 (d, J=9.1, 1H), 4.46–4.37 (m, 3H), 3.79 (ddd, J=15.9, 5.5, 5.3, 1H), 3.63 (ddd, J=15.9, 5.4, 5.3, 1H), 2.82 (dd, J=13.9, 0.3, 1H), 2.71 (dd, J=13.6, 10.7, 1H), 2.16 (s, 3H), 1.76 (s, 3H), 1.51 (s, 3H), 1.36 (s, 3H); Anal. Calcd for C$_{28}$H$_{35}$N$_4$O$_5$S.0.3H$_2$O: C, 63.32; H, 6.76; N, 7.91, Found: C, 63.35; H, 6.70; N, 7.71.

EXAMPLE B35

(R)-3-[(2S,3S)-3-(5-Fluoro-3-hydroxy-2-methyl-benzoylamino)-2-hydroxy-4-phenyl-butyryl]-5,5-dimethyl-thiazolidine-4-carboxylic Acid Allylamide

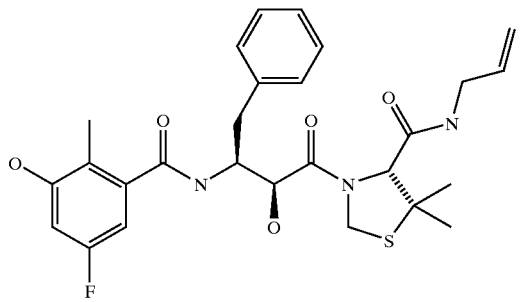

$^1$H NMR (DMSO-d$_6$) δ 9.94 (s, 1H), 8.23 (d, J=8.2, 1H), 8.10 (t, J=5.6, 1H), 7.33–7.17 (m, 5H), 6.58 (dd, J=10.6, 2.5, 1H), 6.32 (dd, J=8.8, 2.5, 1H), 5.78 (m, 1H), 5.54 (br s, 1H), 5.21 (dd, J=17.2, 1.7, 1H), 5.10 (d, J=9.1, 1H), 5.03 (dd, J=10.2, 1.5, 1H), 5.01 (d, J=9.1, 1H), 4.50–4.42 (m, 3H), 3.78 (ddd, J=15.9, 5.4, 5.4, 1H), 3.63 (ddd, J=15.9, 5.4, 5.3, 1H), 2.84 (dd, J=14.5, 3.3, 1H), 2.70 (dd, J=13.5, 10.3, 1H), 1.75 (s, 3H), 1.50 (s, 3H), 1.36 (s, 3H); Anal. Calcd for C$_{27}$H$_{32}$FN$_3$O$_5$S.0.3H$_2$O: C, 60.61; H, 6.14; N, 7.85, Found: C, 60.63; H, 6.08; N, 8.07.

EXAMPLE B36

(R)-3-((2S,3S)-3-{[1-(3-Fluoro-2-methyl-phenyl)-methanoyl]-amino}-2-hydroxy-4-phenyl-butanoyl)-5,5-dimethyl-thiazolidine-4-carboxylic Acid 2-methyl-benzylamide

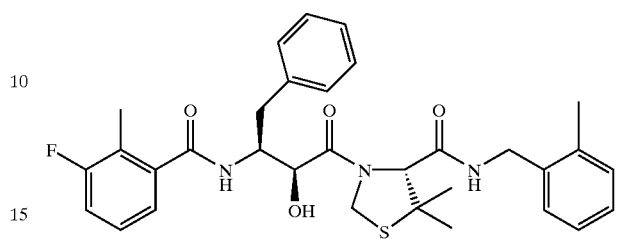

$^1$H NMR (DMSO) δ 8.85–8.35 (m, 2H), 7.38–6.90 (m, 12H), 5.55 (d, J=5.9, 1H), 5.12 (d, J=9.2, 1H), 5.01 (d, J=9.2, 1H), 4.58–4.32 (m, 4H), 4.10 (dd, J=15.0, 4.6, 1H), 2.92–2.62 (m, 2H), 2.24 (s, 3H), 1.90 (s, 3H), 1.49 (s, 3H), 1.34 (s, 3H); HRMS (ESI) m/z calcd for C$_{32}$H$_{37}$N$_3$O$_4$FS (M+H)$^+$ 578.2489, found 578.2486; Anal. Calcd for C$_{32}$H$_{36}$N$_3$O$_4$FS.0.2 EtOAc: C, 66.17; H, 6.37; N, 7.06. Found: C, 66.30; H, 6.54; N, 6.74.

EXAMPLE B37

(R)-3-((2S,3S)-3-{[1-(4-Fluoro-2-methyl-phenyl)-methanoyl]-amino}-2-hydroxy-4-phenyl-butanoyl)-5,5-dimethyl-thiazolidine-4-carboxylic Acid 2-methyl-benzylamide

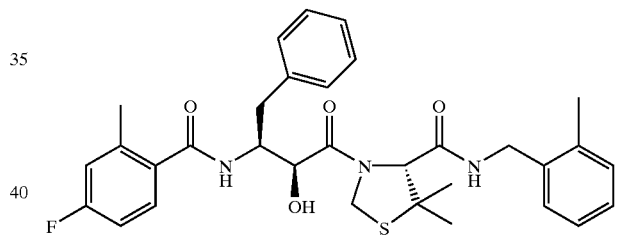

White solid: $^1$H NMR (DMSO) δ 8.40–8.30 (m, 2H), 7.35–6.90 (m, 12H), 5.53 (d, J=6.8, 1H), 5.13 (d, J=9.0, 1H), 5.00 (d, J=9.0, 1H), 4.48 (s, 1H), 4.47–4.45 (m, 2H), 4.38 (dd, J=15.0, 5.9, 1H), 4.10 (dd, J=15.0, 4.8, 1H), 2.90–2.62 (m, 2H), 2.24 (s, 3H), 2.04 (s, 3H), 1.48 (s, 3H), 1.33 (s, 3H); HRMS (ESI) m/z calcd for C$_{32}$H$_{37}$N$_3$O$_4$SF (M+H)$^+$ 578.2463, found 578.2489.

EXAMPLE B38

Nicotinic Acid 3-[(2S,3S)-3-((R)-4-allylcarbamoyl-5,5-dimethyl-thiazolidin-3-yl)-1-benzyl-2-hydroxy-3-oxo-propylcarbamoyl]-2-methyl-phenyl Ester

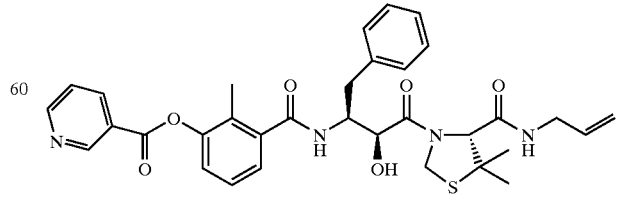

White solid: $^1$H NMR (DMSO) δ 9.26 (dd, J=2.0, 0.9, 1H), 8.90 (dd, J=5.6, 2.0, 1H), 8.47 (dt, J=7.9, 2.0, 1H), 8.40

(d, J=8.2, 1H), 8.1 (t, J=5.7, 1H), 7.65 (ddd, J=7.9, 5.6, 0.9, 1H), 7.40–7.10 (m, 8H), 5.82–5.68 (m, 1H), 5.6 (d, J=6.2, 1H), 5.30–4.90 (m, 4H), 4.50–4.40 (m, 2H), 4.40 (s, 1H), 3.80–3.70 (m, 2H), 3.00–2.60 (m, 2H), 1.85 (s, 3H), 1.49 (s, 3H), 1.34 (s, 3H).

EXAMPLE B39

(R)-3-[(2S,3S)-2-Hydroxy-3-(4-hydroxy-2-methyl-benzoylamino)-4-phenyl-butyryl]-5,5-dimethyl-thiazolidine-4-carboxylic Acid 2-methyl-benzylamide

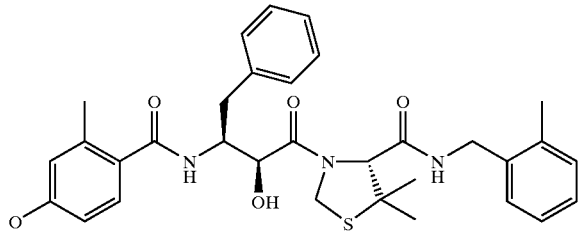

White solid: $^1$H NMR (DMSO) δ 9.55 (s, 1H), 8.32 (t, J=4.9, 1H), 8.00 (d, J=8.4, 1H), 7.36–7.00 (m, 10H), 6.54–6.48 (m, 2H), 5.44 (d, J=6.6, 1H), 5.13 (d, J=9.2, 1H), 4.99 (d, J=9.2, 1H), 4.50–4.32 (m, 4H), 4.11 (dd, J=15.0, 4.8, 1H), 3.50–2.80 (m, 2H), 2.25 (s, 3H), 2.04 (s, 3H), 1.49 (s, 3H), 1.33 (s, 3H); Anal. Calcd for $C_{32}H_{37}N_3O_5S \cdot 0.25 H_2O$: C, 66.24; H, 6.51; N, 7.24. Found: C, 66.25; H, 6.55; N, 7.35.

EXAMPLE B40

6-Amino-pyridine-2-carboxylic Acid {(1S,2S)-1-benzyl-3-[(R)-5,5-dimethyl-4-(2-methyl-benzylcarbamoyl)-thizolidin-3-yl]-2-hydroxy-3-oxo-propyl}-amide

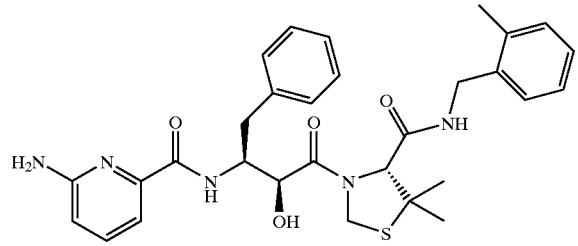

$^1$H NMR (DMSO-$d_6$) δ 8.44 (d, 1H, J=5.6), 8.36 (d, 1H, J=9.3), 7.69–7.49 (t, 1H, J=7.7), 7.34–7.06 (m, 10H), 6.61 (d, 1H, J=8.4), 6.27 (br s, 2H) 5.47 (d, 1H, J=7.1), 5.00 (m, 2H), 4.54–4.43 (m, 2H), 4.50 (s, 1H), 4.38 (dd, 1H, J=6.4, 15.2), 4.19 (dd, 1H, J=4.6, 14.7), 2.87–2.65 (m, 2H), 2.28 (s, 3H), 1.53 (s, 3H), 1.38 (s, 3H). Exact mass calculated for $C_{30}H_{36}N_5O_4S$ (M+H)$^+$ 562.2488, found 562.2493.

EXAMPLE B41

{(1S,2S)-1-Benzyl-3-[(R)-5,5-dimethyl-4-(2-methyl-benzylcarbamoyl)-thiazolidin-3-yl]-2-hydroxy-3-oxo-propyl}-2,3-dichloro-isonicotinamide

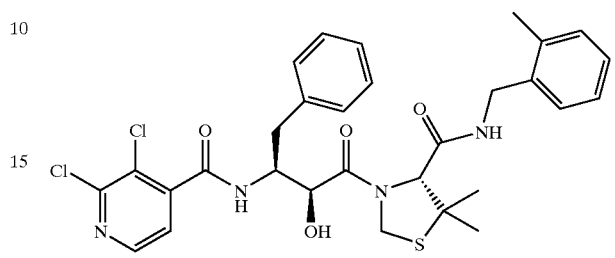

$^1$H NMR (DMSO-$d_6$) δ 8.89 (d, 1H, J=8.42), 8.40 (t, 1H, J=5.5), 8.38 (d, 1H, J=4.8), 7.30–7.08 (m, 10H), 5.58 (d, 1H, J=7.3), 5.07 (d, 1H, J=8.8), 5.00 (d, 1H, J=8.8), 4.54–4.50 (m, 1H), 4.51 (s, 1H), 4.43–4.36 (m, 2H), 4.16 (dd, 1H, J=5.1, 15.0), 2.89–2.85 (m, 1H), 2.71–2.63 (m, 1H), 2.26 (s, 3H), 1.50 (s, 3H), 1.35s (s, 3H). Exact mass calculated for $C_{30}H_{33}N_4O_4SCl_2$ (M+H)$^+$ 615.1600, found 615.1581. Anal. Calcd for $C_{30}H_{32}N_4O_4SCl_2$: C, 58.54; H, 5.24; N, 9.10. Found: C, 58.48; H, 5.10; N, 8.80.

EXAMPLE B42

{(1S,2S)-1-Benzyl-3-[(R)-5,5-dimethyl-4-(2-methyl-benzylcarbamoyl)-thiazolidin-3-yl]-2-hydroxy-3-oxo-propyl}-3-chloro-isonicotinamide

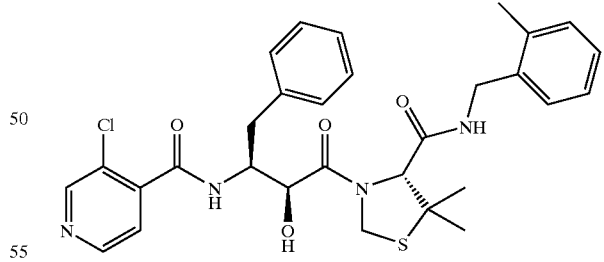

$^1$H NMR (DMSO-$d_6$) δ 8.82 (d, 1H, J=8.6), 8.62 (s, 1H), 8.52 (d, 1H, J=4.9), 8.39 (d, 1H, J=5.1), 7.29–7.09 (m, 10H), 5.54 (d, 1H, J=7.1), 5.09 (d, 1H, J=9.0), 4.99 (d, 1H, J=9.0), 4.56–4.49 (m, 1H), 4.51 (s, 1H), 4.44–4.37 (m, 2H), 4.15 (dd, 1H, J=5.1, 15.0), 2.88–2.83 (m, 1H), 2.74–2.65 (m, 1H), 2.26 (s, 3H), 1.50 (s, 3H), 1.35s (s, 3H). Exact mass calculated for $C_{30}H_{33}N_4O_4SCl$ (M)$^+$ 581.1989, found 581.1983.

EXAMPLE B43

(R)-3-[(2S,3S)-2-Hydroxy-3-(3-hydroxy-2,5-dimethyl-benzoylamino)-4-phenyl-butyryl]-5,5-dimethyl-thiazolidine-4-carboxylic Acid 2-methyl-benzylamide

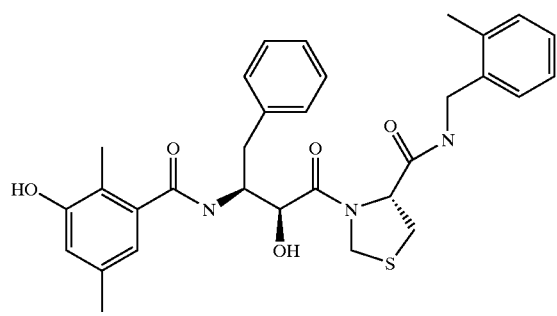

$^1$H NMR (DMSO-d$_6$) δ 9.24 (s, 1H), 8.31 (t, J=5.6, 1H), 8.10 (d, J=8.2, 1H), 7.34–7.09 (m, 9H), 6.60 (s, 1H), 6.38 (s, 1H), 5.42 (br s, 1H), 5.14 (d, J=9.1, 1H), 5.01 (d, J=9.1, 1H), 4.50 (s, 1H), 4.50–4.37 (m, 3H), 4.11 (dd, J=15.1, 4.7, 1H), 2.76 (m, 2H), 2.26 (s, 3H), 2.16 (s, 3H), 1.77 (s, 3H), 1.50 (s, 3H), 1.35 (s, 3H); HRMS (ESI) m/z calcd for C$_{33}$H$_{40}$N$_3$O$_5$S (M+H)$^+$ 590.2689, found 590.2676; Anal. Calcd for C$_{33}$H$_{39}$N$_3$O$_5$S.0.3 H$_2$O: C, 66.60; H, 6.71; N, 7.06. Found: C, 66.65; H, 6.69; N, 7.05.

EXAMPLE B44

N-{(1S,2S)-1-Benzyl-3-[5,5-dimethyl-4-(2-methyl-benzylcarbamoyl)-thiazolidin-3-yl]-2-hydroxy-3-oxo-propyl}-2-methyl-nicotinamide

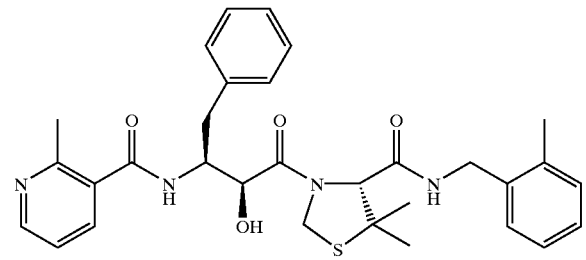

White solid: $^1$H NMR (DMSO-d$_6$) δ 8.53–8.33 (m, 2H), 7.47 (d, J=7.82, 1H), 7.38–7.10 (m, 12H), 5.62 (d, J=7.94, 1H), 5.18 (dd, J=9.6, 7.6, 2H), 4.43–4.37 (m, 3H), 4.17 (dd, J=7.81, 6.99, 1H), 2.87–2.67 (m, 2H), 2.28 (s, 3H), 2.21(s, 3H), 1.49 (s, 3H), 1.34 (s, 3H); Anal. (C$_{31}$H$_{36}$N$_4$O$_4$S.1.0 H$_2$O.1.0 MeCN) calculated C (63.95), H (6.67), N (11.30), found C (63.94), H (6.75), N (11.26). HRMS (ESI) m/z calcd for 561.2544, found 561.2556.

EXAMPLE B45

Pyridine-2-carboxylic acid{(1S,2S)-1-benzyl-3-[5,5-dimethyl-4-(2-methyl-benzylcarbamoyl)-thiazolidin-3-yl]-2-hydroxy-3-oxo-propyl}-amide

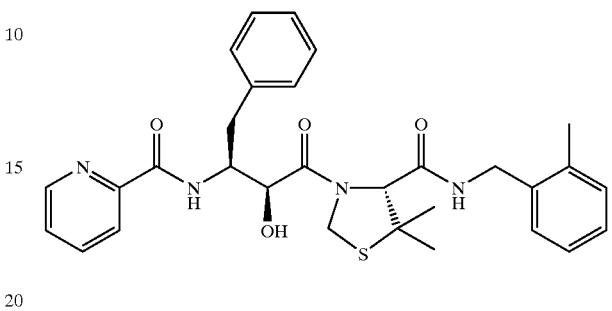

White solid: $^1$H NMR (DMSO-d$_6$) δ 8.89 (d, J=7.86,), 8.66 (d, J=4.2, 1H), 8.39 (t, J=6.54, 1H), 7.89 (m 2H), 7.32–7.12 (m, 9H), 5.68 (d, J=7.28, 1H), 5.03 (dd J=9.7, 8.3, 2H), 4.56(m 3H), 4.40 (d, J=7.5, 1H), 4.35 (d, J=7.5, 1H), 4.21 (d, J=6.7, 1H), 2.87–2.67 (m, 2H), 2.25 (s 3H), 1.49 (s, 3H), 1.34 (s, 3H); Anal. (C$_{30}$H$_{34}$N$_4$O$_4$S.0.1 H$_2$O.0.1 EtOAc) calculated C (65.52), H (6.33), N (10.05), found C (65.78), H (6.69), N (9.66). HRMS (ESI) m/z calcd for 547.2380, found 547.2373.

EXAMPLE B46

Pyridine-2-5-hydroxy-carboxylic acid{(1S,2S)-1-benzyl-3-[5,5-dimethyl-4-(2-methyl-benzylcarbamoyl)-thiazolidin-3-yl]-2-hydroxy-3-oxo-propyl}-amide

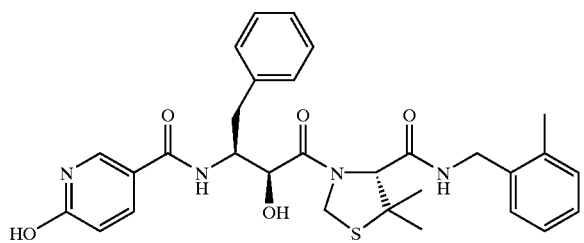

White solid: $^1$H NMR (DMSO-d$_6$) δ 8.89 (d, J=7.9, 1), 8.66 (d, J=4.2, 1H), 8.39 (t, J=6.54, 1H), 7.89 (m 2H), 7.32–7.12 (m, 9H), 5.68 (d, J=7.2, 1H), 5.03 (dd J=9.7, 8.3, 2H), 4.56(m 3H), 4.40 (d, J=7.5, 1H), 4.35 (d, J=7.5, 1H), 4.21 (d, J=6.7, 1H), 2.87–2.67 (m, 2H), 2.25 (s 3H), 1.49 (s, 3H), 1.34 (s, 3H); Anal. (C$_{30}$H$_{34}$N$_4$O$_5$S.0.5 H$_2$O.0.5 EtOAc) calculated C (62.29), H (6.42), N (9.91), found C (62.53), H (6.84), N (10.10). HRMS (ESI) m/z calcd for 563.2325, found 563.2328.

EXAMPLE B47

N-{(1S,2S)-1-Benzyl-3-[5,5-dimethyl-4-(2-methyl-benzylcarbamoyl)-thiazolidin-3-yl]-2-hydroxy-3-oxo-propyl}-nicotinamide

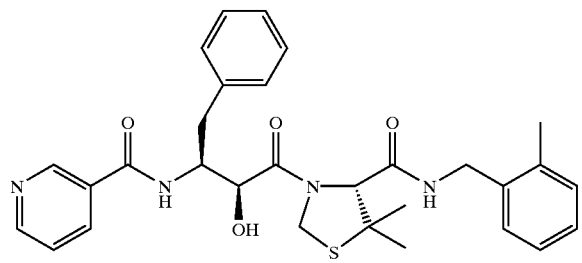

White solid $^1$H NMR (DMSO-d$_6$) δ 8.89 (d, J=7.9, 1H), 8.66 (d, J=4.2, 1H), 8.39 (t, J=6.54, 1H), 7.89 (m 2H), 7.32–7.12 (m, 9H), 5.68 (d, J=7.3, 1H), 5.03 (dd J=9.7, 8.3, 2H), 4.56(m 3H), 4.40 (d, J=7.5, 1H), 4.35 (d, J=7.5,1H), 4.21 (d, J=6.7,1H), 2.87–2.67 (m, 2H), 2.25 (s 3H), 1.49 (s, 3H), 1.34 (s, 3H); Anal. (C$_{30}$H$_{34}$N$_4$O$_4$S.0.5 H$_2$O.0.5 MeCN) calculated C (64.61), H (6.39), N (10.94), found C (65.02), H (6.58), N (10.90). HRMS (ESI) m/z calcd for 547.2372, found 547.2379.

EXAMPLE B48

N-{(1S,2S)-1-Benzyl-3-[5,5-dimethyl-4-(2-methyl-benzylcarbamoyl)-thiazolidin-3-yl]-2-hydroxy-3-oxo-propyl}-nicotinamide

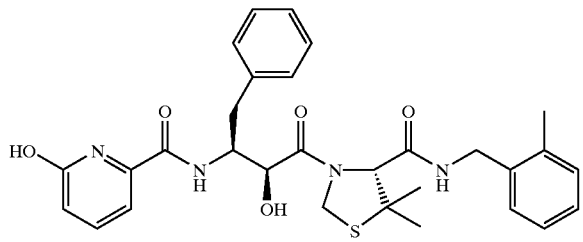

White solid: $^1$H NMR (DMSO-d$_6$) δ 8.89 (d, J=7.9, 1H), 8.66 (d, J=4.2, 1H), 8.39 (t, J=6.54, 1H), 7.89 (m 2H), 7.32–7.12 (m, 9H), 5.68 (d, J=7.28, 1H), 5.03 (dd J=9.7, 8.3, 2H), 4.56(m, 3H), 4.40 (d, J=7.5, 1H), 4.35 (d, J=7.5, 1H), 4.21 (d, J=6.7, 1H), 2.87–2.67 (m, 2H), 2.25 (s 3H), 1.49 (s, 3H), 1.34 (s, 3H); Anal. (C$_{30}$H$_{34}$N$_4$O$_4$S.1.3 H$_2$O) calculated C (61.42), H (6.32), N (9.49), found C (61.64), H (6.17), N (9.12). HRMS (ESI) m/z calcd for 563.2326, found 563.2328.

EXAMPLE B49

N-[(1S,2S)-3-(4-Allylcarbamoyl-5,5-dimethyl-thiazolidin-3-yl)-1-benzyl-2-hydroxy-3-oxo-propyl]-2-methyl-nicotinamide

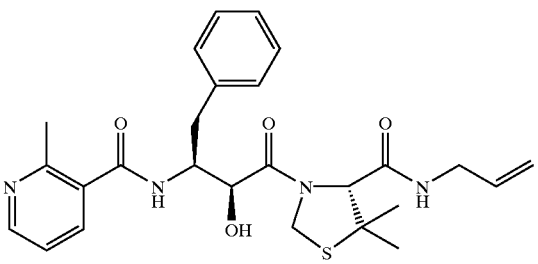

White solid: $^1$H NMR (DMSO-d$_6$), 8.58 (m, 1H), 8.29 (d, J=7.54, 1H), 7.78 (d, J=7.88, 2H), 7.32–7.12 (m, 7H), 5.78 (m, 1H), 5.18 (dd J=9.7, 8.3, 2H), 4.56(m, 3H), 4.40 (m, 4H), 2.87–2.67 (m, 2H), 2.25 (s 3H), 1.49 (s, 3H), 1.34 (s, 3H); Anal. (C$_{26}$H$_{32}$N$_4$O$_4$S.0.5 H$_2$O.0.5 TFA) calculated C (57.68), H (6.66), N (8.31), found C (57.66), H (6.18), N (8.77). HRMS (ESI) m/z calcd for 497.2232, found 497.2223.

General Methods C

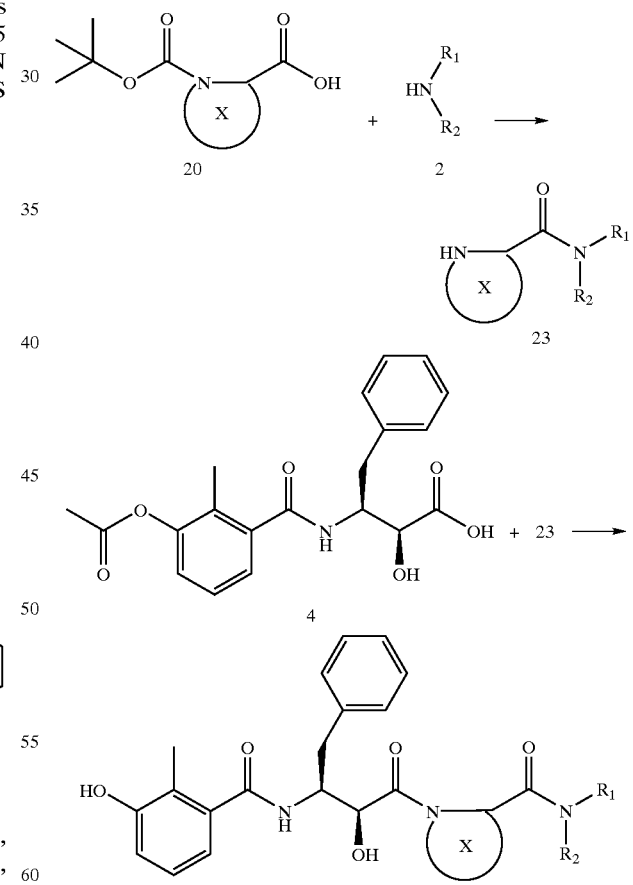

The synthesis of compounds with the general structure 24 is as follows. The boc-protected carboxylic acids 20a–f are coupled to the requisite amines 2 to yield amino amides 23 using a two step process. The process includes treatment of 20 with 2 in the presence of either diphenyl chlorophosphate or EDCI, followed by exposure to HCl or methane sulfonic acid. Final compounds 24 are obtained by a DCC-mediated coupling of 23 and 4 followed by deprotection of the P2 phenol. Final compounds were purified either by flash chromatography or preparative HPLC.

Additional General Method C solution stirred overnight at room temperature. The solution was poured into saturated $NaHCO_3$ and the product was extracted into ethyl acetate. The organic solution was washed with brine, dried over $Na_2SO_4$ and concentrated in vacuo. The crude was used without further purification unless otherwise noted.

$MeSO_3H$ Boc deprotection—To a solution of Boc-amine in ethyl acetate at 0° C. was added methane sulfonic acid and

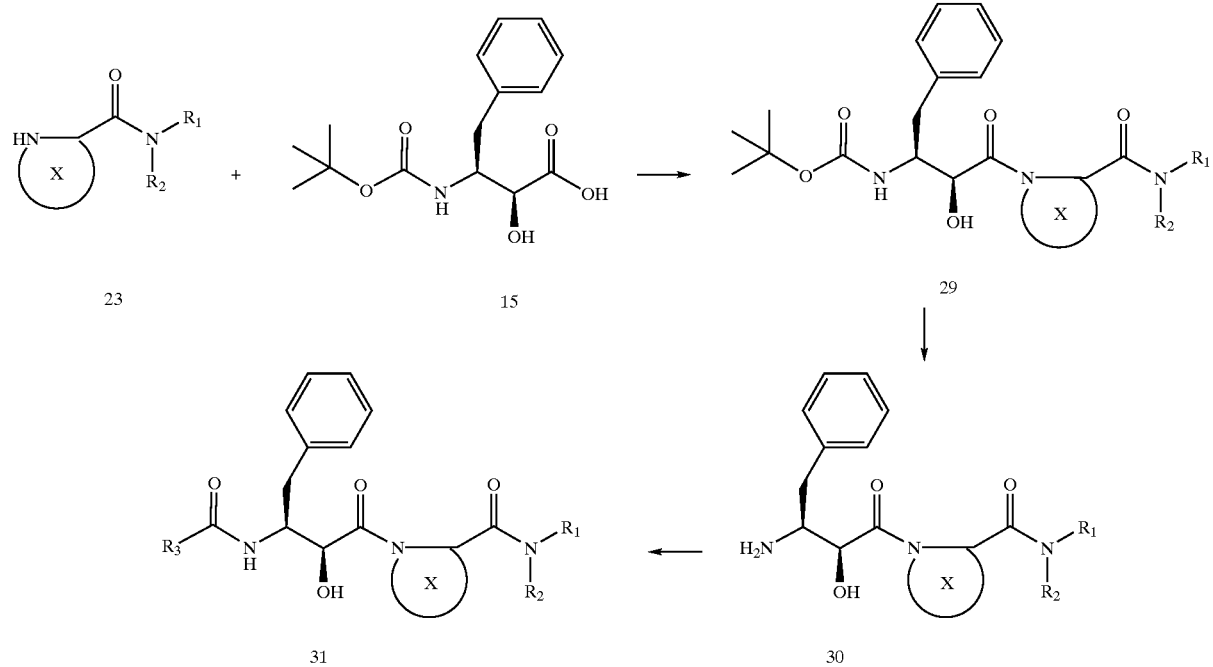

The synthesis of compounds of the general structure 31 (where P2 is not 2-methyl-3-hydroxy benzamide) is as follows. Amino amides of the general structure 23 were coupled to the Boc-acid intermediate 15 using DCC coupling conditions. The resulting intermediate 29 was deprotected under acidic conditions to yield amine of the general structure 30. Final compounds were obtained by modification of amine 30 by methods described in General Methods B section to give P2 amides and ureas.

Methods Used for Synthesis of Compounds with P1 Variations.

EDCI coupling—To a solution of acid, amine and HOBT in $CH_2Cl_2$ was added EDCI and the solution stirred overnight at room temperature. The solution was concentrated in vacuo and the residue dissolved in ethyl acetate and a small portion of water. The solution was washed with saturated $NH_4Cl$ (2×), saturated $NaHCO_3$ (2×), brine (1×), dried with $MgSO_4$ and concentrated in vacuo. The crude used without further purification unless otherwise noted.

DCC coupling—A solution of acid, amine and HOBT was prepared in ethyl acetate. To the solution was then added DCC in an EtOAc solution at 0° C. and the mixture was stirred overnight at room temperature. The mixture was filtered and the filtrate was concentrated in vacuo. The residue dissolved in ethyl acetate washed with saturated $NH_4Cl$ (1×), saturated $NaHCO_3$ (1×), brine (1×), dried over $Na_2SO_4$ and concentrated in vacuo. The crude was used without further purification unless otherwise noted.

4N HCl Boc deprotection—To a solution of Boc-amine in dioxane was added 4N HCl solution in dioxane and the the solution stirred 3–6 h at room temperature. The solution was cooled to 0° C. and sufficient saturated $NaHCO_3$ was added to quench the acid. The solution was diluted with ethyl acetate, washed with saturated $NaHCO_3$ and brine, dried over $Na_2SO_4$ and concentrated in vacuo. The crude used without further purification unless otherwise noted.

KCN Phenolic acetate deprotection—A solution of phenolic acetate and KCN in ethanol was heated at 50° C. overnight. The solution was concentrated in vacuo. The residue was purified by flash chromatography eluted with 0 to 5% methanol in $CH_2Cl_2$ unless otherwise noted.

NaOMe/MeOH Phenolic acetate deprotection—0.5 N $NaOCH_3$/MeOH Phenolic acetate deprotection—A solution of phenolic acetate in EtOAc and methanol was cooled to 0° C. in an ice bath. 0.5 N $NaOCH_3$/MeOH was then added dropwise and then stirred at 0° C. for 1.5–2 hrs following addition. Additional EtOAc was then added, the 0.15 N HCl (4.5 eq.) added dropwise. The phases were separated and organic phase washed with 2.5% $Na_2CO_3$ aqueous solution, then with 0.1 N HCl/brine (2:1), followed with brine, dried with $MgSO_4$ and concentrated in vacuo. The resulting residue subjected to flash silica gel chromatography to afford the desired product unless otherwise noted.

HCl/MeOH Phenolic acetate deprotection—To a solution of phenolic acetate in methanol was added 4N HCl in dioxane and the solution stirred at room temperature ca. 4 h. The solution was concentrated in vacuo. The residue was purified by flash chromatography eluted with 0 to 5% methanol in $CH_2Cl_2$ unless otherwise noted.

Fragments of the General Structure 20.

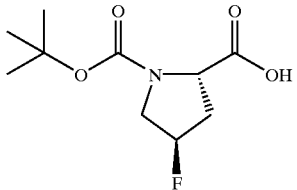
20b

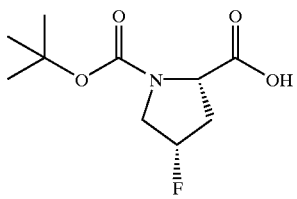
20c

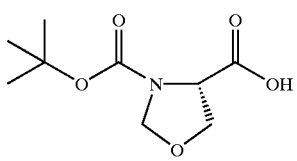
20c

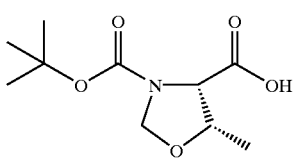
20d

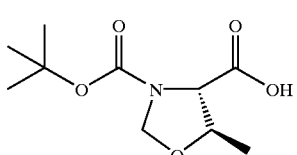
20e

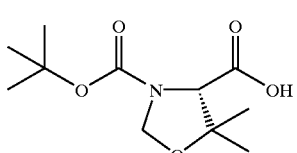
20f

Source of Boc-Carboxylic Acids 20a–f

Boc-acids 20a and 20b were prepared following the procedure of Demange, L.; Ménez, A.; Dugave, C. *Tet. Lett.* 1998, 39, 1169.

Boc-acids 20c, 20d, 20e and 20f were prepared following the procedure of Karanewsky, D.; et al. *J. Med Chem.* 1990, 33, 1459.

Specific Method C

EXAMPLE C1

(S)-4,4-Difluoro-1-[(2S,3S)-2-hydroxy-3-(3-hydroxy-2-methyl-benzoylamino)-4-phenyl-butyryl]-pyrrolidine-2-carboxylic Acid 2-methyl-benzylamide

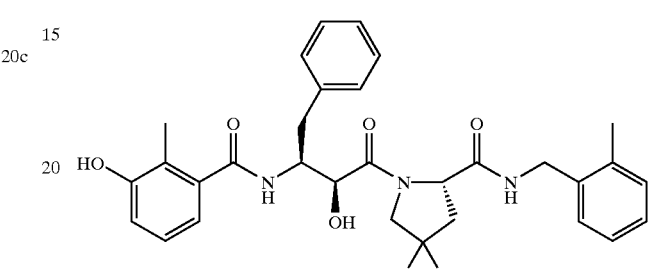

The title compound was prepared according to general methods using the corresponding Boc-protected pyrrolidinic acid (0.96 g, 3.8 mmol), o-methylbenzyl amine (0.57 mL, 4.6 mmol), HOBT (0.62 g, 4.6 mmol), EDCI (0.88 g, 4.6 mmol), $CH_2Cl_2$ (50 mL). To give the crude Boc-amide (MS-APCI (m/z+): 355, 255) (1.35 g, 3.8 mmol). The Boc was removed using the general 4N HCl Boc deprotection. 4N HCl in 1,4-dioxane (5 mL), 1,4-dioxane (5 mL). The result was amino amide of general structure 23. Isolated yield: 0.79 g (71%, 2 steps). $^1$H NMR (400 MHz, DMSO-$d_6$): δ 9.02 (t, 1H), 7.24–7.14 (m, 4H), 4.55 (t, 1H), 4.35 (dd, 1H), 4.30 (dd, 1H), 3.73 (m, 2H), 2.94 (m, 2H), 2.52 (m, 1H), 2.27 (s, 3H); $^{19}$F NMR (376 MHz, DMSO-$d_6$): δ −95.3 (dq, J=235, 15 Hz, 1F), −96.5 (dq, J=235, 12 Hz, 1F); MS-APCI (m/z+): 255.

Amino amide 23 (100 mg, 0.34 mmol) was coupled to carboxylic acid 4 (140 mg, 0.38 mmol) using the general DCC coupling method outlined above. HOBT (51 mg, 0.38 mmol), DCC (78 mg, 0.38 mmol), TEA (50 µL, 0.36 mmol), $CH_2Cl_2$ (10 mL). The crude was purified by chromatography eluted with 10% acetone in $CH_2Cl_2$. Isolated yield: 0.13 g (63%). MS-APCI (m/z+): 608. This material was subjected to the general KCN phenolic acetate deprotection conditions (130 mg, 0.21 mmol), KCN (1 mg, 15 µmol), ethanol (10 mL). The crude was precipitated from diethyl ether and ethyl acetate with hexanes at −78° C. Isolated yield: 0.10 g (84%). $^1$H NMR (400 MHz, DMSO-$d_6$): δ 9.37 (s, 1H), 8.36 (t, 1H), 8.16 (d, 1H), 7.32–7.09 (m, 9H), 6.93 (t, 1H), 6.76 (d, 1H), 6.54 (d, 1H), 5.49 (d, 1H), 4.66 (dd, 1H), 4.34–4.15 (m, 6H), 2.85–2.67 (m, 3H), 2.40 (m, 1H), 2.22 (s, 3H), 1.79 (s, 3H); $^{19}$F NMR (376 MHz, DMSO-$d_6$): δ −98.7 (m, 2F); MS-APCI (m/z+): 566; HPLC Purity: 100%; Rf (min.) 19.01; Anal. $C_{31}H_{33}N_3O_5F_2 \cdot 0.3\ H_2O$ C, H, N calcd: C65.21, H5.93, N7.36; found: C65.11, H5.90, N7.17.

EXAMPLE C2

(2S,3S)-4-Fluoro-1-[(2S,3S)-2-hydroxy-3-(3-hydroxy-2-methyl-benzoylamino)-4-phenyl-butyryl]-pyrrolidine-2-carboxylic Acid 2-methyl-benzylamide

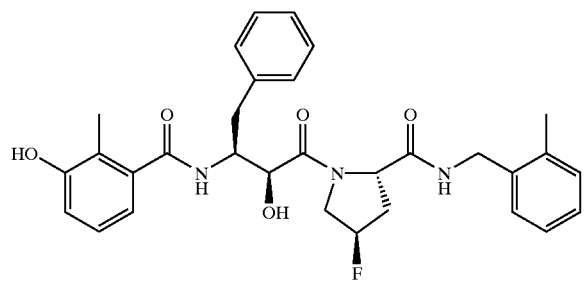

Isolated material was subjected to flash silica gel chromatography, eluting with EtOAc/hexanes (50/50) then with EtOAc EtOAc/hexanes (4:1) to afford the title compound. $^1$H NMR (400 MHz, DMSO-$d_6$): δ 9.37 (s, 1H), 8.46 (t, 1H), 8.21 (d, 1H), 7.34 (d, 2H), 7.26 (d, 2H), 7.21 (t, 2H), 7.15–7.07 (m, 3H), 6.94 (t, 1H), 6.76 (d, 1H), 6.56 (d, 1H), 5.51+5.38 (bs+bs, 1H), 5.06 (d, 1H), 4.58 (t, 1H), 4.45 (dd, 1H), 4.35–4.27 (m, 2H), 4.21–4.09 (m, 3H), 3.94–31.91+3.84–3.81 (m+m, 1H), 2.69 (d, 2H), 2.23 (s, 3H), 2.19–2.01 (m, 1H), 1.83 (s, 3H); MS-APCI (m/z+): 548; HPLC: Rf(min.) 18.72; Purity: 96%. Anal. $C_{31}H_{34}N_3O_5F$·0.3 $H_2O$ calcd: 67.33, 6.31, 7.60, found: 67.37, 6.25, 7.535.

EXAMPLE C3

(2S,3S)-4-Fluoro-1-[(2S,3S)-2-hydroxy-3-(3-hydroxy-2-methyl-benzoylamino)-4-phenyl-butyryl]-pyrrolidine-2-carboxylic Acid 2-methyl-benzylamide

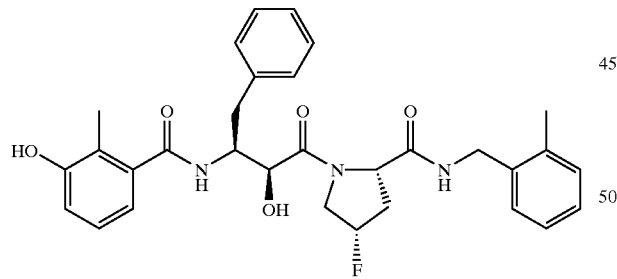

Isolated material was subjected to flash silica gel chromatography, eluting with EtOAc/hexanes (50/50) then with EtOAc to afford the title compound. $^1$H NMR (400 MHz, DMSO-$d_6$): δ 9.37 (s, 1H), 8.21 (d, 1H), 7.96 (t, 1H), 7.29 (d, 2H), 7.23 (t, 2H), 7.18–7.13 (m, 2H), 7.10–7.04 (m, 3H), 6.90 (t, 1H), 6.75 (d, 1H), 6.52 (d, 1H), 5.55 (d, 1H), 5.45+5.32 (bs+bs, 1H), 4.54 (d, 1H), 4.42–4.36 (m, 1H), 4.29–4.40 (m, 5H), 2.98 (t, 1H), 2.73 (t, 1H), 2.32–2.21 (m, 2H), 2.19 (s, 3H), 1.78 (s, 3H); MS-APCI (m/z+): 548; HPLC: Rf(min.) 18.21; Purity: 99%; Anal. $C_{31}H_{34}N_3O_5F$·0.5 $H_2O$ calcd: 66.89, 6.34, 7.55, found: 66.85, 6.22, 7.41.

EXAMPLE C4

(S)-3-((2S,3S)-2-Hydroxy-3-{[1-(3-hydroxy-2-methyl-phenyl)-methanoyl]-amino}-4-phenyl-butanoyl)-oxazolidine-4-carboxylic Acid 2-methyl-benzylamide

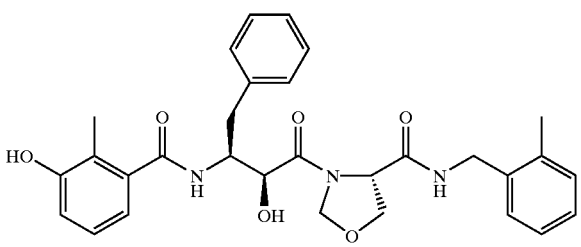

White solid; $^1$H NMR (DMSO-$d_6$) δ 9.36 (s, 1H), 8.80 (dd, J=8.8, 4.8, 1H), 8.30 (t, J=5.5, 1H), 8.12 (d, J=8.6, 1H), 7.30–7.13 (m, 9H), 6.96 (t, J=7.9, 1H), 6.76 (d, J=7.9, 1H), 6.55 (d, J=7.2, 1H), 5.74 (d, J=8.8, 1H), 5.31 (d, J=3.8, 1H), 5.23 (d, J=4.2, 1H), 4.49 (dd, J=6.6, 6.5, 1H), 4.33–4.11 (m, 5H), 2.94–2.68 (m, 2H), 2.24 (s, 3H), 1.78 (s, 3H); HRMS (ESI) m/z calcd for $C_{30}H_{34}N_3O_6$ (M+H)$^+$ 532.2448, found 532.2450.

EXAMPLE C5

(4S,5R)-3-((2S,3S)-2-Hydroxy-3-{[1-(3-hydroxy-2-methyl-phenyl)-methanoyl]-amino}-4-phenyl-butanoyl)-5-methyl-oxazolidine-4-carboxylic Acid 2-methyl-benzylamide

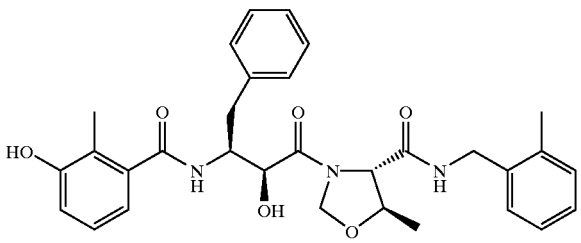

White solid; $^1$H NMR (DMSO-$d_6$) δ 9.38 (s, 1H), 8.51 (t, J=6.0, 1H), 8.15 (d, J=8.4, 1H), 7.33–7.13 (m, 9H), 6.96 (t, J=7.7, 1H), 6.79 (d, J=8.2, 1H), 6.58 (d, J=7.3, 1H), 5.69 (d, J=5.7, 1H), 5.50 (d, J=4.6, 1H), 5.10 (d, J=4.8, 1H), 4.39–4.22 (m, 4H), 4.11–4.01 (m, 2H), 2.90 (m, 1H), 2.74 (m, 1H), 2.27 (s, 3H), 1.82 (s, 3H), 1.37 (d, J=5.9, 1H); HRMS (ESI) m/z calcd for $C_{31}H_{36}N_3O_6$ (M+H)$^+$ 546.2604, found 546.2595.

EXAMPLE C6

(S)-3-((2S,3S)-2-Hydroxy-3-{[1-(3-hydroxy-2-methyl-phenyl)-methanoyl]-amino}-4-phenyl-butanoyl)-5,5-dimethyl-oxazolidine-4-carboxylic Acid 2-methyl-benzylamide

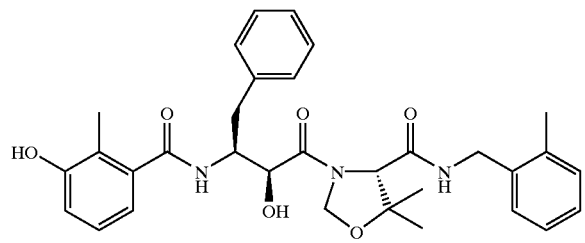

White solid; $^1$H NMR (DMSO-d$_6$) δ 9.34 (s, 1H), 8.32 (t, J=5.8, 1H), 8.11 (J=9.0, 1H), 7.31–7.10 (m, 9H), 6.93 (t, J=7.9, 1H), 6.76 (d, J=8.1, 1H), 6.55 (d, J=6.5, 1H), 5.73 (d, J=4.0, 1H), 5.46 (d, J=4.1, 1H), 5.23 (d, J=3.9, 1H), 4.39–4.32 (m, 2H), 4.18 (m, 3H), 2.92 (m, 1H), 2.69 (m, 1H), 2.27 (s, 3H), 1.81 (s, 3H), 1.28 (s, 3H), 1.18 (s, 3H); HRMS (ESI) m/z calcd for $C_{32}H_{38}N_3O_6$ (M+H)$^+$ 560.2761, found 560.2759; Anal. Calcd for $C_{32}H_{37}N_3O_6$·0.5 $H_2O$: C, 67.59; H, 6.74; N, 7.39. Found: C, 67.74; H, 6.75; N, 7.16.

EXAMPLE C7

(S)-3-((2S,3S)-2-Hydroxy-3-{[1-(3-hydroxy-2-methyl-phenyl)-methanoyl]-amino}-4-phenyl-butanoyl)-5,5-dimethyl-oxazolidine-4-carboxylic Acid Propylamide

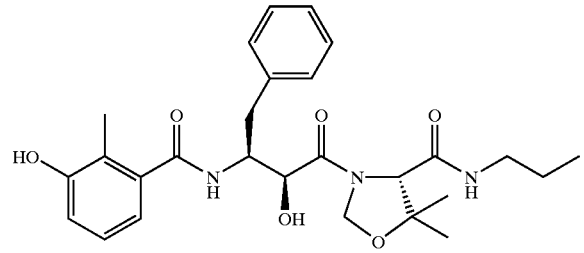

$^1$H NMR (DMSO-d$_6$) δ 9.37 (s, 1H), 8.12 (d, J=9.3, 1H), 7.93 (t, J=5.6, 1H), 7.34–7.18 (m, 5H), 6.96 (t, J=8.1, 1H), 6.79 (d, J=8.1, 1H), 6.56 (d, J=7.1, 1H), 5.73 (d, J=6.2, 1H), 5.44 (d, J=4.0, 1H), 5.24 (d, J=3.8, 1H), 4.36 (m, 1H), 4.18 (m, 1H), 4.11 (s, 1H), 3.10–2.92 (m, 3H), 2.75–2.66 (m, 1H), 1.80 (s, 3H), 1.46–1.39 (m, 2H), 1.31 (s, 3H), 1.22 (s, 3H), 0.86 (t, J=7.2, 3H); HRMS (ESI) m/z calcd for $C_{27}H_{36}N_3O_6$ (M+H)$^+$ 498.2604, found 498.2590.

EXAMPLE C8

(4S,5R)-3-((2S,3S)-2-Hydroxy-3-{[1-(3-hydroxy-2-methyl-phenyl)-methanoyl]-amino}-4-phenyl-butanoyl)-5-methyl-oxazolidine-4-carboxylic Acid 2-methyl-benzylamide

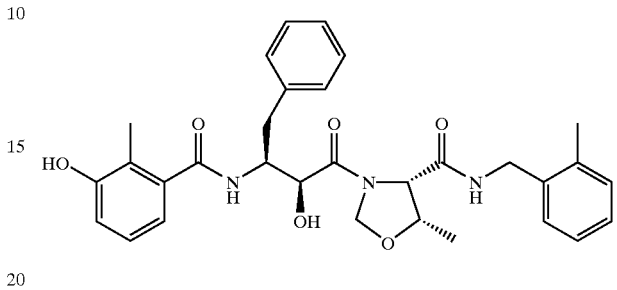

White solid; $^1$H NMR (DMSO-d$_6$) δ 9.36 (s, 1H), 8.26 (t, J=5.5, 1H), 8.09 (d, J=8.8, 1H), 7.30–7.08 (m, 9H), 6.93 (t, J=7.7, 1H), 6.76 (d, J=7.9, 1H), 6.56 (d, J=7.5, 1H), 5.72 (d, J=6.4, 1H), 5.55 (d, J=3.7, 1H), 5.08 (d, J=3.8, 1H), 4.40–4.33 (m, 3H), 4.26–4.11 (m, 3H), 3.10–2.89 (m, 1H), 2.78–2.67 (m, 1H), 2.26 (s, 3H), 1.78 (s, 3H), 1.15 (d, J=6.2, 3H); HRMS (ESI) m/z calcd for $C_{31}H_{36}N_3O_6$ (M+H)$^+$ 546.2604, found 546.2592.

EXAMPLE C9

(S)-3-((2S,3S)-2-Hydroxy-3-{[1-(3-hydroxy-2-methyl-phenyl)-methanoyl]-amino}-4-phenyl-butanoyl)-5,5-dimethyl-oxazolidine-4-carboxylic Acid 5-fluoro-2-methyl-benzylamide

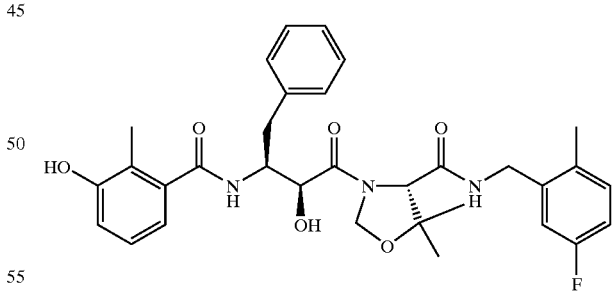

White solid; $^1$H NMR (DMSO-d$_6$) δ 9.35 (s, 1H), 8.41 (t, J=5.6, 1H), 8.12 (d, J=8.9, 1H), 7.28–7.08 (m, 8H), 6.95–6.90 (m, 1H), 6.76 (d, J=8.1, 1H), 6.55 (d, J=7.2, 1H), 5.78 (d, J=6.1, 1H), 5.47 (d, J=3.8, 1H), 5.24 (d, J=3.8, 1H), 4.40–4.25 (m, 2H), 4.20–4.10 (m, 3H), 3.00–2.60 (m, 2H), 2.22 (s, 3H), 1.77 (s, 3H), 1.30 (s, 3H), 1.19 (s, 3H); Anal. Calcd for $C_{32}H_{36}N_3O_6F$: C, 66.54; H, 6.28; N, 7.27. Found: C, 66.37; H, 6.20; N, 7.21.

EXAMPLE C10

(S)-3-((2S,3S)-2-Hydroxy-3-{[1-(3-hydroxy-2-methyl-phenyl)-methanoyl]-amino}-4-phenyl-butanoyl)-5,5-dimethyl-oxazolidine-4-carboxylic Acid cyanomethyl-amide

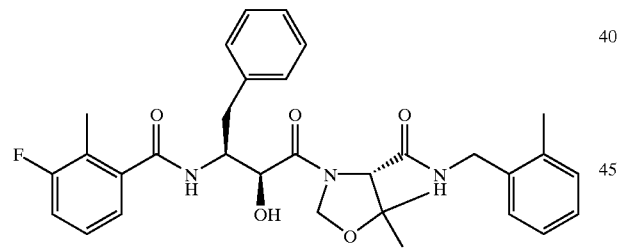

White solid; $^1$H NMR (DMSO-d$_6$) δ 9.36 (s, 1H), 8.72 (t, J=5.3, 1H), 8.11 (d, J=9.0, 1H), 7.29–7.16 (m, 5H), 6.94 (t, J=7.7, 1H), 6.76 (d, J=8.1, 1H), 6.50 (d, J=7.5, 1H), 5.85 (d, J=6.0, 1H), 5.49 (d, J=4.0, 1H), 5.23 (d, J=3.9, 1H), 4.35 (m, 1H), 4.18–4.12 (m, 3H), 4.11 (s, 1H), 2.92 (m, 1H), 2.70 (m, 1H), 1.76 (s, 3H), 1.29 (s, 3H), 1.19 (s, 3H); HRMS (ESI) m/z calcd for $C_{26}H_{31}N_4O_6$ (M+H)$^+$ 495.2244, found 495.2239.

EXAMPLE C11

(S)-3-((2S,3S)-3-{[1-(3-Fluoro-2-methyl-phenyl)-methanoyl]-amino}-2-hydroxy-4-phenyl-butanoyl)-5,5-dimethyl-oxazolidine-4-carboxylic Acid 2-methyl-benzylamide

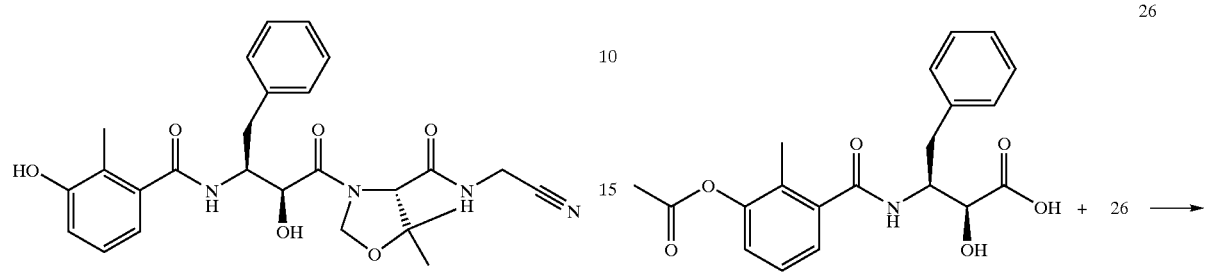

$^1$H NMR (DMSO-d$_6$) δ 8.34 (m, 2H), 7.30–7.13 (m, 11H), 6.95 (d, J=7.1, 1H), 5.82 (d, J=6.4, 1H), 5.45 (d, J=3.9, 1H), 5.23 (d, J=4.0, 1H), 4.38–4.31 (m, 2H), 4.18–4.15 (m, 3H), 2.96 (m, 1H), 2.67 (m, 1H), 2.26 (s, 3H), 1.87 (s, 3H), 1.28 (s, 3H), 1.18 (s, 3H); HRMS (ESI) m/z calcd for $C_{32}H_{37}N_3O_5F$ (M+H)$^+$ 562.2717, found 562.2713.

General Methods D

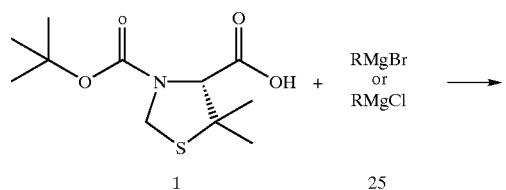

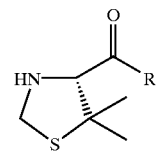

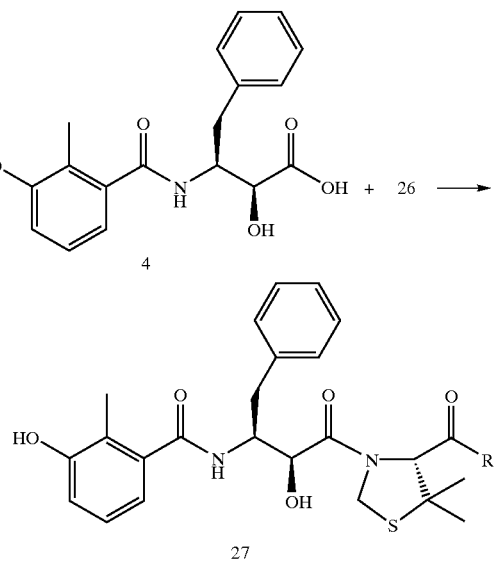

The synthesis of compounds with the general structure 27 is as follows. The boc-protected thiazolidine carboxylic acid 1 is converted to amino-ketones 26 with requisite grignard reagents 25 in the presence of oxalyl chloride. Final compounds 27 are obtained by a DCC-mediated coupling of 26 and 4 followed by deprotection of the P2 phenol. Final compounds were purified either by flash chromatography or preparative HPLC.

Specific Method D

EXAMPLE D1

N-[(1S,2S)-1-Benzyl-3-((R)-5,5-dimethyl-4-pent-4-enoyl-thiazolidin-3-yl)-2-hydroxy-3-oxo-propyl]-3-hydroxy-2-methyl-benzylamide

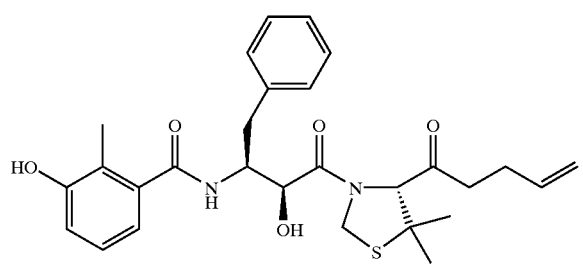

The title compound was prepared as follows. (R)-5,5-Dimethyl-thiazolidine-3,4-dicarboxylic acid 3-tert-butyl ester 1 (1.0 g, 3.80 mmol) was dissolved in benzene (10 mL) and cooled to 0° C. with magnetic stirring. Two drops of DMF were added followed by a drop wise addition of oxalyl chloride (0.33 mL, 3.80 mmol). When gas evolution ceased, the solution was concentrated to a yellow/red residue. The material was dissolved in dry THF (10 mL) and cooled to −78° C. with magnetic stirring. The grignard reagent, 3-butenylmagnesium bromide (7.7 mL, 3.80 mmol) was added dropwise over 10 min. The result was stirred at −78° C. for 1 h then at −55° C. for 30 min. The reaction was quenched at −55° C. with sat NH$_4$Cl soln.(3 mL) and then poured into H$_2$O (50 mL). The mixture was extracted with EtOAc (2×50 mL). The combined organics were washed with brine (1×100 mL), dried over Na$_2$SO$_4$, filtered, and concentrated. The result was the amino ketone 26 that was sufficiently pure to use in the subsequent step. The clear oil 26 (0.24 g, 1.15 mmol) was dissolved in EtOAc (10 mL). AMB-AHPBA 4 (0.40 g, 1.09 mmol) was added followed by HOBt (0.15 g, 1.09 mmol). The mixture was stirred at room temperature 1 h, then cooled to 0° C. DCC (0.24 g, 1.15 mmol) was slowly added as solution in EtOAc (6 mL). The mixture was warmed to room temperature and stirred overnight. The mixture was filtered and the filtrate was washed with 1N HCl (10 mL), saturated NaHCO$_3$ (11 mL), brine (10 mL), dried over Na$_2$SO$_4$ and concentrated to give a crude white solid (contaminated with DCU). The DCU was removed by flash chromatography (30% to 50% EtOAc in hexanes) to provide a white solid, which was dissolved in MeOH (2 mL) and treated with 4N HCl in 1,4-dioxane (0.26 mL, 1.1 mmol). The reaction was stirred at room temperature overnight then partitioned between 1N HCl (10 mL) and EtOAc (10 mL). The organic layer was washed with saturated sat. NaHCO$_3$ (1×25 mL) dried over Na$_2$SO$_4$, filtered, and concentrated to a residue which was purified by flash chromatography (60% EtOAc in hexanes) to provide the title compound as a white amorphous solid: $^1$H NMR (DMSO-d$_6$) δ 9.36 (s, 1H), 8.23 (d, J=8.1, 1H), 7.35–7.14 (m, 5H), 6.96 (t, J=7.5, 1H), 6.78 (d, J=8.2, 1H), 6.52 (d, J=7.5, 1H), 5.81–5.69 (m, 2H), 5.32 (d, J=9.7, 1H), 5.11–5.91 (m, 3H), 4.40 (m, 3H), 2.89–2.61 (m, 4), 2.37–2.14 (m, 2H), 1.81 (s, 3H), 1.55 (s, 3H), 1.30 (s, 3H); Anal. Calcd for C$_{28}$H$_{34}$N$_2$O$_5$S: C, 65.86; H, 6.71; N, 5.49. Found: C, 65.52; H, 6.55; N, 5.81.

The following examples were synthesized using the specific method outlined above using the appropriate grignard reagent for the desired compound.

EXAMPLE D2

N-{1-Benzyl-3-[5,5-dimethyl-4-(4,4,4-trifluoro-butanoyl)-thiazolidin-3-yl]-2-hydroxy-3-oxo-propyl}-3-hydroxy-2-methyl-benzamide

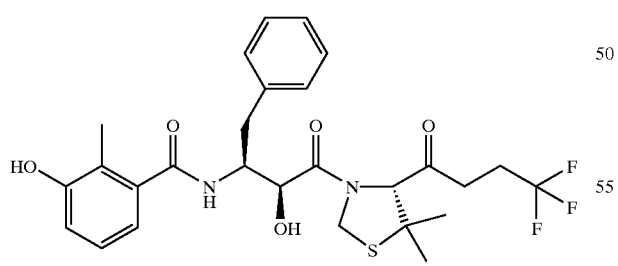

$^1$H NMR (DMSO-d$_6$) δ 9.34 (s, 1H), 8.16 (d, 1H, J=8.6), 7.29–6.49 (m, 8H), 5.88 (d, 1H, J=6.1), 5.33 (d, 1H, J=9.5), 5.10 (d, 1H, J=9.5), 4.56 (s br, 3H), 2.98–2.57 (m, 6H), 1.74 (s, 3H), 1.55 (s, 3H), 1.30 (s, 3H); HRMS (ESI) m/z calcd for C$_{27}$H$_{32}$N$_2$O$_5$SF$_3$ (M+H)$^+$ 553.1984, found 553.1984; Anal. Calcd for C$_{27}$H$_{31}$N$_2$O$_5$SF$_3$·0.5H$_2$O: C, 58.59; H, 5.66; N, 5.06; S, 5.79. Found: C, 58.96; H, 6.02; N, 5.58; S, 5.33.

EXAMPLE D3

N-{1-Benzyl-2-hydroxy-3-[4-(4-methoxy-butanoyl)-5,5-dimethyl-thiazolidin-3-yl]-3-oxo-propyl}-3-hydroxy-2-methyl-benzamide

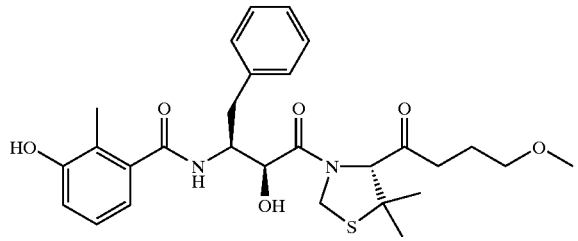

$^1$H NMR (DMSO-d$_6$) δ 9.34 (s, 1H), 8.18 (d, 1H, J=8.2), 7.32–6.51 (m, 8H), 5.56 (d, 1H, J=7.8), 5.26 (d, 1H, J=9.5), 5.08 (d, 1H, J=9.5), 4.45–4.38 (m, 2H), 4.36 (s, 1H), 3.15 (s, 3H), 2.93–2.61 (m, 2H), 1.87–1.00 (m, 6H), 1.80 (s, 3H), 1.55 (s, 3H), 1.36 (s, 3H); HRMS (ESI) m/z calcd for C$_{28}$H$_{37}$N$_2$O$_6$S (M+H)$^+$ 529.2165, found 529.2372; Anal. Calcd for C$_{28}$H$_{36}$N$_2$O$_6$S·0.5H$_2$O: C, 62.55; H, 6.94; N, 5.21; S, 5.96. Found C, 62.89; H, 7.32; N. 5.96; S, 5.59.

EXAMPLE D4

(R)-3-[(2S,3S)-2-Hydroxy-3-(3-hydroxy-2,5-dimethyl-benzoylamino)-4-phenyl-butyryl]-5,5-dimethyl-thiazolidine-4-carboxylic Acid Allylamide

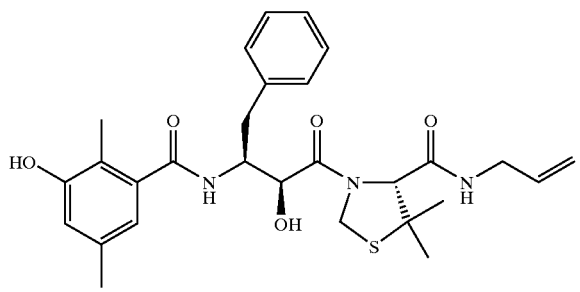

White solid: $^1$H NMR (DMSO-d$_6$) δ 9.23 (s, 1H), 8.09 (m, 2H), 7.35–7.17 (m, 5H), 6.60 (s, 1H), 6.37 (s, 1H), 5.82–5.68 (m, 1H), 5.41 (br s, 1H), 5.20 (dd, 1H, J=1.6, 17.2), 5.11 (d, 1H, J=9.2), 5.02 (dd, 1H, J=1.5, 10.2), 5.00 (d, 1H, J=9.1), 4.46–4.37 (m, 3H), 3.79 (ddd, 1H, J=5.3, 5.5, 15.9), 3.63 (ddd, 1H, J=5.4, 5.3, 15.9), 2.82 (dd, 1H, J=0.3, 13.9), 2.71 (dd, 1H, J=10.7, 13.6), 2.16 (s, 3H), 1.76 (s, 3H), 1.51 (s, 3H), 1.36 (s, 3H); HRMS (ESI) m/z calcd for C$_{28}$H$_{36}$N$_3$O$_5$S (M+H)$^+$ 526.6670, found 526.2376; Anal. Calcd for C$_{28}$H$_{35}$N$_3$O$_5$S·0.3 H$_2$O: C, 63.32; H, 6.76; N, 7.91, Found: C, 63.35; H, 6.70; N, 7.71.

Combinatorial Chemistry Approach to HIV Protease P2' Inhibitors

General Method E

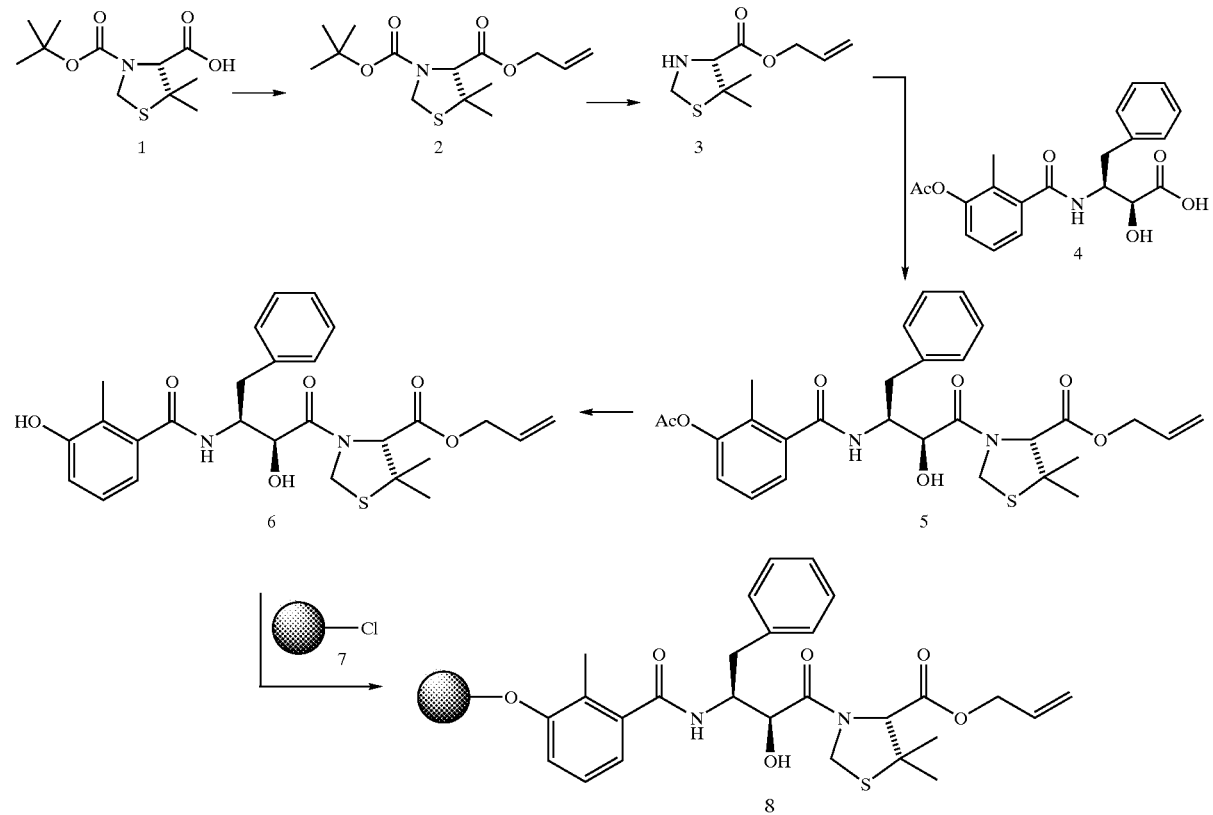

The combinatorial building block, 8, is prepared using the following method. The boc-protected thiazolidine carboxylic acid, 1, is treated with allyl bromide in the presence of NaHCO₃ to yield the boc-protected thiazolidine allyl ester, 2. Deprotection of boc-protected allyl ester, 2, with HCl (g) in EtOAc gives the HCl salt of the thiazolidine allyl ester amine, 3, which is treated with TEA and coupled to 4 in the presence of HOBT and DCC to give the building block precursor, 5. Deprotection of the building block, 5, with 4N HCl yields the phenol, 6. Loading the building block, 6, on to activated cross-linked trityl chloride polystyrene beads, 7, was accomplished in the following manner. The polystyrene cross-linked trityl alcohol was activated to the trityl chloride, 7, by treatment with 20% acetyl chloride in anhydrous CH₂Cl₂ at room temperature. The trityl chloride beads were combined with the phenol 6 in the presence of Hunig's base in anhydrous CH₂Cl₂ to yield the substrate loaded polystyrene beads 8. Intermediates were purified either by flash chromatography or preparative HPLC.

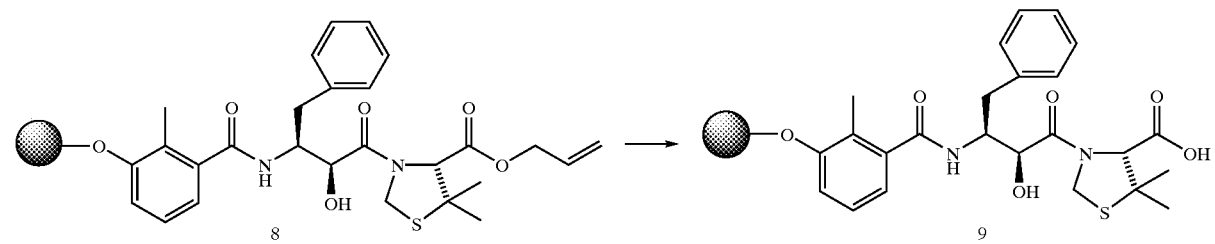

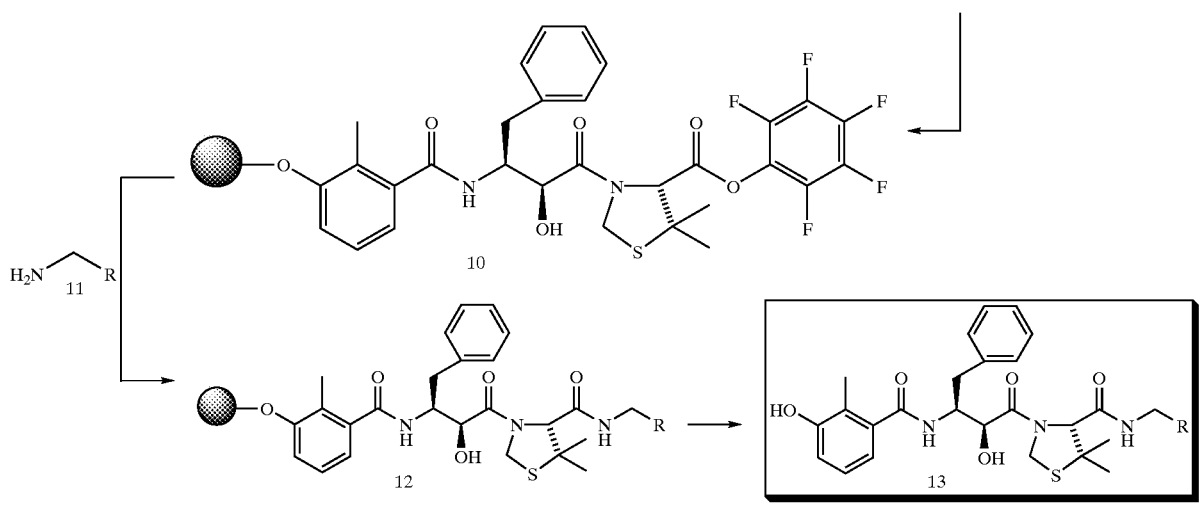

The synthesis of the HIV protease combinatorial library was carried out in the following fashion. The allyl ester was removed by treatment with Pd[PPh$_3$]$_4$ and NMM in anhydrous THF to give carboxylate 9, which was treated with pentafluorophenol, pentafluorophenol trifluoromethyl acetate and pyridine in DMF to yield the pentafluoro ester, 10. The pentafluoro ester 10 was treated with various primary amines in a 96-well plate format to give amides 12. The final products were cleaved from the polystyrene crowns with TFA to give products 13. Each product was analyzed by LCMS and HPLC. The following table typifies compounds synthesized by this combinatorial method.

TABLE 1

| P2' | Expected Mass (LCMS) | Observed Mass | % Inhibition |
|---|---|---|---|
| HO–CH(CH$_3$)–CH$_2$–NH$_2$ | 529 | 552(Na$^+$) | 38 |
| H$_2$N–CH$_2$CH$_2$–N(CH$_3$)H | 528 | 529(MH$^+$) | 4 |
| H$_2$N–CH$_2$CH$_2$–C$_6$H$_4$–OH | 591 | 614(Na$^+$) | 18 |
| H$_3$C–C(CH$_3$)$_2$–CH$_2$CH$_2$–NH$_2$ | 555 | 578(Na$^+$) | 19 |

TABLE 1-continued

| P2' | Expected Mass (LCMS) | Observed Mass | % Inhibition |
|---|---|---|---|
| NH$_2$–CH$_2$CH$_2$–C$_6$H$_3$(OCH$_3$)$_2$ | 635 | 658(Na$^+$) | 5 |
| ClH·H$_2$N–CH$_2$CH$_2$–C$_6$H$_4$–NO$_2$ | 656 | 656(MH$^+$) | 8 |
| H$_2$N–CH$_2$–C$_6$H$_4$–CH$_3$ (o-) | 575 | 598(Na$^+$) | 86 |
| H$_3$C–C(CH$_3$)$_2$–CH$_2$–NH$_2$ | 541 | 564(Na$^+$) | 63 |
| H$_2$N–CH$_2$CH$_2$CH$_2$–OH | 529 | 552(Na$^+$) | 49 |

Scheme 3:
Solid Phase Synthesis Of HIV Protease Inhibitors (AG 1776 Analogs)

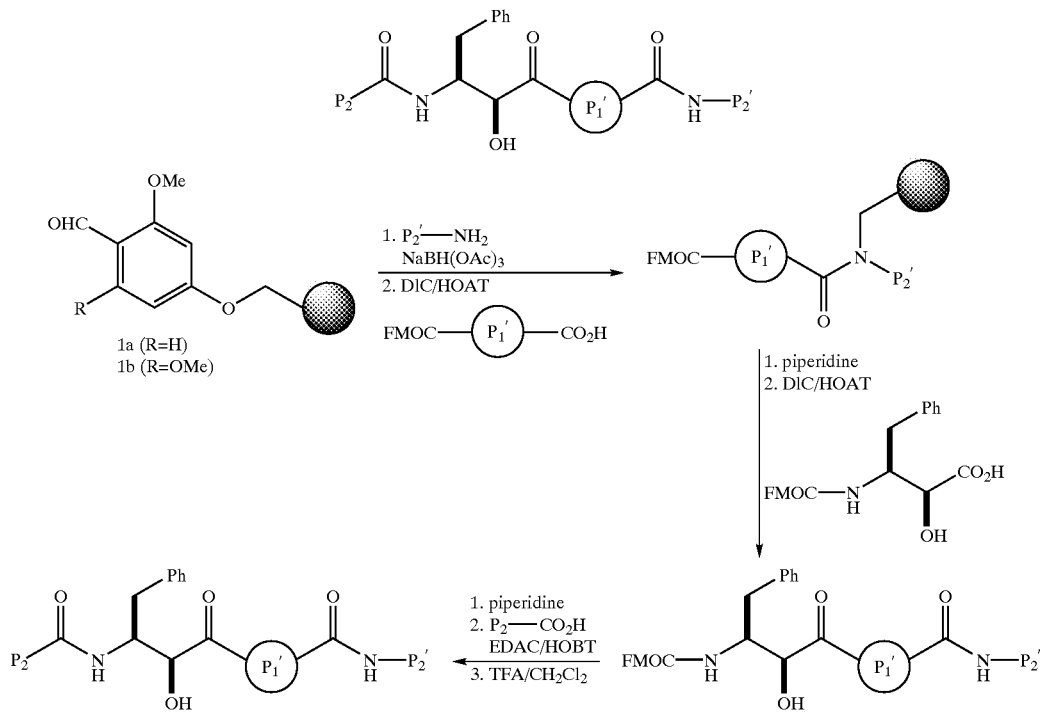

The solid phase combinatorial synthesis of HIV protease inhibitors was performed using the IRORI Directed Sorting Technology. Commercial 4-formyl-3-methoxyphenoxymethyl polystyrene resin 1a (PS-MB-CHO, Argonaut Technologies) or 4-formyl-3,5-dimethoxyphenoxymethyl polystyrene resin 1b (PL-FDMP resin, Polymer Laboratories) was loaded into individual Minikans.

Step A. Reductive Amination With $P_2'$ Amines

To separate flasks containing sorted MiniKans was added DCM (3 mL/MiniKan). The appropriate primary $P_2'$ amine (3 eq), sodium triacetoxyborohydride (5 eq), and acetic acid (3 eq) were added, and the mixtures were placed under argon, agitated with periodic venting at room temperature for 1–2 hours, and allowed to react overnight. For resin 1a, the filtrates were poured off and the MiniKans were washed with DCM, MeOH (2×), DCM (2×), Et$_3$N/DCM (1:3, 3×), DCM (2×), MeOH (3×), and DCM (4×). For resin 1b, a washing sequence of DCM, MeOH (2×), DCM (2×), Et$_3$N/DCM (1:3, 3×), DCM (2×), DMF, 1M NaOH/DMF (1:5, 3×), DMF (3×), MeOH (3×), and DCM (3×) was used. The MiniKans were dried under vacuum and taken on in Step B.

Step B. Peptide Coupling With $P_1'$ Amino Acids

To separate flasks containing the sorted MiniKans was added DMF (3 mL/MiniKan). The appropriate FMOC-protected amino acid (2.5 eq) and 1-hydroxy-7-azabenzotriazole (HOAT) (3 eq) were added and mixed until dissolved, and 1,3-diisopropylcarbodiimide (DIC) (3 eq) was added. The containers were placed under argon and agitated at room temperature overnight. The filtrates were poured off, and the MiniKans were washed with DMF (3×), MeOH (3×), DCM (2×), and DMF (2×). The MiniKans were taken directly on to Step C.

Step C. FMOC Deprotection

A container of MiniKans in DMF and piperidine (25%) with a total reaction volume of 3 mL/MiniKan was agitated under argon at room temperature for 45 minutes. The filtrate was removed, and the reaction procedure was repeated. The MiniKans were filtered and washed with DMF (3×), MeOH (2×), DCM (3×), and DMF, and taken directly on to Step D.

Step D. Peptide Coupling With FMOC-APNS

FMOC-Allophenylnorstatine (APNS) (3 eq) was added to the flask of MiniKans in DMF (3 mL/MiniKan). After dissolution, HOAT (3.5 eq) and DIC (3.5 eq) were added. The mixture was placed under argon and agitated at room temperature overnight. The reaction was filtered and the MiniKans were washed with DMF (3×), MeOH (3×), DCM (3×), and DMF. FMOC deprotection was carried out as in Step C, and the MiniKans were washed with DMF (3×), MeOH (2×), DCM (3×), dried under vacuum and taken on to Step E or F.

Step E. Peptide Coupling With $P_2$ Acids

To separate flasks containing the sorted MiniKans in DMF (3 mL/MiniKan) was added the appropriate $P_2$ acid (3 eq), HOBT hydrate (4 eq), and (3-(dimethylamino)propyl) ethylcarbodiimide hydrochloride (EDAC) (3.5 eq). The reaction was agitated under argon at room temperature for 3 hours. After filtration, the MiniKans were washed with DMF (3×), MeOH (3×), and DCM (3×), dried under vacuum, and taken on to Step G.

Step F. Cleavage and Processing of the HIV Analogs

The individual MinKans were sorted into cleavage racks and a solution of 25% TFA in DCM (3 mL/MinKan) was added. The racks were agitated for 1.5 hours. The individual filtrates and DCM rinses were collected, concentrated, and purified by HPLC to provide the final compounds.

TABLE 2
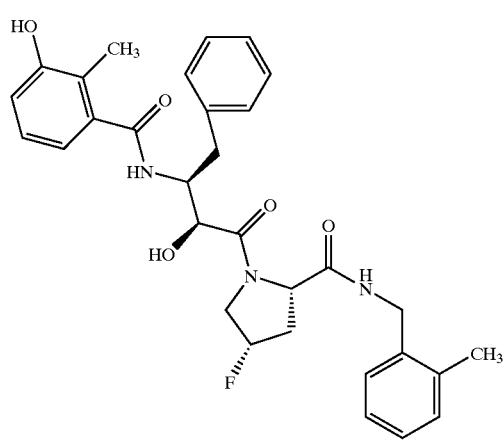
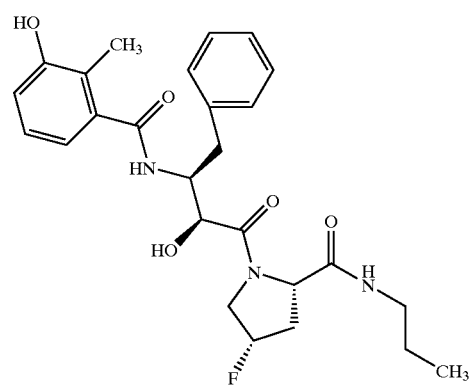
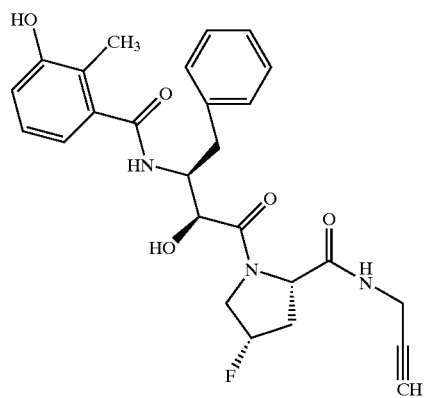
TABLE 2-continued
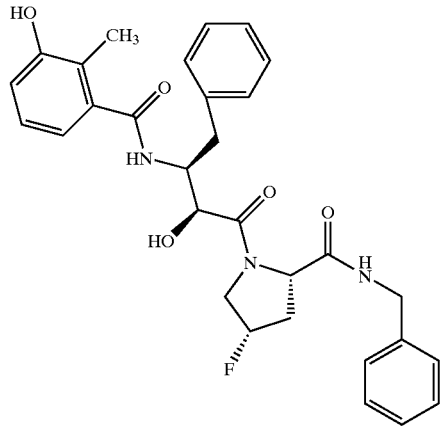
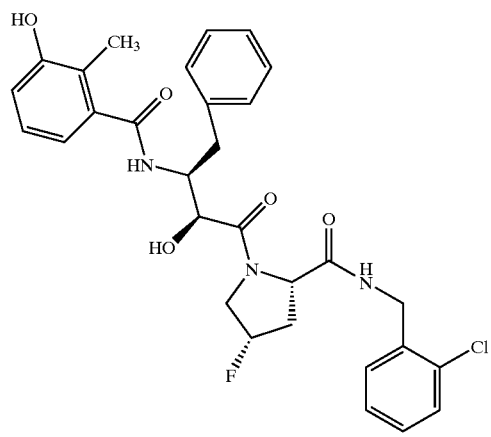
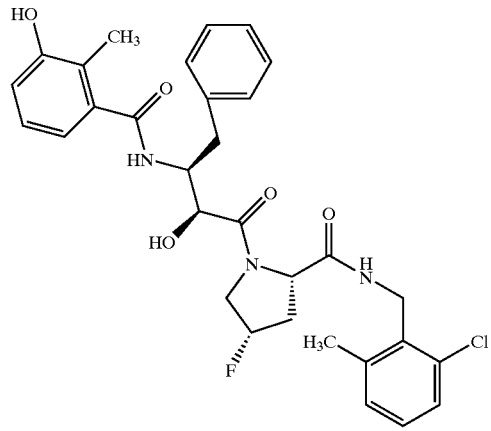

TABLE 2-continued

TABLE 2-continued
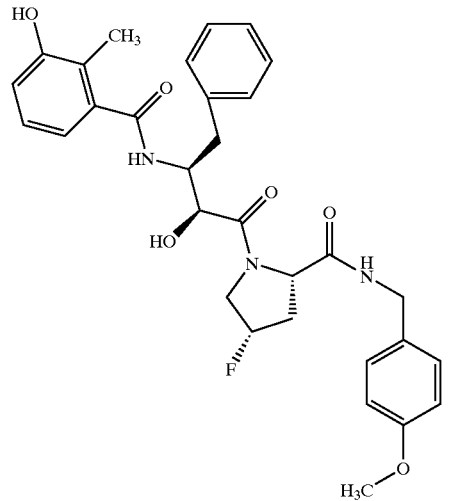
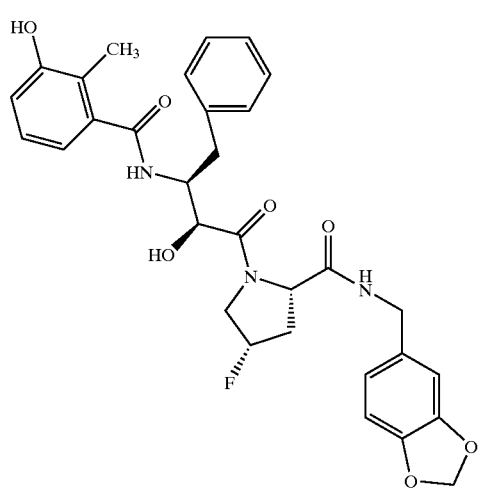
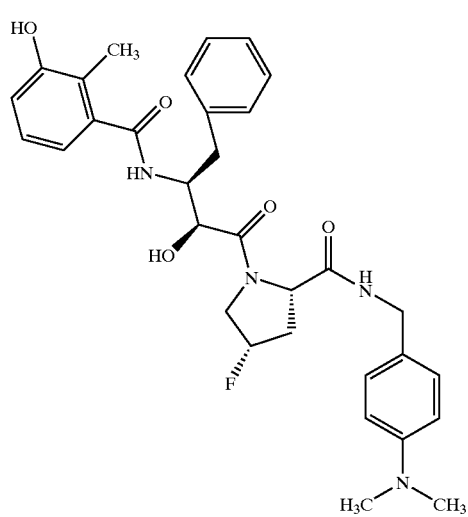
TABLE 2-continued
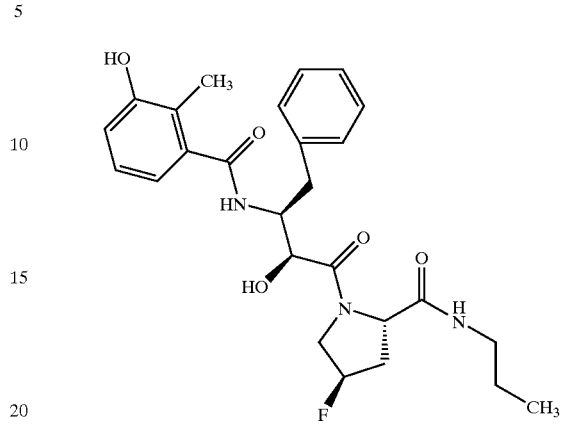
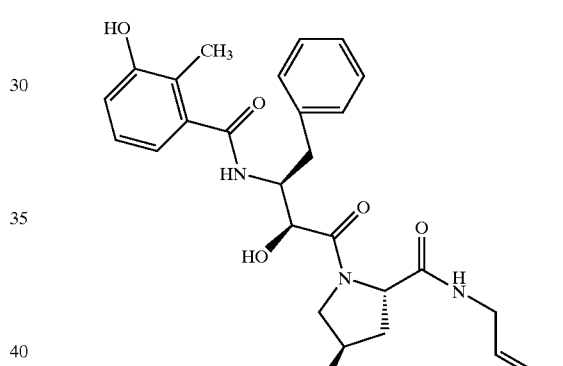
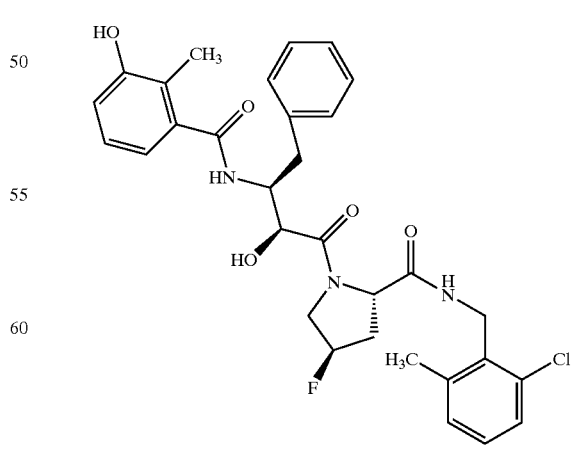

TABLE 2-continued
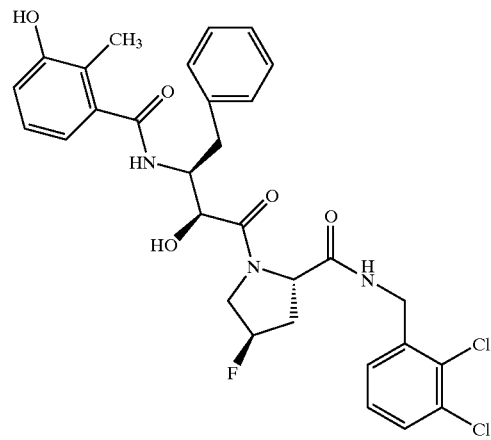
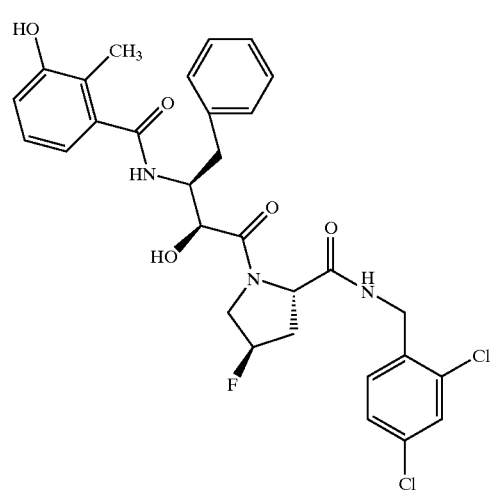
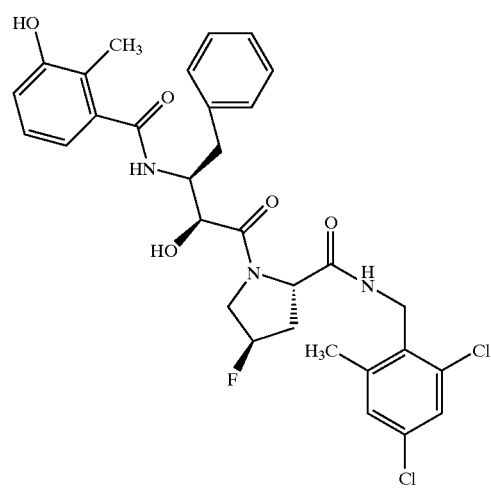
TABLE 2-continued
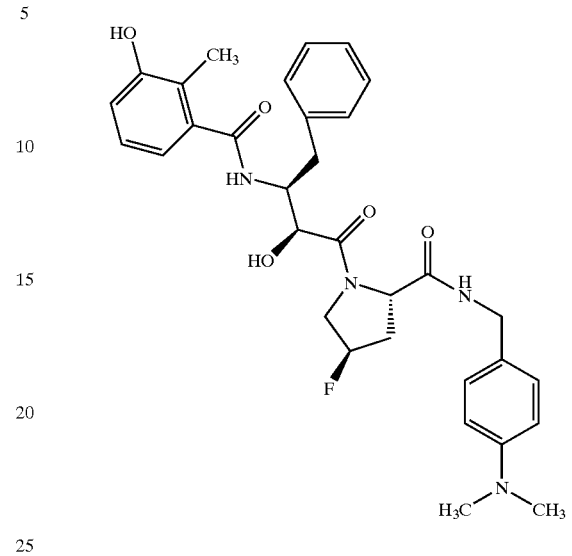
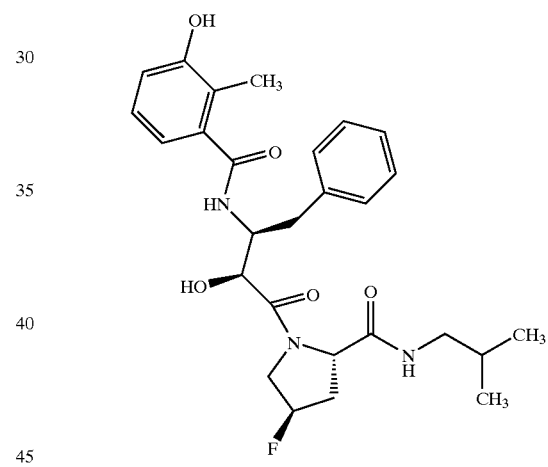
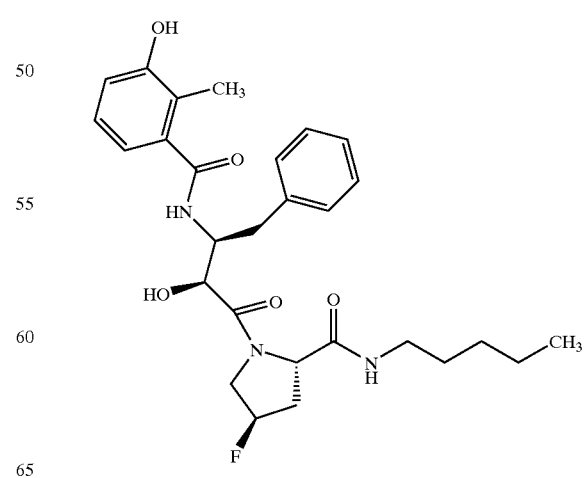

TABLE 2-continued
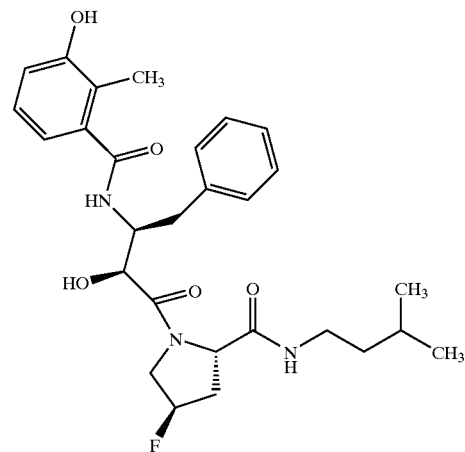
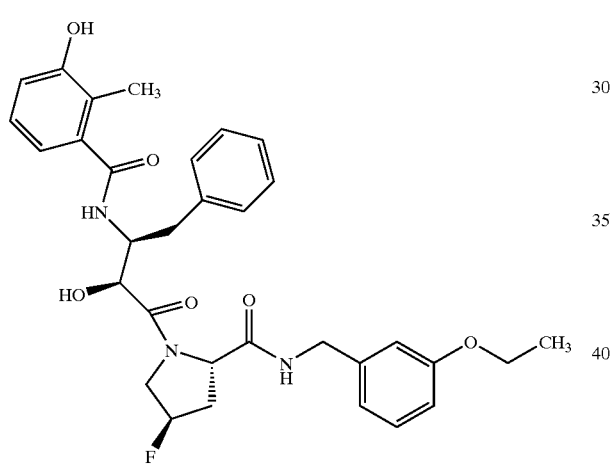
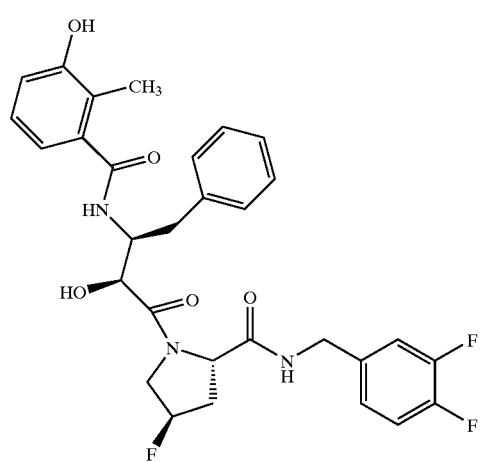
TABLE 2-continued
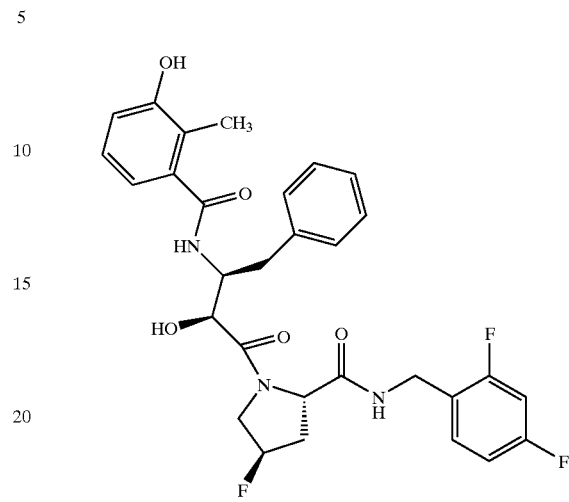
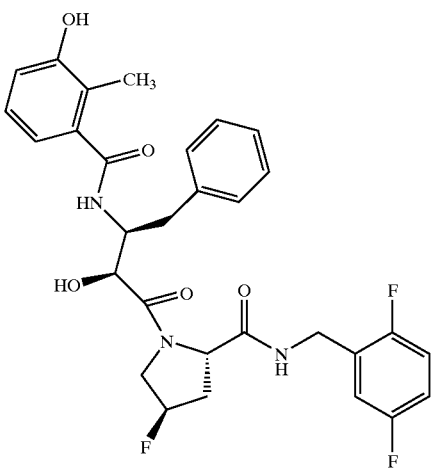
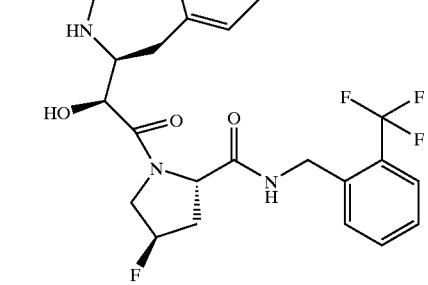

TABLE 2-continued
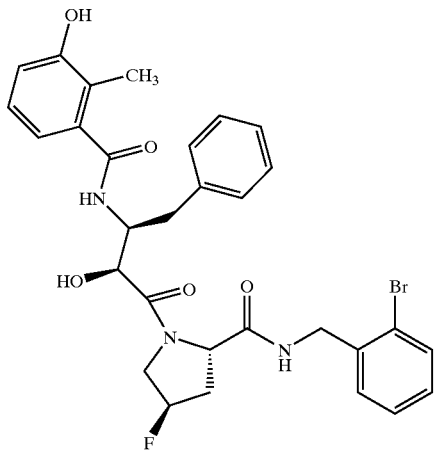
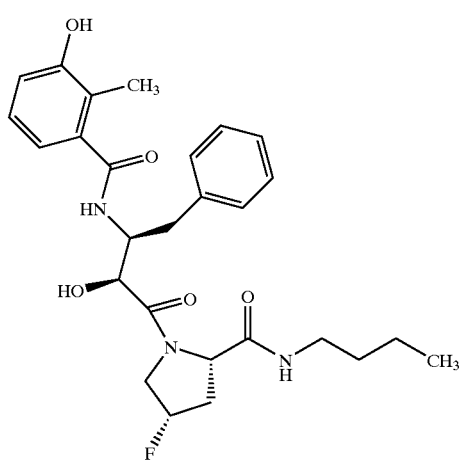
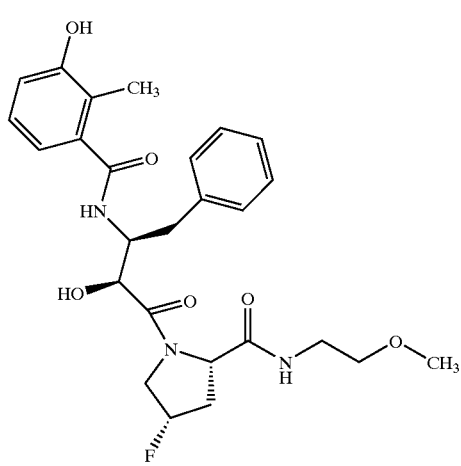
TABLE 2-continued
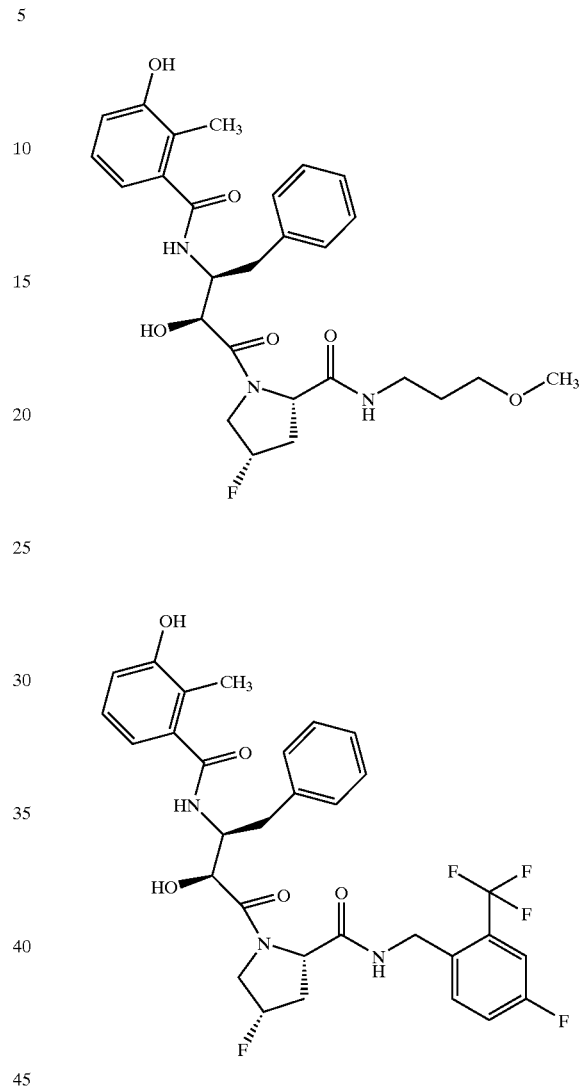
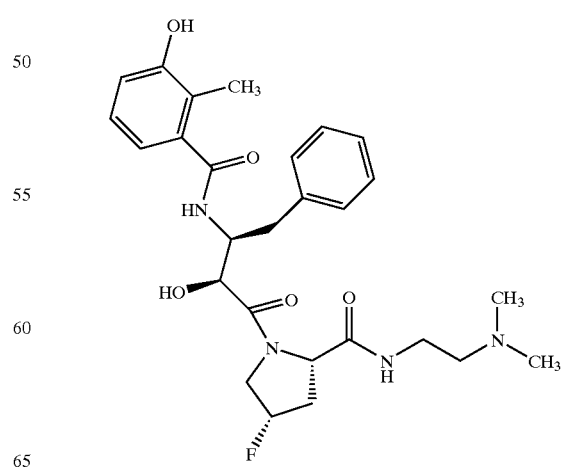

TABLE 2-continued
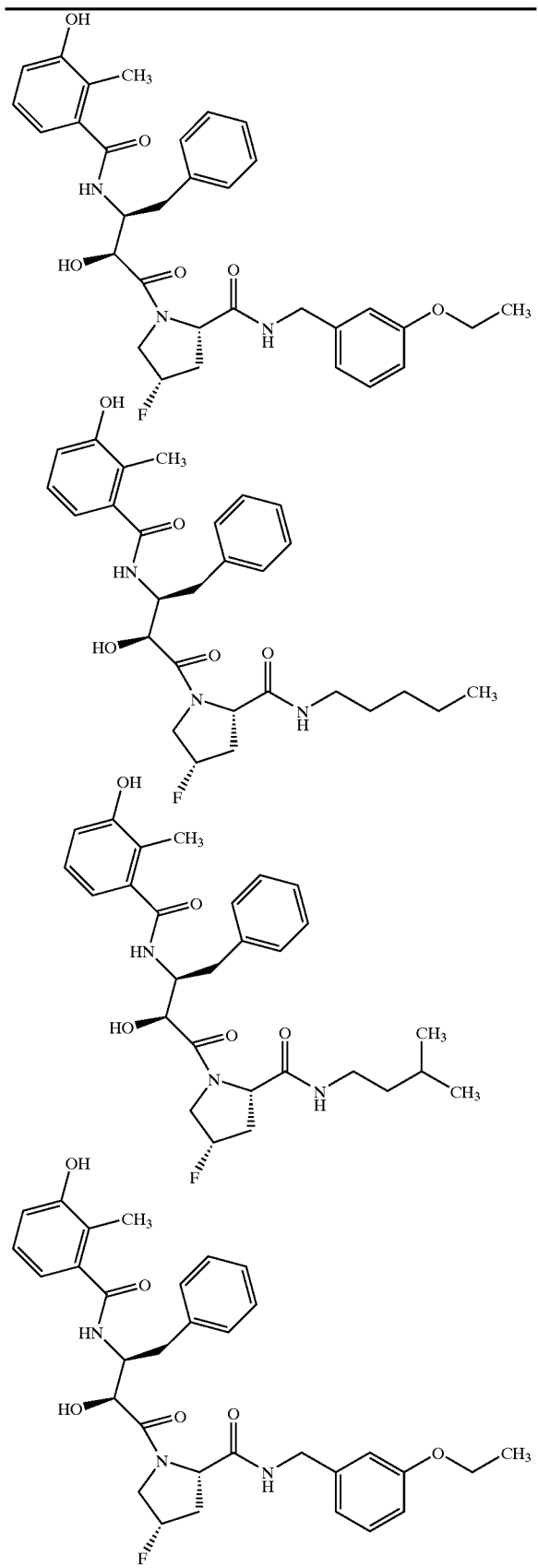
TABLE 2-continued
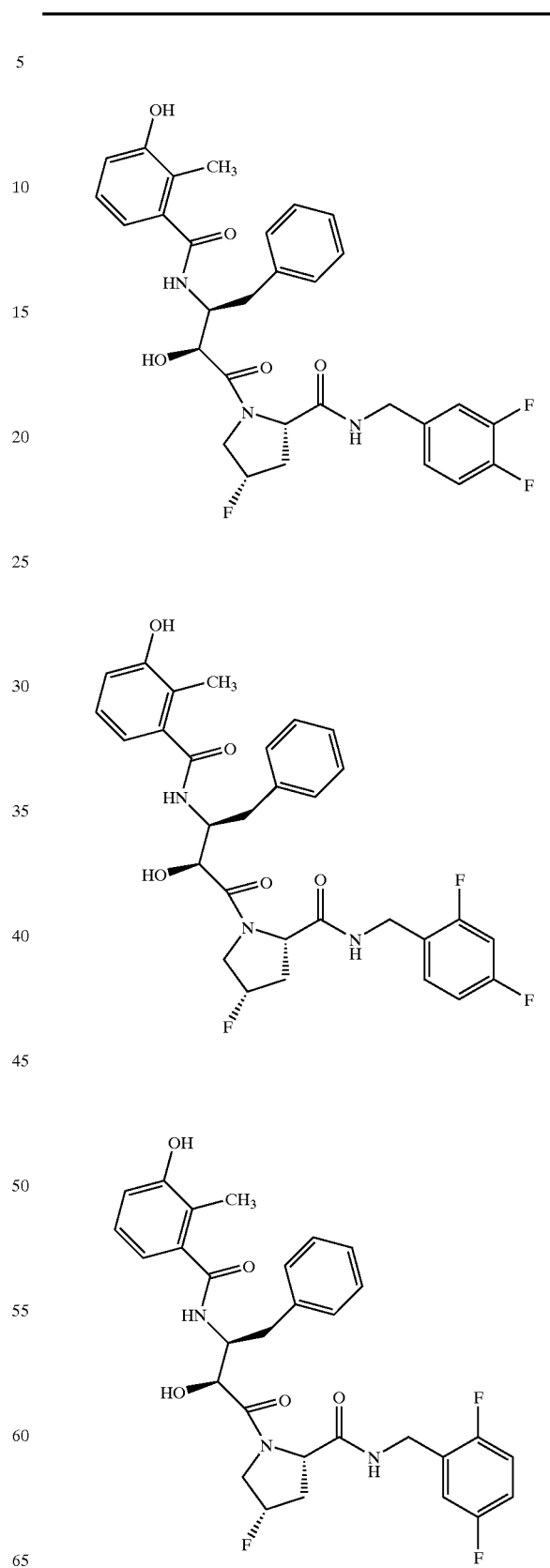

TABLE 2-continued
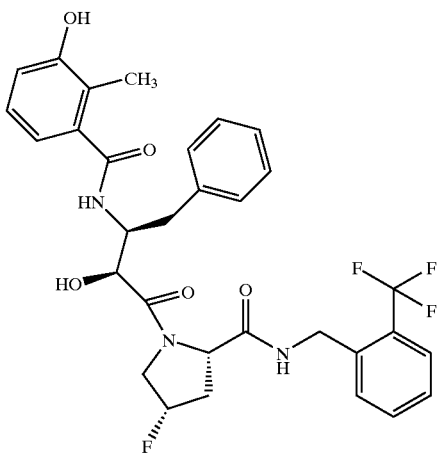
TABLE 2-continued
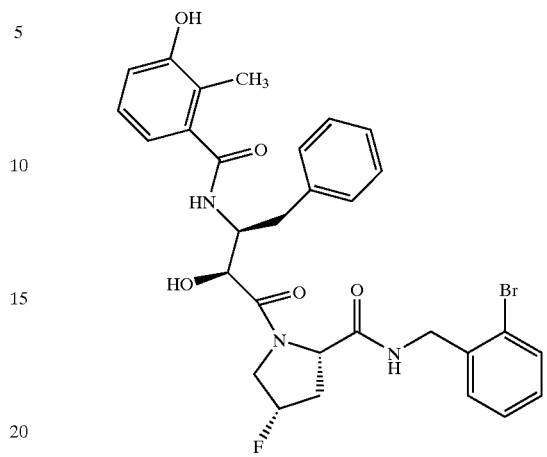
Scheme 3: Solid Phase Synthesis of HIV Protease Inhibitors
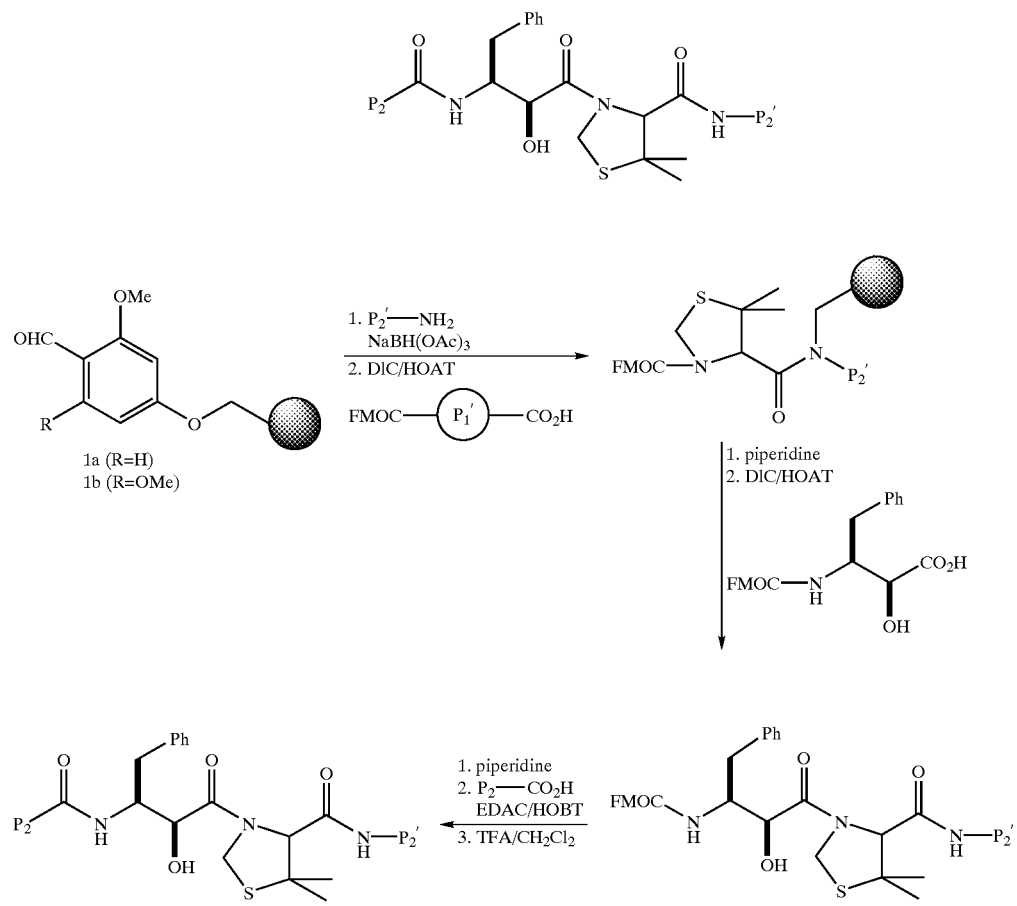

Scheme 3 Experimental

The solid phase combinatorial synthesis of HIV protease inhibitors was performed using the IRORI Directed Sorting Technology. Commercial 4-formyl-3-methoxyphenoxymethyl polystyrene resin 1a (PS-MB-CHO, Argonaut Technologies) or 4-formyl-3,5-dimethoxyphenoxymethyl polystyrene resin 1b (PL-FDMP resin, Polymer Laboratories) was loaded into individual Minikans.

Step A. Reductive Amination With P$_2$' Amines

To separate flasks containing sorted MiniKans was added DCM (3 mL/MiniKan). The appropriate primary P$_2$' amine (3 eq), sodium triacetoxyborohydride (5 eq), and acetic acid (3 eq) were added, and the mixtures were placed under argon, agitated with periodic venting at room temperature for 1–2 hours, and allowed to react overnight. For resin 1a, the filtrates were poured off and the MiniKans were washed with DCM, MeOH (2×), DCM (2×), Et$_3$N/DCM (1:3, 3×), DCM (2×), MeOH (3×), and DCM (4×). For resin 1b, a washing sequence of DCM, MeOH (2×), DCM (2×), Et$_3$N/DCM (1:3, 3×), DCM (2×), DMF, 1M NaOH/DMF (1:5, 3×), DMF (3×), MeOH (3×), and DCM (3×) was used. The MiniKans were dried under vacuum and taken on in Step B.

Step B. Peptide Coupling With P$_1$' Amino Acids

To separate flasks containing the sorted MiniKans was added DMF (3 mL/MiniKan). The appropriate FMOC-protected amino acid (2.5 eq) and 1-hydroxy-7-azabenzotriazole (HOAT) (3 eq) were added and mixed until dissolved, and 1,3-diisopropylcarbodiimide (DIC) (3 eq) was added. The containers were placed under argon and agitated at room temperature overnight. The filtrates were poured off, and the MiniKans were washed with DMF (3×), MeOH (3×), DCM (2×), and DMF (2×). The MiniKans were taken directly on to Step C.

Step C. FMOC Deprotection

A container of MiniKans in DMF and piperidine (25%) with a total reaction volume of 3 mL/MiniKan was agitated under argon at room temperature for 45 minutes. The filtrate was removed, and the reaction procedure was repeated. The MiniKans were filtered and washed with DMF (3×), MeOH (2×), DCM (3×), and DMF, and taken directly on to Step D.

Step D. Peptide Coupling With FMOC-APNS

FMOC-Allophenylnorstatine (APNS) (3 eq) was added to the flask of MiniKans in DMF (3 mL/MiniKan). After dissolution, HOAT (3.5 eq) and DIC (3.5 eq) were added. The mixture was placed under argon and agitated at room temperature overnight. The reaction was filtered and the MiniKans were washed with DMF (3×), MeOH (3×), DCM (3×), and DMF. FMOC deprotection was carried out as in Step C, and the MiniKans were washed with DMF (3×), MeOH (2×), DCM (3×), dried under vacuum and taken on to Step E or F.

Step E. Peptide Coupling With P$_2$ Acids

To separate flasks containing the sorted MiniKans in DMF (3 mL/MiniKan) was added the appropriate P$_2$ acid (3 eq), HOBT hydrate (4 eq), and (3-(dimethylamino)propyl)ethylcarbodiimide hydrochloride (EDAC) (3.5 eq). The reaction was agitated under argon at room temperature for 3 hours. After filtration, the MiniKans were washed with DMF (3×), MeOH (3×), and DCM (3×), dried under vacuum, and taken on to Step G.

Step F. Cleavage and Processing of the HIV Analogs

The individual MinKans were sorted into cleavage racks and a solution of 25% TFA in DCM (3 mL/MinKan) was added. The racks were agitated for 1.5 hours. The individual filtrates and DCM rinses were collected, concentrated, and purified by HPLC to provide the final compounds.

TABLE 3

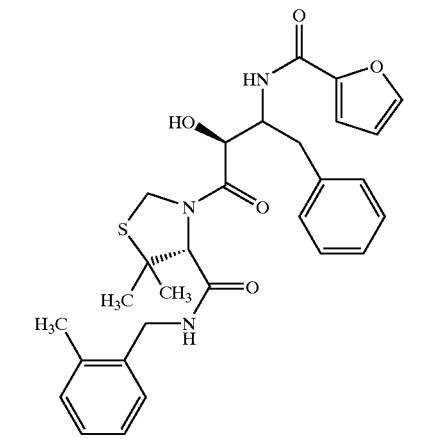

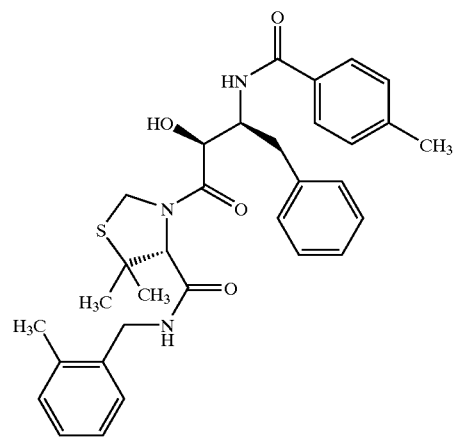

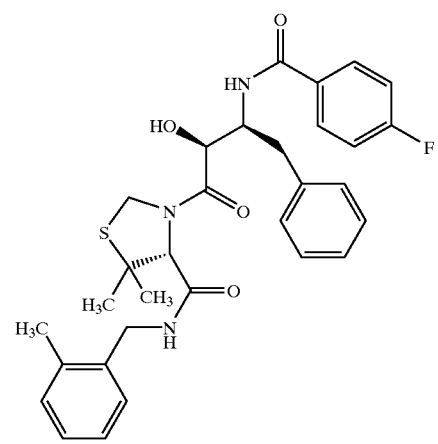

TABLE 3-continued
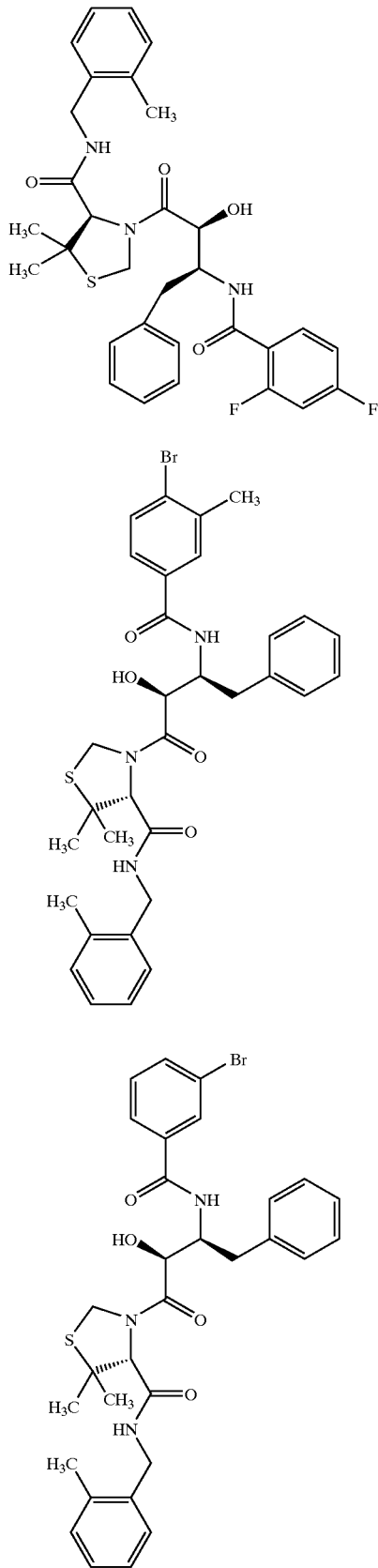
TABLE 3-continued
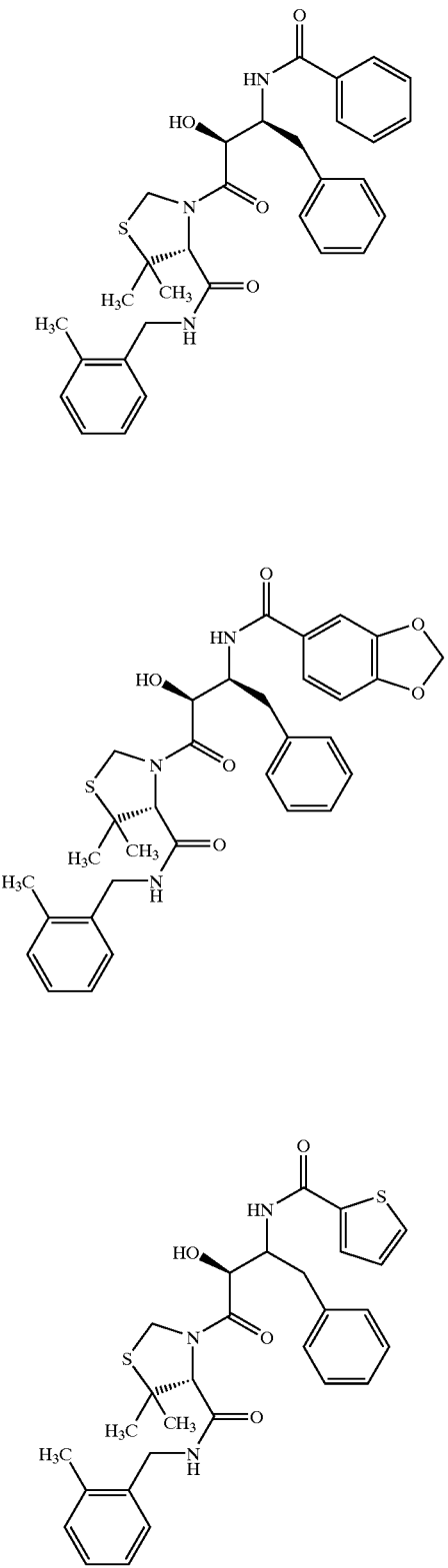

TABLE 3-continued
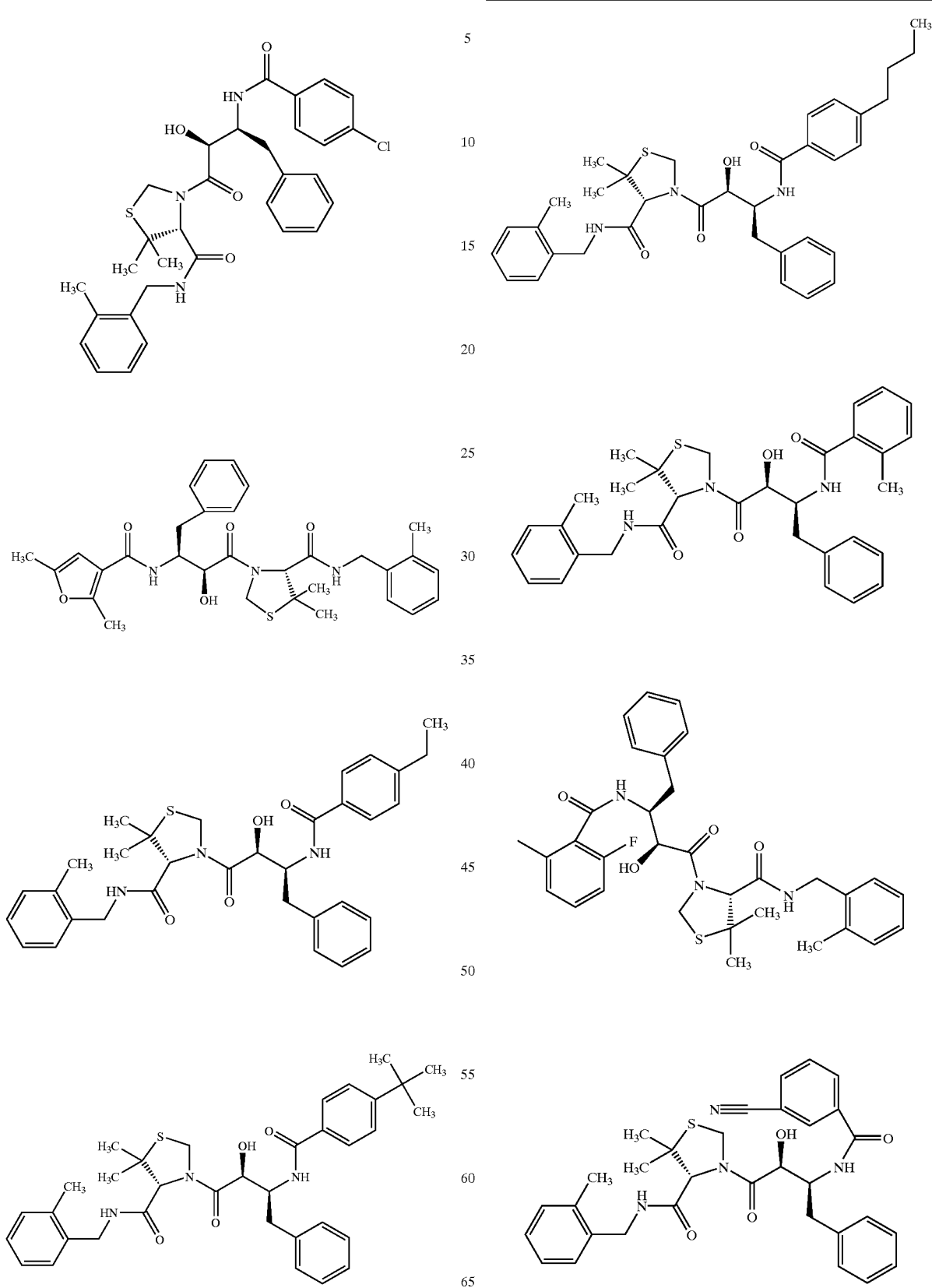

TABLE 3-continued
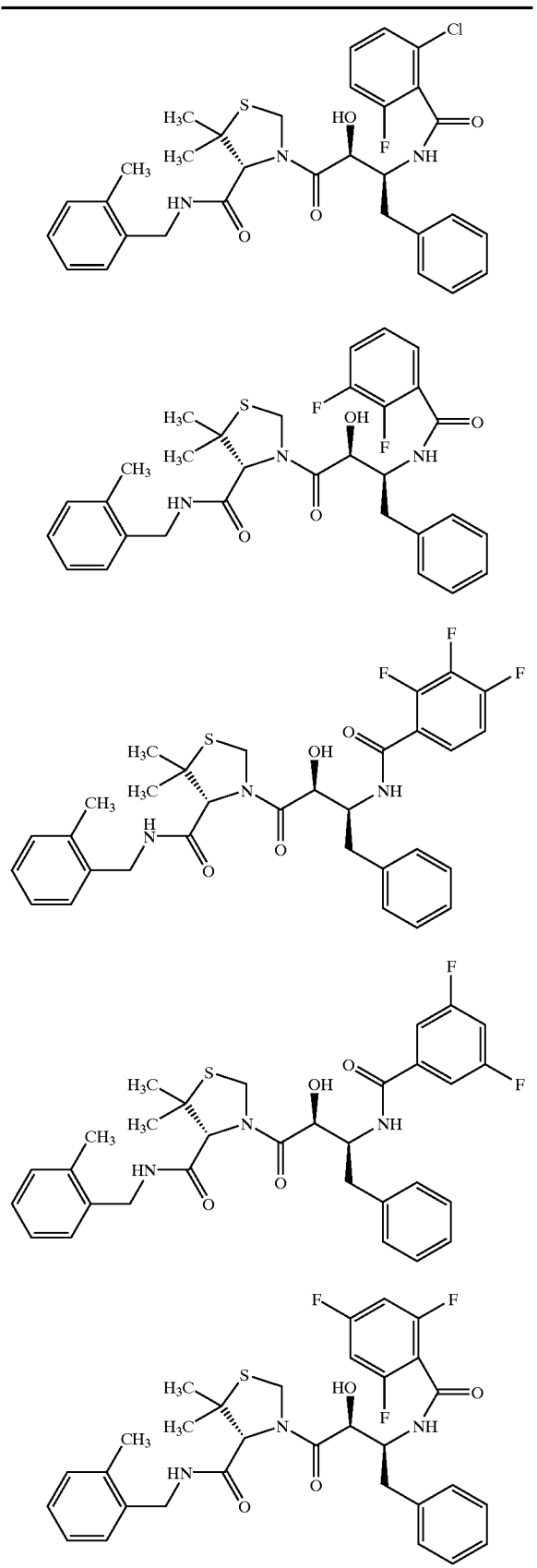
TABLE 3-continued
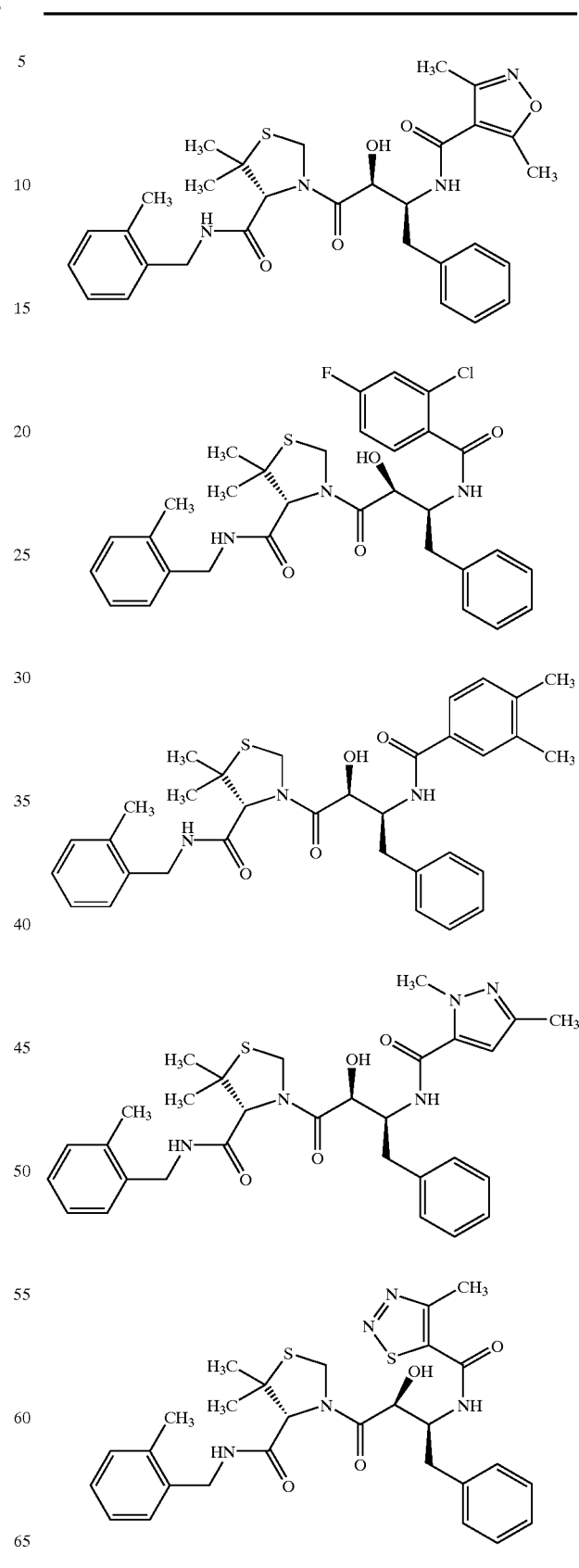

TABLE 3-continued
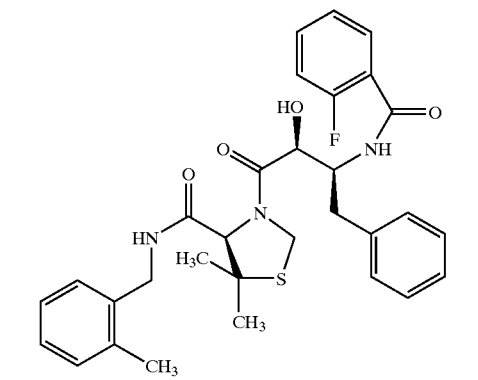
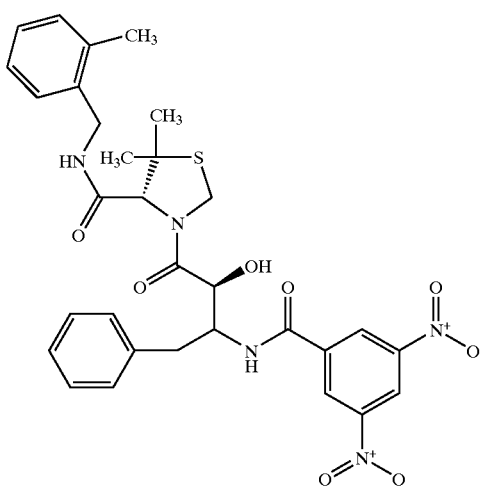
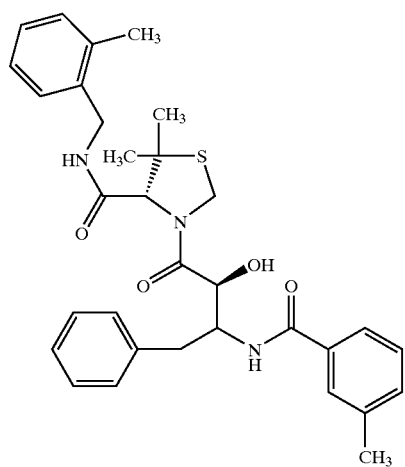
TABLE 3-continued
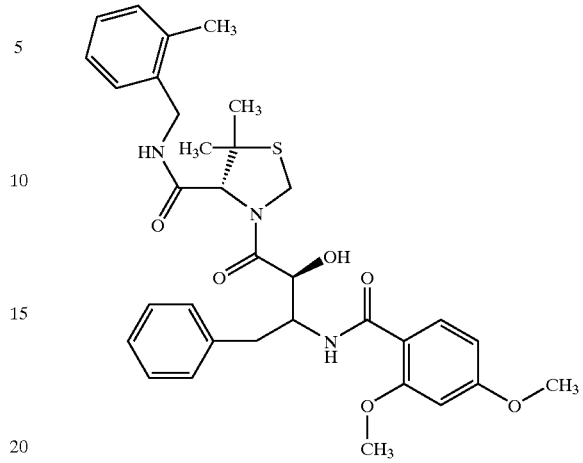
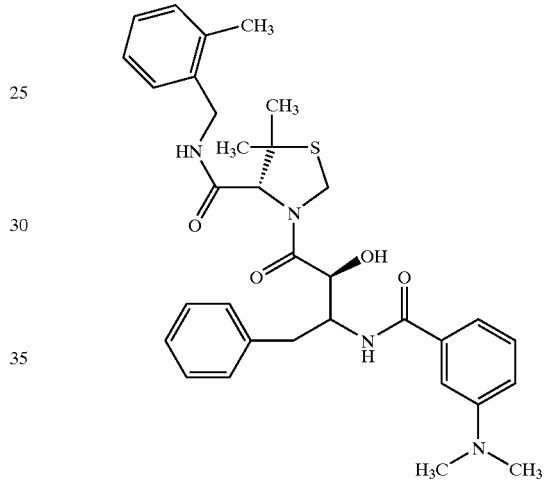
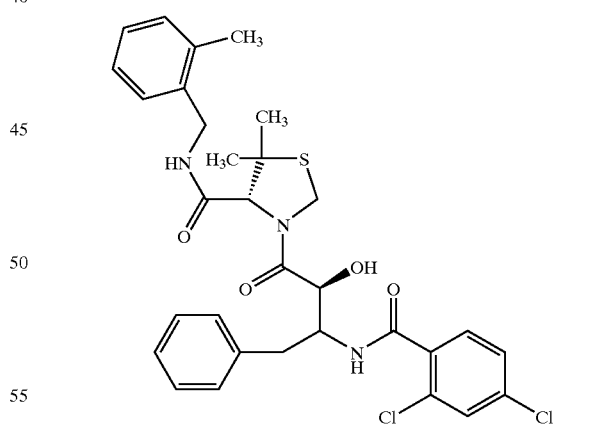
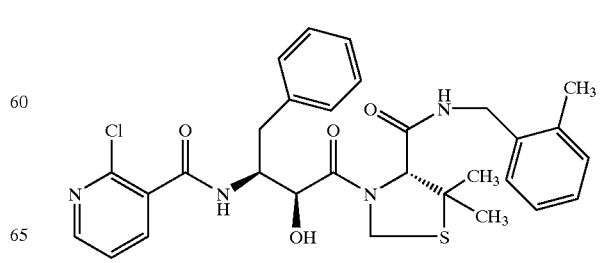

TABLE 3-continued
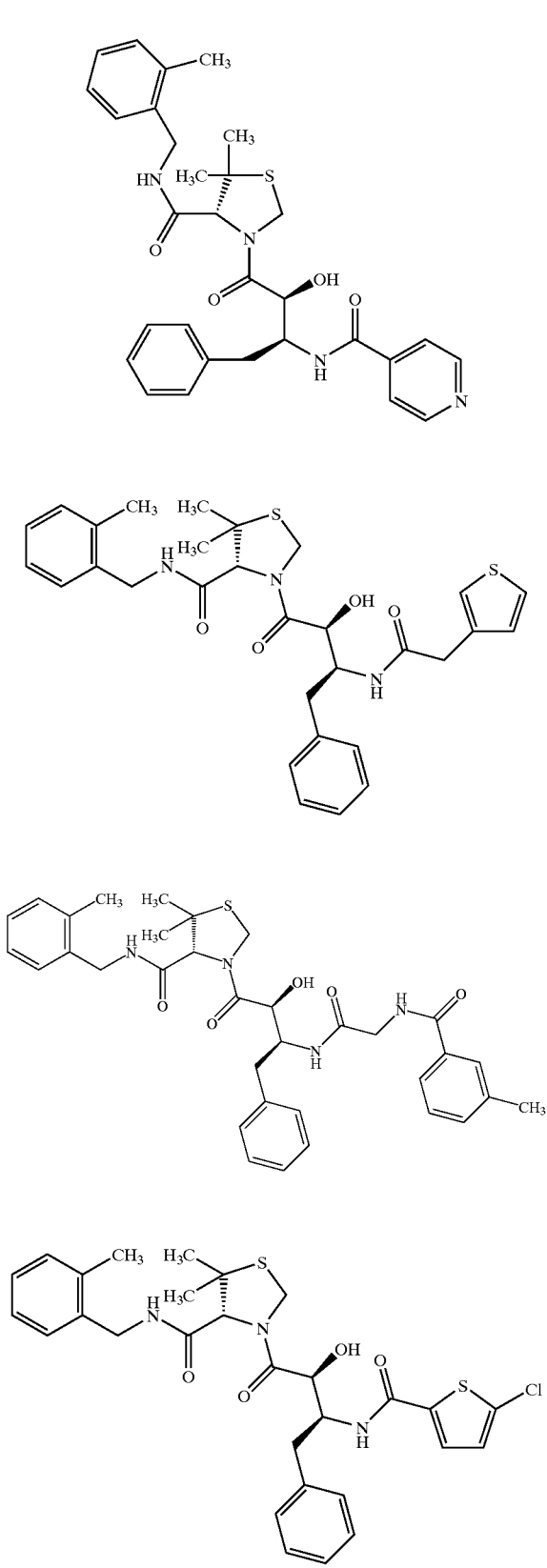
TABLE 3-continued
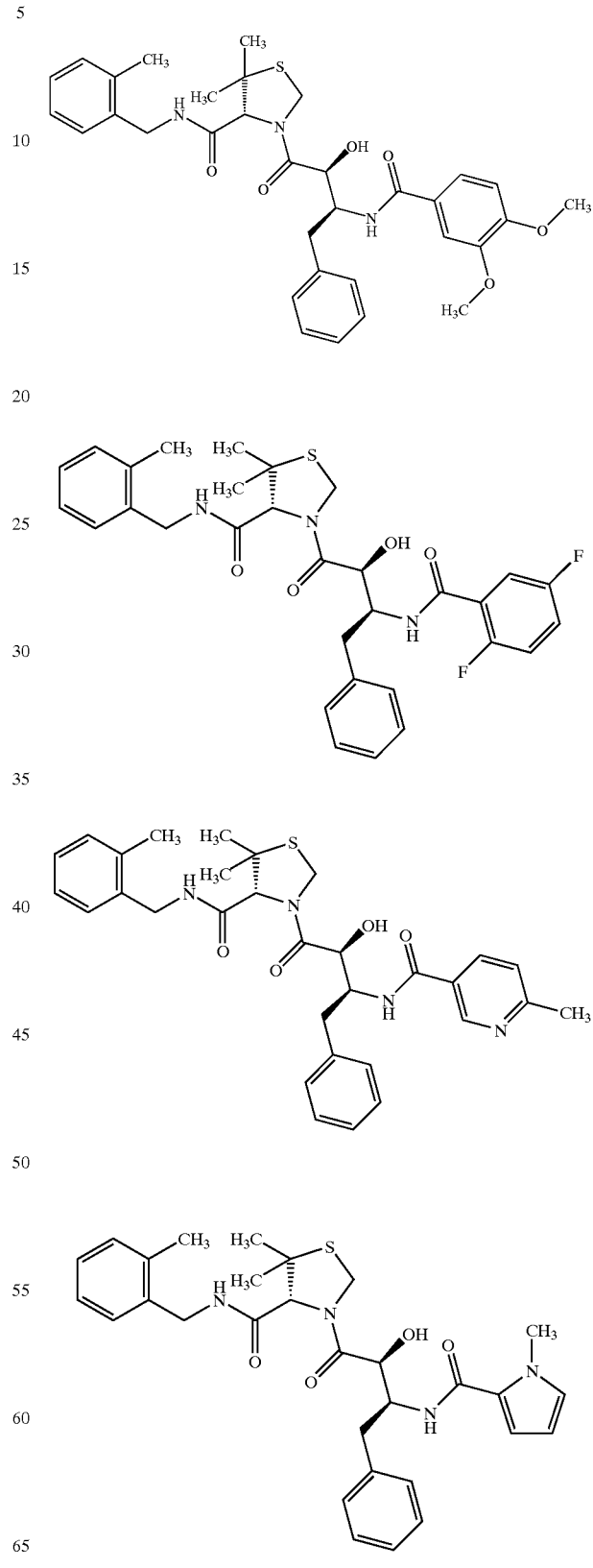

TABLE 3-continued

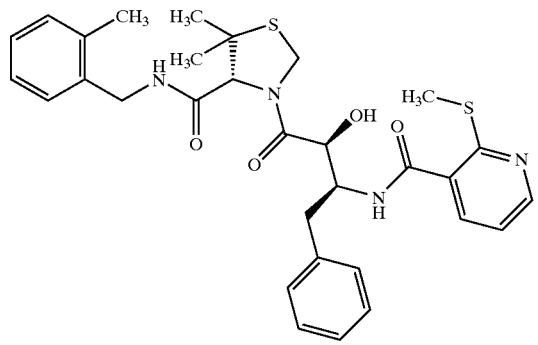

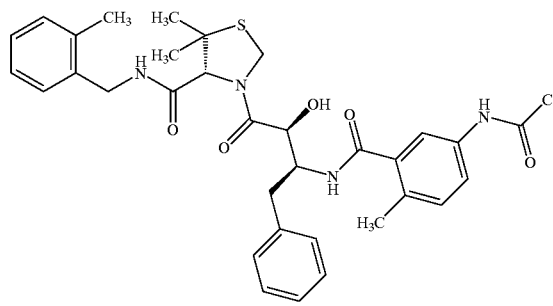

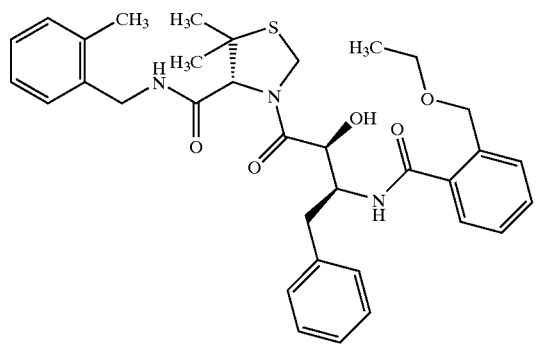

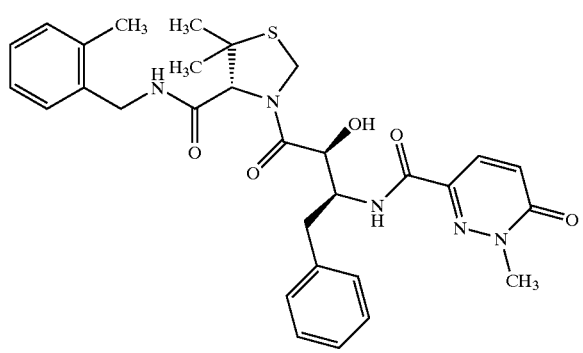

TABLE 3-continued

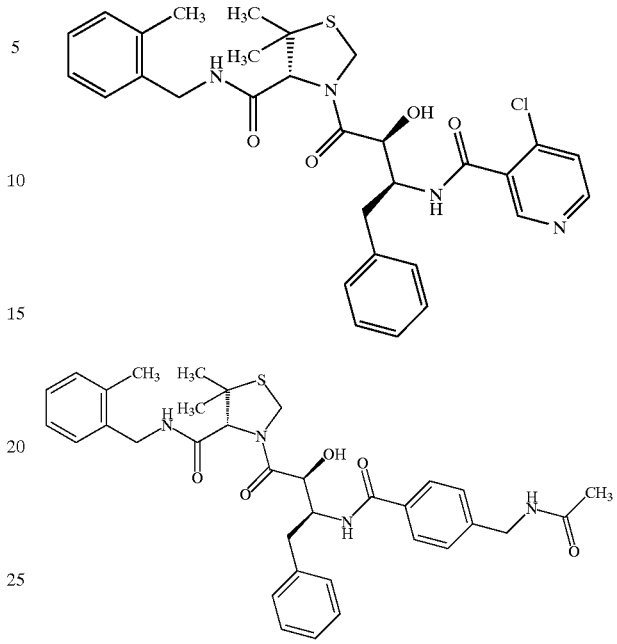

Biological Evaluation

Cells and Virus

T-cell lines, CEM-SS, and MT-2, and viruses HIV-1 RF and HIV-1 NL4-3 (pNL4-3) were obtained from the National Institutes of Health (AIDS Research and Reference Reagent Program, Bethesda, Md.). HIV-1 NL4-3(I84V/L90M) was derived from a clinical isolate that exhibited the protease inhibitor-resistance associated substitutions I84V and L90M, by cloning of an reverse transcriptase-polymerase chain reaction amplified fragment into the unique Age I and Spe I restriction sites of pNL4-3.

Cytopathic Effect (CPE) Inhibition Assays

The ability of compounds to protect cells against HIV infection was measured by the MTT dye reduction method, essentially as described (See Pauwels, R. Balzarini, J. Baba, M. Snoeck, R. Schols, D. Herdewijn, P. Desmyter, J. and De Clercq, E. 1988, "Rapid and automated tetrazolium-based calorimetric assay for the detection of anti-HIV compounds, ". *J. Virol. Methods.,* 20: 309–321 and Weislow, O. S. Kiser, R. Fine, D. L. Bader, J. Shoemaker, R. H. and Boyd, M. R. 1989. "New soluble-formazan assay for HIV-1 cytopathic effects: application to high-flux screening of synthetic and natural products for AIDS-antiviral activity". *J. Natl. Cancer Inst.* 81:577–586). Subject cells were infected with test virus at an moi of 0.025 to 0.819 or mock infected with medium only and added at $2\times10^4$ cells per well into 96 well plates containing half-log dilutions of test compounds. Six days later, 50 μl of XTT (1 mg/ml XTT tetrazolium, 0.02 nM phenazine methosulfate) was added to the wells and the plate was reincubated for four hours. Viability, as determined by the amount of XTT formazan produced, was quantified spectrophotometrically by absorbance at 450 nm.

Data from CPE assays were expressed as the percent of formazan produced in compound-treated cells compared to formazan produced in wells of uninfected, compound-free cells. The fifty percent effective concentration ($EC_{50}$) was calculated as the concentration of compound that effected an increase in the percentage of formazan production in infected, compound-treated cells to 50% of that produced by uninfected, compound-free cells. The 50% cytotoxicity concentration ($CC_{50}$) was calculated as the concentration of compound that decreased the percentage of formazan produced in uninfected, compound-treated cells to 50% of that produced in uninfected, compound-free cells. The therapeutic index was calculated by dividing the cytotoxicity ($CC_{50}$) by the antiviral activity ($EC_{50}$).

Susceptibility Assays

Compounds were tested in phenotypic susceptibility assays at Virologic, Inc., (See Petropoulos C. J., Parkin N. T., Limoli K. L., Lie Y. S., Wrin T., Huang W., Tian H., Smith D., Winslow G. A., Capon D J, Whitcomb J M. 2000, "A novel phenotypic drug susceptibility assay for human immunodeficiency virus type 1," Antimicrob Agents Chemother 44(4):920–928) or using the assay described here. MT-2 cells were infected with either HIV-1 NL4-3 or HIV-1 NL4-3(I84V/L90M) and incubated in the presence of serial 0.5 log dilutions of test compounds. Three days later, culture supernatants were collected and virus production, as determined by p24 ELISA, was assayed. Percent inhibition was calculated as p24 concentration in compound-treated samples as compared to infected, compound-free controls. Inhibition of viral replication is determined by measuring reduction in HIV p24 present in the culture supernatant, using a Beckman-Coulter p24 HIV-1 Ag EIA kit and following the supplied protocol. Absorbance is read on a MRX microplate reader (Dynex Technologies). The $EC_{50}$ was calculated as the concentration of compound that effected a decrease in the p24 production by infected, compound-treated cells to 50% of that produced by infected, compound-free cells.

HIV-1 Protease RET Assay

Ki's for the inhibitors of HIV-1 protease were determined using a resonance energy transfer (RET) assay. A mutant form of this enzyme (Q7S) is used for this assay because it is more stable against auto-proteolysis than the wild-type protein. This enzyme is first partially purified as inclusion bodies from cell lysate. It is then solublized in 8M urea and passed through a Q-Sepharose column (Pharmacia) for further purification. To refold this protein, samples containing Q7S is dialyzed into 50 mM sodium phosphate pH 7.0, 50 mM NaCl, 10 mM DTT, and 10% glycerol.

The commercially available peptide substrate (Molecular Probes Cat. #H-2930) RE(EDANS)SQNYPIVQK (DABCYL)R is used to assess activity and Ki's. This peptide is cleaved quantitatively by HIV-1 Pr at the Tyr-Pro bond. The EDANS fluorophore absorbs at 340 nm and emits at 490 nm. The reaction is carried out in a 96 well plate in a total volume of 100 $\mu$L and is run for 12 minutes at 37 C under steady-state conditions with 5$\mu$M substrate and 2 nM active dimer enzyme concentration. The literature value Km for this substrate and enzyme is 103 +/−8$\mu$M (See Matayoshi, et al., "Novel Fluorogenic Substrates for Assaying Retroviral Proteases by Resonance Energy Transfer," Science 247, 954 (1990)). The buffer for this reaction is 0.1M sodium acetate pH 4.8, 1M NaCl, 1 mM EDTA, 5 mM dithiothreitol, 10% dimethyl sulfoxide and 1 mg/ml bovine serum albumin. Inhibition curves are fit using the Morrison tight binding equation.

| Example No. | Ave. $K_i$ (nM) | Ave CPE $EC_{50}$ (mM) | $EC_{50}$ or $IC_{50}$ (mM) |
|---|---|---|---|
| A3 | 1.7 | 0.37 | |
| A4 | 4.1 | 0.591 | |
| A5 | 2 | 0.433 | |
| A6 | 0.22 | 0.036 | |
| A7 | 0.49 | 0.104 | 0.832 |
| A8 | 0.23 | 0.036 | |
| A9 | 4 | 0.565 | |
| A10 | 51 | >1 | |
| A11 | 19 | 0.93 | |
| A12 | 1.7 | 1.09 | |
| A13 | 44.1 | >1 | |
| A14 | 0.44 | 0.052 | 0.071* |
| A15 | 10.9 | 0.13 | |
| A16 | 0.63 | 0.134 | |
| A17 | <0.1 | 0.045 | 0.102* |
| A18 | 0.38 | 0.193 | |
| A19 | 10 | 0.442 | |
| A20 | 0.13 | 0.037 | 0.147* |
| A21 | 1.9 | 0.717 | |
| A22 | 0.32 | 0.061 | 0.226* |
| A23 | 0.65 | 0.072 | |
| A24 | 0.18 | 0.104 | 0.831 |
| A25 | 5.8 | 0.248 | |
| A26 | 0.38 | 0.119 | 0.321* |
| A27 | 0.62 | 0.072 | |
| A28 | <0.1 | 0.041 | |
| A29 | <0.1 | 0.117 | |
| A30 | 1.1 | 0.507 | 0.829* |
| A31 | <0.1 | 0.041 | |
| A32 | <0.1 | 0.045 | 0.486 |
| A33 | <0.1 | 0.577 | |
| A34 | <0.1 | 0.036 | |
| A35 | <0.1 | 0.017 | 0.063 |
| A36 | 0.59 | 0.519 | |
| A37 | 0.13 | 0.161 | |
| A38 | 0.17 | 0.078 | 0.401 |
| A39 | 0.27 | 0.367 | |
| A40 | 1.2 | 0.275 | |
| A41 | 1.6 | 0.527 | |
| A42 | 0.23 | 0.126 | 0.307 |
| A43 | 0.35 | 0.561 | |
| A44 | 0.14 | 0.022 | 0.472 |
| A45 | 0.51 | 0.165 | |
| A46 | 0.31 | 0.091 | 0.79 |
| A47 | 2.3 | 1.813 | |
| A48 | 0.19 | 0.417 | |
| A49 | 1.2 | 0.13 | |
| A50 | 0.26 | 0.224 | |
| A51 | 1.3 | 0.667 | |
| A52 | 37 | | |
| B1 | 2.5 | 0.905 | |
| B2 | 0.78 | 0.369 | |
| B3 | 4 | 0.409 | |
| B8 | 0.31 | 0.095 | 0.405* |
| B4 | 1.7 | 0.551 | |
| B5 | 1.6 | 0.508 | |
| B6 | 1.6 | 0.589 | |
| B7 | 1.9 | 0.68 | |
| B8 | 1.5 | 0.552 | |
| B10 | <0.1 | 1.1 | |
| B11 | 1.2 | 1.175 | 1.716* |
| B12 | 0.45 | 1.398 | |
| B13 | 19%@ 64 nM | | |
| B14 | 3.7 | 3.054 | |
| B15 | 2 | 1.086 | |
| B16 | <0.1 | 0.298 | 1.754 |
| B17 | 0.42 | 0.534 | 1.579 |
| B18 | 0.29 | 0.457 | |
| B19 | <0.1 | 0.124 | 1.369 |
| B20 | 2.1 | 0.427 | |
| B21 | 4.6 | 0.598 | |
| B22 | 1.8 | 1.613 | |
| B23 | 0.42 | 1.42 | |
| B24 | 5.5 | 2.316 | |
| B25 | 2.7 | 1.794 | |
| B26 | 2.9 | 1.712 | |

| Example No. | Ave. $K_i$ (nM) | Ave CPE $EC_{50}$ (mM) | $EC_{50}$ or $IC_{50}$ (mM) |
|---|---|---|---|
| B27 | 3.5 | | |
| B28 | 153 | | |
| B29 | 0.12 | 1.256 | |
| B30 | 1.1 | 1.227 | |
| B31 | 1.5 | 1.316 | |
| B32 | 4.9 | | |
| B33 | 1.2 | 1.286 | |
| B34 | | | |
| B35 | | | |
| B36 | <0.1 | 0.615 | |
| B37 | 0.11 | 0.736 | |
| B38 | | | |
| B39 | 0.16 | | |
| B40 | 2.8 | 1.396 | |
| B41 | 0.15 | | |
| B42 | 0.73 | | |
| B43 | 0.2 | | |
| B44 | 0.76 | 0.629 | |
| B45 | 19.7 | | |
| B46 | 12.5 | | |
| B47 | 6.9 | | |
| B48 | 12 | >3.2 | |
| B49 | 17.2 | | |

| Example No. | Ave. $K_i$ (nM) | Ave CPE $EC_{50}$ (mM) | $EC_{50}$ or $IC_{50}$ (mM) |
|---|---|---|---|
| C1 | 0.38 | 0.627 | 0.427 |
| C3 | 1.3 | 0.5 | |
| C4 | 4.2 | | |
| C4 | 69 | | |
| C5 | 3.2 | | |
| C6 | <0.1 | 0.164 | 1.475 |
| C7 | 7.9 | | |
| C8 | 0.26 | 0.447 | |
| C9 | 0.34 | 0.233 | |
| C10 | 36 | | |
| C11 | 1.1 | 1.562 | |
| D1 | <0.01 | 0.052 | 0.601 |
| D3 | 0.5 | 0.162 | 1.954 |
| D4 | 0.7 | 0.016 | 1.954 |

*$IC_{50}$ (mM) Data was determined at Virologic Inc against the 46I, 84V, 90M virus The following compounds have been prepared according to the procedures described herein and have demonstrated the noted activity:

| MOLSTRUCTURE | $K_i$ | $EC_{50}$ |
|---|---|---|
| 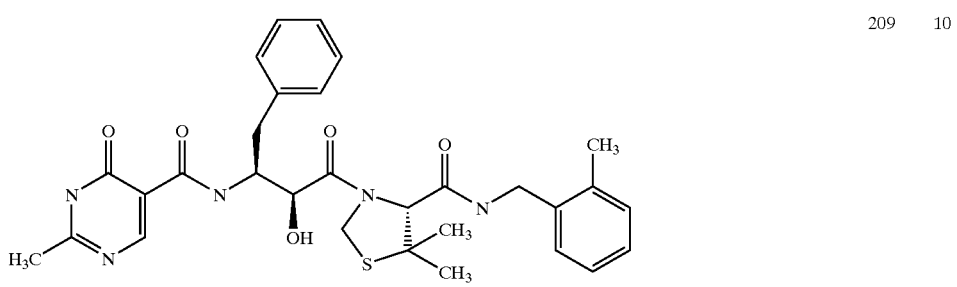 | 209 | 10 |
| 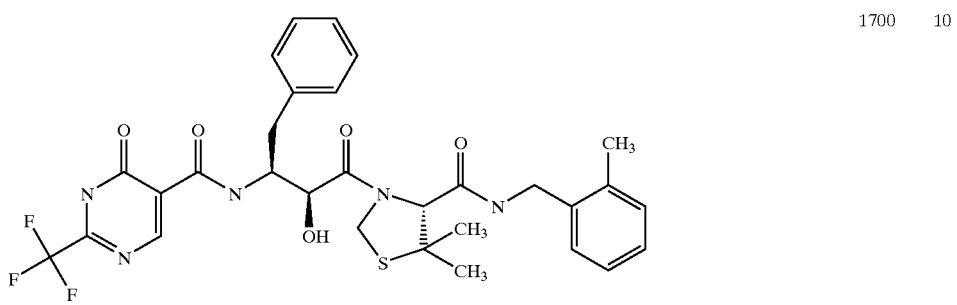 | 1700 | 10 |
| 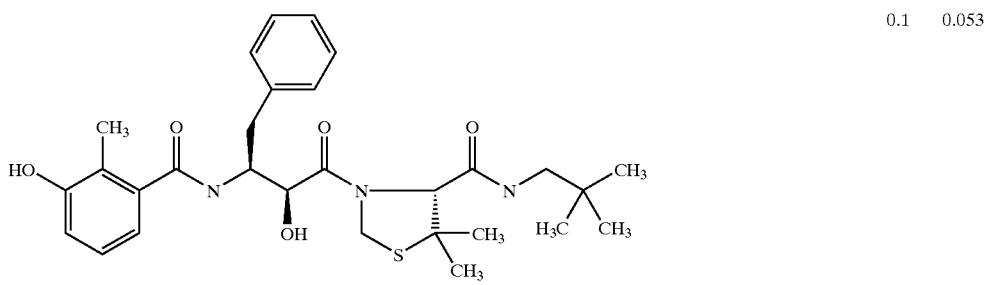 | 0.1 | 0.053 |

-continued
| MOLSTRUCTURE | $K_i$ | $EC_{50}$ |
|---|---|---|
| 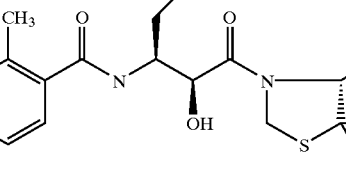 | 62 | |
| 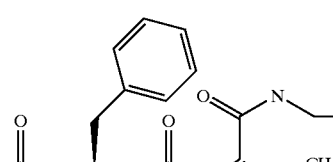 | 0.75 | |
| 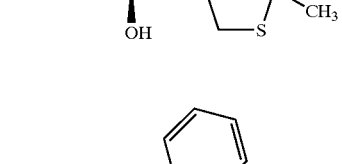 | 0.1 | 0.072 |
| 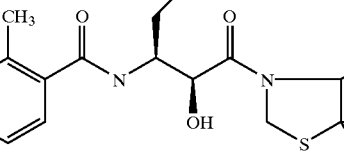 | 1.5 | 0.076 |
| 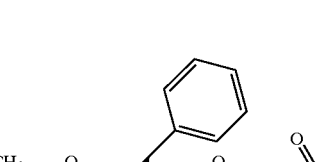 | 0.2 | 0.113 |
| 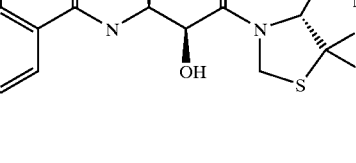 | | |

-continued
| MOLSTRUCTURE | $K_i$ | $EC_{50}$ |
|---|---|---|
| 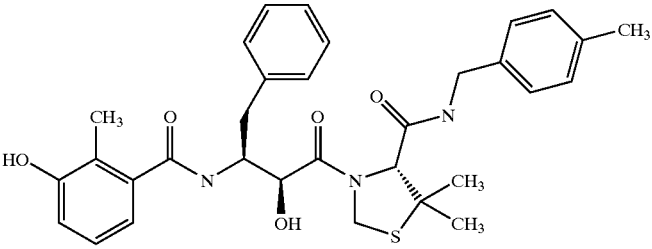 | 0.73 | 0.141 |
| 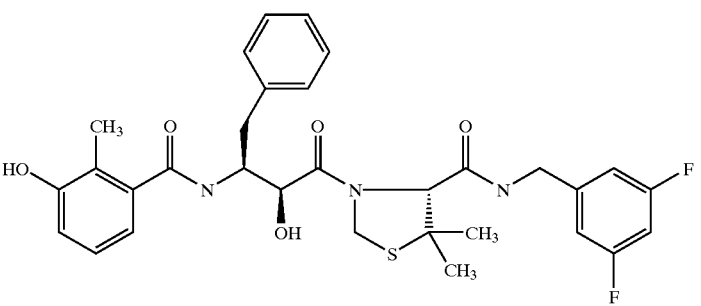 | 0.36 | 0.144 |
| 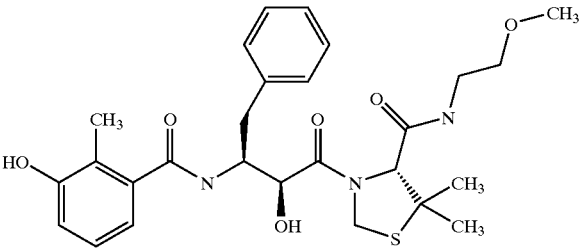 | 0.24 | 0.158 |
| 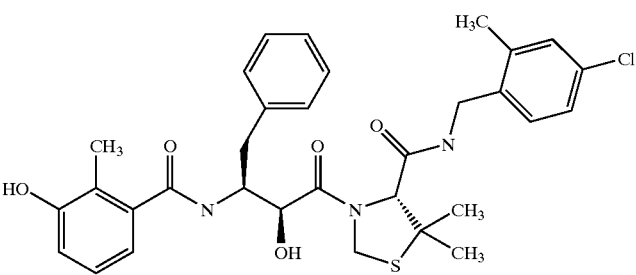 | 0.26 | 0.207 |
| 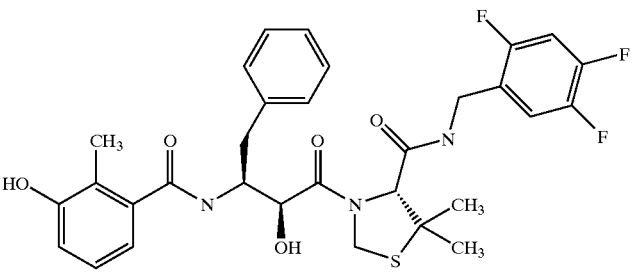 | 0.17 | 0.289 |

| MOLSTRUCTURE | $K_i$ | $EC_{50}$ |
| --- | --- | --- |
| | 0.11 | 0.334 |
| | 0.2 | 0.585 |
| | 9.6 | 0.723 |
| | 4.7 | 1.064 |
| | 1.1 | 1.114 |

| MOLSTRUCTURE | $K_i$ | $EC_{50}$ |
|---|---|---|
| 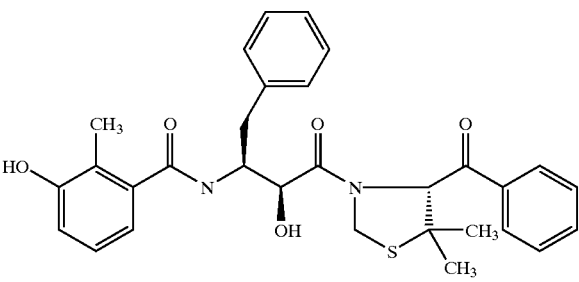 | 2.5 | 1.221 |
| 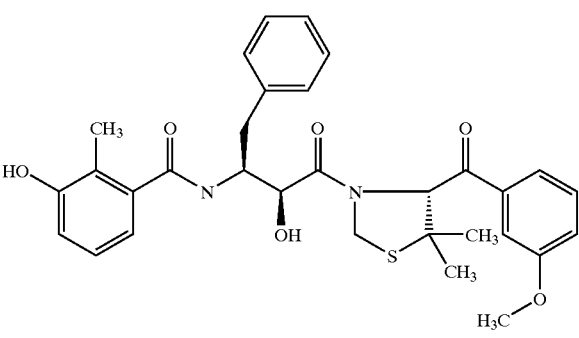 | 7.4 | |
| 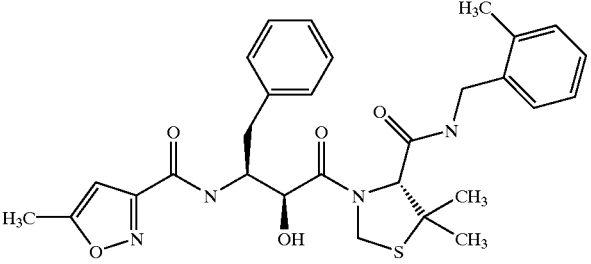 | 2.6 | 1.3095 |
| 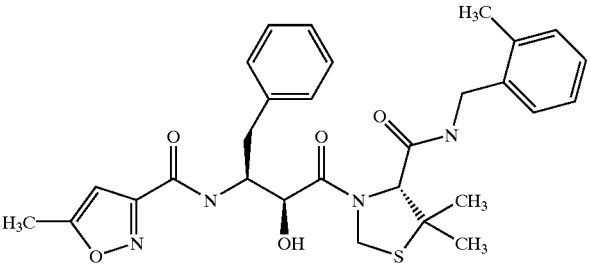 | 2.6 | 1.3095 |
| 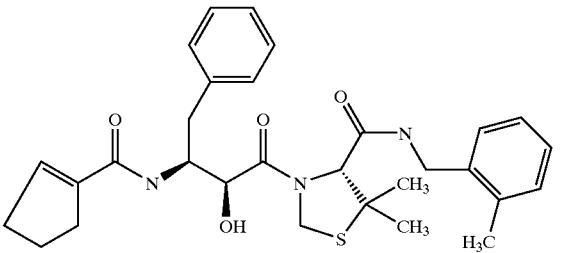 | 3.4 | |

| MOLSTRUCTURE | $K_i$ | $EC_{50}$ |
|---|---|---|
| 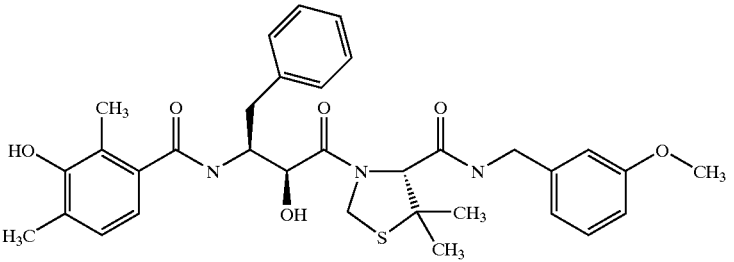 | 3.7 | 1.332 |
| 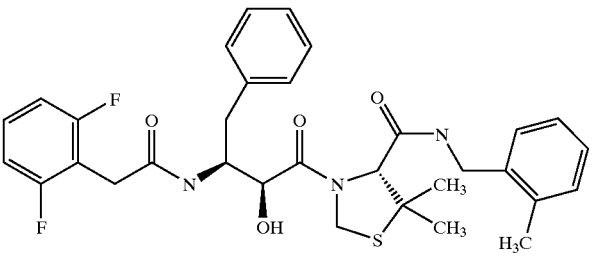 | 72 | |
| 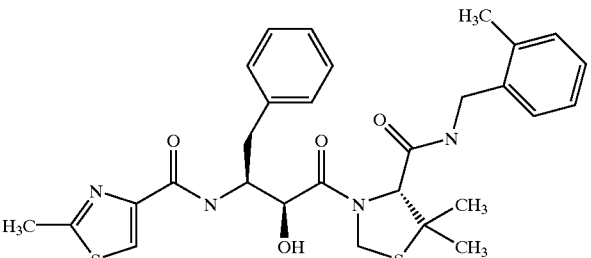 | 2.3 | 1.378 |
| 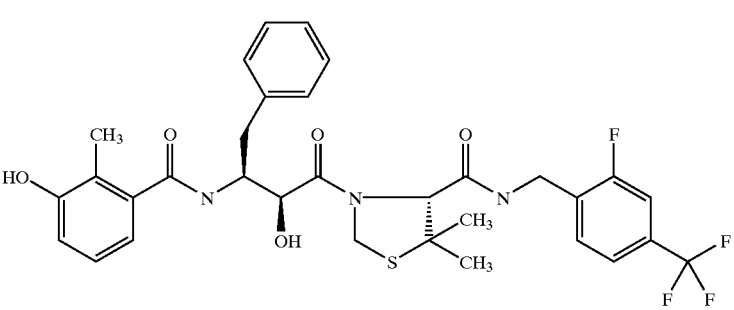 | 11.1 | 1.401 |
| 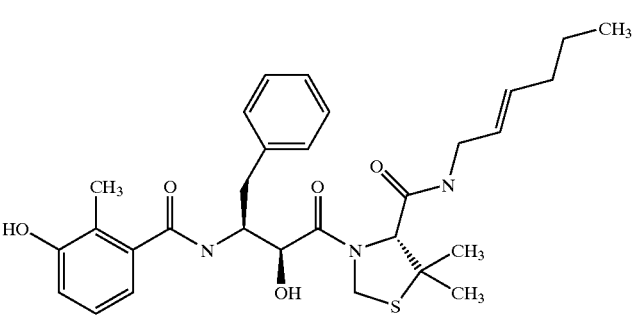 | 2.6 | 1.416 |

| MOLSTRUCTURE | $K_i$ | $EC_{50}$ |
|---|---|---|
| | 2.1 | 1.488 |
| | 14 | 1.512 |
| | 18.5 | |
| | 19.5 | 3 |
| | 12.1 | |

| MOLSTRUCTURE | $K_i$ | $EC_{50}$ |
|---|---|---|
| 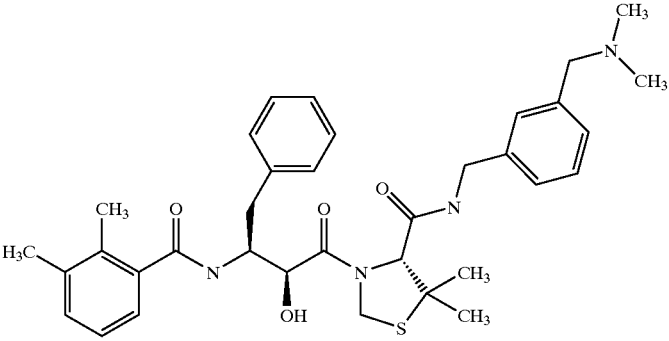 | 10.5 | 3.2 |
| 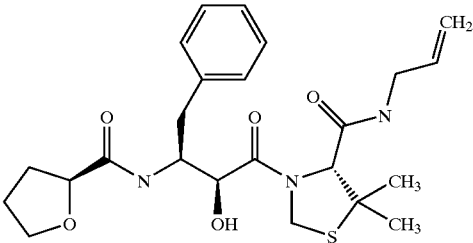 | 17.3 | 3.303 |
| 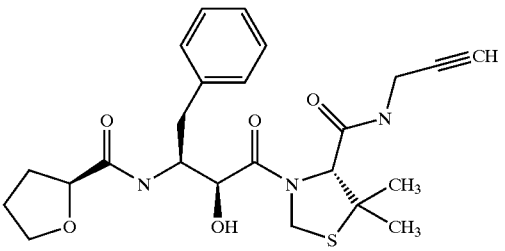 | 16.8 | 3.745 |
| 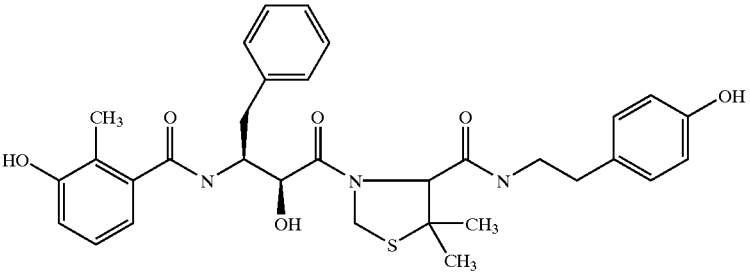 | 13.1 | |
| 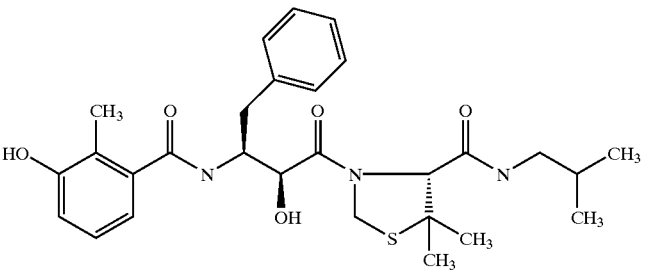 | 0.1 | |

| MOLSTRUCTURE | $K_i$ | $EC_{50}$ |
|---|---|---|
| | 28 | 4.132 |
| | 0.1 | |
| | 24.6 | 4.951 |
| | 55.8 | 10 |
| | 214 | 10 |

The following compounds have been prepared according to the procedures described herein and have demonstrated the noted activity:

While the invention has been described in terms of preferred embodiments and specific examples, those skilled in the art will recognize that various changes and modifications can be made through routine experimentation without departing from the spirit and scope of the invention. Thus, the invention should be understood as not being limited by the foregoing detailed description, but as being defined by the appended claims and their equivalents.

We claim:
1. A compound having the formula

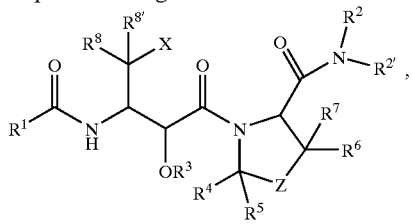

which includes all the possible stereoisomers,
wherein:
$R^1$ is phenyl, where said phenyl is substituted with one or more substituents independently selected from alkyl, halogen or hydroxyl;
$R^2$ is a $C_2$–$C_6$ alkenyl group or a $C_2$–$C_6$ alkynyl group, wherein said alkenyl or alkynyl group is a straight or branched chained group, and
where said alkenyl or alkynyl group is unsubstituted or is substituted by one or more halogen substituents;
$R^{2'}$ is H;
X is

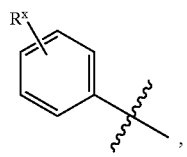

wherein $R^x$ is H;
Z is S, SO or $SO_2$;
$R^3$, $R^4$, $R^5$, $R^8$ and $R^{8'}$ are each H; and
$R^6$ and $R^7$ are each methyl;
or a prodrug, pharmaceutically acceptable salt or solvate thereof.

2. The compound, prodrug, pharmaceutically acceptable salt, or pharmaceutically acceptable solvate according to claim 1, having the formula:

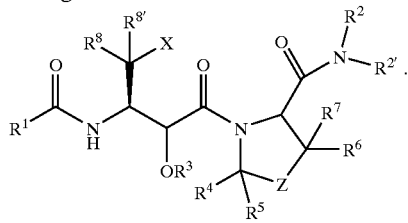

3. The compound, prodrug, pharmaceutically acceptable salt, or pharmaceutically acceptable solvate according to claim 1, having the formula:

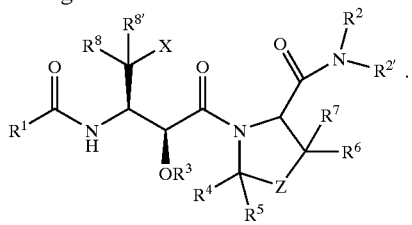

4. The compound, prodrug, pharmaceutically acceptable salt, or pharmaceutically acceptable solvate according to claim 1, having the formula:

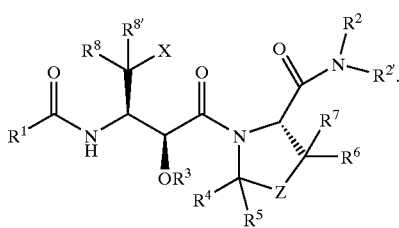

5. The compound according to claim 1, wherein $R^2$ is a $C_2$–$C_6$ alkenyl group.

6. The compound according to claim 1, wherein $R^2$ is a $C_2$–$C_6$ alkynyl group.

7. A compound selected from:

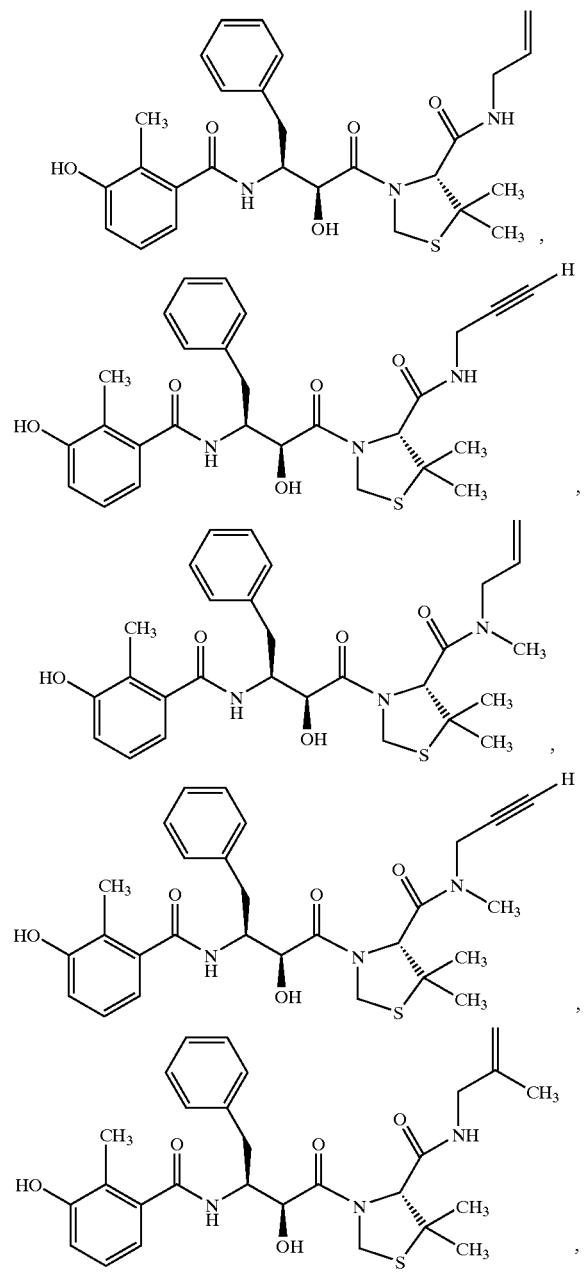

-continued
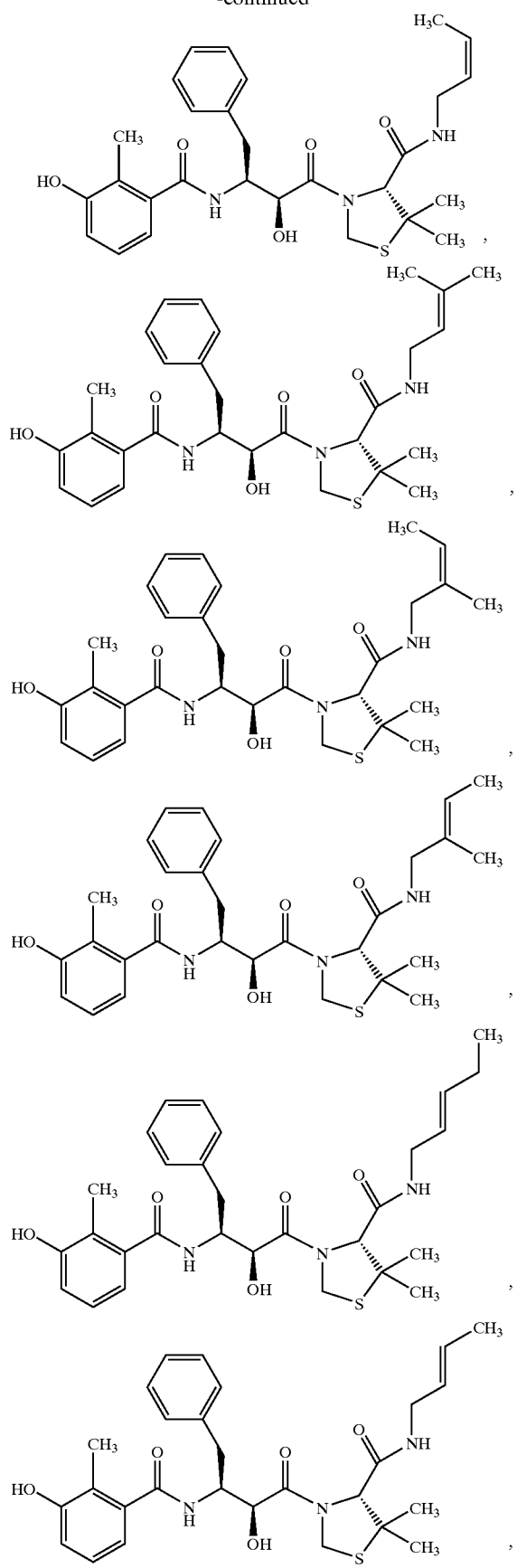
-continued
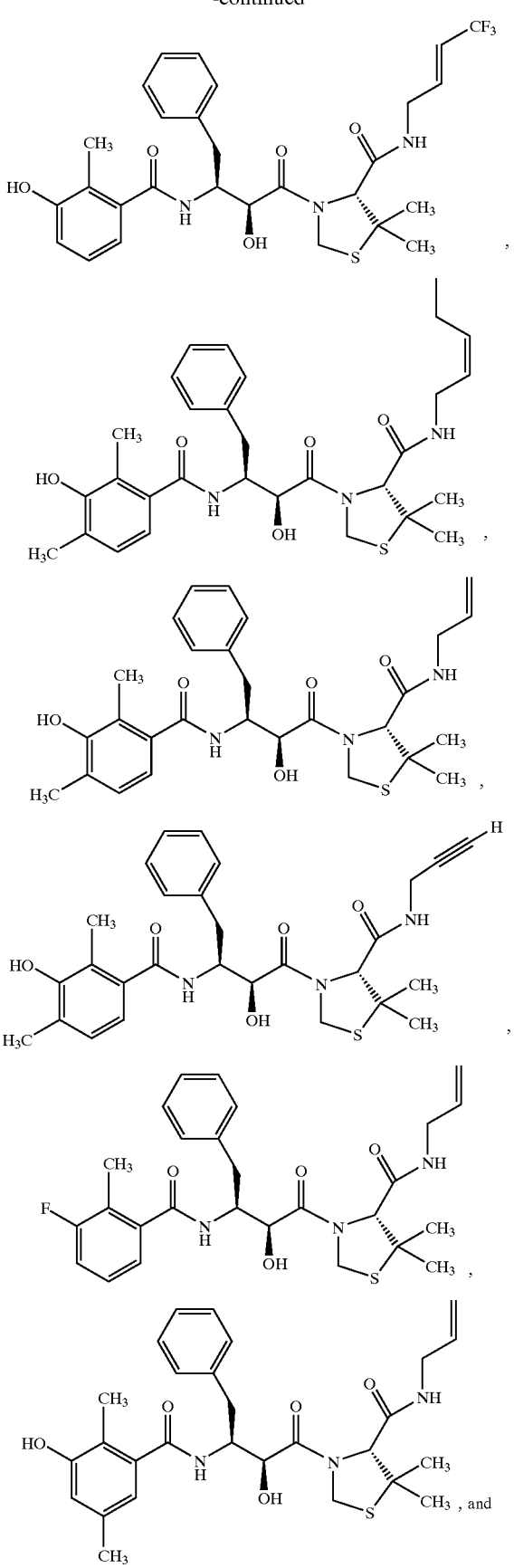

-continued

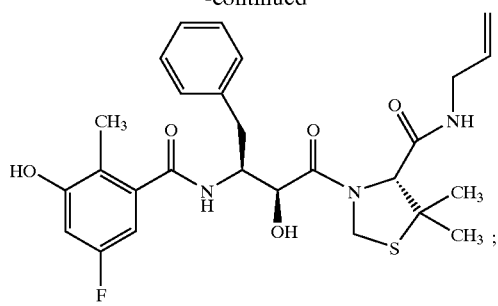

or a prodrug, pharmaceutically acceptable salt or solvate thereof.

8. A compound of formula:

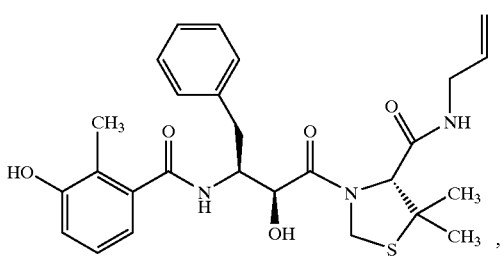

or pharmaceutically acceptable salt or solvate thereof.

9. A compound of formula:

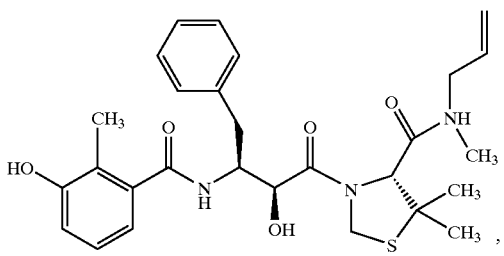

or pharmaceutically acceptable salt or solvate thereof.

10. A compound of formula:

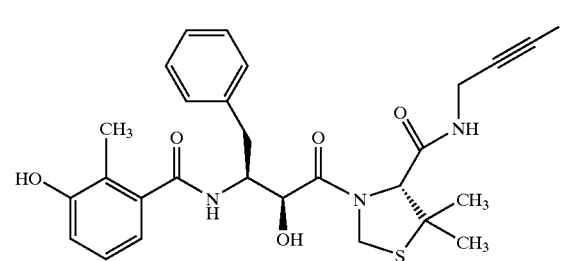

or pharmaceutically acceptable salt or solvate thereof.

11. A compound of formula:

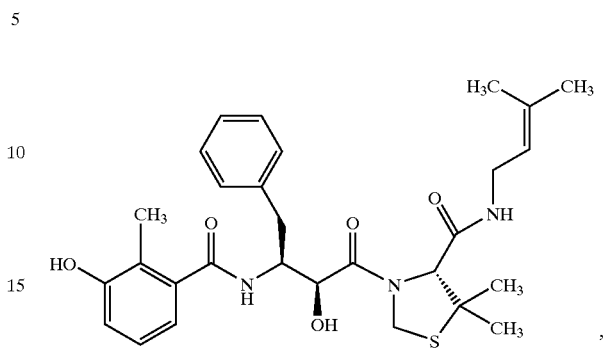

or pharmaceutically acceptable salt or solvate thereof.

12. A compound of formula:

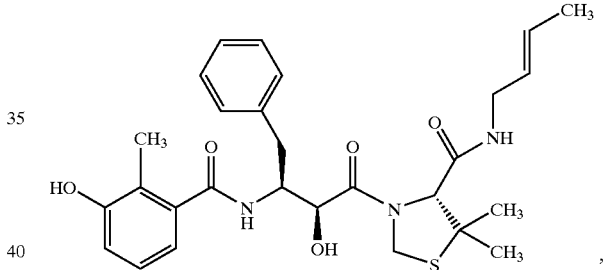

or pharmaceutically acceptable salt or solvate thereof.

13. A compound of formula:

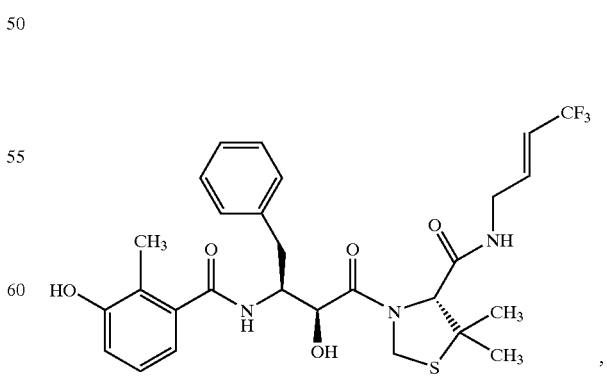

or pharmaceutically acceptable salt or solvate thereof.

14. A compound of formula:
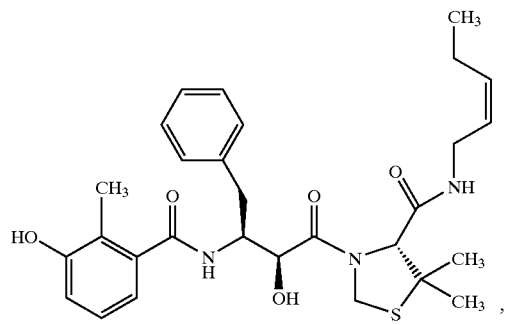
or pharmaceutically acceptable salt or solvate thereof.
15. A compound of formula:
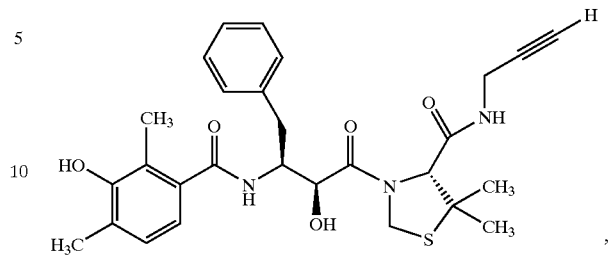
or pharmaceutically acceptable salt or solvate thereof.
16. The compound of claim 4, wherein Z is S.
* * * * *